United States Patent
Gérard et al.

(10) Patent No.: US 10,370,389 B2
(45) Date of Patent: *Aug. 6, 2019

(54) METHODS OF PREPARING CYTOTOXIC BENZODIAZEPINE DERIVATIVES

(71) Applicant: IMMUNOGEN, INC., Waltham, MA (US)

(72) Inventors: Baudouin Gérard, Belmont, MA (US); Manami Shizuka, Belmont, MA (US); Michael Louis Miller, Framingham, MA (US); Richard A. Silva, Needham, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/837,832

(22) Filed: Dec. 11, 2017

(65) Prior Publication Data

US 2018/0201626 A1    Jul. 19, 2018

Related U.S. Application Data

(63) Continuation of application No. 15/216,512, filed on Jul. 21, 2016, now Pat. No. 9,873,708.

(60) Provisional application No. 62/327,973, filed on Apr. 26, 2016, provisional application No. 62/195,023, filed on Jul. 21, 2015.

(51) Int. Cl.
*C07D 519/00* (2006.01)
*C07D 487/04* (2006.01)
*C07K 5/083* (2006.01)

(52) U.S. Cl.
CPC ......... *C07D 519/00* (2013.01); *C07D 487/04* (2013.01); *C07K 5/0804* (2013.01)

(58) Field of Classification Search
CPC .................................................. C07D 519/00
See application file for complete search history.

(56) References Cited

U.S. PATENT DOCUMENTS

| | | |
|---|---|---|
| 9,353,127 B2 | 5/2016 | Fishkin et al. |
| 2016/0106863 A1 | 4/2016 | Chari et al. |
| 2017/0050985 A1 | 2/2017 | Gerard et al. |

FOREIGN PATENT DOCUMENTS

| | | |
|---|---|---|
| EP | 2511260 A1 | 10/2012 |
| WO | 2010/091150 A1 | 8/2010 |
| WO | 2011/064141 A1 | 6/2011 |
| WO | 2012/128868 A1 | 9/2012 |
| WO | 2015/051045 A2 | 4/2015 |
| WO | 2016/036794 A1 | 3/2016 |
| WO | 2016/036801 A1 | 3/2016 |

OTHER PUBLICATIONS

Behrens et al., Synthesis of achiral linker reagents for direct labelling of oligonucleotides on solid supports. Nucleosides Nucleotides. Feb. 1999;18(2):291-305.

Ueno et al., Synthesis and properties of nucleic acid analogues consisting of a benzene-phosphate backbone. J Org Chem. Sep. 30, 2005;70(20):7925-35.

*Primary Examiner* — Bruck Kifle

(74) *Attorney, Agent, or Firm* — McCarter & English, LLP; Steven G. Davis; Xin Zhang

(57) ABSTRACT

The invention relates to novel methods for preparing indolinobenzodiazepine dimer compounds and their synthetic precursors.

22 Claims, 19 Drawing Sheets ns described herein can be combined with one or more other
METHODS OF PREPARING CYTOTOXIC BENZODIAZEPINE DERIVATIVES

REFERENCE TO RELATED APPLICATIONS

This application is a continuation of U.S. patent application Ser. No. 15/216,512, filed on Jul. 21, 2016, which claims the benefit of the filing date, under 35 U.S.C. § 119(e), of U.S. Provisional Application No. 62/327,973, filed on Apr. 26, 2016, and U.S. Provisional Application No. 62/195,023, filed on Jul. 21, 2015. The entire contents of each of the above-referenced applications are incorporated.

FIELD OF THE INVENTION

The present invention relates to novel methods for preparing cytotoxic indolinobenzodiazepine derivatives.

BACKGROUND OF THE INVENTION

It has been shown that cell-binding agent conjugates of indolinobenzodiazepine dimers that have one imine functionality and one amine functionality display a much higher therapeutic index (ratio of maximum tolerated dose to minimum effective dose) in vivo compared to previously disclosed benzodiazepine derivatives having two imine functionalities. See, for example, WO 2012/128868. The previously disclosed method for making the indolinobenzodiazepine dimers with one imine functionality and one amine functionality involves partial reduction of indolinobenzodiazepine dimers having two imine functionalities. The partial reduction step generally leads to the formation of fully reduced by-product and unreacted starting material, which requires cumbersome purification step and results in low yield.

Thus, there exists a need for improved methods for preparing the indolinobenzodiazepine dimers that are more efficient and suitable for large scale manufacturing process.

SUMMARY OF THE INVENTION

The present invention provides various methods for preparing indolinobenzodiazepine dimer compounds and their synthetic precursors. Compared to the previously disclosed method, the methods of the present invention can produce the desired dimer compounds with higher yield without the need of cumbersome purification steps. These methods are more suitable for large scale manufacturing process.

The present invention provides methods of the first through forty-fourth embodiments described in detail below.

DETAILED DESCRIPTION OF THE INVENTION

Figure 1:
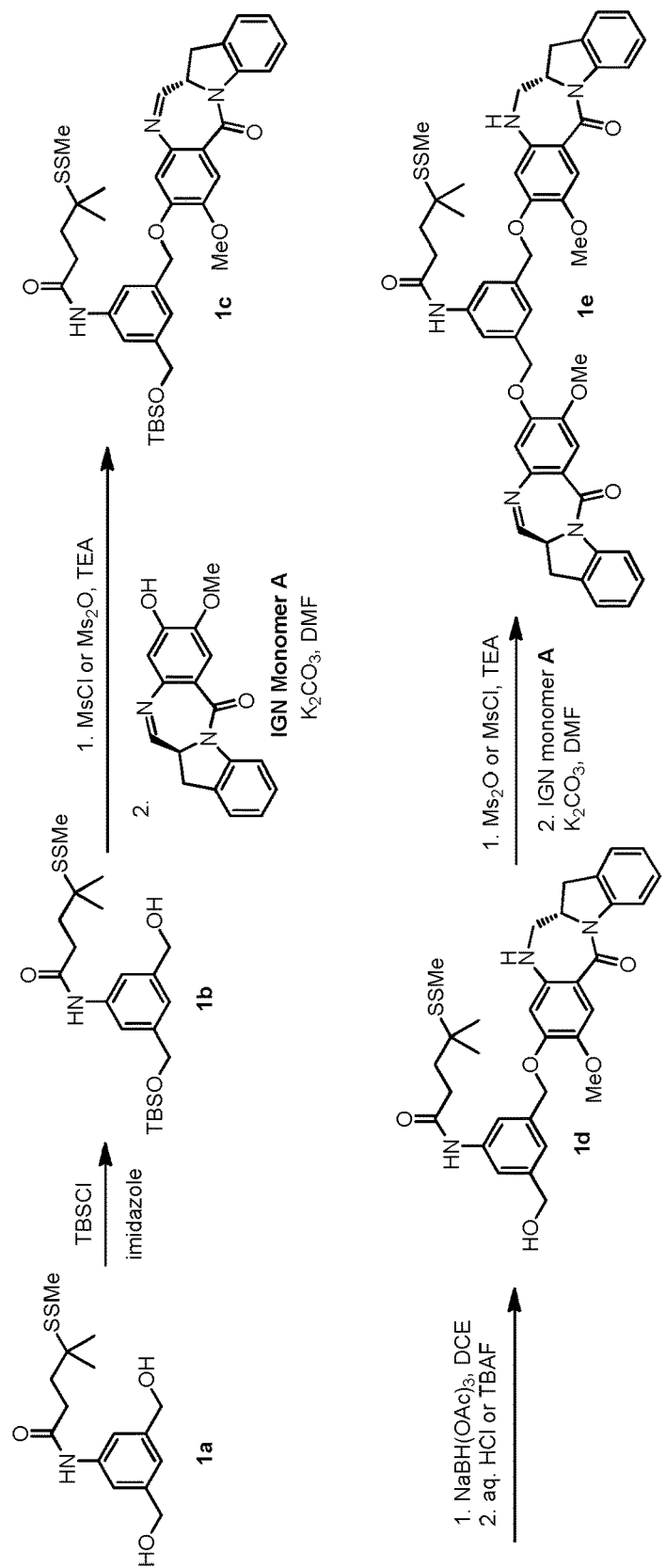
FIGS. 1-19 show exemplary schemes for the methods of the present invention.
Figure 2:
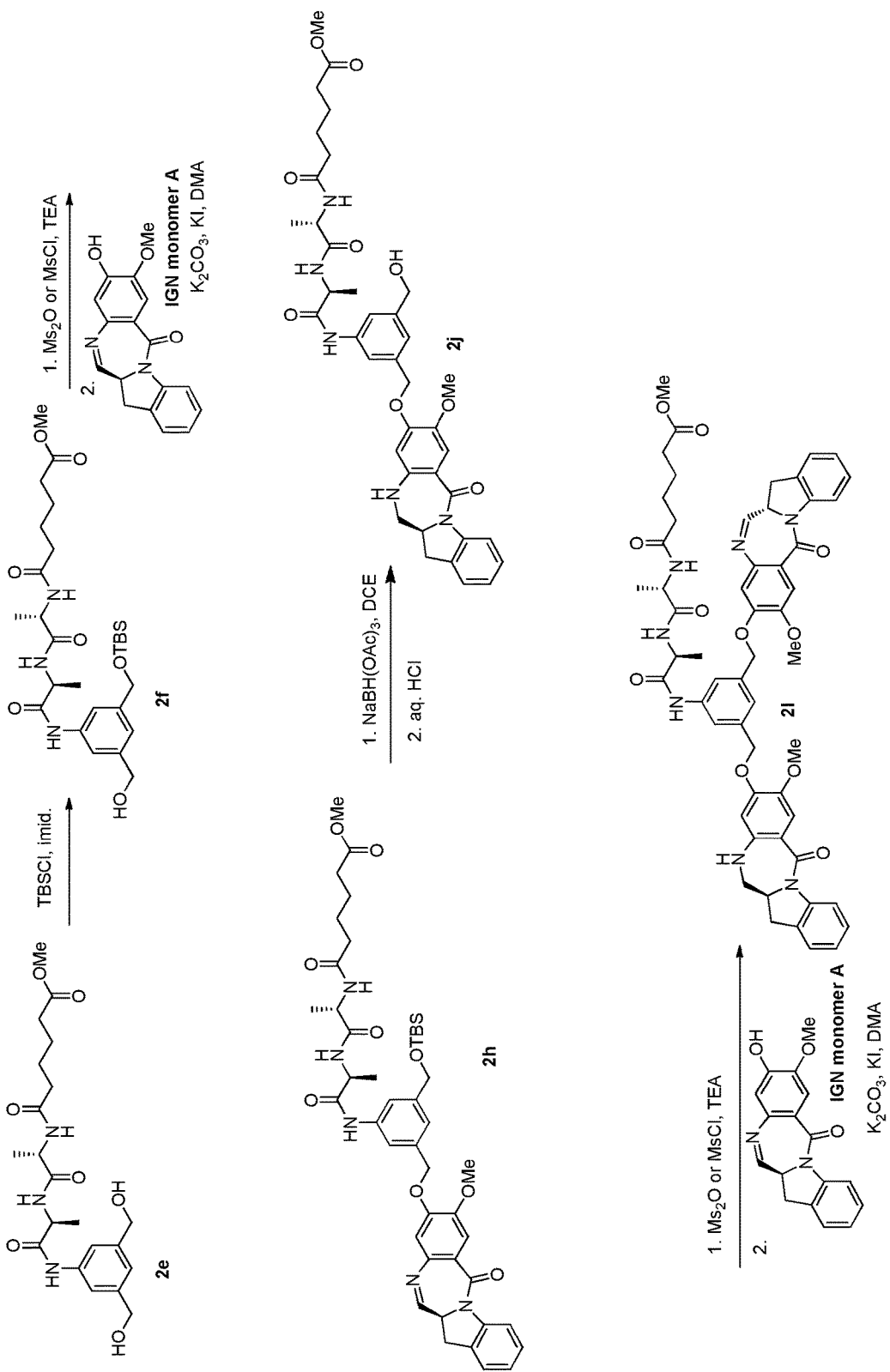
Figure 3:
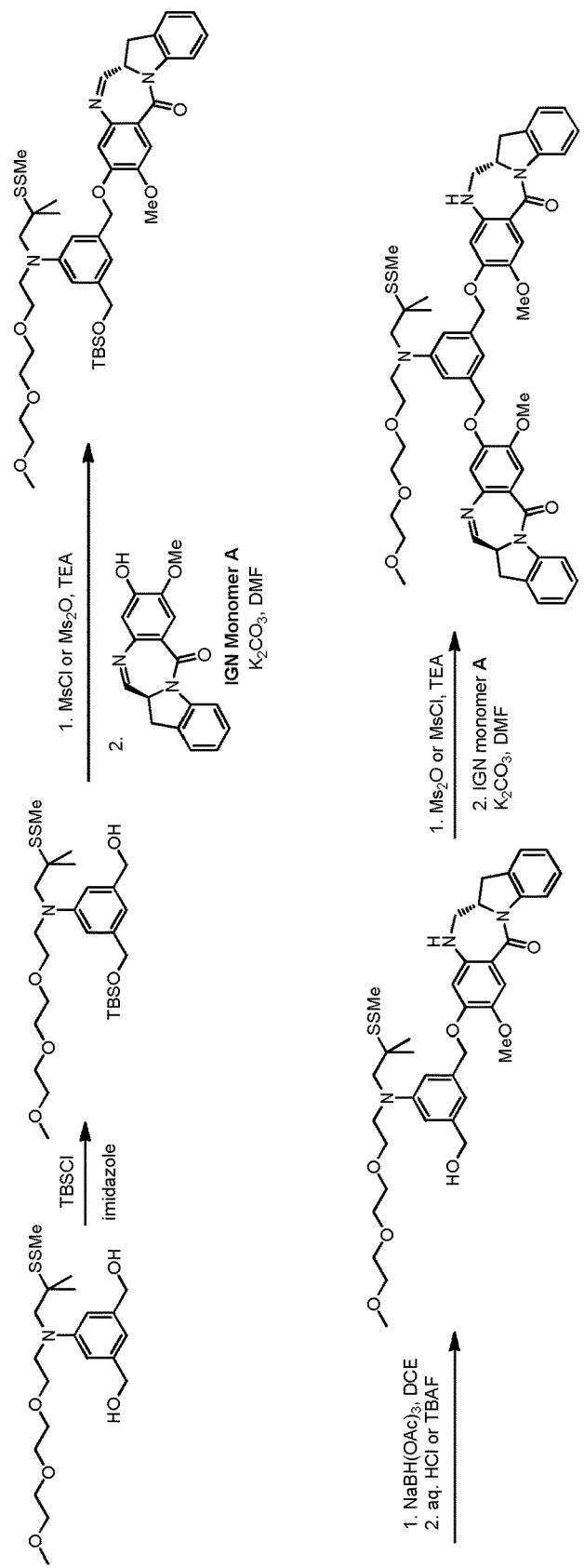
Figure 4:
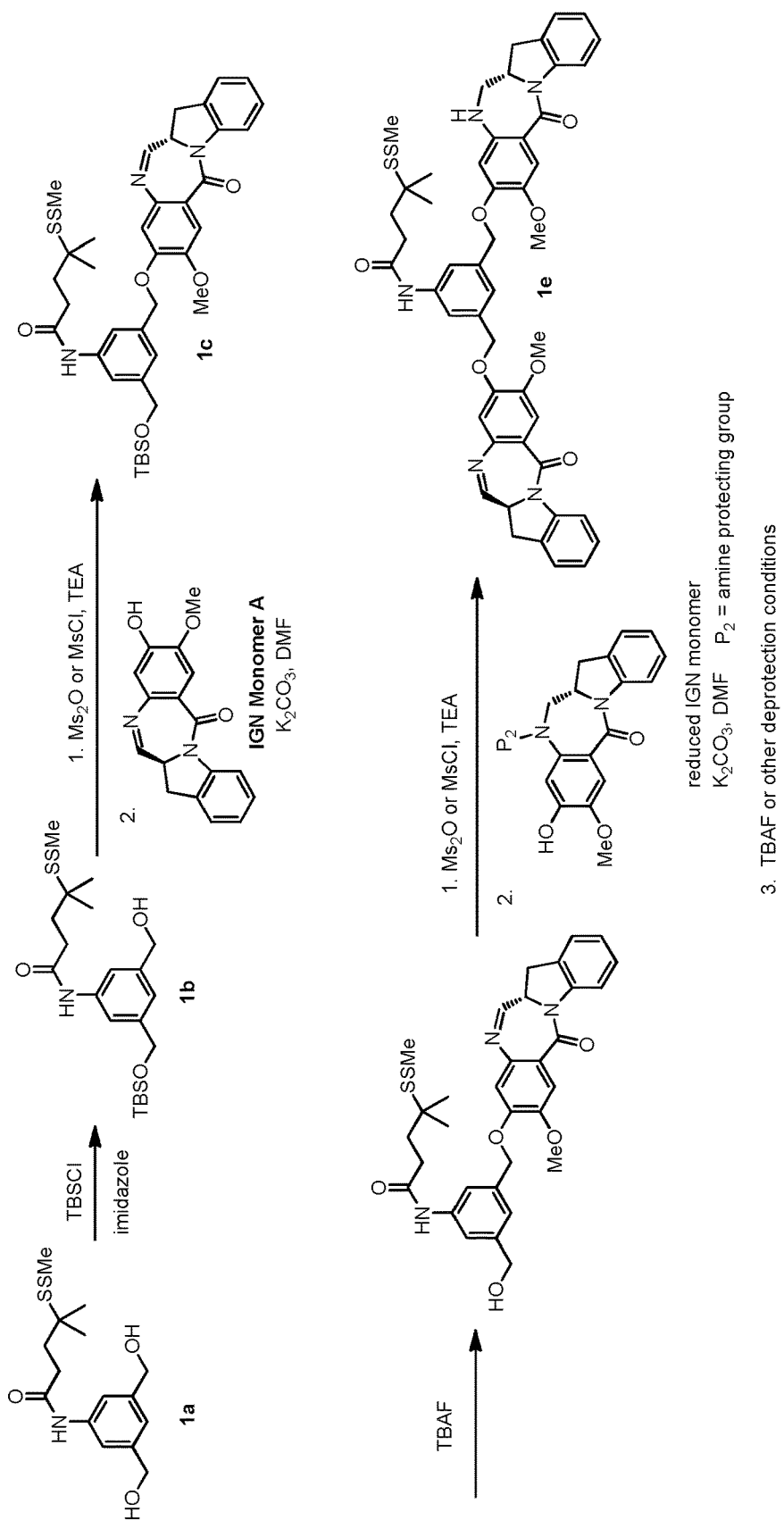
Figure 5:
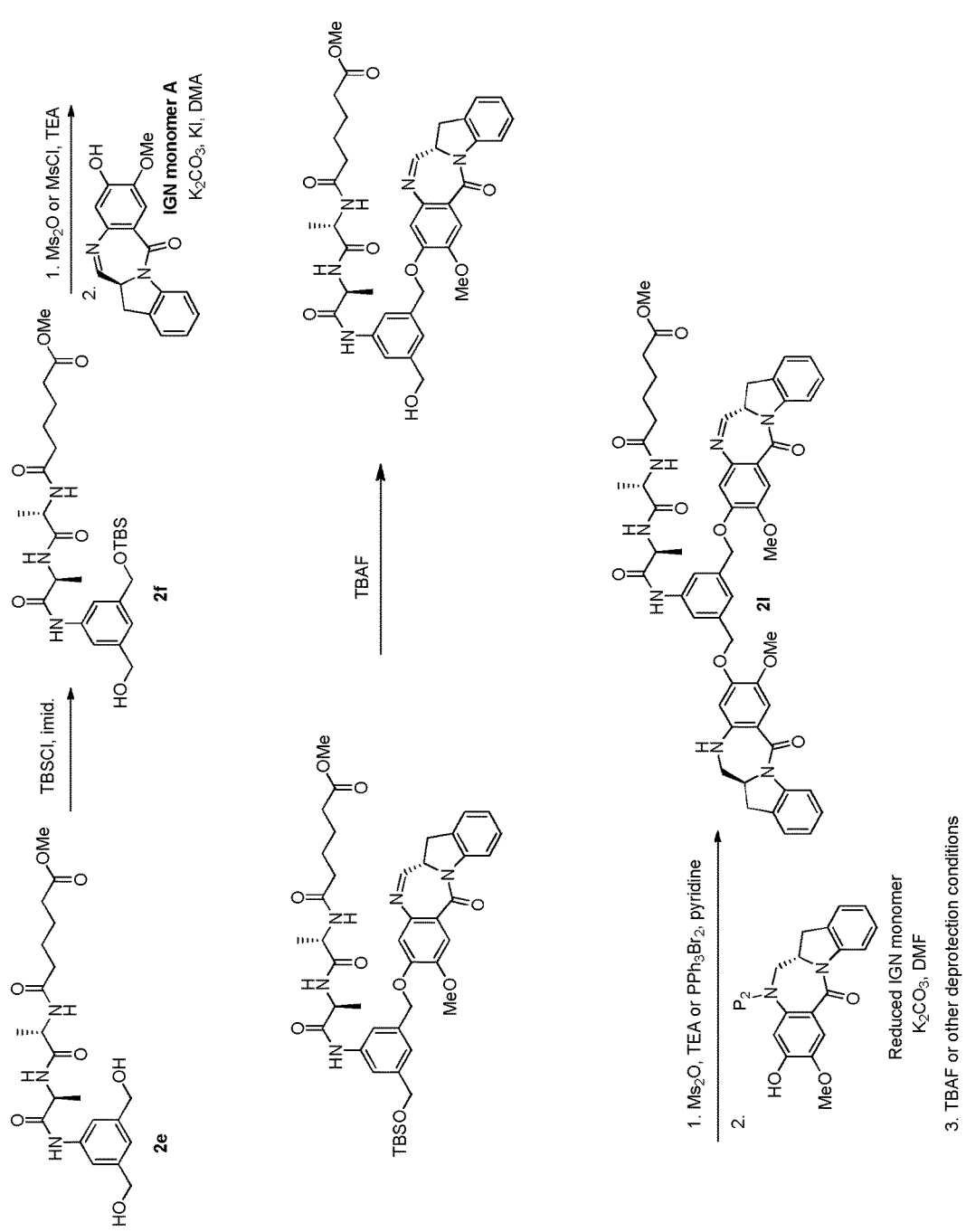
Figure 6:
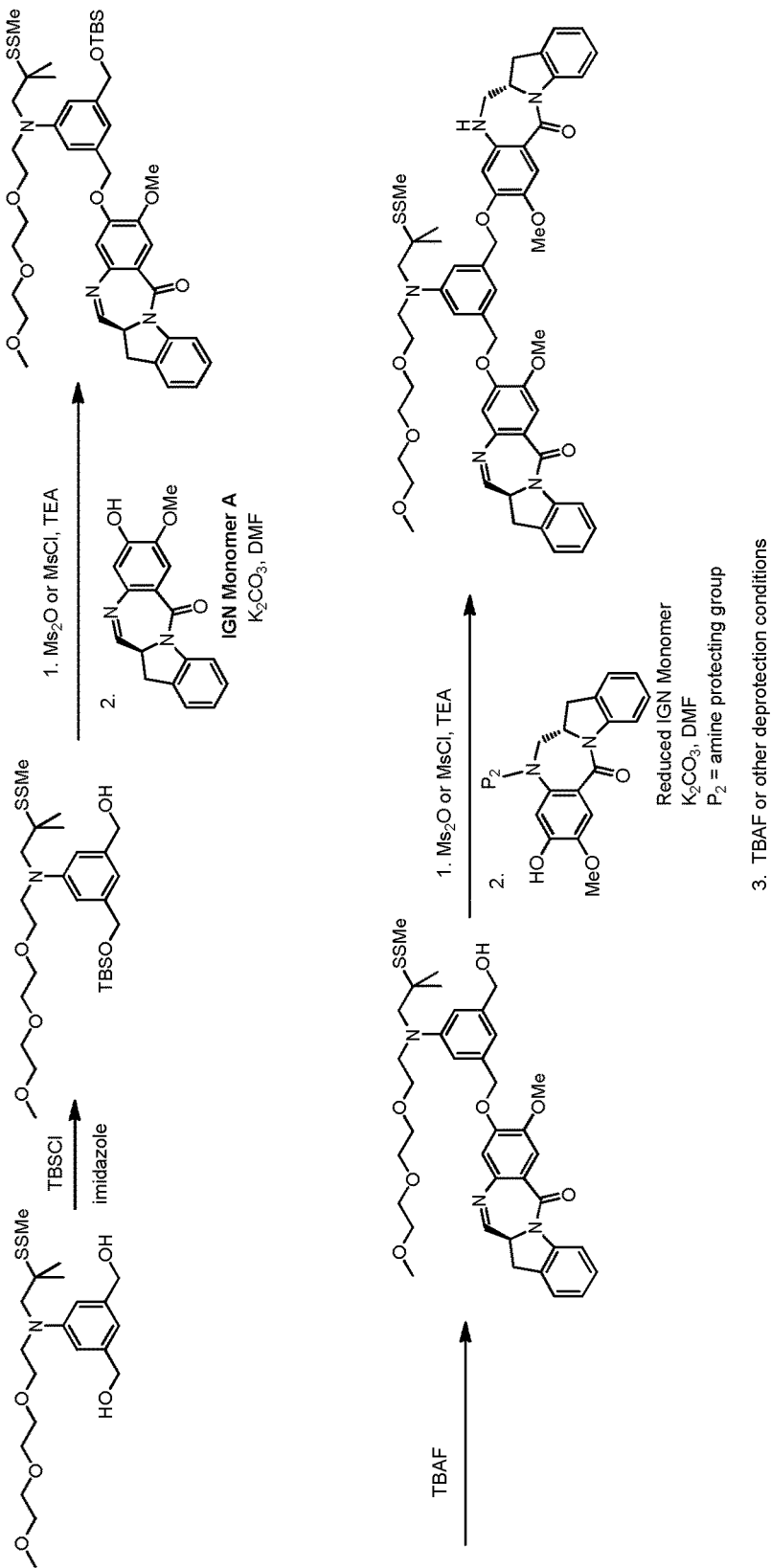
Figure 7:
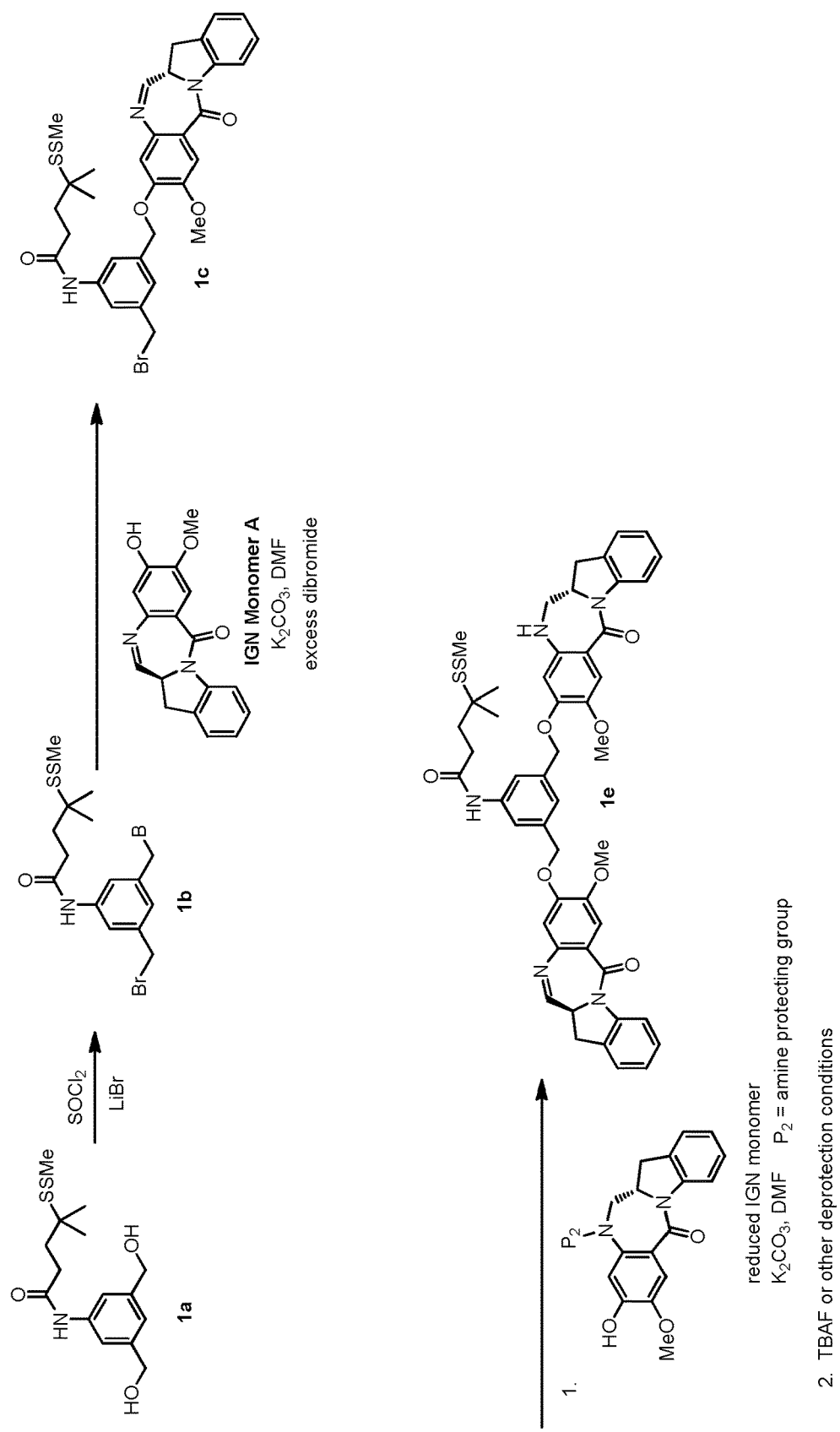
Figure 8:
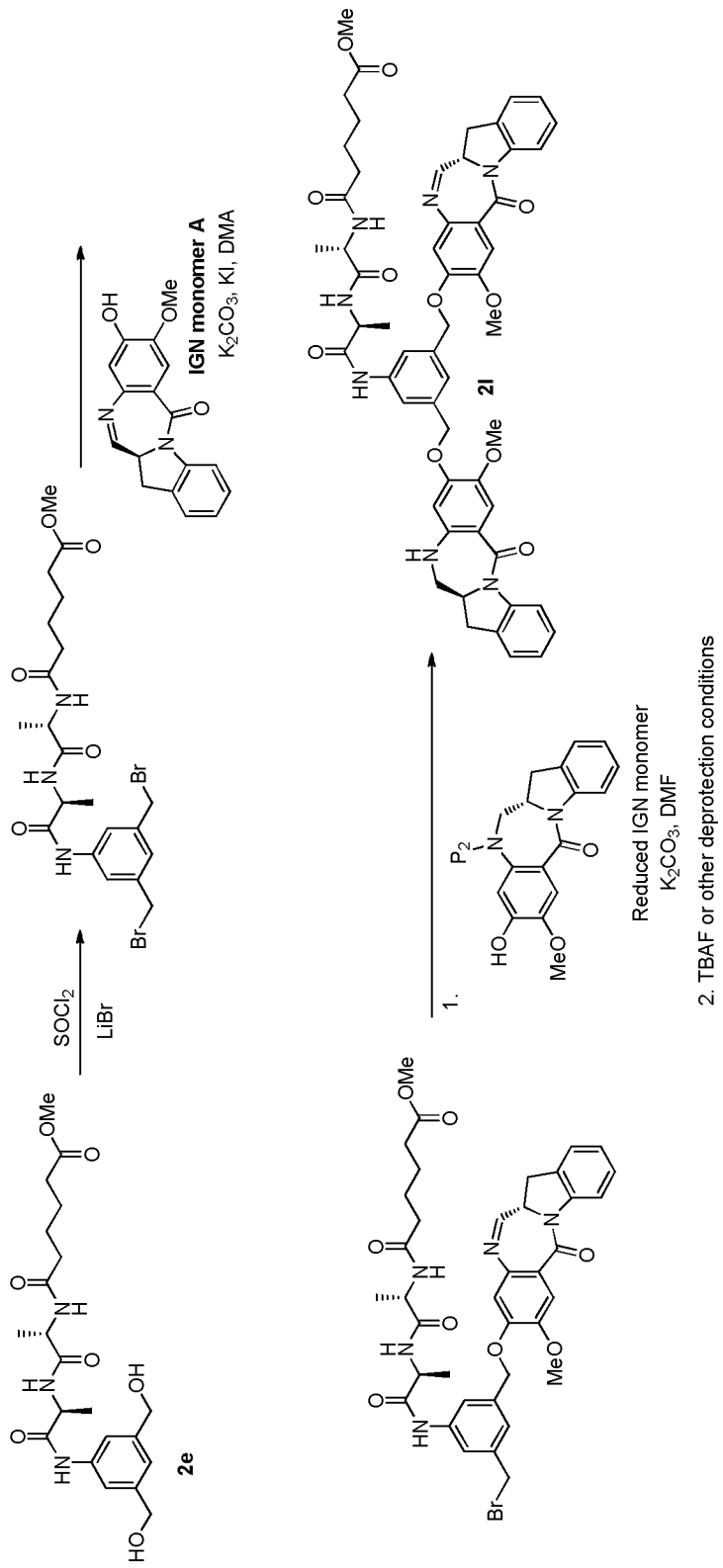
Figure 9:
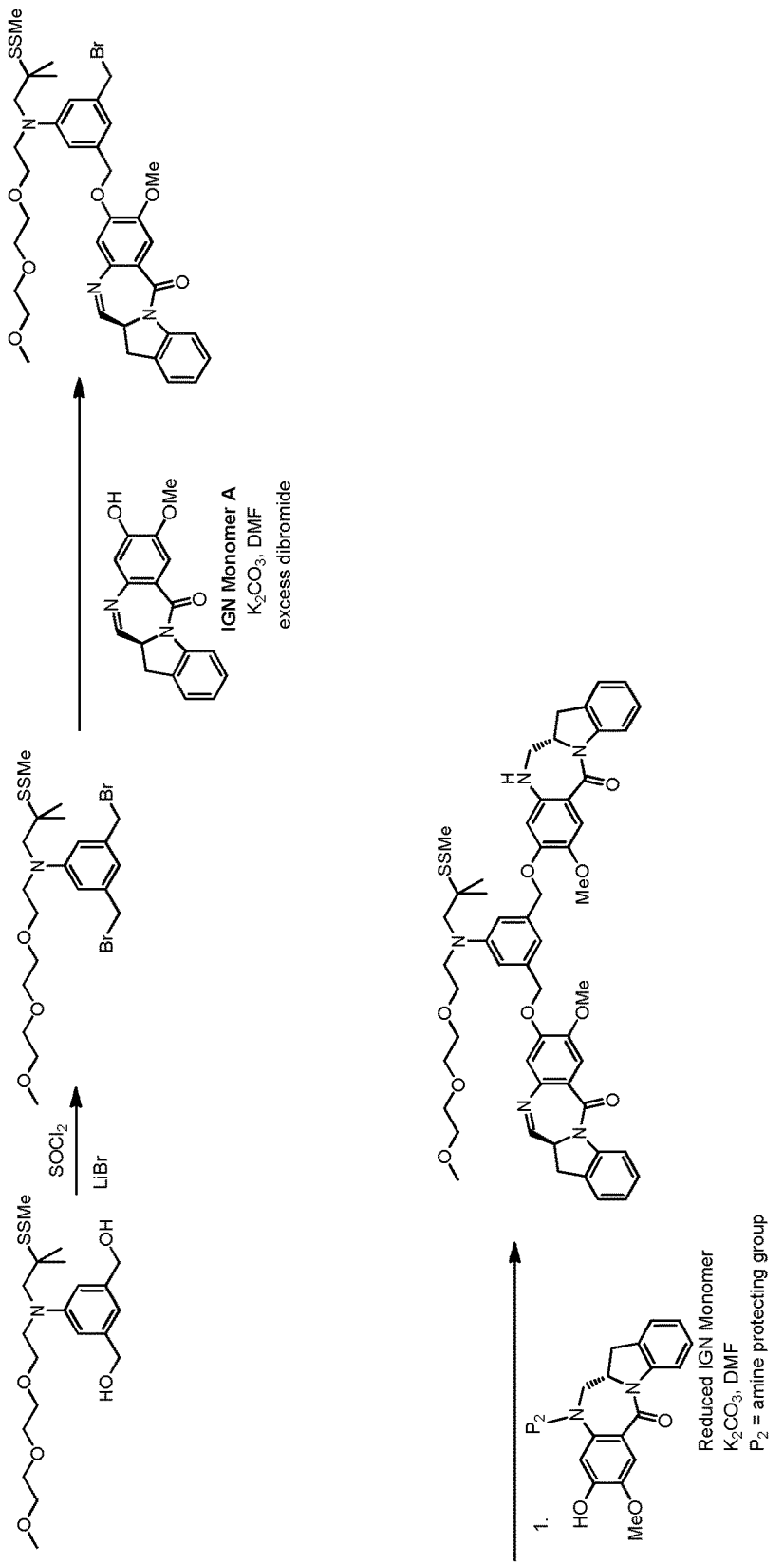
Figure 10:
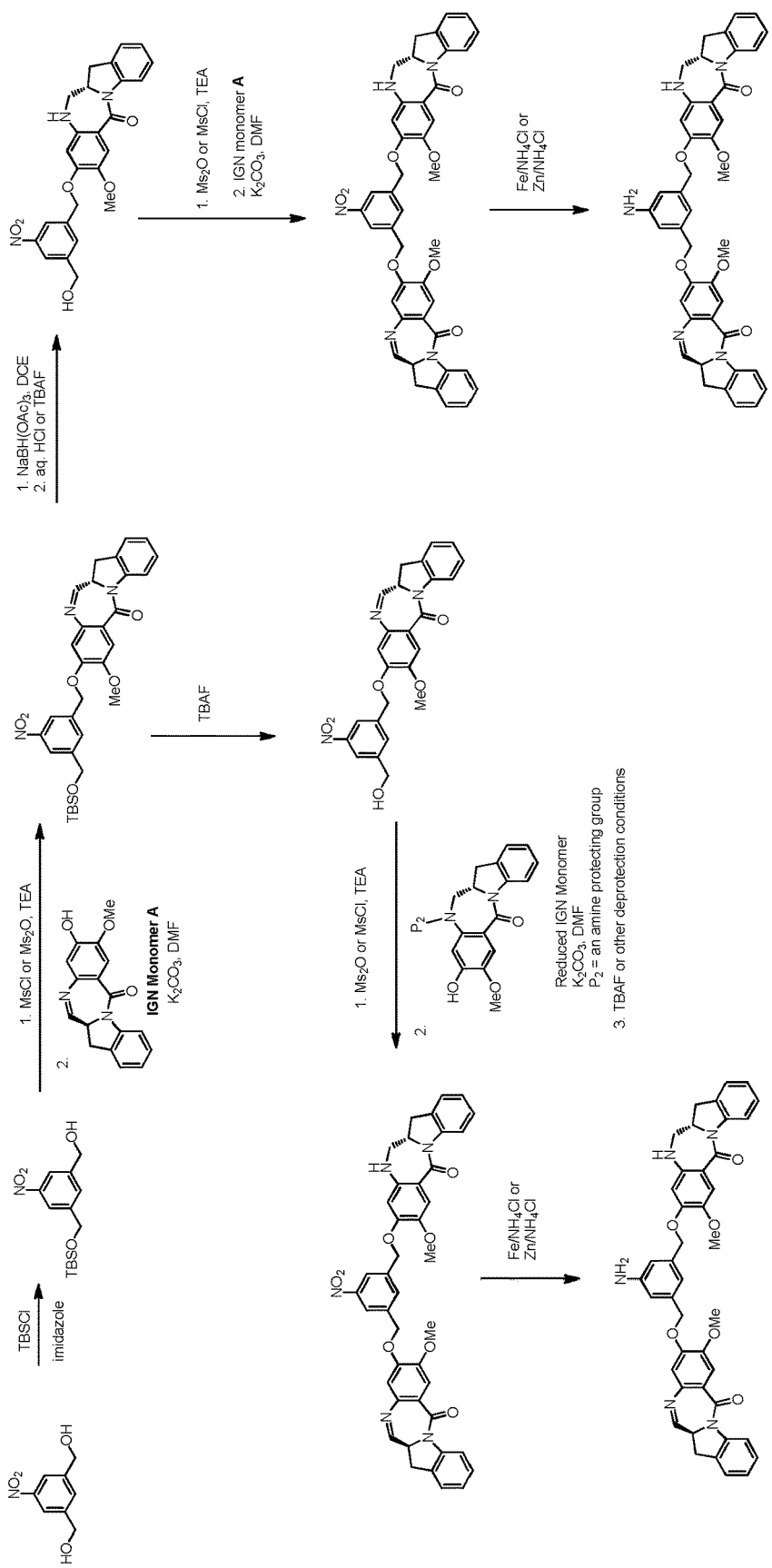
Figure 11:
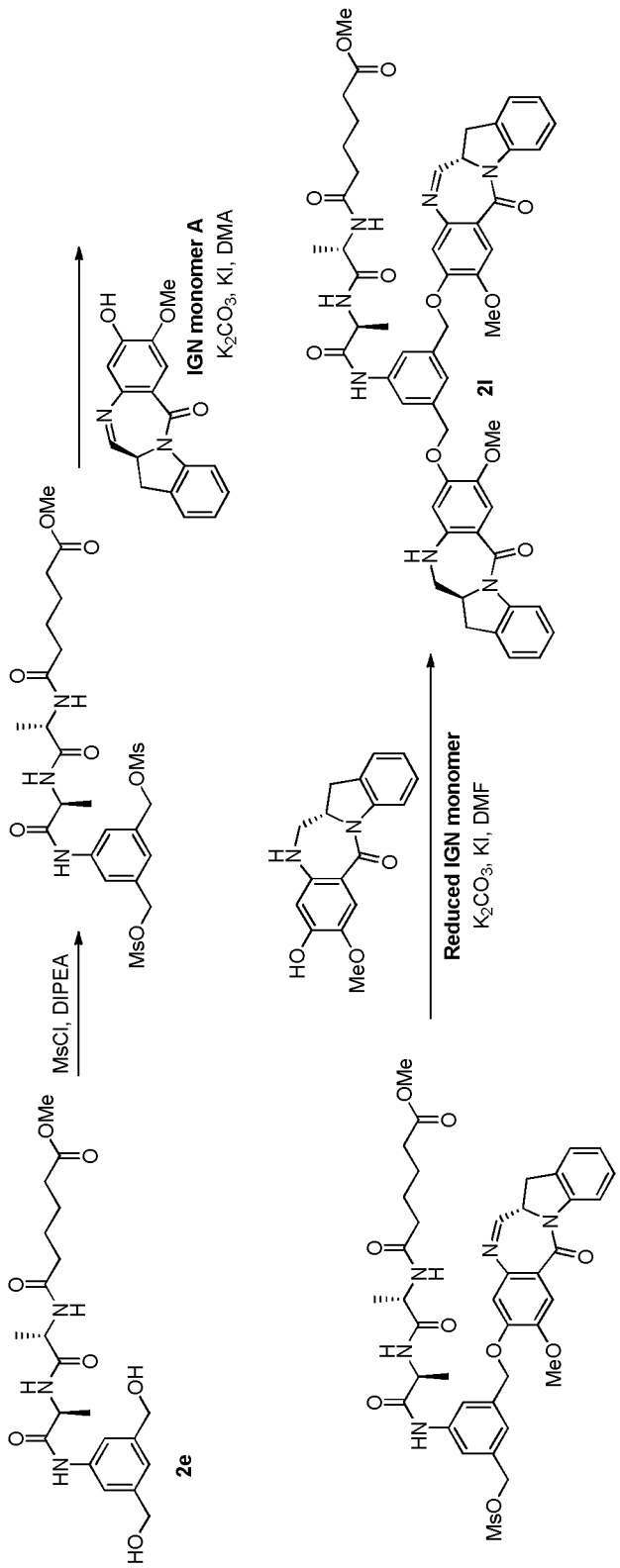
Figure 12:
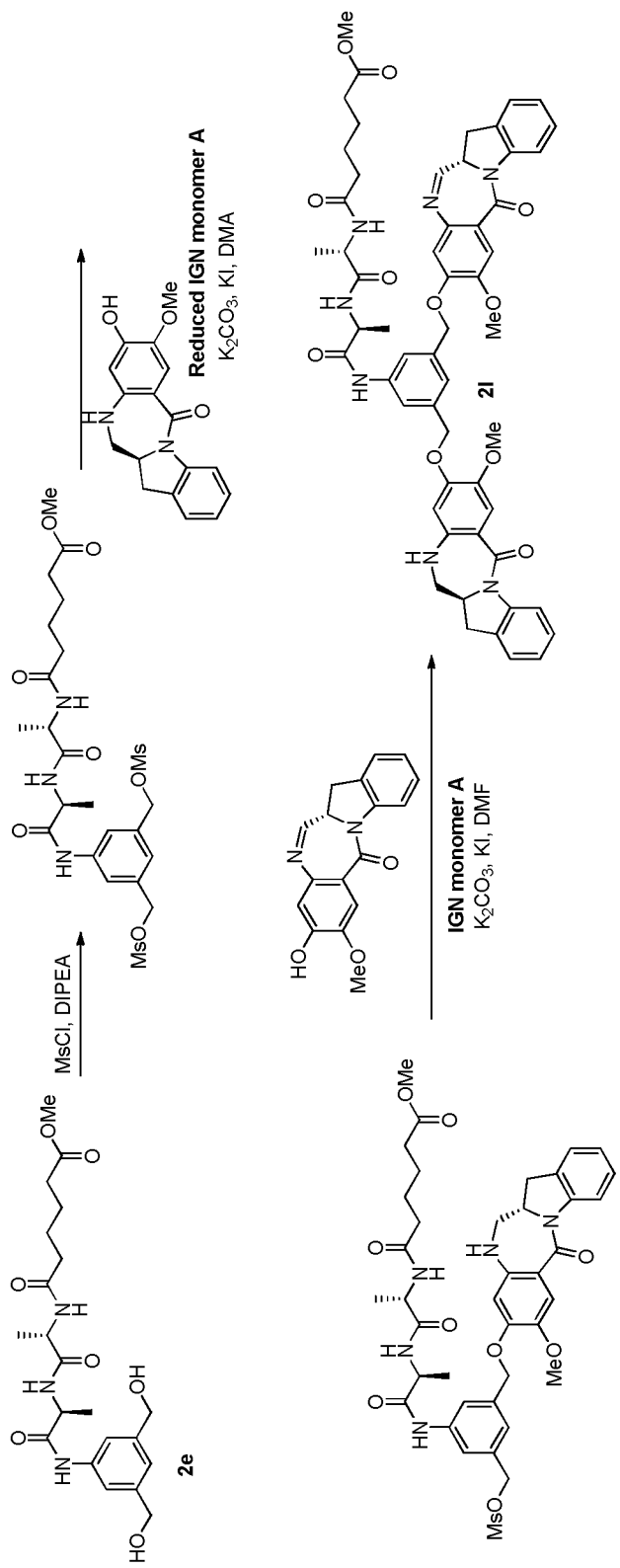
Figure 13:
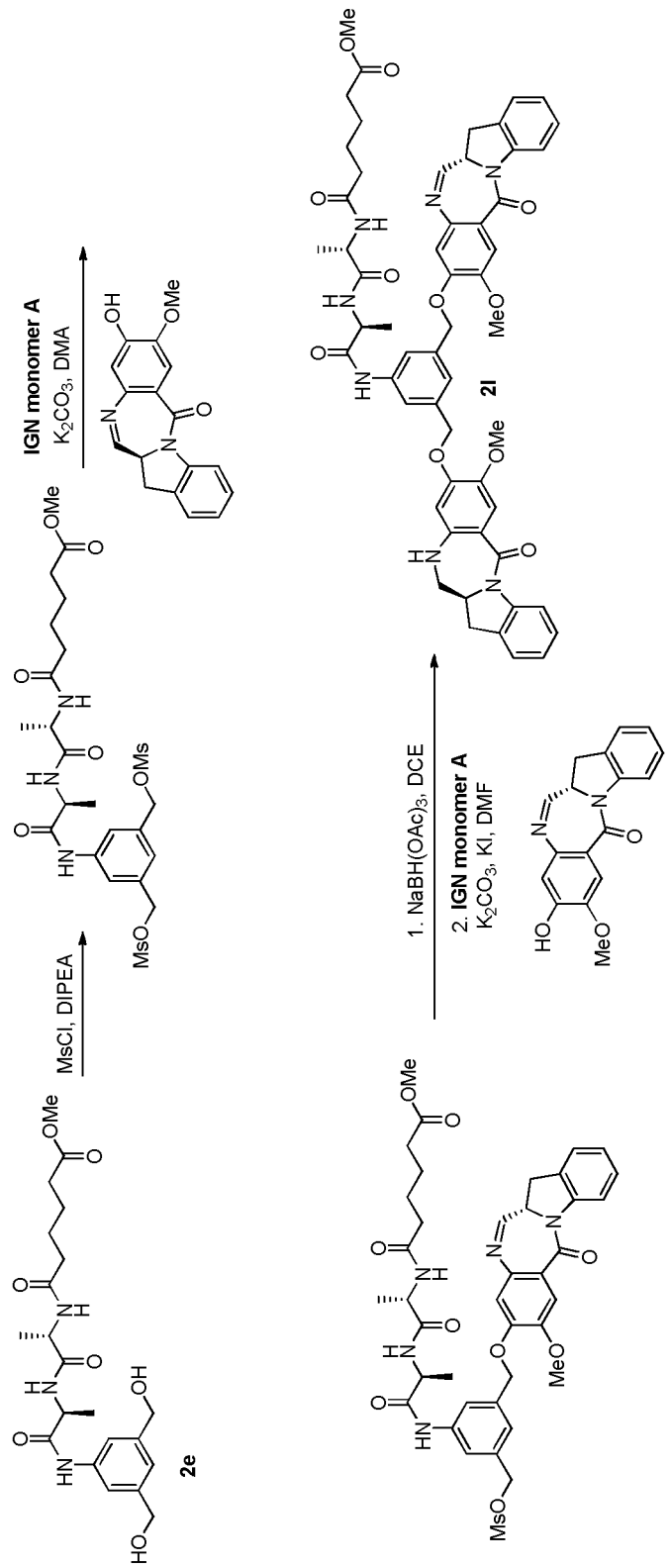
Figure 14:
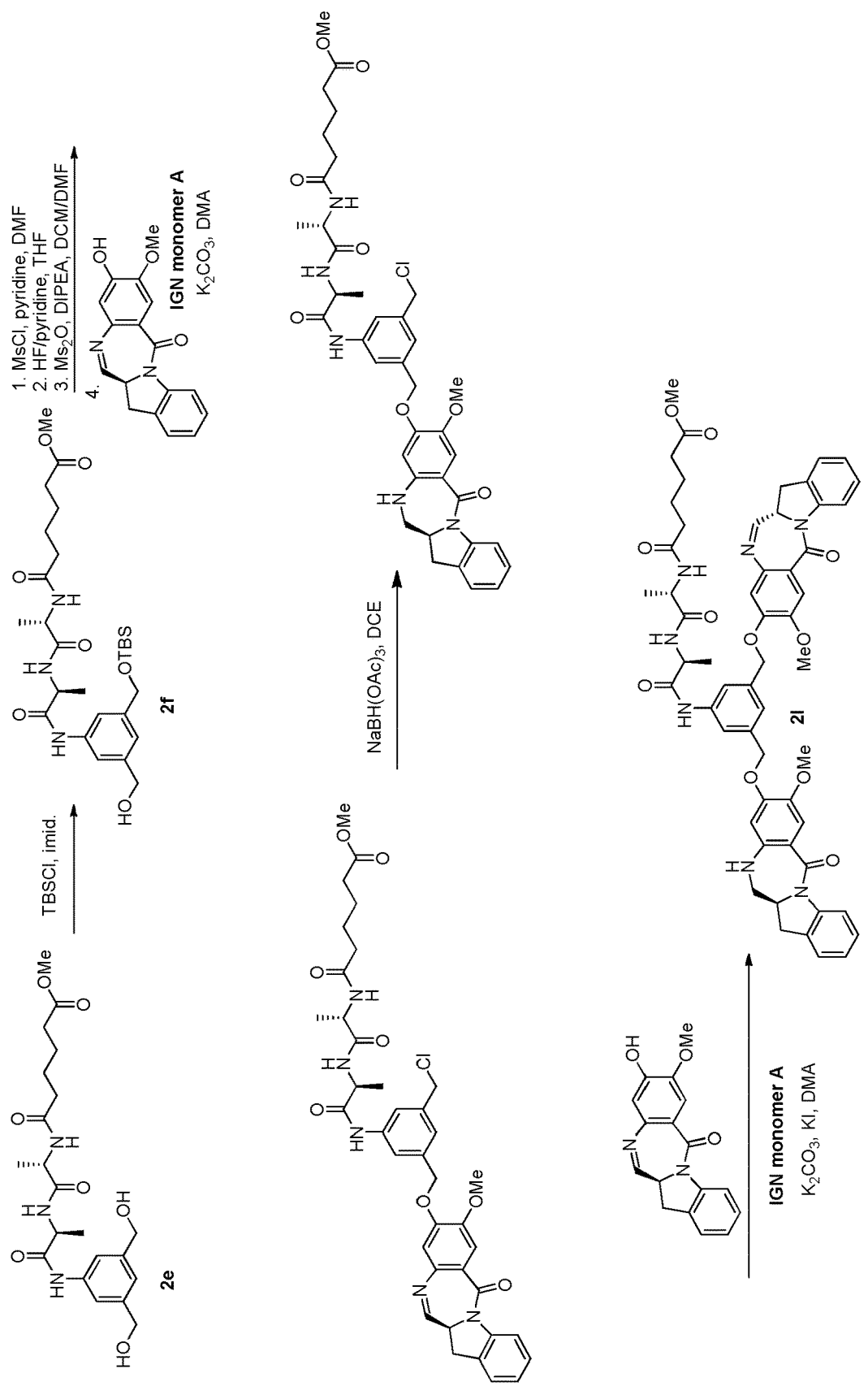
Figure 15:
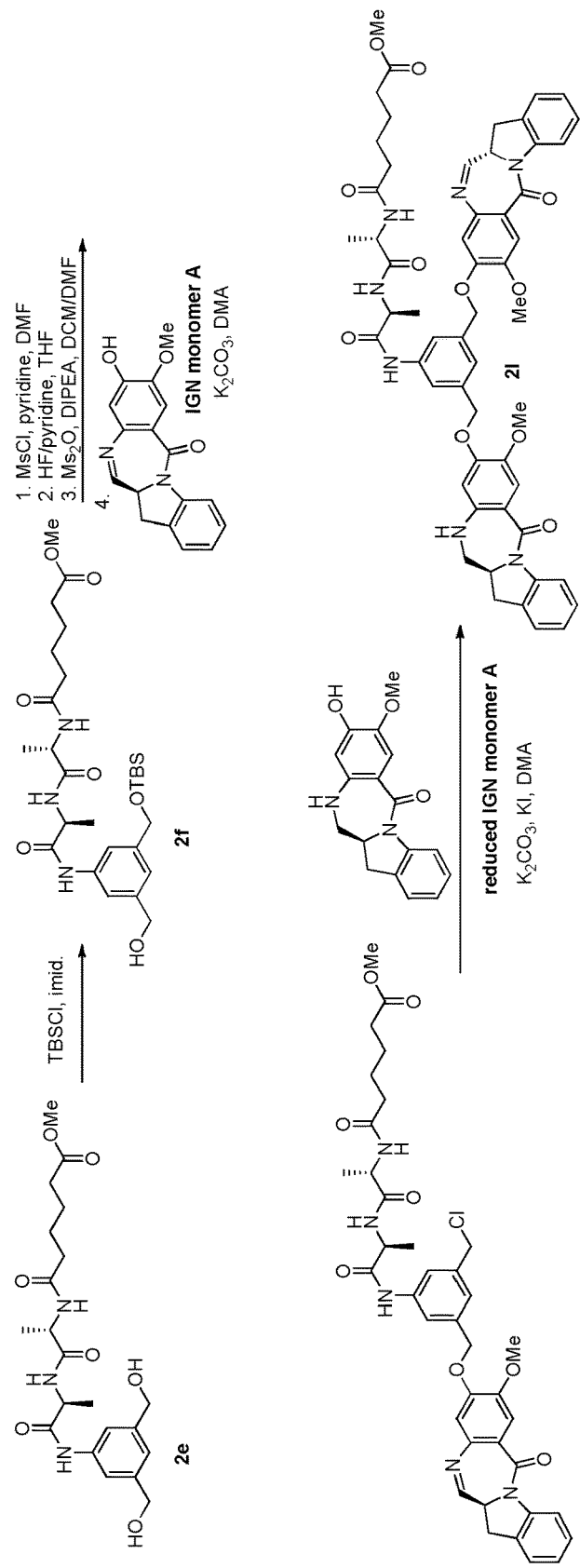
Figure 16:
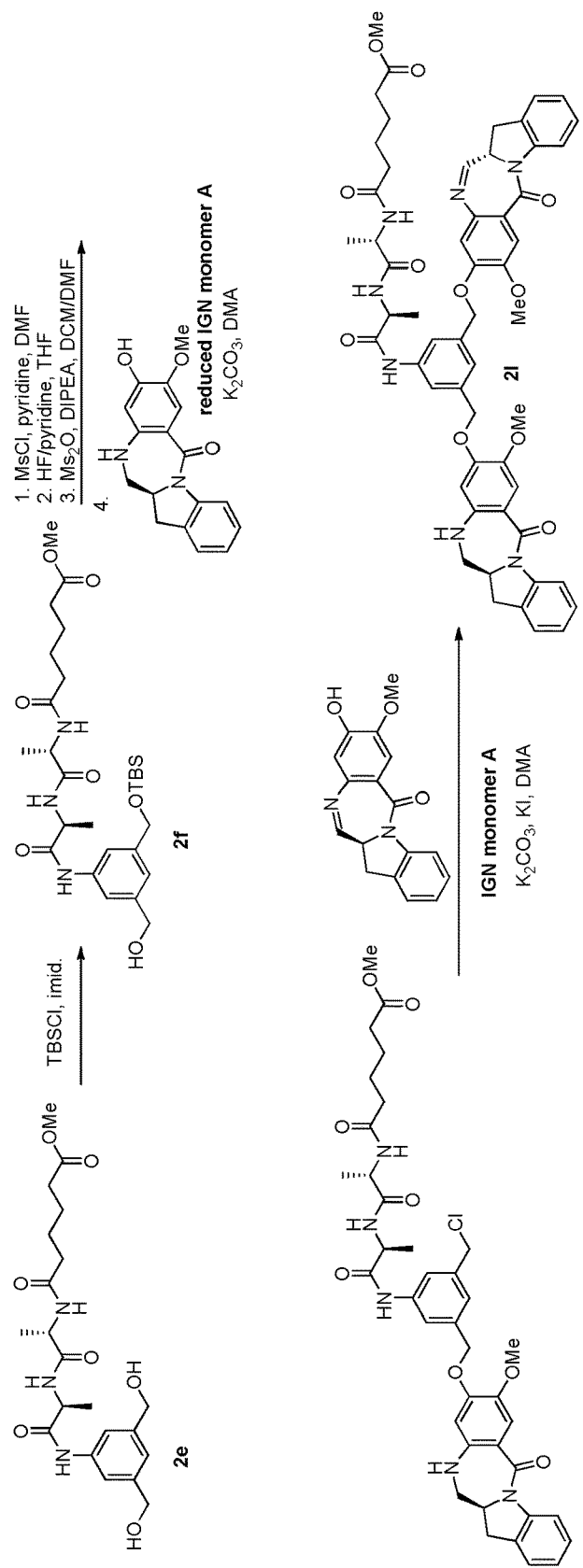
Figure 17:
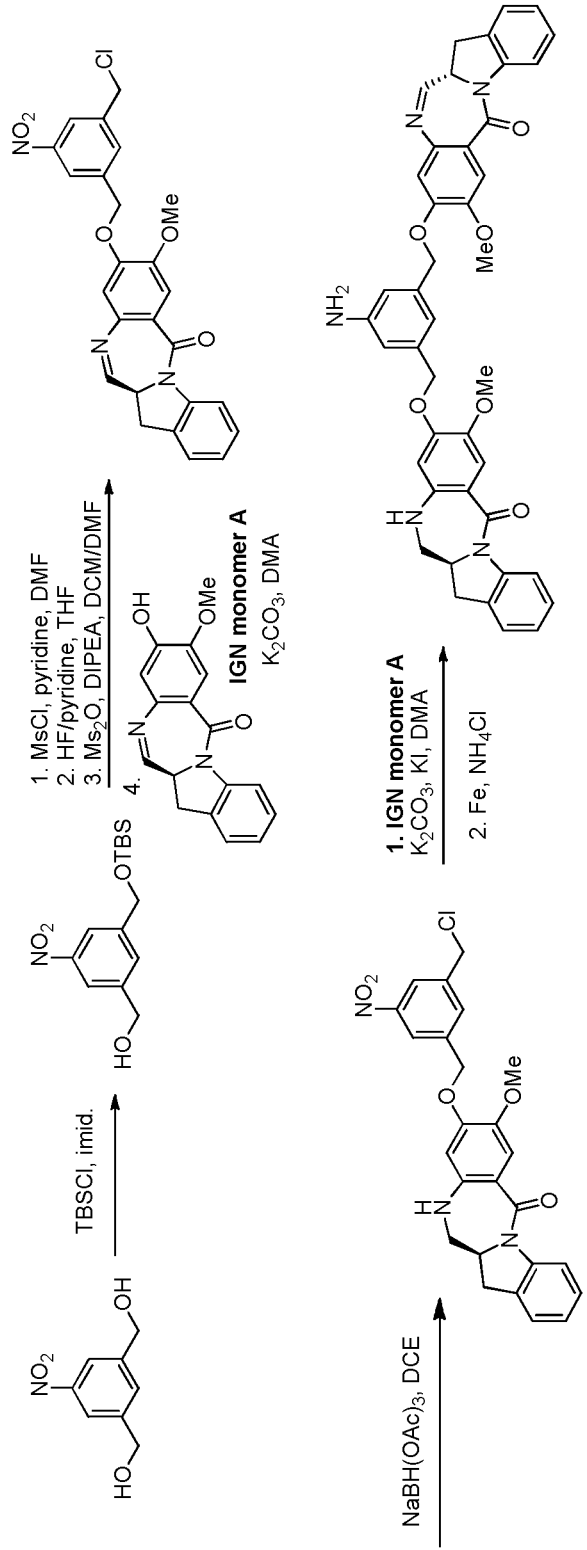
Figure 18:
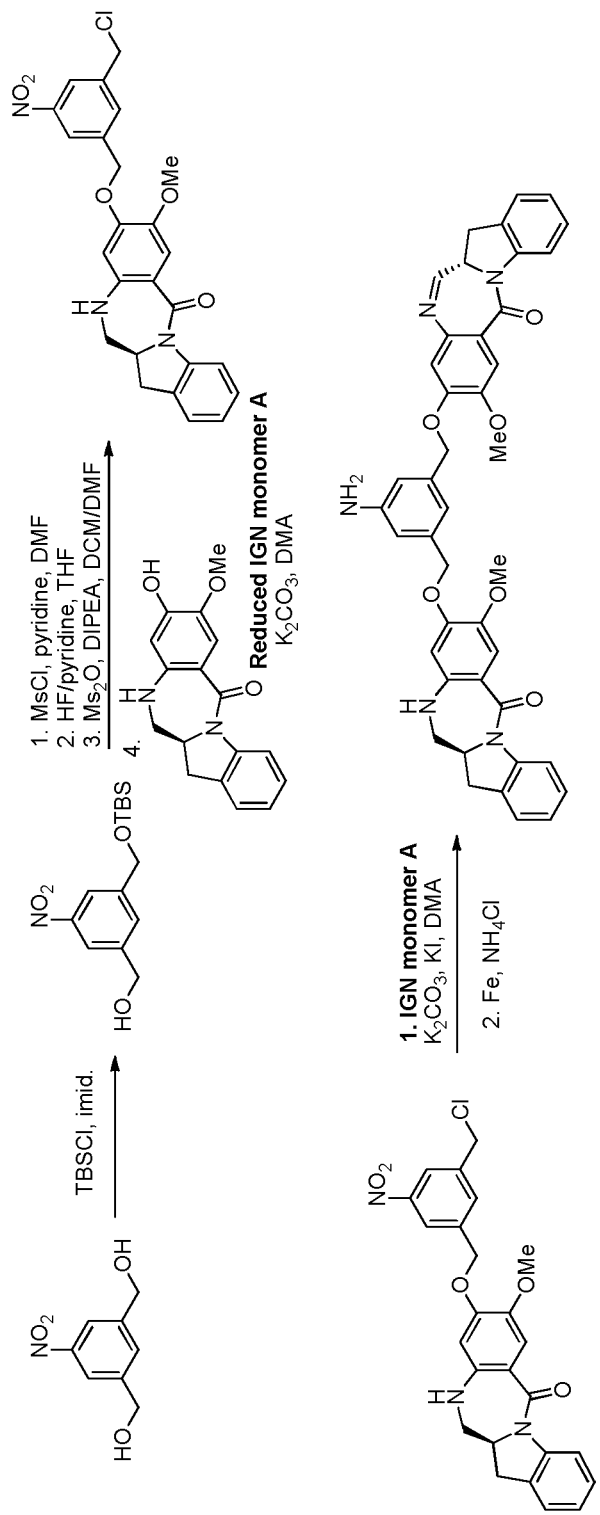
Figure 19:
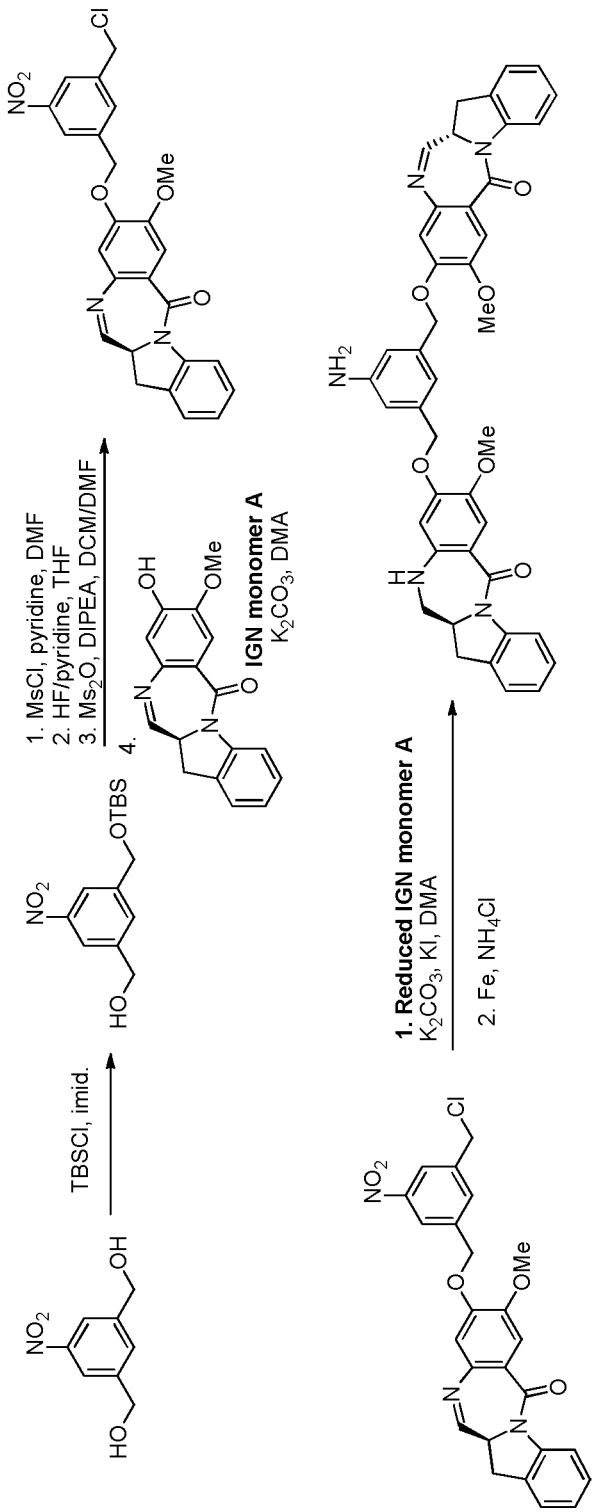

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein can be combined with one or more other embodiments of the invention, unless explicitly disclaimed or improper. Combination of embodiments are not limited to those specific combinations claimed via the multiple dependent claims.

Definitions

As used herein, the term "cell-binding agent" or "CBA" refers to a compound that can bind a cell (e.g., on a cell-surface ligand) or bind a ligand associated with or proximate to the cell, preferably in a specific manner. In certain embodiments, binding to the cell or a ligand on or near the cell is specific. The CBA may include peptides and non-peptides.

"Linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Linear or branched alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like. Preferably, the alkenyl has two to ten carbon atoms. More preferably, the alkyl has two to four carbon atoms.

"Linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The term "carbocycle," "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6], or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. They refer to a monovalent saturated carbocyclic ring radical. Preferably, the cyclic alkyl is 3 to 7 membered monocyclic ring radical. More preferably, the cyclic alkyl is cyclohexyl.

The term "cyclic alkenyl" refers to a carbocyclic ring radical having at least one double bond in the ring structure.

The term "cyclic alkynyl" refers to a carbocyclic ring radical having at least one triple bond in the ring structure.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl," and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclyl include the oxidized forms such as NO, SO, and $SO_2$.

The term "halo" or "halogen" refers to F, Cl, Br or I.

The alkyl, alkenyl, alkynyl, cyclic alkyl, cyclic alkenyl, cyclic alkynyl, carbocyclyl, aryl, heterocyclyl and heteroaryl described above can be optionally substituted with one more (e.g., 2, 3, 4, 5, 6 or more) substituents.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached, may form a heterocyclic ring. The heterocyclic ring formed from R' and R" together with the nitrogen atom to which they are attached may be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less.

Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—CH$_2$CH$_2$O)$_n$R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—CH$_2$CH$_2$O)$_n$—R$^{104}$ wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$, R$^{103}$ and R$^{14}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocyclyl, —SR$^{101}$, —SOR$^{101}$, —SO$_2$R$^{101}$ and —SO$_3$M.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "linkable to a cell binding agent" or "capable of covalently linking a cytotoxic compound to a cell binding agent" as used herein refers to the compounds described herein or derivates thereof comprising at least one linking group or a precursor thereof suitable to bond these compounds or derivatives thereof to a cell binding agent.

The term "precursor" of a given group refers to any group which may lead to that group by any deprotection, a chemical modification, or a coupling reaction.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "imine reactive reagent" refers to a reagent that is capable of reacting with an imine group. Examples of imine reactive reagent includes, but is not limited to, sulfites ($H_2SO_3$, $H_2SO_2$ or a salt of $HSO_3^-$, $SO_3^{2-}$ or $HSO_2$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i$), $R^iSH$, $R^iSOH$, $R^iSO_2H$, $R^iSO_3H$), various amines (hydroxyl amine (e.g., $NH_2OH$), hydrazine (e.g., $NH_2NH_2$), $NH_2$—$R^i$, $R^i$, $NH$—$R^i$, $NH_2$—$R^i$), $NH_2$—CO—$NH_2$, $NH_2$—C(=S)—$NH_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(=S)(OR^k)(SH)(OH) or a salt thereof formed with a cation), hydroxamic acid ($R^kC$(=O)NHOH or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-$ $Na^+$), glycated nucleotide (such as GDP-mannose), fludarabine or a mixture thereof, wherein $R^i$ and $R^{i'}$ are each independently a linear or branched alkyl having 1 to 10 carbon atoms and are substituted with at least one substituent selected from —N($R^j$)$_2$, —$CO_2H$, —$SO_3H$, and —$PO_3H$; $R^i$ and $R^{i'}$ can be further optionally substituted with a substituent for an alkyl described herein; $R^j$ is a linear or branched alkyl having 1 to 6 carbon atoms; and $R^k$ is a linear, branched or cyclic alkyl, alkenyl or alkynyl having 1 to 10 carbon atoms, aryl, heterocyclyl or heteroaryl (preferably, $R^k$ is a linear or branched alkyl having 1 to 4 carbon atoms; more preferably, $R^k$ is methyl, ethyl or propyl). Preferably, the cation is a monovalent cation, such as $Na^+$ or $K^+$. Preferably, the imine reactive reagent is selected from sulfites, hydroxyl amine, urea and hydrazine. More preferably, the imine reactive reagent is $NaHSO_3$ or $KHSO_3$.

As used herein, the term "imine reducing reagent" refers to a reagent that is capable of reducing an imine functional group to an amine functional group. In certain embodiments, the imine reducing reagent is a hydride reducing reagent. Examples of such imine reducing reagents include, but are not limited to, borohydrides (e.g., sodium borohydride, sodium triacetoxy borohydride, sodium cyanoborohydride, lithium borohydride ($LiBH_4$), potassium borohydride ($KBH_4$)), hydrogen gas, and lithium aluminum hydride, ammonium formate, borane, 9-borabicyclo[3.3.1]nonane (9-BBN), diisobutylaluminium hydride (DIBAL), and sodium bis(2-methoxyethoxy)aluminumhydride (Red-Al). In certain embodiments, the imine reducing reagent is sodium triacetoxy borohydride.

The term "protecting group" or "protecting moiety" refers to a substituent that is commonly employed to block or protect a particular functionality while reacting other functional groups on the compound, a derivative thereof, or a conjugate thereof. For example, an "amine protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc), 2-trimethylsilylethyl, (2-phenyl-2-trimethylsilyl)ethyl, triisopropylsiloxy, 2-(trimethylsilyl)ethoxymethyl, allyloxycarbonyl, 9-fluorenylmethoxycarbonyl, 2-(trimethylsilyl)ethoxycarbonyl, or 2,2,2,2-trichloroethoxycarbonyl. For a general description of protecting groups and their use, see P. G. M. Wuts & T. W. Greene, Protective Groups in Organic Synthesis, John Wiley & Sons, New York, 2007.

An "alcohol protecting group" or an "alcohol-protecting moiety" is a substituent attached to an alcohol group that blocks or protects the alcohol functionality in the compound. Such groups are well known in the art (see for example, P. Wuts and T. Greene, 2007, Protective Groups in Organic Synthesis, Chapter 2, J. Wiley & Sons, NJ). Suitable alcohol protecting group include, but are not limited to, pivaloyl, methoxymethyl, 2-methoxyethoxymethyl, p-methoxybenzyl, 3,4-dimethyoxybenzyl, 2,6-dimethyoxybenzyl, diphenylmethyl, benzyloxymethyl, 2,2,2-trichloroethoxycarbonyl, tetrahydrofuranyl, tetrahydropyranyl, benzyl, benzoyl, para-phenylbenzoyl, 2,4,6-trimethylbenzoyl, para-bromobenzoyl, para-nitrobenzoyl, picolinoyl, nicotinoyl, 5-dibenzosuberyl, trityl/triphenylmethyl, or tris(4-tert-butylphenyl)methyl and various silyl protecting groups (for example, dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl). In certain embodiments, the alcohol protecting group is sterically hindered. In certain embodiments, the alcohol protecting group is preferably methoxymethyl, tetrahydropyranyl, 2-methoxyethoxymethyl, p-methoxybenzyl, benzyloxymethyl, or 2,2,2-trichloroethoxycarbonyl. More preferably, the alcohol protecting group is 2,2,2-trichloroethoxycarbonyl. In certain embodiments, the alcohol protecting group is a silyl protecting group, preferably, triethylsilyl, triisopropylsilyl, or tert-butyldimethylsilyl. More preferably, the alcohol protecting group is tert-butyldimethylsilyl.

An "alcohol protecting reagent" as used herein refers to a reagent that introduces an alcohol protecting group onto an alcohol group.

An "acid labile alcohol protecting group" is an alcohol protecting group that is not stable under acidic condition and releases the alcohol protecting group to form free alcohol. Examples of an acid labile alcohol protecting group include, but are not limited to, acetate, allyl, methoxymethyl, tetrahydrofuranyl, tetrahydropyranyl, 5-dibenzosuberyl, 1-ethoxyethyl, 1-methyl-1methoxylethyl, 2-(phenylselenyl) ethyl, trityl/triphenylmethyl, tris(4-tert-butylphenyl)methyl, and various silyl protecting group (for example, dimethylisopropylsilyl, diethylisopropylsilyl, dimethylhexylsilyl, trimethylsilyl, triethylsilyl, triisopropylsilyl, tribenzylsilyl, triphenylsilyl, 2-norbornyldimethylsilyl, tert-butyldimethylsilyl, tert-butyldiphenylsilyl, or 2-trimethyethylsilyl (TEOC), [2-(trimethylsilyl)ethoxy]methyl). In certain embodiments, the alcohol protecting group is a silyl protecting group, preferably, triethylsilyl, triisopropylsilyl, or tert-butyldimethylsilyl. More preferably, the alcohol protecting group is tert-butyldimethylsilyl.

As used herein, the term "alcohol deprotecting reagent" refers to a reagent that is capable of cleaving an alcohol protecting group to form free alcohol. Such reagents are well known in the art (see for example P. Wuts and T. Greene, 2007, Protective Groups in Organic Synthesis, Chapter 2, J. Wiley & Sons, NJ). Examples of such alcohol deprotecting reagents include, but are not limited to, tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, trifluoroacetic acid, pyridinium p-toluensulfonate, p-toluenesulfonic acid (p-TsOH), formic acid, periodic acid. In certain embodiments, the alcohol deprotecting reagent is hydrochloric acid or tetra-n-butylammonium fluoride (TBAF). In certain embodiments, the alcohol deprotecting agent is hydrogen fluoride-pyridine (HF-pyridine).

As used herein, "amine deprotecting group" refers a reagent that is capable of cleaving an amine protecting group to form free amine. Such reagents are well known in the art (see for example P. Wuts and T. Greene, 2007, Protective Groups in Organic Synthesis, Chapter 7, J. Wiley & Sons, NJ). Examples of such amine deprotecting reagents include, but are not limited to, tetra-n-butylammonium fluoride, acetic acid, hydrogen fluoride pyridine, cesium fluoride, piperidine, morpholine, or trifluoroacetic acid.

As used herein, "alcohol activating agent" refers a reagent that increases the reactivity of a hydroxyl group thereby making the hydroxyl group a better leaving group. Examples of such alcohol activating agents include p-toluenesulfonyl chloride, thionyl chloride, triflic anhydride, mesyl chloride, mesyl anhydride, triphenylphosphine, acyl chloride, 4-dimethylaminopyridine, and others. In certain embodiments, the alcohol activating agent is thionyl chloride. In certain embodiment, the alcohol activating agent is triphenylphosphine.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

The term "leaving group" refers to a group of charged or uncharged moiety that departs during a nucleophilic substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" or "crosslinking agents" refers to modifying agents that possess two reactive groups; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. In certain embodiments, the linking group is a part of the cytotoxic compound described herein. The linking group may comprise a reactive group, which can react with a cell binding agent, or a precursor thereof. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Non-cleavable linking moiety can also be used.

A "reactive group" or "reactive moiety" as defined herein refers to a moiety that readily forms a covalent bond with a cell binding agent, e.g., an amide bond with lysine amine group on an antibody, or a bifunctional crosslinking agent, e.g. through thioether or disulfide bond. The reactive group is inert to reactions described in the methods of the present invention. Also included is functional groups that can be converted to the reactive group. For example, a reactive group can be a N-hydroxysuccinimide ester or an methyl ester group that can be converted to a N-hydroxysuccinimide ester. In another example, a reactive group can be a thiol (—SH) group that can readily forms a covalent bond with a bifunctional crosslining agent through a disulfide bond or a thioether bond. It can also be an alkyldisulfide or pyridyldisulfide (R—S—S—, wherein R is alkyl or pyridyl) that can be converted to a thiol group.

In one embodiment, the linking group with a reactive group attached at one end, such as a reactive ester, is selected from the following:

—O$(CR_{20}R_{21})_m(CR_{22}R_{23})_n(OCH_2CH_2)_p(CR_{40}R_{41})_{p''}$Y"$(CR_{24}R_{25})_q(CO)_rX''$,

—O$(CR_{20}R_{21})_m(CR_{26}=CR_{27})_{m'}(CR_{22}R_{23})_n(OCH_2CH_2)_p$ $(CR_{40}R_{41})_{p''}$Y"$(CR_{24}R_{25})_q(CO)_rX''$,

—O$(CR_{20}R_{21})_m(alkynyl)_n(CR_{22}R_{23})_n(OCH_2CH_2)_p$ $(CR_{40}R_{41})_{p''}$Y"$(CR_{24}R_{25})_q(CO)_rX''$, —O$(CR_{20}R_{21})_m(piperazino)_t(CR_{22}R_{23})_n(OCH_2CH_2)_p$ $(CR_{40}R_{41})_{p''}$Y"$(CR_{24}R_{25})_q(CO)_rX''$, —O$(CR_{20}R_{21})_m(pyrrolo)_t(CR_{22}R_{23})_n(OCH_2CH_2)_p$ $(CR_{40}R_{41})_{p''}$Y"$(CR_{24}R_{25})_q(CO)_rX''$, —O$(CR_{20}R_{21})_mA''_{m''}(CR_{22}R_{23})_n(OCH_2CH_2)_p(CR_{40}R_{41})_{p''}$Y"$(CR_{24}R_{25})_q(CO)_rX''$, —S$(CR_{20}R_{21})_m(CR_{22}R_{23})_n(OCH_2CH_2)_p(CR_{40}R_{41})_{p''}$Y"$(CR_{24}R_{25})_q(CO)_rX''$, —S$(CR_{20}R_{21})_m(CR_{26}=CR_{27})_m(CR_{22}R_{23})_n(OCH_2CH_2)_p$ $(CR_{40}R_{41})_{p''}$Y"$(CR_{24}R_{25})_q(CO)_rX''$, —S$(CR_{20}R_{21})_m(alkynyl)_n(CR_{22}R_{23})_n(OCH_2CH_2)_p$ $(CR_{40}R_{41})_{p''}$Y"$(CR_{24}R_{25})_q(CO)_rX''$, —S$(CR_{20}R_{21})_m(piperazino)_t(CR_{22}R_{23})_n(OCH_2CH_2)_p$ $(CR_{40}R_{41})_{p''}$Y"$(CR_{24}R_{25})_q(CO)_rX''$, —S$(CR_{20}R_{21})_m(pyrrolo)_t(CR_{22}R_{23})_n(OCH_2CH_2)_p$ $(CR_{40}R_{41})_{p''}$Y"$(CR_{24}R_{25})_q(CO)_rX''$, —S$(CR_{20}R_{21})_mA''_{m''}(CR_{22}R_{23})_n(OCH_2CH_2)_p(CR_{40}R_{41})_{p''}$Y"$(CR_{24}R_{25})_q(CO)_rX''$, —NR$_{33}$(C=O)$_{p'}(CR_{20}R_{21})_m(CR_{22}R_{23})_n(OCH_2CH_2)_p$ $(CR_{40}R_{41})_{p''}$Y"$(CR_{24}R_{25})_q(CO)_rX''$, —NR$_{33}$(C=O)$_{p'}(CR_{20}R_{21})_m(CR_{26}=CR_{27})_m(CR_{22}R_{23})_n$ $(OCH_2CH_2)_p(CR_{40}R_{41})_{p''}$Y"$(CR_{24}R_{25})_q(CO)_rX''$, —NR$_{33}$(C=O)$_{p'}(CR_{20}R_{21})_m(alkynyl)_n(CR_{22}R_{23})_n$ $(OCH_2CH_2)_p(CR_{40}R_{41})_{p''}$Y"$(CR_{24}R_{25})_q$—$(CO)_rX''$, —NR$_{33}$(C=O)$_{p'}(CR_{20}R_{21})_m(piperazino)_t(CR_{22}R_{23})_n$ $(OCH_2CH_2)_p(CR_{40}R_{41})_{p''}$Y"$(CR_{24}R_{25})_q'(CO)_rX''$, —NR$_{33}$(C=O)$_{p'}(CR_{20}R_{21})_m(pyrrolo)_t(CR_{22}R_{23})_n$ $(OCH_2CH_2)_p(CR_{40}R_{41})_{p''}$Y"$(CR_{24}R_{25})_q$—$(CO)_rX''$, —NR$_{33}$(C=O)$_{p'}(CR_{20}R_{21})_mA''_{m''}(CR_{22}R_{23})_n(OCH_2CH_2)_p$ $(CR_{40}R_{41})_{p''}$Y"$(CR_{24}R_{25})_q$—$(CO)_rX''$, —$(CR_{20}R_{21})_m(CR_{22}R_{23})_n(OCH_2CH_2)_p(CR_{40}R_{41})_{p''}$Y"$(CR_{24}R_{25})_q(CO)_rX''$, —$(CR_{20}R_{21})_m(CR_{26}=CR_{27})_m(CR_{22}R_{23})_n(OCH_2CH_2)_p$ $(CR_{40}R_{41})_{p''}$Y"$(CR_{24}R_{25})_q(CO)_rX''$, —$(CR_{20}R_{21})_m(alkynyl)_n(CR_{22}R_{23})_n(OCH_2CH_2)_p$ $(CR_{40}R_{41})_{p''}$Y"$(CR_{24}R_{25})_q(CO)_rX''$, —$(CR_{20}R_{21})_m(piperazino)_t(CR_{22}R_{23})_n(OCH_2CH_2)_p$ $(CR_{40}R_{41})_{p''}$Y"$(CR_{24}R_{25})_q(CO)_rX''$, —$(CR_{20}R_{21})_mA''_{m''}(CR_{22}R_{23})_n(OCH_2CH_2)_p(CR_{40}R_{41})_{p''}$Y"$(CR_{24}R_{25})_q(CO)_rX''$, —$(CR_{20}R_{21})_m(CR_{29}=N-NR_{30})_n(CR_{22}R_{23})_n(OCH_2CH_2)_p(CR_{40}R_{41})_{p''}$Y"$(CR_{24}R_{25})_q(CO)_rX''$, —$(CR_{20}R_{21})_m(CR_{29}=N-NR_{30})_n(CR_{26}=CR_{27})_{m'}$ $(CR_{22}R_{23})_n(OCH_2CH_2)_p(CR_{40}R_{41})_{p''}$Y"$(CR_{24}R_{25})_q(CO)_rX''$, —$(CR_{20}R_{21})_m(CR_{29}=N-NR_{30})_n(alkynyl)_n(CR_{22}R_{23})_n$ $(OCH_2CH_2)_p(CR_{40}R_{41})_{p''}$Y"$(CR_{24}R_{25})_q$-$(CO)_rX''$, —$(CR_{20}R_{21})_m(CR_{29}=N-NR_{30})_n''A''_{m''}(CR_{22}R_{23})_n$ $(OCH_2CH_2)_p(CR_{40}R_{41})_{p''}$Y"$(CR_{24}R_{25})_q$—$(CO)_rX''$, wherein:

m, n, p, q, m', n', t' are integer from 1 to 10, or are optionally 0;

t, m", n", and p" are 0 or 1;

X" is selected from $OR_{36}$, $SR_{37}$, $NR_{38}R_{39}$, wherein $R_{36}$, $R_{37}$, $R_{38}$, $R_{39}$ are H, or linear, branched or cyclic alkyl, alkenyl or alkynyl having from 1 to 20 carbon atoms and, or, a polyethylene glycol unit —$(OCH_2CH_2)_n$, $R_{37}$, optionally, is a thiol protecting group when t=1, COX" forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation;

Y" is absent or is selected from O, S, S—S or $NR_{32}$, wherein $R_{32}$ has the same definition as given above for R; or when Y" is not S—S and t=0, X" is selected from a maleimido group, a haloacetyl group or $SR_{37}$, wherein $R_{37}$ has the same definition as above;

A" is an amino acid residue or a polypeptide containing between 2 to 20 amino acid residues;

$R_{20}$, $R_{21}$, $R_{22}$, $R_{23}$, $R_{24}$, $R_{25}$, $R_{26}$, and $R_{27}$ are the same or different, and are —H or a linear or branched alkyl having from 1 to 5 carbon atoms;

$R_{29}$ and $R_{30}$ are the same or different, and are —H or alkyl from 1 to 5 carbon atoms;

$R_{33}$ is —H or linear, branched or cyclic alkyl, alkenyl or alkynyl having from 1 to 12 carbon atoms, a polyethylene glycol unit R—$(OCH_2CH_2)_n$—, or $R_{33}$ is —$COR_{34}$, —$CSR_{34}$, —$SOR_{34}$, or —$SO_2R_{34}$, wherein $R_{34}$ is H or linear, branched or cyclic alkyl, alkenyl or alkynyl having from 1 to 20 carbon atoms or, a polyethylene glycol unit —$(OCH_2CH_2)_n$; and one of $R_{40}$ and $R_{41}$ is optionally a negatively or positively charged functional group and the other is H or alkyl, alkenyl, alkynyl having 1 to 4 carbon atoms. Any of the above linking groups may be present in any of the compounds, drug-linker compounds, or conjugates of the invention, including replacing the linking groups of any of the formulas described herein.

The term "amino acid" refers to naturally occurring amino acids or non-naturally occurring amino acid. In one embodiment, the amino acid is represented by $NH_2$—$C(R^{aa'}R^{aa})$—$C(=O)OH$, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl, or $R^{aa}$ and the N-terminal nitrogen atom can together form a heteroycyclic ring (e.g., as in proline). The term "amino acid residue" refers to the corresponding residue when one hydrogen atom is removed from the amine and/or carboxy end of the amino acid, such as —NH—$C(R^{aa'}R^{aa})$—$C(=O)O$—.

The term "cation" refers to an ion with positive charge. The cation can be monovalent (e.g., $Na^+$, $K^+$, etc.), bi-valent (e.g., $Ca^{2+}$, $Mg^{2+}$, etc.) or multi-valent (e.g., $Al^{3+}$ etc.). Preferably, the cation is monovalent.

As used herein, the term "halogenating reagent" refers to a reagent that converts an alcohol group to a halide group. A "brominating reagent" is a reagent that converts an alcohol group to a bromide group. A "iodinating reagent" is a reagent that converts an alcohol group to a iodide group. A "chlorinating reagent" is a reagent that converts an alcohol group to a chloride group. Exemplary brominating reagents include, but are not limited to, bromine, hydrobromic acid, carbon tetrabromide, phosphorus tribromide, and potassium bromide. Exemplary iodinating reagent include, but are not limited to, hydroiodic acid, iodine, carbon tetraiodide, phosphorus triiodide, sodium iodide, or potassium iodide. Exemplary chlorinating reagent include, but are not limited to, carbon tetrachloride, methanesulfonyl chloride, sulfuryl chloride, thionyl chloride, cyanuric chloride, N-chlorosuccinimide, phosphorus(V) oxychloride, phosphorus pentachloride, and phosphorus trichloride. In a specific embodiment, the chlorinating reagent is methanesulfonyl chloride.

As used herein, a "sulfonating reagent" refers to a reagent that converts an alcohol group to a sulfonate ester group. Preferably, the sulfonating reagent is a sulfonic anhydride, such as methanesulfonic anhydride, or a sulfonic chloride, such as methanesulfonyl chloride (MsCl).

As used herein, an "activated ester" refers to an ester group that is readily displaced by a hydroxyl or an amine group. Exemplary activated esters include, but are not limited to nitrophenyl (e.g., 2 or 4-nitrophenyl) ester, dinitrophenyl (e.g., 2,4-dinitrophenyl) ester, sulfo-tetraflurophenyl (e.g., 4-sulfo-2,3,5,6-tetrafluorophenyl) ester, pentafluorophenyl ester, nitropyridyl (e.g., 4-nitropyridyl) ester, trifluoroacetate, and acetate.

As used herein, an "esterification reagent" refers to a reagent that converts an alcohol group to an ester group. Exemplary esterification reagent include, but are not limited to, nitrobenzoid acid (e.g., 2 or 4-nitrobenzoic acid), dinitrobenzoid acid (e.g., 2,4-dinitrobenzoic acid), sulfo-tetraflurobenzoid acid (e.g., 4-sulfo-2,3,5,6-tetrafluorobenzoic acid), pentafluorobenzoic acid, nitropyridine carboxylic acid (e.g., 4-nitro-2-pyridine carboxylic acid, trifluoroacetic acid, and acetic acid, or acyl chloride, acid anhydride or other activated carboxylic acid derivatives thereof.

Methods of the Present Invention

The present invention provides novel methods for preparing indolinobenzodiazepine dimer compounds that have one imine functionality and one amine functionality. As compared to the methods known in the art, the present methods can produce the desired dimer compounds with higher yield and without the use of HPLC purification.

In a first embodiment, the present invention provides a method of preparing a compound of formula (2),

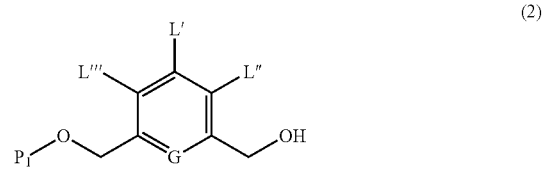

(2)

or a salt thereof, comprising introducing an alcohol protecting group onto one of the primary alcohols of a compound of formula (1) by reacting the compound of formula (I) with an alcohol protecting reagent,

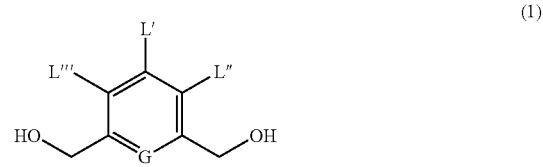

(1)

wherein:

L', L", and L'" are the same or different, and are independently —H, an optionally substituted linear, branched or cyclic alkyl, alkenyl or alkynyl having from 1 to 10 carbon atoms, a polyethylene glycol unit —$(OCH_2CH_2)_{n'}$—$R^c$, halogen, guanidinium [—NH(C=NH)NH$_2$], —OR, —NR'R", —NO$_2$, —NR'COR", —SR, —SOR', —SO$_2$R', —SO$_3$M, —OSO$_3$M, —SO$_2$NR'R", cyano, an azido, —COR', —OCOR', —OCONR'R", or a linking group with a reactive group bonded thereto capable of covalently linking a cytotoxic compound to a cell binding agent (CBA), provided that only one of L', L", and L'" is the linking group with the reactive group bonded thereto;

M is —H or a cation;

R, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —N(R)$_2$, —COR, an optionally substituted linear, branched or cyclic alkyl, alkenyl or alkynyl having from 1 to 10 carbon atoms, a polyethylene glycol unit —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms, or the linking group with the reactive group bonded thereto;

n' is an integer from 1 to 24;

G is selected from —CH— or —N—; and

P$_1$ is the alcohol protecting group.

In one embodiment, the compound of formula (1) is represented by a formula selected from the following:

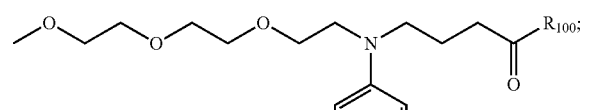

(1b)

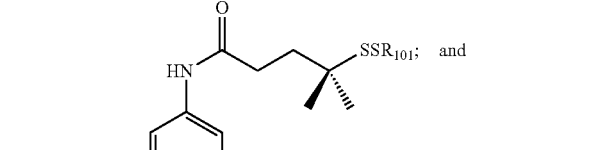

(1c)

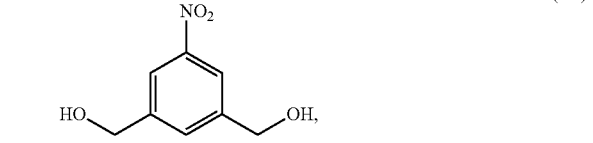

(1A)

wherein R$_{100}$ is a (C$_1$-C$_3$)alkoxy; and R$_{101}$ is a (C$_1$-C$_3$)alkyl, pyridyl or nitropyridyl (e.g., 4-nitropyridyl).

In a specific embodiment, the alcohol protecting group is sterically hindered. In another specific embodiment, the alcohol protecting group is pivaloyl, methoxymethyl, 2-methoxyethoxymethyl, p-methoxybenzyl, 3,4-dimethyoxybenzyl, 2,6-dimethyoxybenzyl, diphenylmethyl, benzyloxymethyl, 2,2,2-trichloroethoxycarbonyl, tetrahydrofuranyl, tetrahydropyranyl, benzyl, benzoyl, para-phenylbenzoyl, 2,4,6-trimethylbenzoyl, para-bromobenzoyl, para-nitrobenzoyl, picolinoyl, nicotinoyl, 5-dibenzosuberyl, trityl/triphenylmethyl, or tris(4-tert-butylphenyl)methyl. Preferably, the alcohol protecting group is methoxymethyl, tetrahydropyranyl, 2-methoxyethoxymethyl, p-methoxybenzyl, benzyloxymethyl, or 2,2,2-trichloroethoxycarbonyl. Even more preferably, the alcohol protecting group is 2,2,2-trichloroethoxycarbonyl.

In another specific embodiment, the alcohol protecting group is a silyl protecting group. For example, the silyl protecting group is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl. Preferably, the silyl protecting group is triethylsilyl, triisopropylsilyl, or tert-butyldimethylsilyl. More preferably, the silyl protecting group is tert-butyldimethylsilyl.

The silyl protecting group can be introduced by reacting the compound of formula (1) with R$^3$—Cl, R$^3$—Br, R$^3$—I or R$^3$—OSO$_2$CF$_3$ (collectively the alcohol protecting reagent) in the presence of a base, wherein R$^3$ is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl or [2-(trimethylsilyl)ethoxy]methyl. In certain embodiments, the molar ratio of the alcohol protecting reagent to the compound of formula (1) is between 0.8-1.2, between 1 to 5, between 1 to 2, between 1 to 1.5, between 1 to 1.4, between 1 to 1.3, between 1 to 1.2, or between 1 to 1.1. In certain embodiment, less than 2 molar equivalents of the alcohol protecting reagent is used relative to the compound of formula (I). Preferably, 1.5, 1.4, 1.3, 1.2, 1.1 or 1.0 molar equivalent of the alcohol protecting reagent relative to the compound of formula (1) is used.

In one embodiment, the base can be a non-nucleophilic base. Examples of non-nucleophilic base include, but are not limited to, imidazole, triethylamine, diisopropylethylamine, pyridine, 2,6-lutidine, 1,8-diazabicycloundec-7-ene, or tetramethylpiperidine. Preferably, the non-nucleophilic base is imidazole. Molar excess amount of the base can be used. In certain embodiments, more than 2 molar equivalents of the base (e.g., non-nucleophilic base) are used relative to the compound of formula (1).

In another embodiment, the reaction between the compound of formula (1) and R$^3$—Cl, R$^3$—Br, R$^3$—I or R$^3$—OSO$_2$CF$_3$ is carried out in the presence of a catalyst that facilitates the introduction of the silyl protecting group. Any suitable catalysts known in the art (see, for example, P. Wuts and T. Greene, 2007, Protective Groups in Organic Synthesis, Chapter 2, J. Wiley & Sons, NJ) can be used in the reaction. Exemplary catalysts include, but are not limited to, 4-dimethylaminopyridine (DMAP), 1,1,3,3-tetramethylguanidine and 1,8-diazabicyclo[5.4.0]undec-7-ene (DBU).

Any suitable organic solvents can be used for the methods of the first embodiment. Exemplary solvents include, but are not limited to, DMF, CH$_2$Cl$_2$, dichloroethane, THF, dimethylacetamide, etc. In certain embodiments, DMF is used as the solvent.

In a second embodiment, the present invention provides a method of preparing a compound of formula (3),

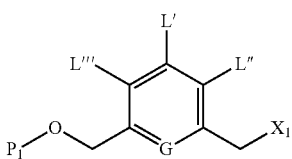

(3)

or a salt thereof, comprising reacting the compound of formula (2) with a halogenating reagent, a sulfonating reagent or an esterification reagent,

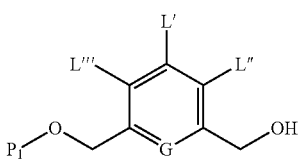

(2)

wherein L', L", L'", G and $P_1$ are as defined in the first embodiment, and $X_1$ is a leaving group selected from the group consisting of: —Br, —I, —Cl, a sulfonate ester, and an activated ester.

In a specific embodiment, the compound of formula (2) is represented by a formula selected from the following:

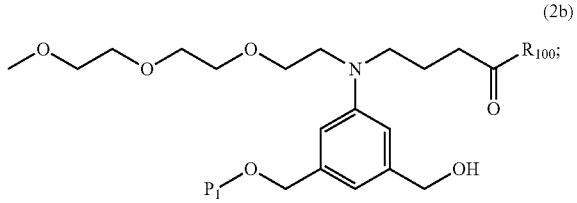

(2b)

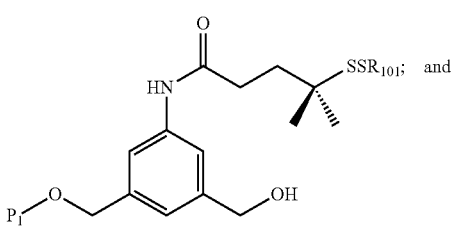

(2c)

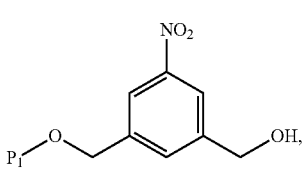

(2A)

wherein $R_{100}$ is a ($C_1$-$C_3$)alkoxy; and $R_{101}$ is a ($C_1$-$C_3$)alkyl, pyridyl or nitropyridyl (e.g., 4-nitropyridyl).

In another specific embodiment, for methods of preparing compound of formula (3d) or (3A) described above, $X_1$ is —Br, —I or a sulfonate ester.

In another specific embodiment, $X_1$ is mesylate, tosylate, brosylate, or triflate. Preferably, $X_1$ is mesylate.

In another specific embodiment, the method of the second embodiment comprises reacting the compound of formula (2) with a halogenating reagent. Exemplary halogenating reagents include, but are not limited to, bromine, hydrobromic acid, carbon tetrabromide, phosphorus tribromide, potassium bromide, hydroiodic acid, iodine, carbon tetraiodide, phosphorus triiodide, sodium iodide, or potassium iodide.

In yet another specific embodiment, the method of the second embodiment comprises reacting the compound of formula (2) with a sulfonating reagent. Preferably, the sulfonating reagent is a sulfonic anhydride, such as methanesulfonic anhydride, or a sulfonic chloride, such as methanesulfonyl chloride (MsCl).

In certain embodiment, the reaction between the compound of formula (2) and the sulfonating reagent can be carried out in the presence of a base. In one embodiment, the base is a non-nucleophilic base. Exemplary non-nucleophilic bases include, but are not limited to, triethylamine, imidazole, triethylamine, diisopropylethylamine, pyridine, 2,6-lutidine, dimethylformamide, 1,8-diazabicyclo[5.4.0]undec-7-ene (DBU), or tetramethylpiperidine. Preferably, the base is triethylamine or diisopropylethylamine.

Any suitable organic solvents can be used in the method of the second embodiment. In one embodiment, the solvent is dichloromethane.

In a third embodiment, the present invention provides a method of preparing a compound of formula (4),

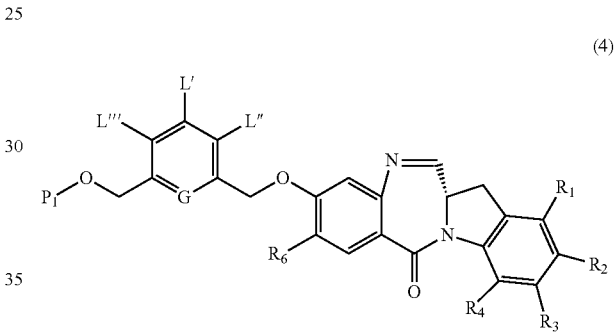

(4)

or a salt thereof, said method comprising reacting a compound of formula (3)

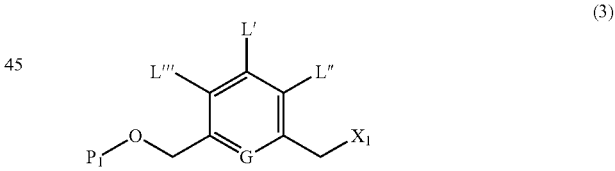

(3)

with a monomer compound of the formula (a),

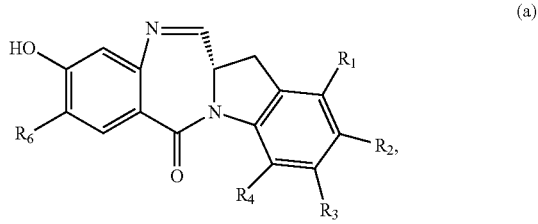

(a)

wherein:

$R_1$, $R_2$, $R_3$, and $R_4$ are each independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$_c$, halogen, guanidinium [—NH(C=NH)NH$_2$], —OR, —NR'R", —NO$_2$, —NCO, —NR'COR", —SR, —SOR', —SO$_2$R', —SO$_3^-$H, —OSO$_3$H, —SO$_2$NR'R", cyano, an azido, —COR', —OCOR', and —OCONR'R"; and R$_6$ is —H, —R, —OR, —SR, —NR'R", —NO$_2$, or halogen; and the remaining variables are as described in the second embodiment.

Alternatively, the third embodiment provides a method of preparing a compound of formula (8),

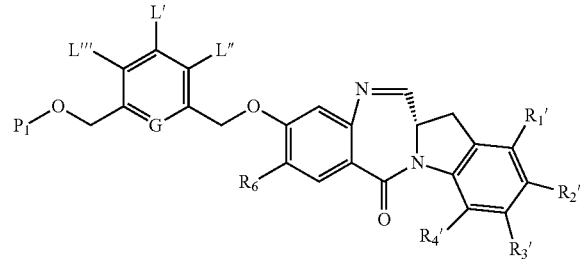

(8)

or a salt thereof, said method comprising reacting a compound of formula (3')

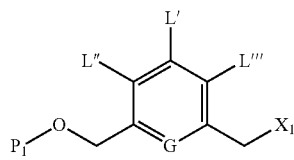

(3')

with a monomer compound of the formula (b),

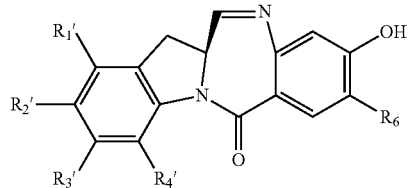

(b)

wherein R$_1$', R$_2$', R$_3$', and R$_4$' are each independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$_c$, halogen, guanidinium [—NH(C=NH)NH$_2$], —OR, —NR'R", —NO$_2$, —NCO, —NR'COR", —SR, —SOR', —SO$_2$R', —SO$_3^-$H, —OSO$_3$H, —SO$_2$NR'R", cyano, an azido, —COR', —OCOR', and —OCONR'R"; R$_6$ is —H, —R, —OR, —SR, —NR'R", —NO$_2$, or halogen; and the remaining variables are as described in the second embodiment.

In a specific embodiment, the compound of formula (3) is represented by a formula selected from the following:

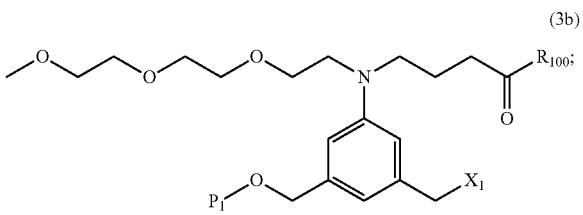

(3b)

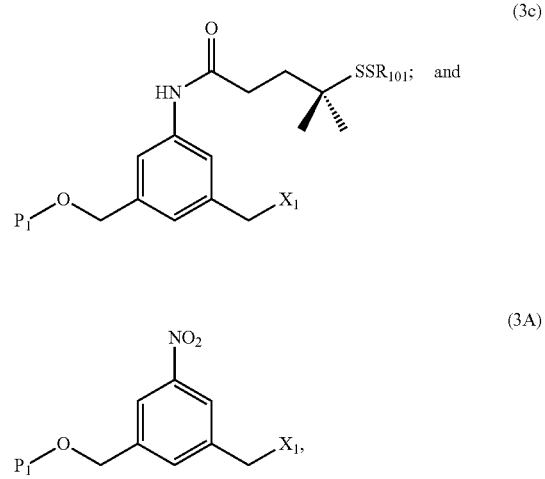

(3c)

(3A)

wherein R$_{100}$ is a (C$_1$-C$_3$)alkoxy; and R$_{101}$ is a (C$_1$-C$_3$)alkyl, pyridyl or nitropyridyl (e.g., 4-nitropyridyl).

In a specific embodiment, for methods of the third embodiment, X$_1$ is —Br, —I, or a sulfonate ester.

In a specific embodiment, the compound of formula (3) is reacted with the monomer compound of formula (b) in the presence of a base. Any suitable base can used. Exemplary bases include, but are not limited to, sodium carbonate, potassium carbonate, cesium carbonate, sodium hydride, or potassium hydride. In one embodiment, the base is potassium carbonate.

In a fourth embodiment, the present invention provides a method of preparing a compound of formula (5),

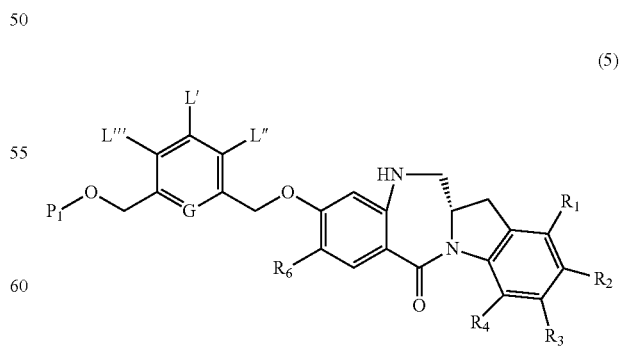

(5)

or a salt thereof, said method comprising reacting a compound of formula (4), (4)

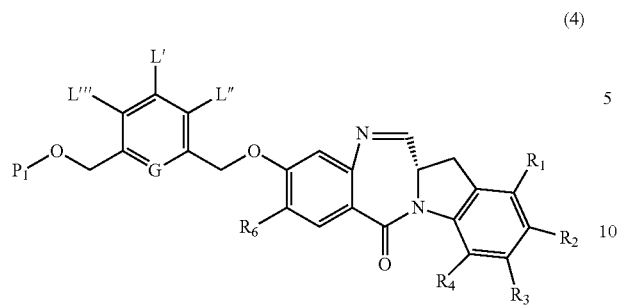

with an imine reducing agent, wherein the variables are as described above in the third embodiment.

In a specific embodiment, the compound of formula (4) is represented by a formula selected from the following:

(4b)

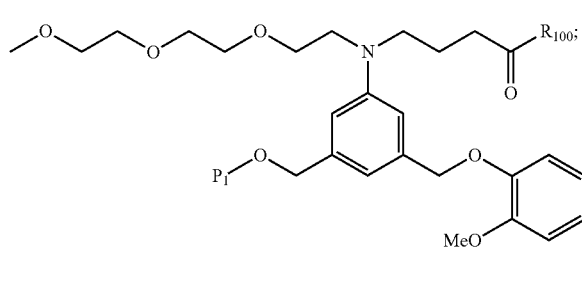

(4c)

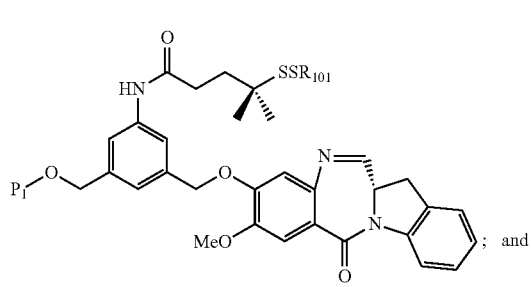

wherein $R_{100}$ is a $(C_1-C_3)$alkoxy; and $R_{101}$ is a $(C_1-C_3)$alkyl, pyridyl or nitropyridyl (e.g., 4-nitropyridyl).

In a specific embodiment, the imine reducing reagent is a hydride reducing reagent.

In another specific embodiment, the imine reducing reagent is sodium borohydride, sodium triacetoxy borohydride, sodium cyanoborohydride, lithium aluminum hydride, hydrogen gas, ammonium formate, borane, 9-borabicyclo[3.3.1]nonane (9-BBN), diisobutylaluminium hydride (DIBAL), lithium borohydride (LiBH$_4$), potassium borohydride (KBH$_4$), or sodium bis(2-methoxyethoxy)aluminumhydride (Red-Al). Preferably, the imine reducing reagent is sodium triacetoxy borohydride (NaBH(OAc)$_3$).

Any suitable solvents can be use in the method of fourth embodiment. In one embodiment, the solvent is dichloroethane.

In a fifth embodiment, the present invention provides a method preparing a compound of formula (6), (6)

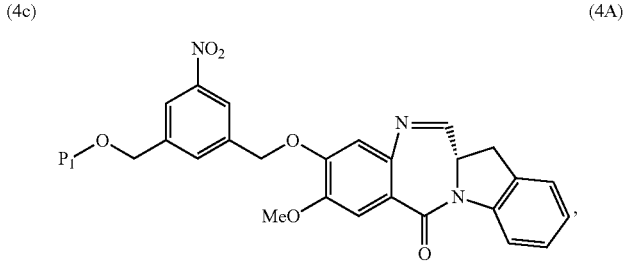

or a salt thereof, said method comprising reacting a compound of formula (5), (4A)

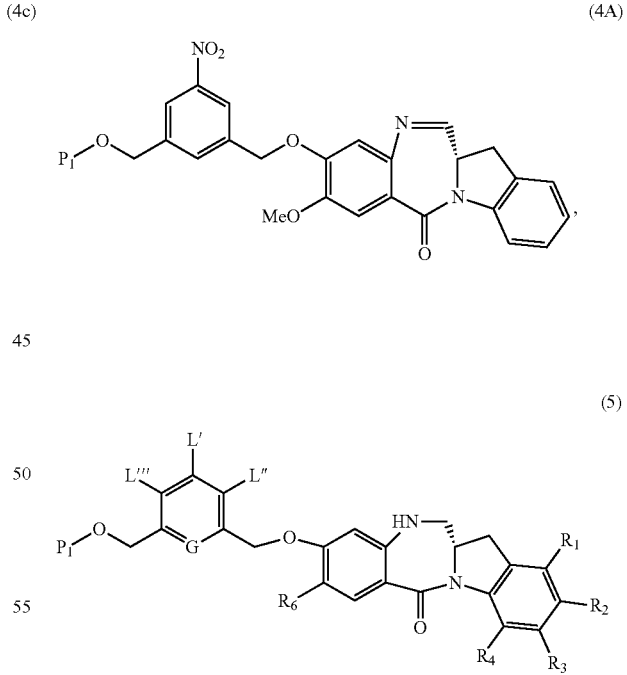

(5)

with an alcohol deprotecting reagent, wherein the variables are as described above in the fourth embodiment.

In a specific embodiment, the compound of formula (5) is represented by a formula selected from the following:

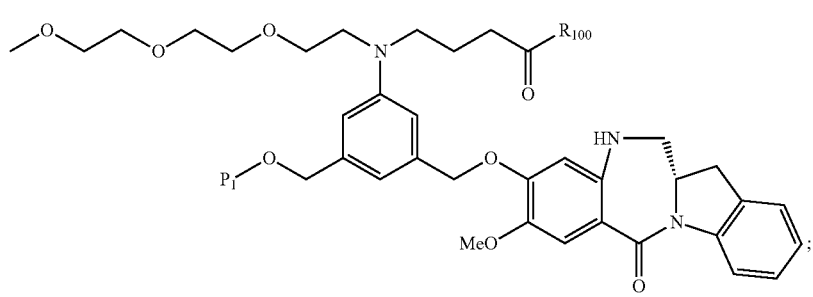

(5b)

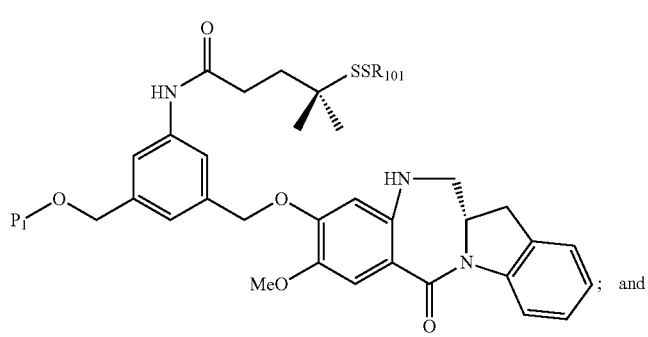

(5c)

; and

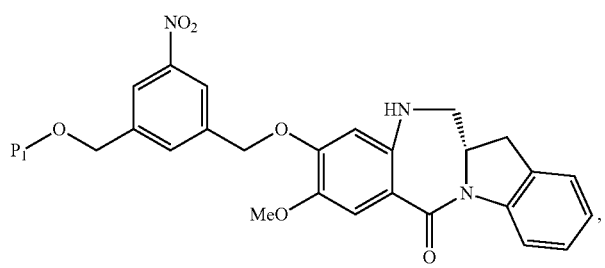

(5A)

;

wherein $R_{100}$ is a $(C_1-C_3)$alkoxy; and $R_{101}$ is a $(C_1-C_3)$alkyl, pyridyl or nitropyridyl (e.g., 4-nitropyridyl).

In a specific embodiment, the alcohol deprotecting reagent is tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, trifluoroacetic acid, pyridinium p-toluensulfonate, p-toluenesulfonic acid (p-TsOH), formic acid, or periodic acid. Preferably, the alcohol deprotecting reagent is hydrochloric acid or tetra-n-butylammonium fluoride.

Any suitable solvents can be used in the deprotection reaction described above. In one embodiment, the solvent is THF.

In a sixth embodiment, the present invention provides a method of preparing a compound of formula (7), (7)

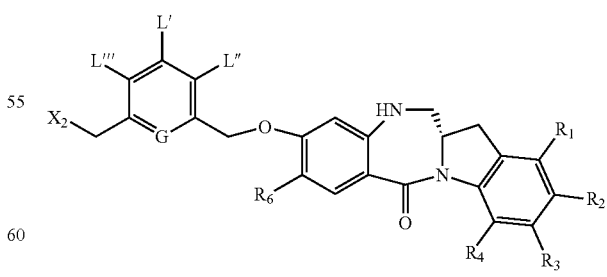

or a salt thereof, said method comprising reacting a halogenating reagent, a sulfonating reagent or an esterification reagent with the primary alcohol compound of formula (6), (6)

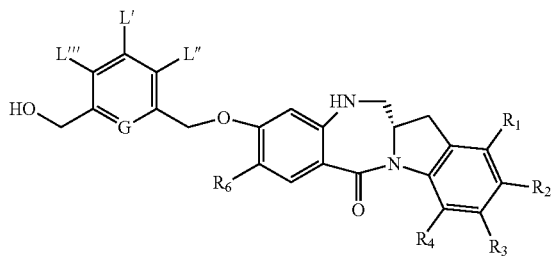

wherein $X_2$ is —Br, —I, —Cl, a sulfonate ester or an activated ester; and the remaining variables are as described above in the fifth embodiment.

In a specific embodiment, the compound of formula (6) is represented by a formula selected from the following:

(6b)

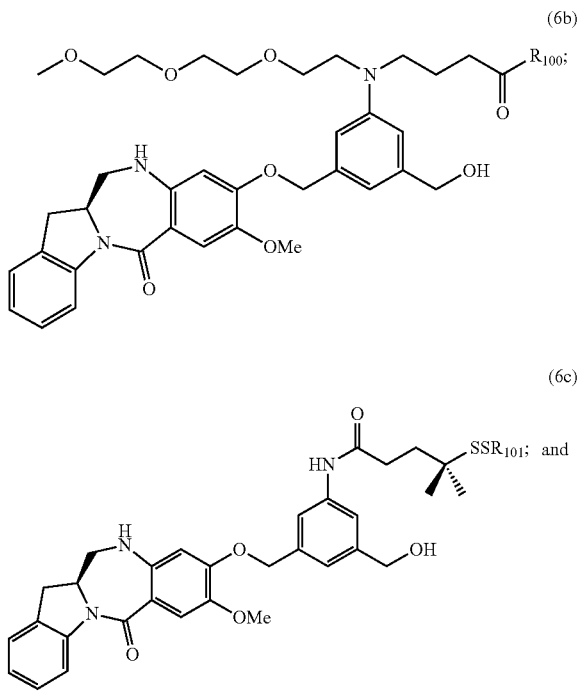

(6c)

(6A)

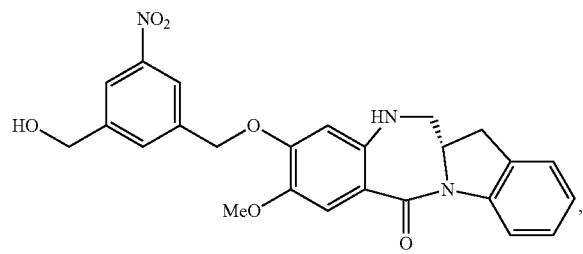

wherein $R_{100}$ is a $(C_1-C_3)$alkoxy; and $R_{101}$ is a $(C_1-C_3)$alkyl, pyridyl or nitropyridyl (e.g., 4-nitropyridyl).

In a specific embodiment, for methods of the sixth embodiment, $X_2$ is —Br, —I or a sulfonate ester.

In a specific embodiment, $X_2$ is mesylate, tosylate, brosylate, or triflate. Preferably, $X_2$ is mesylate.

In another specific embodiment, the method of the sixth embodiment comprises reacting the compound of formula (6) with a halogenating reagent. Exemplary halogenating reagent include, but are not limited to, bromine, hydrobromic acid, carbon tetrabromide, phosphorus tribromide, potassium bromide, hydroiodic acid, iodine, carbon tetraiodide, phosphorus triiodide, sodium iodide, or potassium iodide. In yet another specific embodiment, the method of the sixth embodiment comprises reacting the compound of formula (6) with a sulfonating reagent. Preferably, the sulfonating reagent is a sulfonic anhydride, such as methanesulfonic anhydride, or a sulfonic chloride, such as methanesulfonyl chloride (MsCl).

In one embodiment, the reaction between the compound of formula (6) and the sulfonating reagent is carried out in the presence of a base. Preferably, the base is a non-nucleophiclic base. Exemplary non-nucleophic base include, but are not limited to, triethylamine, imidazole, triethylamine, diisopropylethylamine, pyridine, 2,6-lutidine, dimethylformamide, 1,8-diazabicyclo[5.4.0]undec-7-ene (DBU), or tetramethylpiperidine. Preferably, the base is triethylamine or diisopropylethylamine. Any suitable solvents can be used in reaction described above. In one embodiment, the solvent is dichloromethane.

In a seventh embodiment, the present invention provides a method of preparing a compound of formula (7″)

(7″)

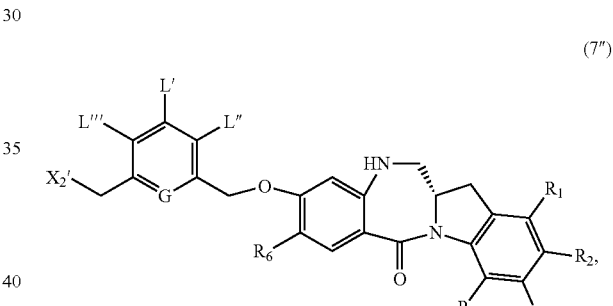

or a salt thereof, said method comprising reacting a compound of formula (5″)

(5″)

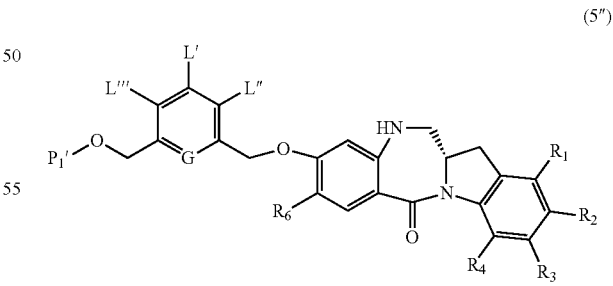

with an alcohol deprotecting reagent and a halogenating reagent, wherein $P_1'$ is an acid labile alcohol protecting group; $X_2'$ is —Br or —I; and the remaining variables are as described above in the sixth embodiment.

In a specific embodiment, the compound of formula (5″) is represented by a formula selected from the following:

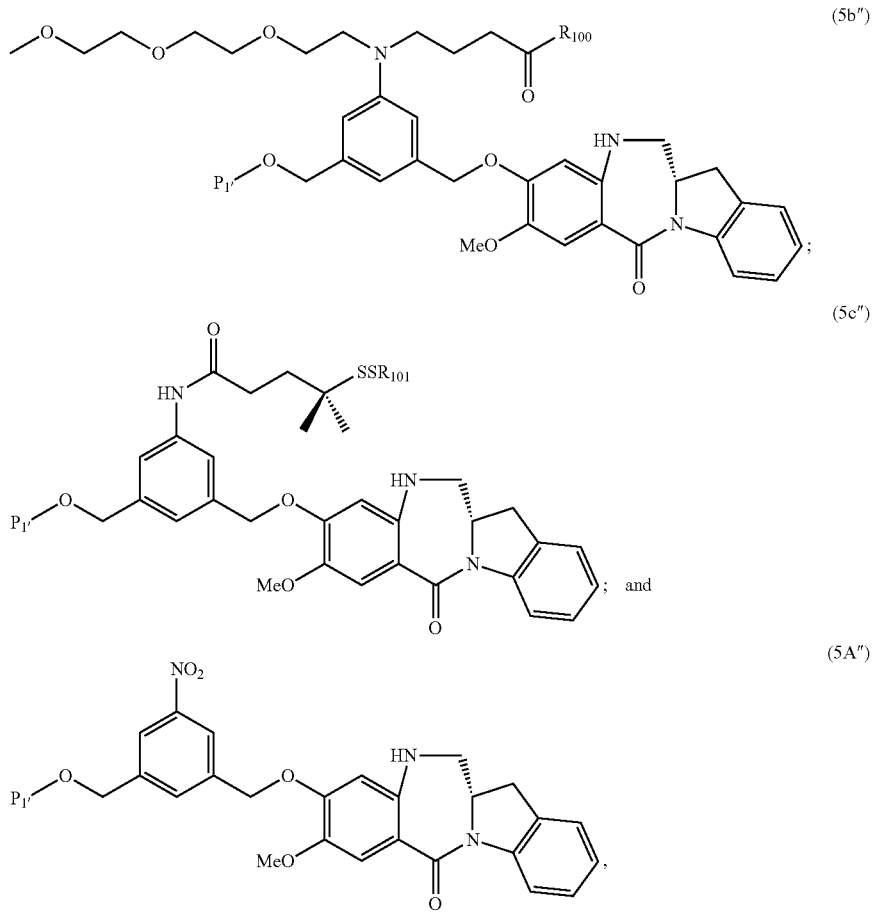

wherein $R_{100}$ is a $(C_1-C_3)$alkoxy; and $R_{101}$ is a $(C_1-C_3)$alkyl, pyridyl or nitropyridyl (e.g., 4-nitropyridyl).

The method of the seventh embodiment combines the alcohol deprotection step described in the fifth embodiment and the halogenation reaction of the resulting alcohol described in the sixth embodiment into one step.

In a specific embodiment, for the method of the seventh embodiment, the compound of formula (7″) is represented by the following formula:

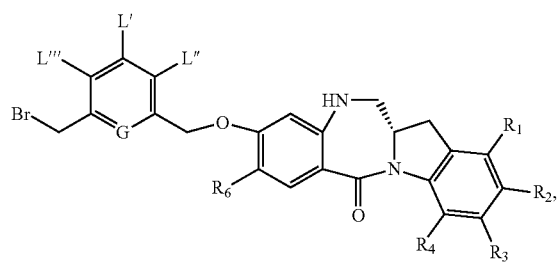

and the method comprising reacting the compound of formula (5″) with an alcohol deprotecting reagent and a bromination reagent.

In one embodiment, the acid labile alcohol protecting group is acetate, allyl, methoxymethyl, tetrahydrofuranyl, tetrahydropyranyl, 5-dibenzosuberyl, 1-ethoxyethyl, 1-methyl-1 methoxyethyl, 2-(phenylselenyl)ethyl, trityl/triphenylmethyl, or tris(4-tert-butylphenyl)methyl.

In another embodiment, the acid labile alcohol protecting group is a silyl protecting group. Exemplary silyl protecting groups include, but are not limited to, dimethylisopropylsilyl, diethylisopropylsilyl, dimethylhexylsilyl, trimethylsilyl, triethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl. Preferably, the silyl protecting group is triethylsilyl, triisopropylsilyl, or tert-butyldimethylsilyl. More preferably, the silyl protecting group is tert-butyldimethylsilyl.

In one embodiment, the alcohol deprotecting reagent is tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, pyridinium p-toluensulfonate, formic acid, periodic acid, trifluoroacetic acid, or .p-toluenesulfonic acid (p-TsOH). Preferably, the alcohol deprotecting reagent is acetic acid.

In yet another embodiment, the bromination reagent is HBr.

In one specific embodiment, the method of the seventh embodiment comprises reacting the compound of formula (5″) with a mixture of acetic acid and HBr to give the compound of formula (7″).

In an eighth embodiment, the present invention provides a method of preparing a compound of formula (I'),

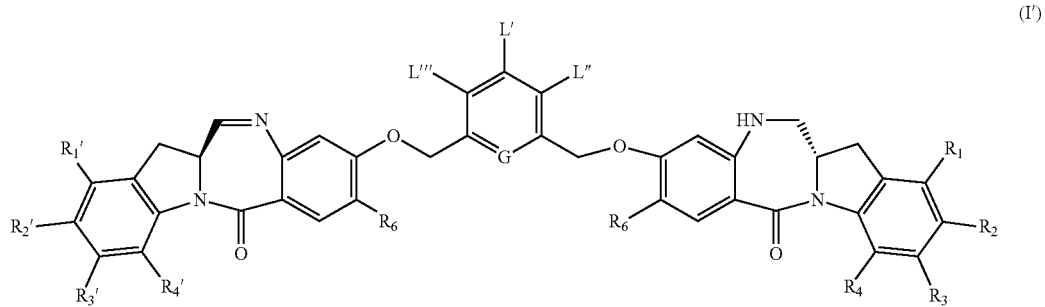

or a pharmaceutically acceptable salt thereof, said method comprising reacting a compound of formula (7)

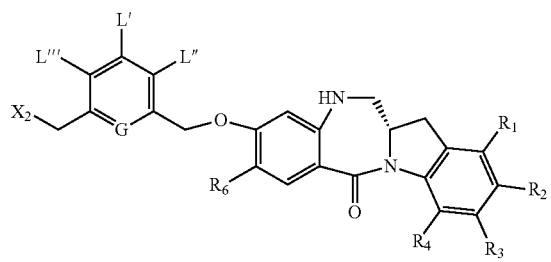

with a monomer compound of the formula (b),

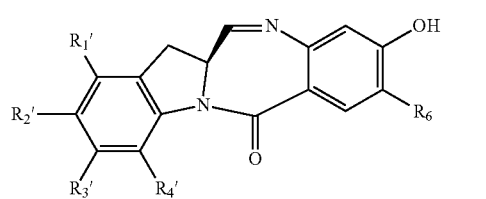

wherein $R_1'$, $R_2'$, $R_3'$, and $R_4'$ are each independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R_c$, halogen, guanidinium [—NH(C=NH)NH$_2$], —OR, —NR'R", —NO$_2$, —NCO, —NR'COR", —SR, —SOR', —SO$_2$R', —SO$_3$H, —OSO$_3$H, —SO$_2$NR'R", cyano, an azido, —COR', —OCOR', and —OCONR'R"; and the remaining variables are as describe above in the seventh embodiment.

In a specific embodiment, the compound of formula (7) is represented by a formula selected from the following:

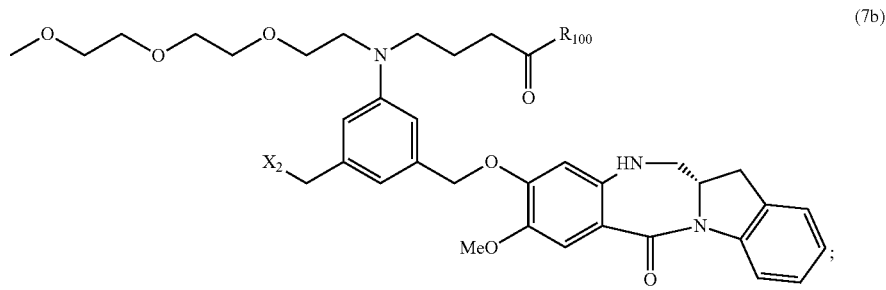

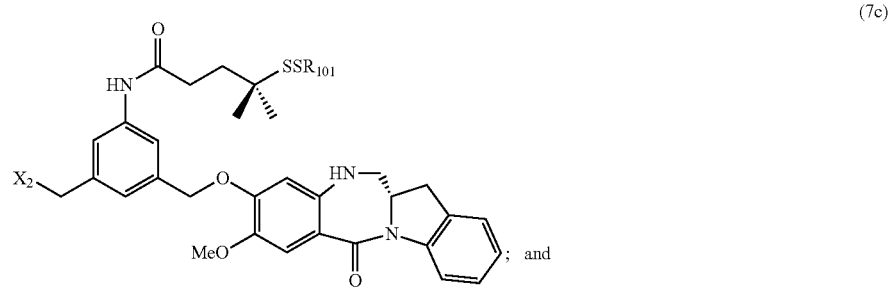

; and

-continued (7A)

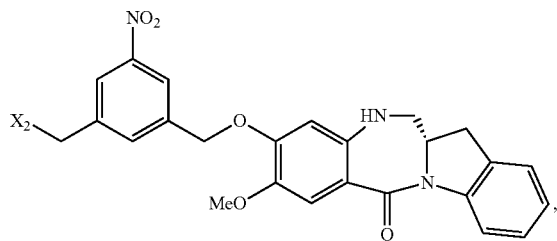

wherein $X_2$ is a leaving group selected from the group consisting of: —Br, —I, —Cl, a sulfonate ester, and an activated ester; $R_{100}$ is a $(C_1-C_3)$alkoxy; and $R_{101}$ is a $(C_1-C_3)$alkyl, pyridyl or nitropyridyl (e.g., 4-nitropyridyl).

In one embodiment, for methods of the eighth embodiment, $X_2$ is —Br, —I or a sulfonate ester.

In one embodiment, the compound of formula (7) is reacted with the monomer compound of formula (b) in the presence of a base. Examples of the base include, but are not limited to, sodium carbonate, potassium carbonate, cesium carbonate, sodium hydride, or potassium hydride. In one embodiment, the base is potassium carbonate.

Any suitable solvents can be used in the methods described above. In one embodiment, the solvent is DMF.

In a ninth embodiment, the present invention provides a method of preparing a compound of formula (I'), (I')

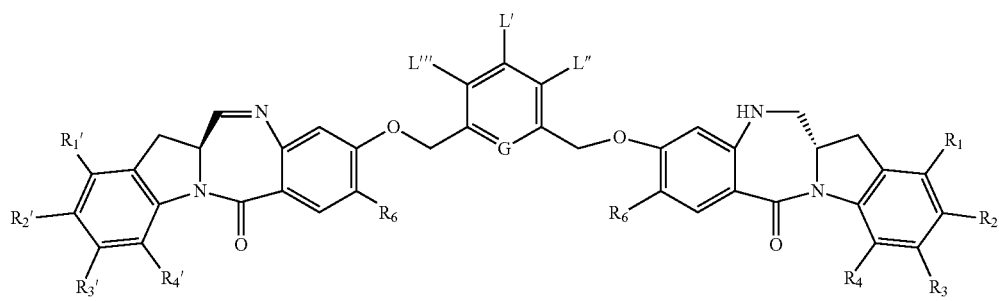

or a pharmaceutically acceptable salt thereof, said method comprising the steps of:

(1) introducing an alcohol protecting group onto one of the primary alcohols of a compound of formula (1), (1)

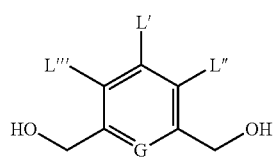

to form a compound of formula (2), (2)

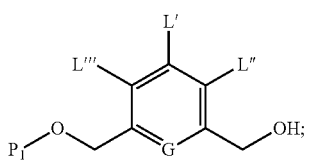

(2) reacting the compound of formula (2) with a halogenating reagent, a sulfonating reagent or an esterification reagent to form a compound of formula (3), (3)

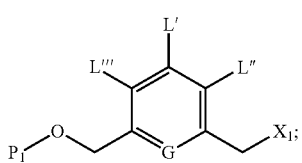

(3) reacting the compound of formula (3) with a monomer compound of the formula (a), (a)

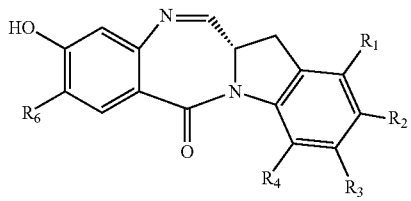

to form a compound of formula (4), (4)

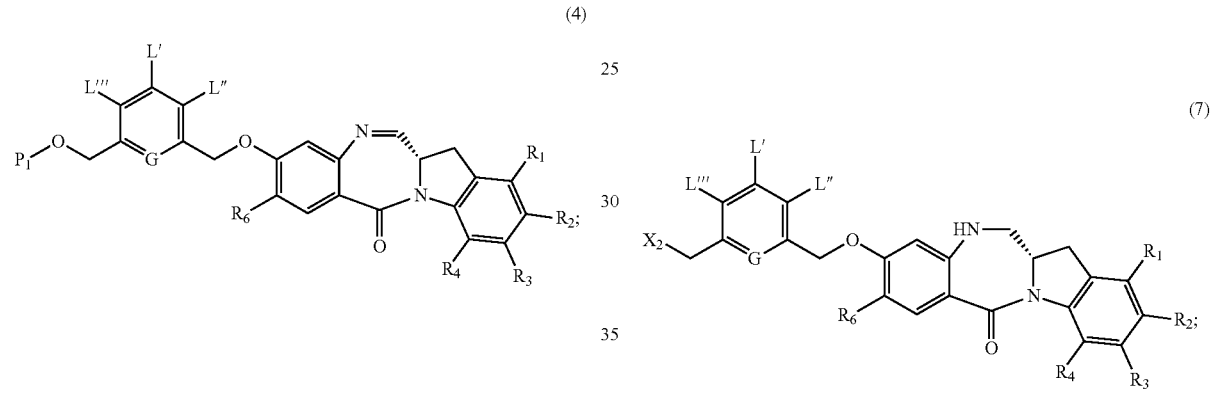

(4) reacting the compound of formula (4) with an imine reducing agent to form a compound of formula (5), (5)

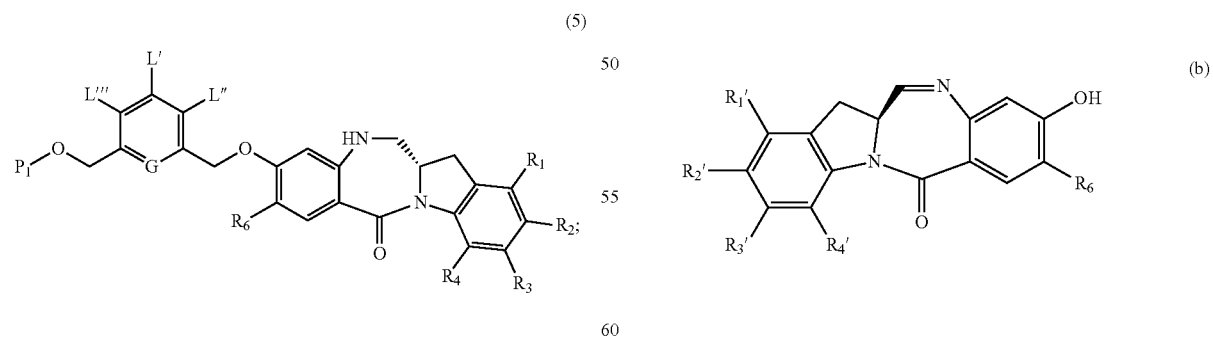

(5) reacting the compound of formula (5) with an alcohol deprotecting reagent to form a compound of formula (6), (6) reacting a second halogenating reagent, a second sulfonating reagent or a second esterification reagent with the compound of formula (6) to form a compound of formula (7), (6)

(7)

and
(7) reacting the compound of formula (7) with a monomer compound of the formula (b), (b)

to form the compound of formula (I'), wherein the variables are as described above in the first, second, third, fourth, fifth, sixth, and eighth embodiments.

In one specific embodiment, the method of the ninth embodiment involves preparing a compound of formula (Ib')

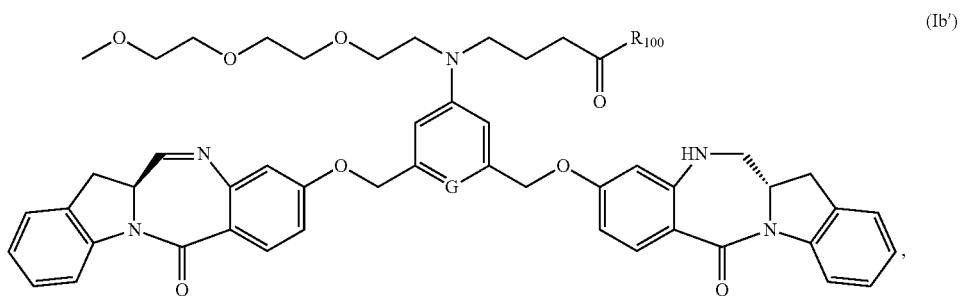

or a pharmaceutically acceptable salt thereof, said method comprising the steps of:

(1) introducing an alcohol protecting group onto one of the primary alcohols of a compound of formula (1b) to form a compound of formula (2b);

(2) reacting the compound of formula (2b) with a halogenating reagent, a sulfonating reagent or an esterification reagent to form a compound of formula (3b);

(3) reacting the compound of formula (3b) with a monomer compound of the formula (a), to form a compound of formula (4b), (4) reacting the compound of formula (4b) with an imine reducing agent to form a compound of formula (5b), (5) reacting the compound of formula (5b) with an alcohol deprotecting reagent to form a compound of formula (6b), (6) reacting the compound of formula (6b) with a second halogenating reagent, a second sulfonating reagent or a second esterification reagent to form a compound of formula (7b), (7) reacting the compound of formula (7b) with a monomer compound of the formula (b), to form the compound of formula (Ib').

In one specific embodiment, the method of the ninth embodiment involves preparing a compound of formula (Ic')

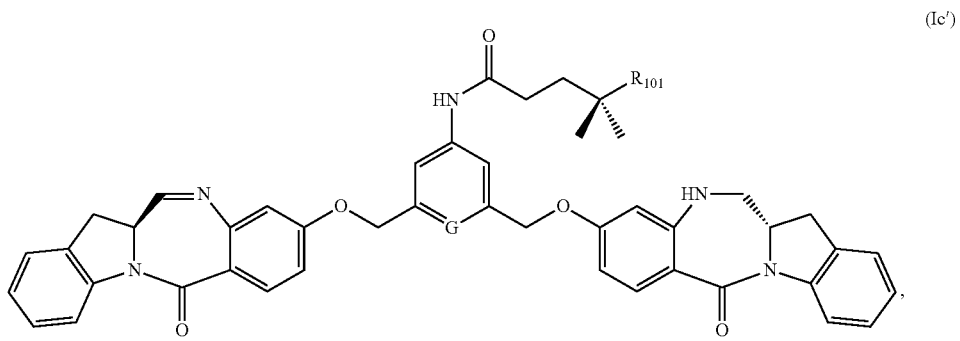

or a pharmaceutically acceptable salt thereof, said method comprising the steps of:

(1) introducing an alcohol protecting group onto one of the primary alcohols of a compound of formula (1c) to form a compound of formula (2c);

(2) reacting the compound of formula (2c) with a halogenating reagent, a sulfonating reagent or an esterification reagent to form a compound of formula (3c);

(3) reacting the compound of formula (3c) with a monomer compound of the formula (a), to form a compound of formula (4c), (4) reacting the compound of formula (4c) with an imine reducing agent to form a compound of formula (5c), (5) reacting the compound of formula (5c) with an alcohol deprotecting reagent to form a compound of formula (6c), (6) reacting the compound of formula (6c) with a second halogenating reagent, a second sulfonating reagent or a second esterification reagent to form a compound of formula (7c), (7) reacting the compound of formula (7c) with a monomer compound of the formula (b), to form the compound of formula (Ic').

In one specific embodiment, the method of the ninth embodiment involves preparing a compound of formula (IA)

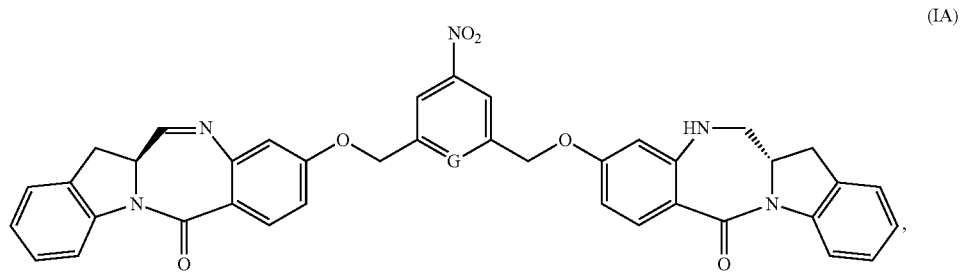

(IA)

or a pharmaceutically acceptable salt thereof, said method comprising the steps of (1) introducing an alcohol protecting group onto one of the primary alcohols of a compound of formula (1A) to form a compound of formula (2A);

(2) reacting the compound of formula (2A) with a halogenating reagent, a sulfonating reagent or an esterification reagent to form a compound of formula (3A);

(3) reacting the compound of formula (3A) with a monomer compound of the formula (a), to form a compound of formula (4A), (4) reacting the compound of formula (4A) with an imine reducing agent to form a compound of formula (5A), (5) reacting the compound of formula (5A) with an alcohol deprotecting reagent to form a compound of formula (6A), (6) reacting the compound of formula (6A) with a second halogenating reagent, a second sulfonating reagent or a second esterification reagent to form a compound of formula (7A), (7) reacting the compound of formula (7A) with a monomer compound of the formula (b), to form the compound of formula (IA).

In one embodiment, for methods of the ninth embodiment, $X_1$ and $X_2$ are each independently —Br, —Cl or a sulfonate ester.

The reaction conditions and reagents for each step in the method of the ninth embodiment are as described in the first, second, third, fourth, fifth, sixth and/or eighth embodiment or any specific embodiments described therein.

In a tenth embodiment, the present invention provides a method of preparing a compound of formula (I'), or a pharmaceutically acceptable salt thereof, said method comprising the steps of:

(1) introducing an alcohol protecting group onto one of the primary alcohols of a compound of formula (1),

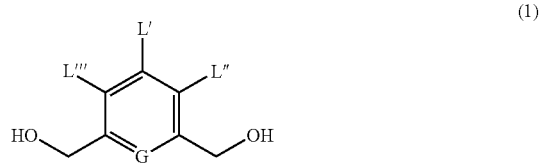

(1)

to form a compound of formula (2"),

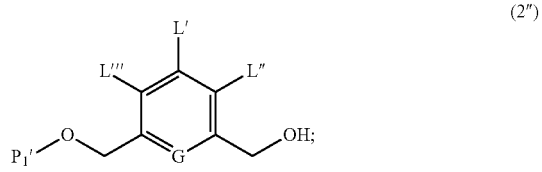

(2")

(2) reacting the compound of formula (2") with a halogenating reagent, a sulfonating reagent or an esterification reagent to form a compound of formula (3"),

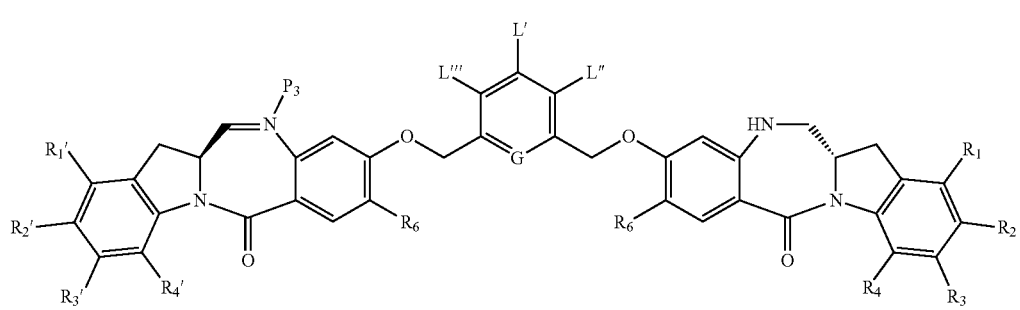

(I')

(3")

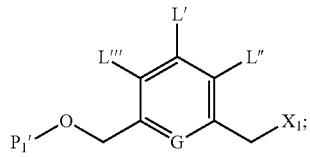

(3) reacting the compound of formula (3") with a monomer compound of the formula (a),

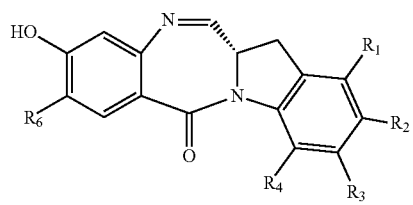
(a)

to form a compound of formula (4"),

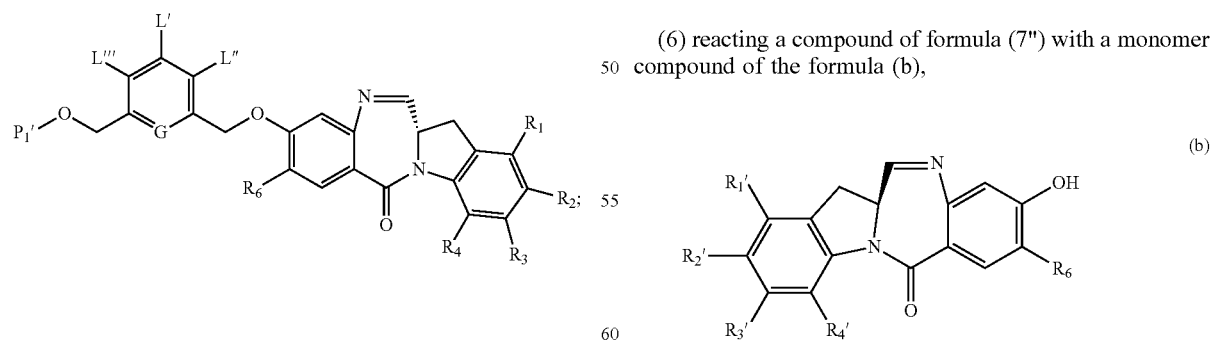
(4")

(4) reacting the compound of formula (4") with an imine reducing agent to form a compound of formula (5"),

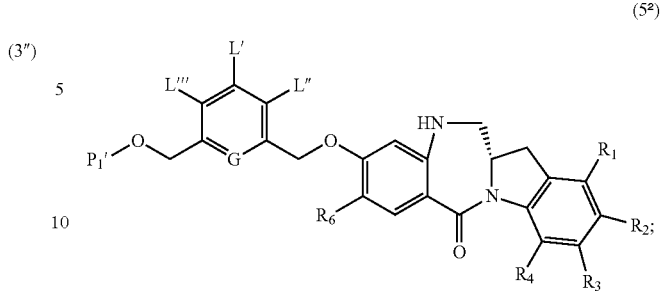
(5²)

(5) reacting the compound of formula (5") with an alcohol deprotecting reagent and a halogenating reagent to form a compound of formula (7"),

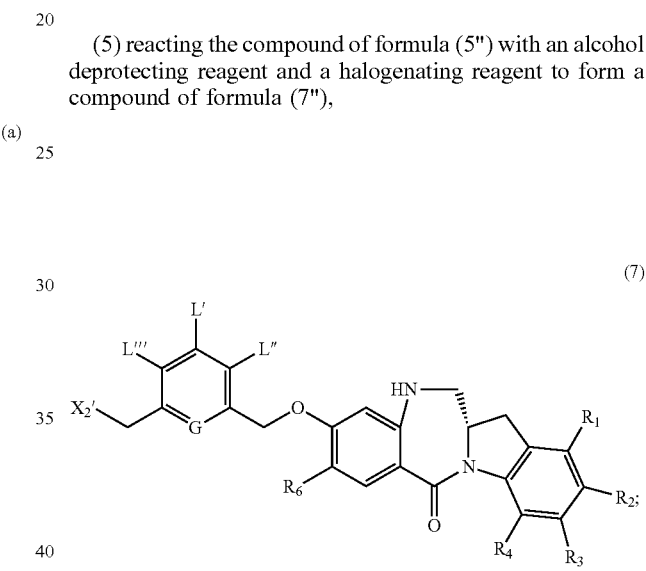
(7)

(6) reacting a compound of formula (7") with a monomer compound of the formula (b), (b)

to form the compound of formula (I'), wherein $X_2'$ is —Br or —I; and the remaining variables are as described above in the ninth embodiment.

In one embodiment, the method of the tenth embodiment involves preparing a compound of formula (Ib'),

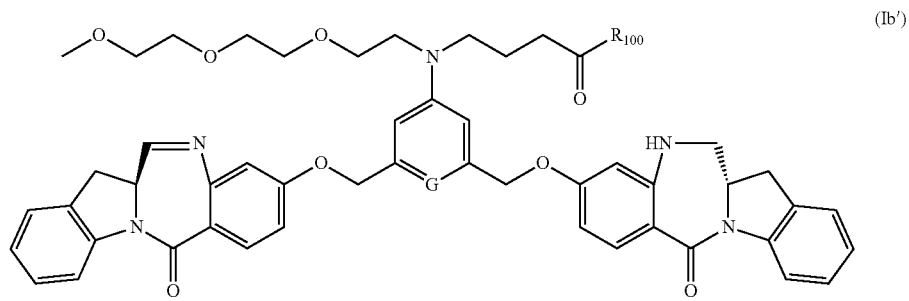
(Ib')

or a pharmaceutically acceptable salt thereof, said method comprising the steps of:

(1) introducing an alcohol protecting group onto one of the primary alcohols of a compound of formula (1b), to form a compound of formula (2b″)

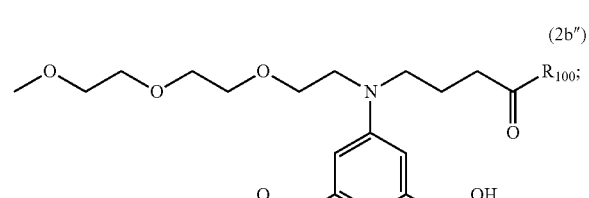
(2b″)

(2) reacting the compound of formula (2b″) with a halogenating reagent or a sulfonating reagent to form a compound of formula (3b″);

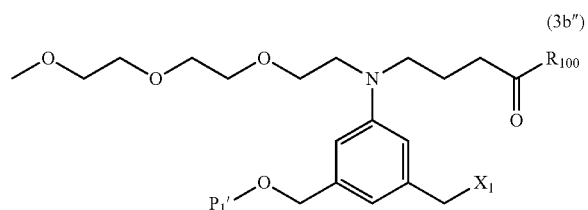
(3b″)

(3) reacting the compound of formula (3b″) with a monomer compound of the formula ($a_1$):

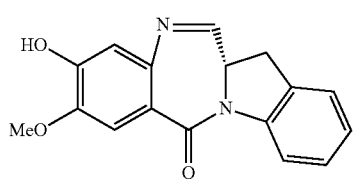
($a_1$)

to form a compound of formula (4b″);

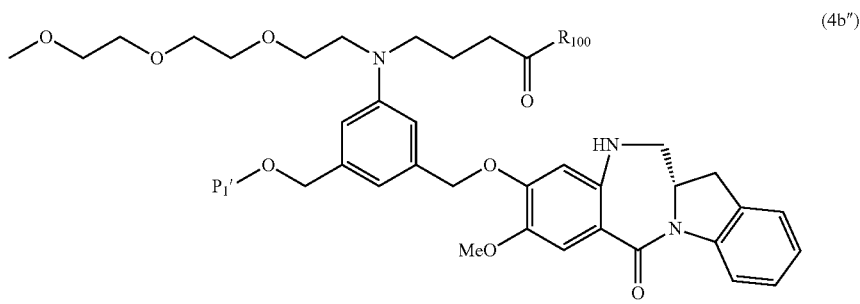
(4b″)

(4) reacting the compound of formula (4b″) with an imine reducing agent to form a compound of formula (5b″);

(5) reacting the compound of formula (5b″) with an alcohol deprotecting reagent and a halogenating reagent to form a compound of formula (7b″);

(6) reacting a compound of formula (7b″) with a monomer compound of the formula ($a_1$), to form the compound of formula (Ib′).

In another embodiment, the method of the tenth embodiment involves preparing a compound of formula (Ic′),

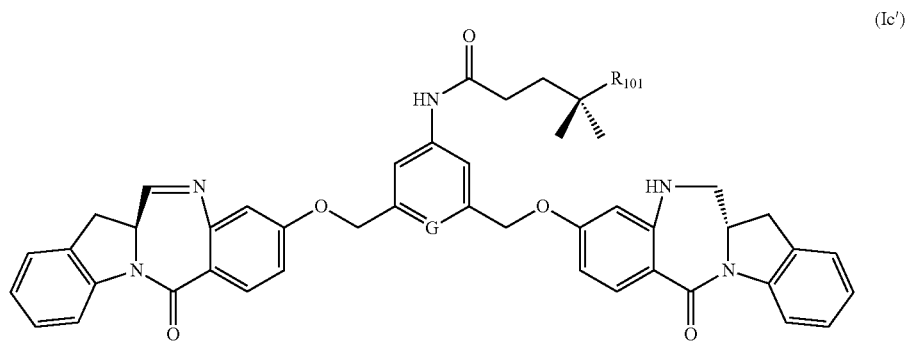

(Ic′)

or a pharmaceutically acceptable salt thereof, said method comprising the steps of:

(1) introducing an alcohol protecting group onto one of the primary alcohols of a compound of formula (1c), to form a compound of formula (2c″);

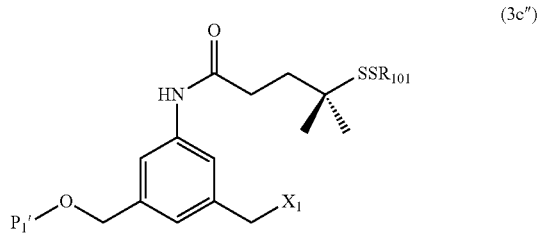

(2c″)

(2) reacting the compound of formula (2c″) with a halogenating reagent or a sulfonating reagent to form a compound of formula (3c″);

(3c″)

(3) reacting the compound of formula (3c″) with a monomer compound of the formula ($a_1$) to form a compound of formula (4c″);

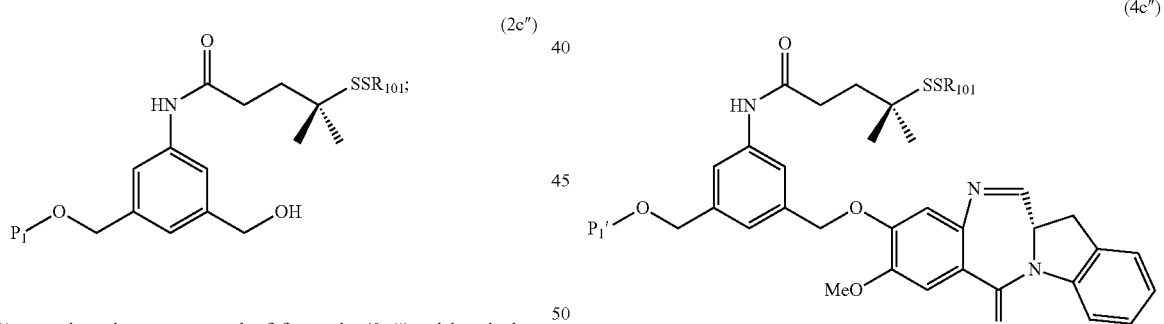

(4c″)

(4) reacting the compound of formula (4c″) with an imine reducing agent to form a compound of formula (5c″);

(5) reacting the compound of formula (5c″) with an alcohol deprotecting reagent and a halogenating reagent to form a compound of formula (7c″);

(6) reacting a compound of formula (7c″) with a monomer compound of the formula ($a_1$), to form the compound of formula (Ic′).

In still another embodiment, the method of the tenth embodiment involves preparing a compound of formula (IA),

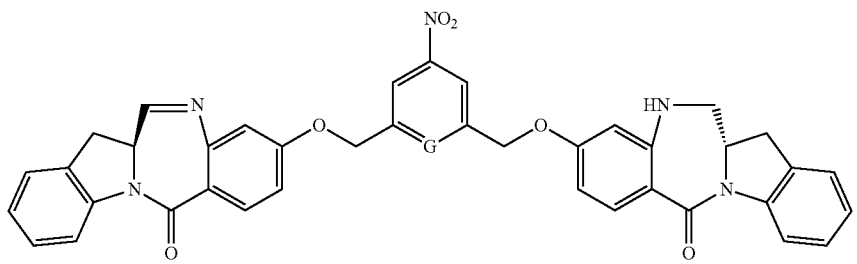

(IA)

or a pharmaceutically acceptable salt thereof, said method comprising the steps of:

(1) introducing an alcohol protecting group onto one of the primary alcohols of a compound of formula (1A), to form a compound of formula (2A″);

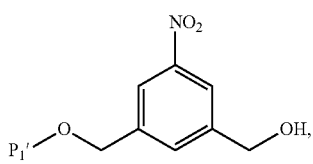

(2A″)

(2) reacting the compound of formula (2A″) with a halogenating reagent or a sulfonating reagent to form a compound of formula (3A″);

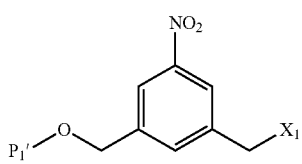

(3A″)

(3) reacting the compound of formula (3A″) with a monomer compound of the formula ($a_1$) to form a compound of formula (4A″);

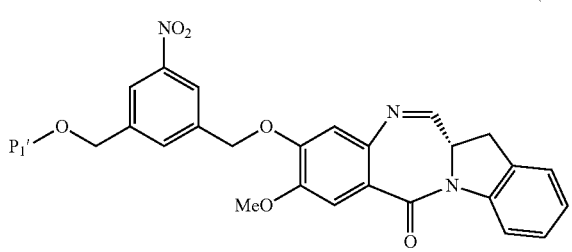

(4A″)

(4) reacting the compound of formula (4A″) with an imine reducing agent to form a compound of formula (5A″);

(5) reacting the compound of formula (5A″) with an alcohol deprotecting reagent and a halogenating reagent to form a compound of formula (7A″);

(6) reacting a compound of formula (7A″) with a monomer compound of the formula ($a_1$), to form the compound of formula (IA′).

The conditions and reagents for the method of tenth embodiment are as described above in the first, second, third, fourth, seventh and/or eighth embodiment(s) and any specific embodiments described therein.

In an eleventh embodiment, the present invention provides a method of preparing a compound of formula (9),

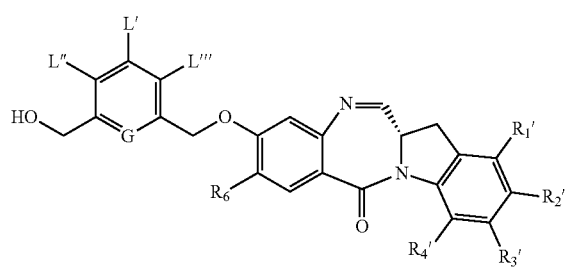

(9)

or a salt thereof, said method comprising reacting a compound of formula (8),

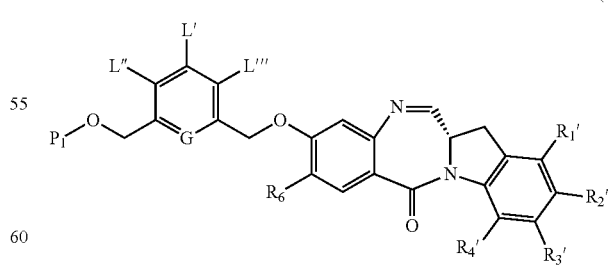

(8)

with an alcohol deprotecting reagent, wherein the variables are as described above in the third embodiment.

In a specific embodiment, the compound of formula (8) is represented by a formula selected from the following:

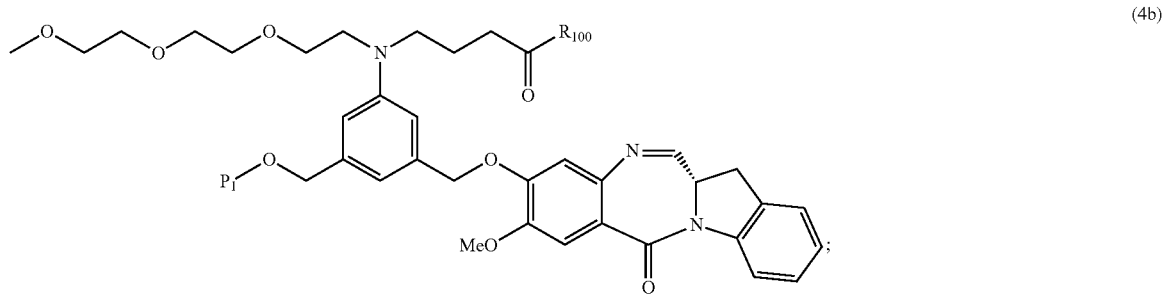

(4b)

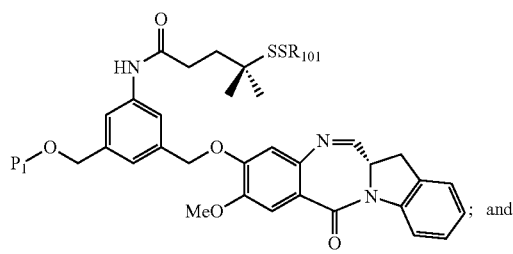

(4c)

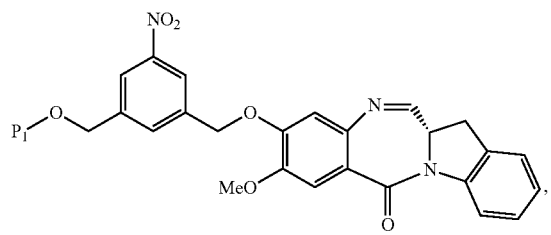

(4A)

wherein $R_{100}$ is a ($C_1$-$C_3$)alkoxy; and $R_{101}$ is a ($C_1$-$C_3$)alkyl, pyridyl or nitropyridyl (e.g., 4-nitropyridyl).

In a specific embodiment, the alcohol deprotecting reagent is tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, pyridinium p-toluensulfonate, formic acid, periodic acid, trifluoroacetic acid, or p-toluenesulfonic acid (p-TsOH). More specifically, the alcohol deprotecting reagent is hydrochloric acid or tetra-n-butylammonium fluoride.

In a twelfth embodiment, the present invention provides a method of preparing a compound of formula (10),

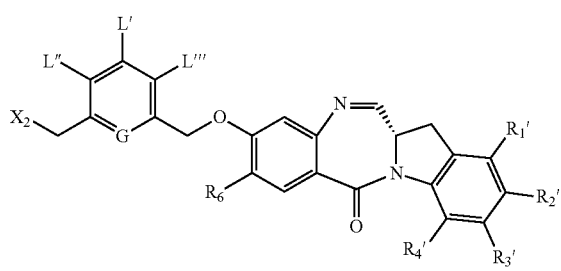

(10)

or a salt thereof, said method comprising reacting the compound of formula (9) with a halogenating reagent, a sulfonating reagent or an esterification reagent,

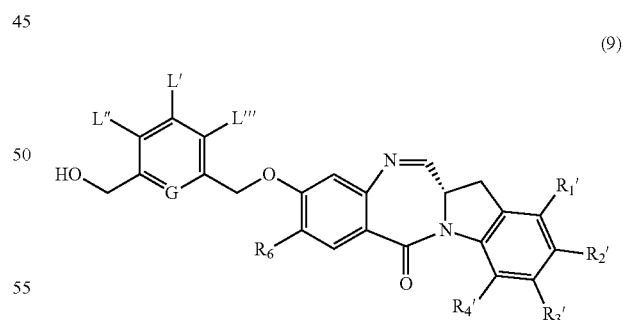

(9)

wherein $X_2$ is —Br, —I, —Cl, a sulfonate ester or an activated ester; and the remaining variables are as described above in the eleventh embodiment.

In one embodiment, the compound of formula (9) is represented by a formula selected from the following:

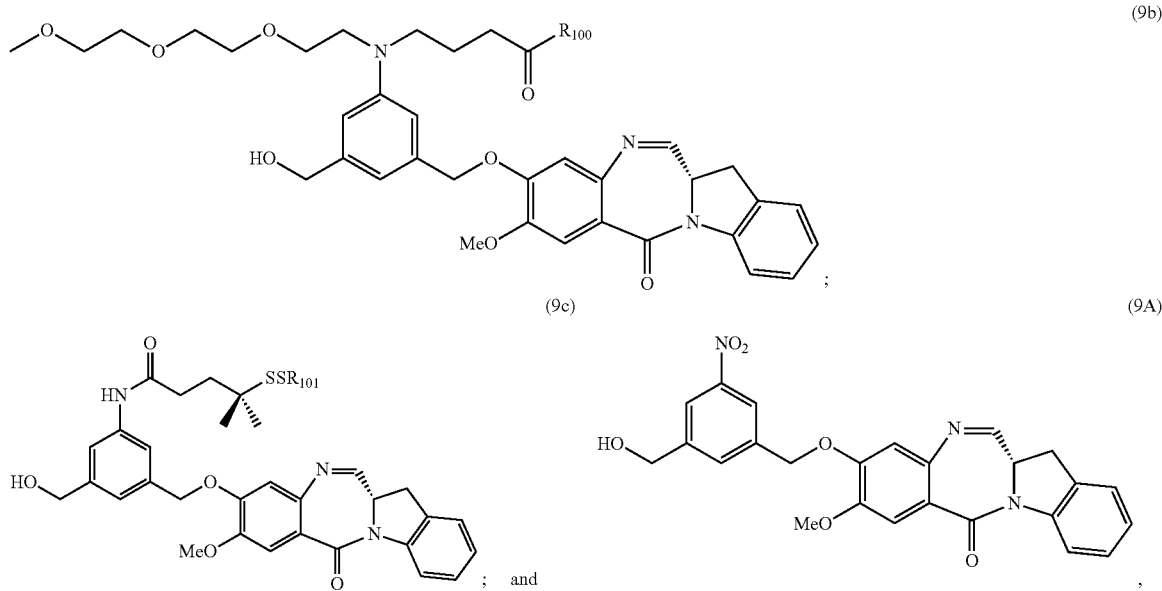

wherein R$_{100}$ is a (C$_1$-C$_3$)alkoxy; and R$_{101}$ is a (C$_1$-C$_3$)alkyl, pyridyl or nitropyridyl (e.g., 4-nitropyridyl).

In a specific embodiment, for the methods of the twelfth embodiment, X$_2$ is —Br, —I or a sulfonate ester.

In a specific embodiment, X$_2$ is mesylate, tosylate, brosylate, or triflate. Preferably, X$_2$ is mesylate.

In another specific embodiment, the method described in the sixth embodiment comprises reacting the compound of formula (9) with a halogenating reagent. Exemplary halogenating reagent include, but are not limited to, bromine, hydrobromic acid, carbon tetrabromide, phosphorus tribromide, potassium bromide, hydroiodic acid, iodine, carbon tetraiodide, phosphorus triiodide, sodium iodide, or potassium iodide.

In yet another specific embodiment, the method of the sixth embodiment comprises reacting the compound of formula (9) with a sulfonating reagent. Preferably, the sulfonating reagent is a sulfonic anhydride, such as methanesulfonic anhydride, or a sulfonic chloride, such as methanesulfonyl chloride (MsCl).

In one embodiment, the reaction between the compound of formula (9) and the sulfonating reagent is carried out in the presence of a base. Preferably, the base is a non-nucleophiclic base. Exemplary non-nucleophic base include, but are not limited to, triethylamine, imidazole, triethylamine, diisopropylethylamine, pyridine, 2,6-lutidine, dimethylformamide, 1,8-diazabicyclo[5.4.0]undec-7-ene (DBU), or tetramethylpiperidine. Preferably, the base is triethylamine or diisopropylethylamine.

In a thirteenth embodiment, the present invention provides a method of preparing a compound of formula (18),

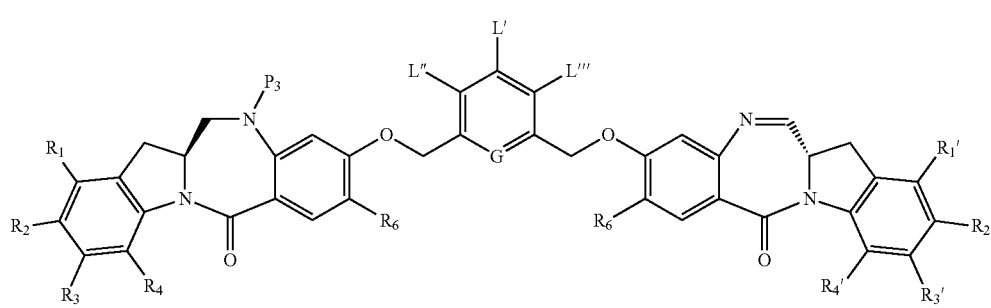

or a salt thereof, said method comprising reacting compound of formula (10)

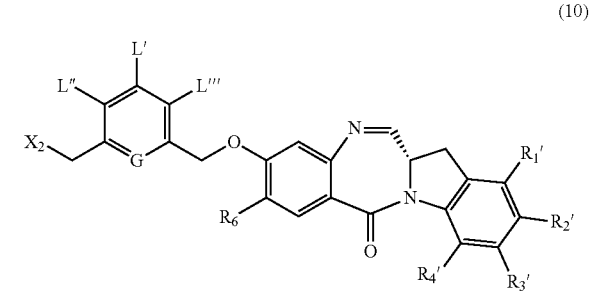

with a monomer compound of the formula (d),

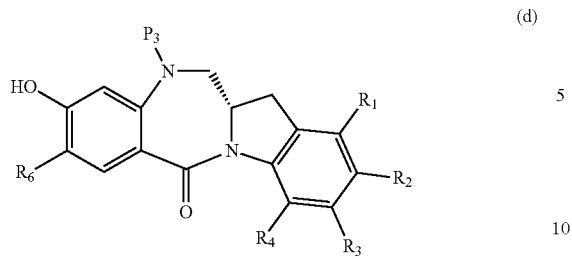

(d)

wherein $X_2$ is a leaving group selected from the group consisting of: —Br, —I, —Cl, a sulfonate ester and an activated ester; $P_3$ is H or $P_2$; $P_2$ is an amine protecting group; $R_1'$, $R_2'$, $R_3'$, and $R_4'$ are each independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R_c$, halogen, guanidinium [—NH(C=NH)NH$_2$], —OR, —NR'R", —NO$_2$, —NCO, —NR'COR", —SR, —SOR', —SO$_2$R', —SO$_3^-$H, —OSO$_3$H, —SO$_2$NR'R", cyano, an azido, —COR', —OCOR', and —OCONR'R"; and the remaining variables are as describe above in the twelfth embodiment. In one embodiment, $X_2$ is —Br, —I, or a sulfonate ester.

In a specific embodiment, the compound of formula (10) is represented by a formula selected from the following:

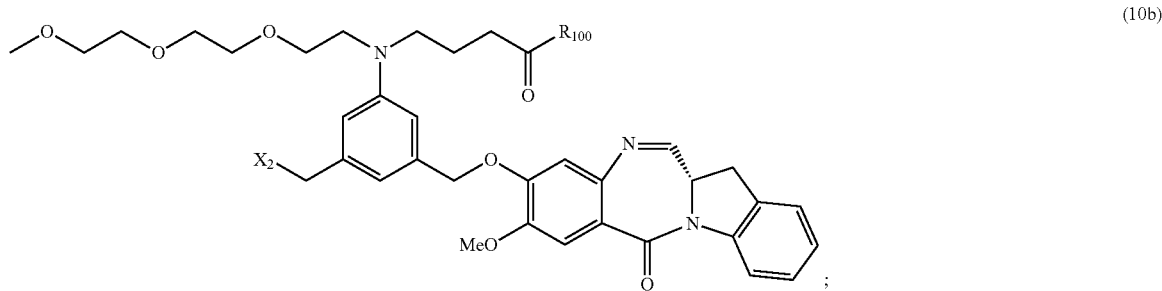

(10b)

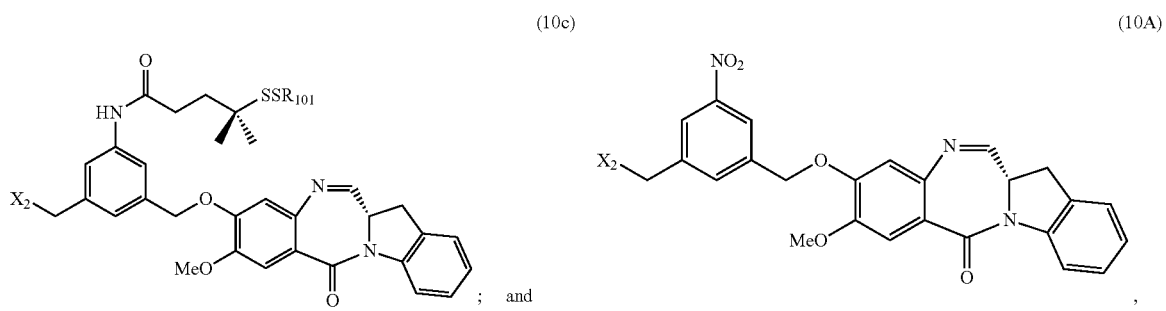

(10c) and (10A)

wherein $R_{100}$ is a $(C_1$-$C_3)$alkoxy; and $R_{101}$ is a $(C_1$-$C_3)$alkyl, pyridyl or nitropyridyl (e.g., 4-nitropyridyl).

In a specific embodiment, $P_3$ is H and the compound of (10) is reacted with the monomer compound of (d) to form a compound of (I'):

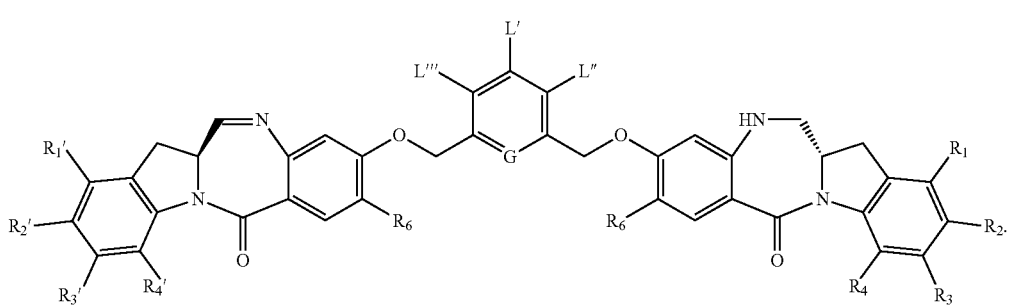

(I')

In another specific embodiment, P$_3$ is P$_2$; the monomer compound is represented by formula (c):

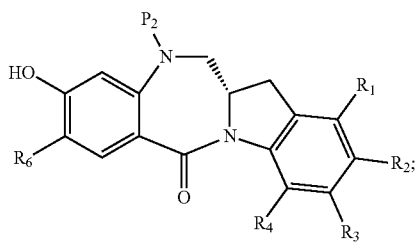

(c)

and the compound of formula (18) is represented by formula (11), protecting group is 2-trimethylsilylethyl, (2-phenyl-2-trimethylsilyl)ethyl, triisopropylsiloxy, 2-(trimethylsilyl)ethoxymethyl, allyloxycarbonyl, 9-fluorenylmethoxycarbonyl, 2-(trimethylsilyl)ethoxycarbonyl, or 2,2,2-trichloroethoxycarbonyl.

In a specific embodiment, the compound of formula (10) is reacted with the monomer compound of formula (d) or (c) in the presence of a base. Examples of the base include, but are not limited to sodium carbonate, potassium carbonate, cesium carbonate, sodium hydride, or potassium hydride.

Any suitable solvents can be used in the reaction described above. In one embodiment, the solvent is DMF.

In a fourteenth embodiment, the present invention provides a method of preparing a compound of formula (I'),

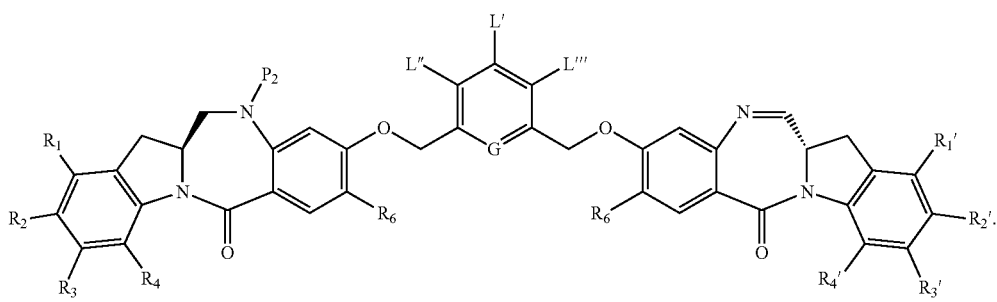

(11)

Any suitable amine protecting group can be used in the method described above. In one embodiment, the amine

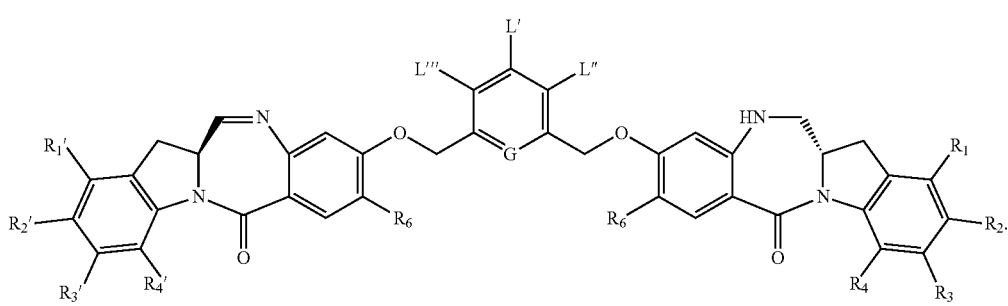

(I')

or a pharmaceutically acceptable salt thereof, said method comprising reacting a compound of formula (11),

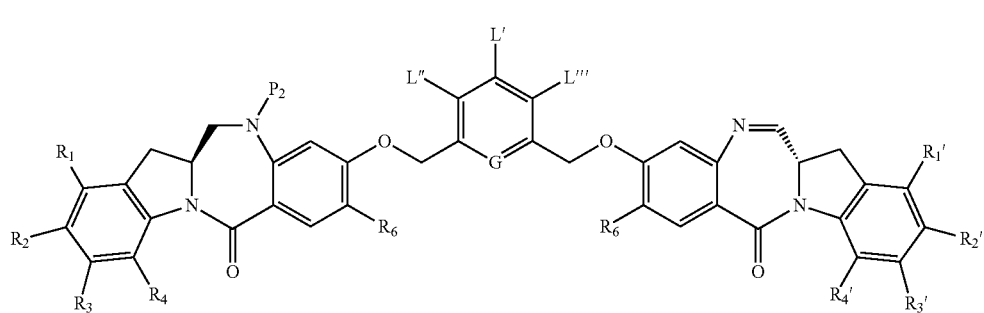

(11)

with an amine deprotecting reagent, wherein the variables are as described above in the thirteenth embodiment.

In a specific embodiment, the compound of formula (11) is represented by a formula selected from the following:

Any suitable amine deprotecting reagent can be used in the method described above. In one embodiment, the amine deprotecting reagent is tetra-n-butylammonium fluoride, acetic acid, hydrogen fluoride pyridine, cesium fluoride, piperidine, morpholine, or trifluroacetic acid.

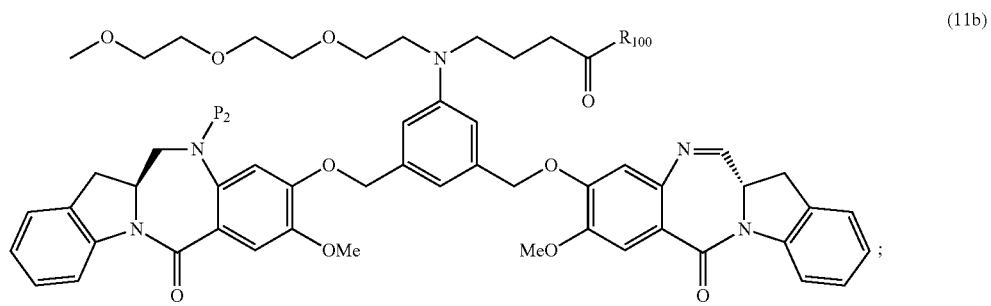

(11b)

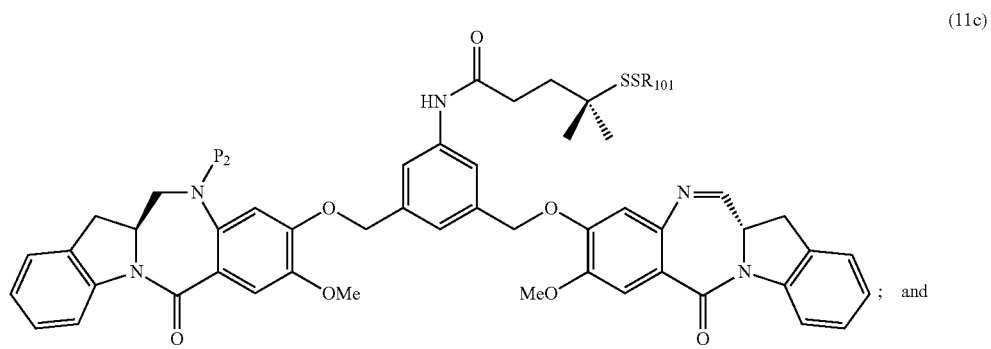

(11c)

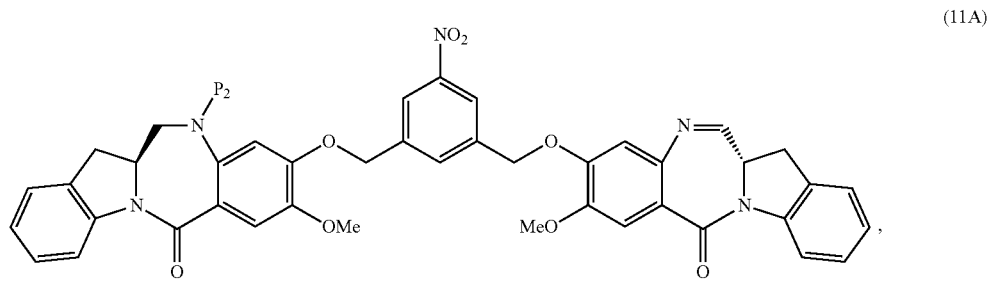

(11A)

wherein $R_{100}$ is a $(C_1-C_3)$alkoxy; and $R_{101}$ is a $(C_1-C_3)$alkyl, pyridyl or nitropyridyl (e.g., 4-nitropyridyl).

In a fifteenth embodiment, the present invention provides a method of preparing a compound of formula (I'),

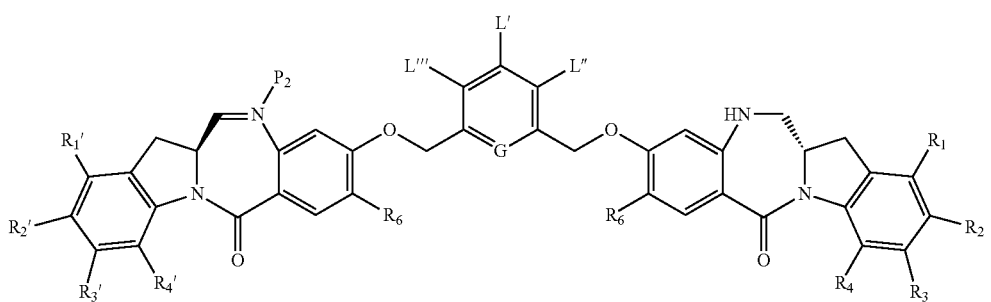

(I')

or a pharmaceutically acceptable salt thereof, said method comprising the steps of:

(1) introducing an alcohol protecting group onto one of the primary alcohols of the compound of formula (1),

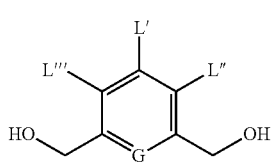

(1)

to form a compound of formula (2),

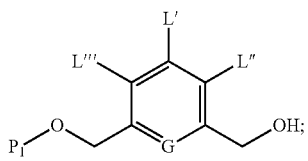

(2)

(2) reacting a halogenating reagent, a sulfonating reagent or an esterification reagent with the compound of formula (2) to form a compound of formula (3),

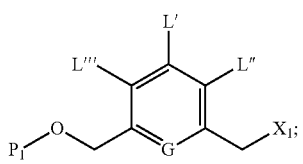

(3)

(3) reacting the compound of formula (3) with a monomer compound of the formula (b),

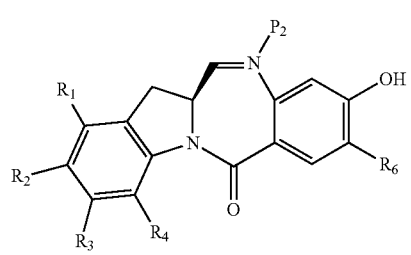

(b)

to form a compound of formula (8),

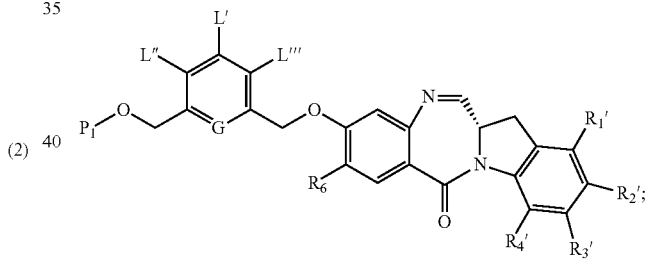

(8)

(4) reacting the compound of formula (8) with an alcohol deprotecting reagent to form a compound of formula (9),

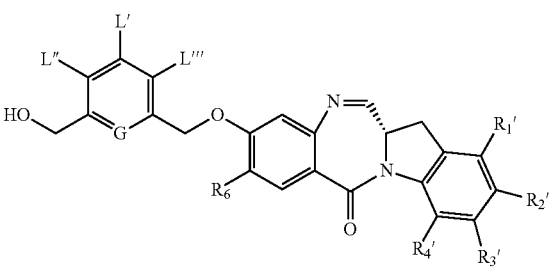

(9)

(5) reacting a second halogenating reagent, a second sulfonating reagent or a second esterification reagent with the compound of formula (9) to form a compound of formula (10),

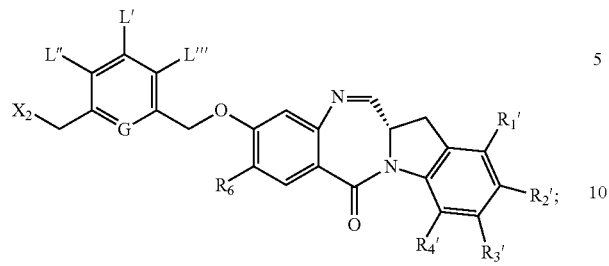

(6) reacting the compound of formula (10) with a monomer compound of the formula (d)

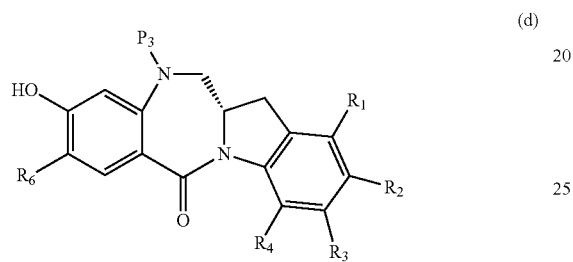

to form a compound of formula (18),

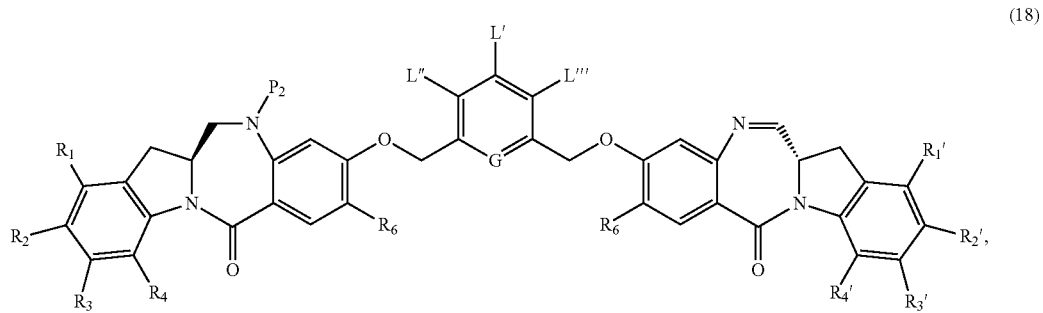

(7) when $P_3$ is an amine protecting group; reacting the compound of formula (18) with an amine deprotecting reagent to form the compound of formula (I'), wherein the variables are as described above in the fourteenth embodiment. In one embodiment, $X_1$ and $X_2$ are each independently —Br, —I or a sulfonate ester.

In one embodiment, the method of the fifteenth embodiment involves preparing a compound of formula (Ib'),

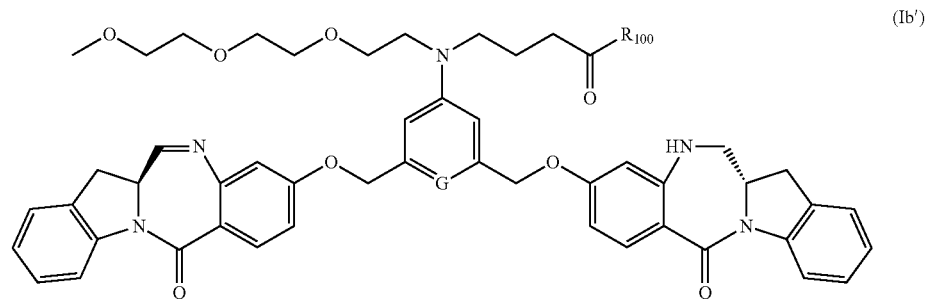

or a pharmaceutically acceptable salt thereof, said method comprising the steps of:

(1) introducing an alcohol protecting group onto one of the primary alcohols of the compound of formula (1b), to form a compound of formula (2b);

(2) reacting a halogenating reagent or a sulfonating reagent with the compound of formula (2b) to form a compound of formula (3b);

(3) reacting the compound of formula (3b) with a monomer compound of the formula (b₁), to form a compound of formula (4b);

(4) reacting the compound of formula (4b) with an alcohol deprotecting reagent to form a compound of formula (9b);

(5) reacting a second halogenating reagent or a second sulfonating reagent with the compound of formula (9b) to form a compound of formula (10b);

(6) reacting the compound of formula (10b) with a monomer compound of the formula (d₁):

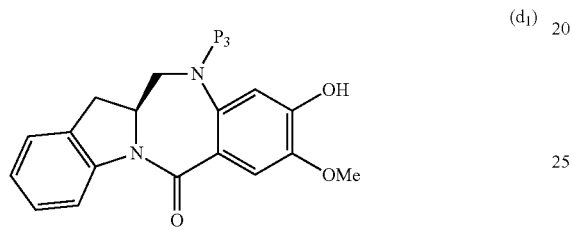

(d₁)

to form a compound of formula (18b);

(7) when $P_3$ is an amine protecting group; reacting the compound of formula (18b):

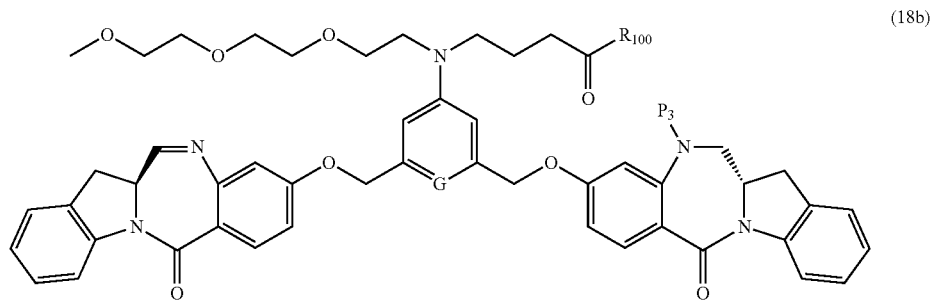

(18b)

with an amine deprotecting reagent to form the compound of formula (Ib'),

In another embodiment, the method of the fifteenth embodiment involves preparing a compound of formula (Ic'),

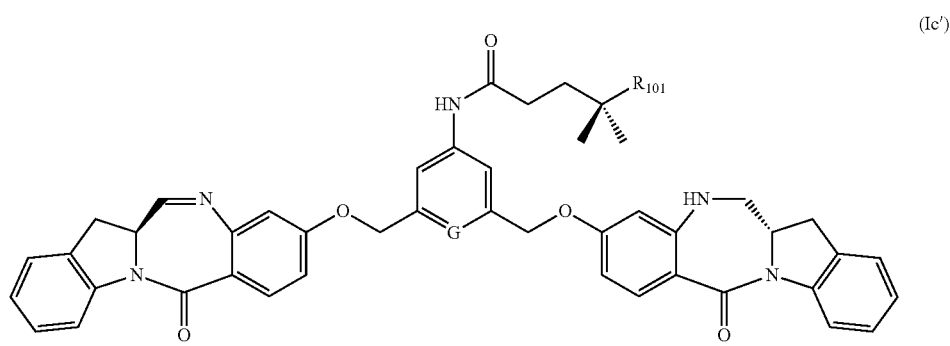

(Ic')

or a pharmaceutically acceptable salt thereof, said method comprising the steps of:

(1) introducing an alcohol protecting group onto one of the primary alcohols of the compound of formula (1c), to form a compound of formula (2c);

(2) reacting a halogenating reagent or a sulfonating reagent with the compound of formula (2c) to form a compound of formula (3c);

(3) reacting the compound of formula (3b) with a monomer compound of the formula ($b_1$), to form a compound of formula (4c);

(4) reacting the compound of formula (4c) with an alcohol deprotecting reagent to form a compound of formula (9c);

(5) reacting a second halogenating reagent or a second sulfonating reagent with the compound of formula (9c) to form a compound of formula (10c);

(6) reacting the compound of formula (10c) with a monomer compound of the formula ($d_1$) to form a compound of formula (18c);

(7) when $P_3$ is an amine protecting group; reacting the compound of formula (18c):

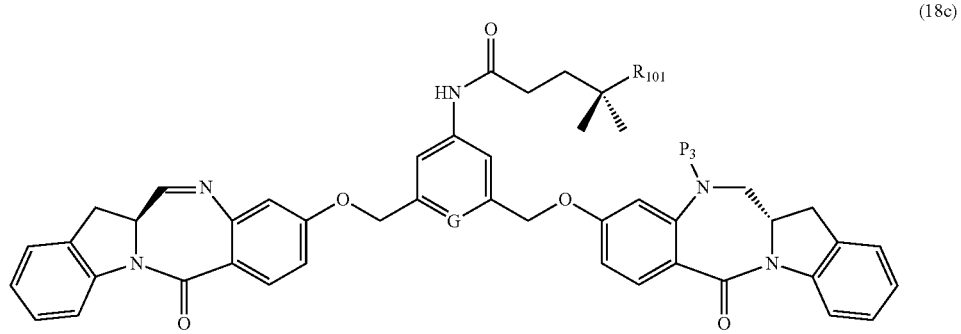

(18c)

with an amine deprotecting reagent to form the compound of formula (Ic').

In still another embodiment, the method of the fifteenth embodiment involves preparing a compound of formula (IA),

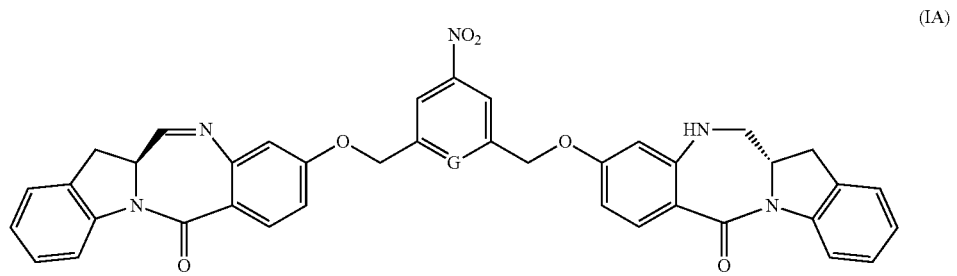

(IA)

or a pharmaceutically acceptable salt thereof, said method comprising the steps of:

(1) introducing an alcohol protecting group onto one of the primary alcohols of the compound of formula (1A), to form a compound of formula (2A);

(2) reacting a halogenating reagent or a sulfonating reagent with the compound of formula (2A) to form a compound of formula (3A);

(3) reacting the compound of formula (3A) with a monomer compound of the formula ($b_1$), to form a compound of formula (4A);

(4) reacting the compound of formula (4A) with an alcohol deprotecting reagent to form a compound of formula (9A);

(5) reacting a second halogenating reagent or a second sulfonating reagent with the compound of formula (9A) to form a compound of formula (10A);

(6) reacting the compound of formula (10A) with a monomer compound of the formula ($d_1$) to form a compound of formula (18A):

(18A)

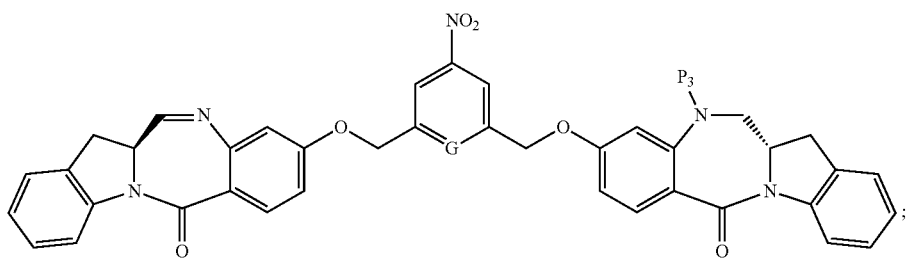

(7) when P₃ is an amine protecting group; reacting the compound of formula (18A) with an amine deprotecting reagent to form the compound of formula (IA').

In one embodiment, P₃ is H and the compound of (10) is reacted with the monomer compound of (d) to form a compound of (I').

In another embodiment, P₃ is P₂; the monomer compound is represented by formula (c):

(c)

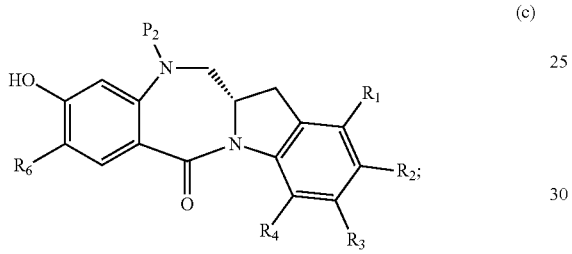

and the compound of formula (18) is represented by formula (11), (1)

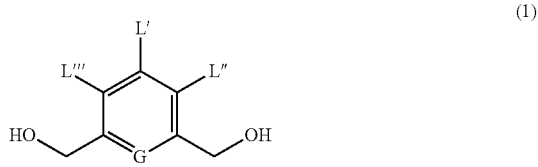

with a halogenating reagent, a sulfonating reagent or an esterification reagent, wherein $X_1$ is —Br, —I, —Cl, a sulfonate ester or an activated ester; and the remaining variables are as described above in the first embodiment. In one embodiment, $X_1$ is —Br, —I, or a sulfonate ester.

(11)

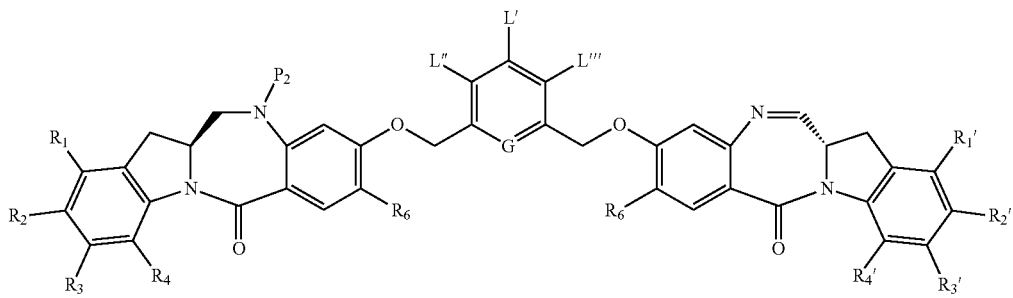

wherein P₂ is an amine protecting group.

In a sixteenth embodiment, the present invention provides a method of preparing a compound of formula (12), (12)

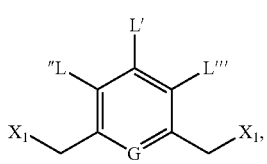

or a salt thereof, said method comprising reacting a compound of formula (1),

In one embodiment, the compound of formula (1) is represented by a formula selected from the following:

(1b)

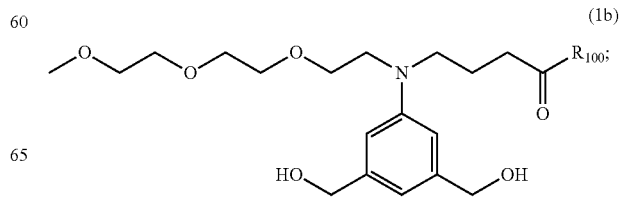

-continued (1c)

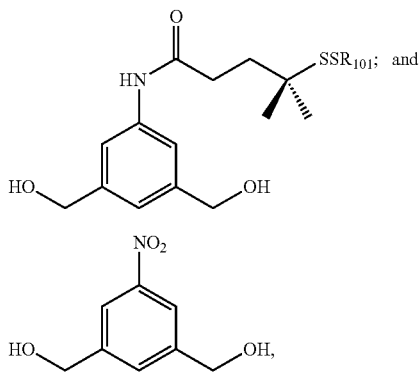

(1A)

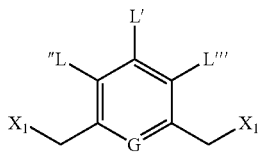

wherein $R_{100}$ is a $(C_1-C_3)$alkoxy; and $R_{101}$ is a $(C_1-C_3)$alkyl, pyridyl or nitropyridyl (e.g., 4-nitropyridyl).

In a specific embodiment, $X_1$ is —Br or —I. In another specific embodiment, $X_1$ is —Cl.

In another specific embodiment, the halogenating reagent reacts with the primary alcohols of the compound of formula (1) in the presence of an alcohol activating agent. In one embodiment, the alcohol activating agent is thionyl chloride. In another specific embodiment, halogenating reagent is lithium bromide, sodium bromide, potassium bromide, potassium iodide, or sodium iodide. In another specific embodiment, the halogenating reagent is carbon tetrachloride/triphenylphosphine, methanesulfonyl (mesyl) chloride/lithium chloride, or methanesulfonyl (mesyl) chloride/pyridine.

In yet another specific embodiment, the method comprises reacting the compound of formula (1) with LiBr in the presence of thionyl chloride.

Any suitable solvents can be used in the method described above. Exemplary solvents include, but are not limited to, DMF, $CH_2Cl_2$, THF, dichloroethane, etc.

In a seventeenth embodiment, the present invention provides a method of preparing a compound of formula (10'), (10')

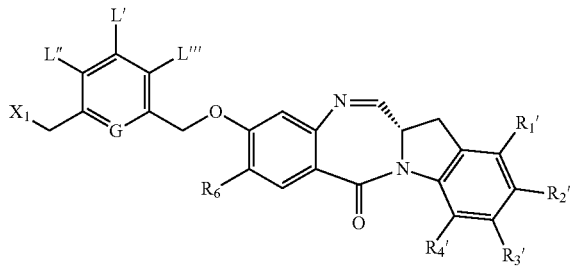

or a salt thereof, said method comprising reacting a compound of formula (12), (12)

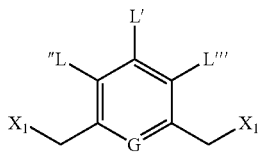

with a monomer compound of the formula (b), (b)

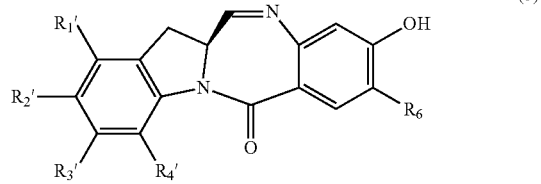

wherein L', L", L'", $X_1$, G are as described above in the seventeenth embodiment; and $R_1'$, $R_2'$, $R_3'$, $R_4'$ and $R_6$ are as describe above in the eleventh embodiment. In one embodiment, $X_1$ is —Br, —I, or a sulfonate ester.

In a specific embodiment, the compound of formula (12) is represented by a formula selected from the following:

(12b)

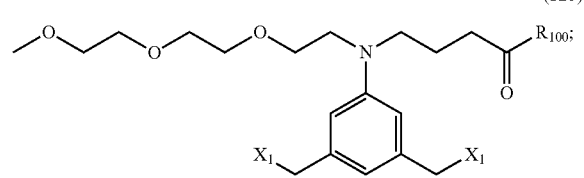

(12c)

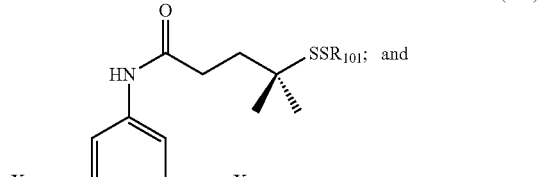

(12A)

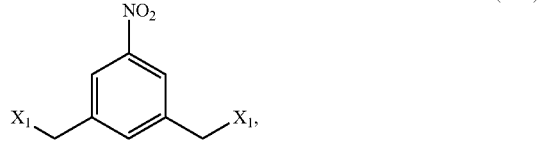

wherein $R_{100}$ is a $(C_1-C_3)$alkoxy; and $R_{101}$ is a $(C_1-C_3)$alkyl, pyridyl or nitropyridyl (e.g., 4-nitropyridyl).

Also provided in the seventeenth embodiment is a method of preparing a compound of formula (7-1)

(7-1)

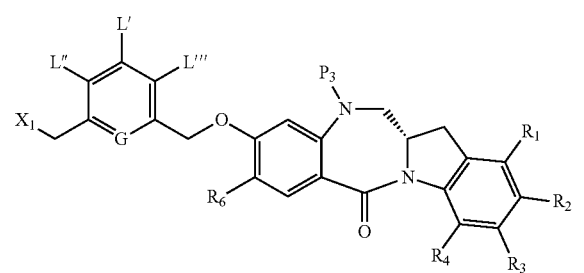

or a salt thereof, said method comprising reacting a compound of formula (12) with a monomer compound of formula (d), wherein $X_1$ is —Br, —I, —Cl, a sulfonate ester or an activated ester; $P_3$ is H or an amine protecting group; and $R_{100}$ is a $(C_1-C_3)$alkoxy.

In a specific embodiment, the compound of formula (12) is represented by formula (12b), (12c) or (12A).

In a specific embodiment, for formula (7-1'), $P_3$ is H. In another specific embodiment, $P_3$ is an amine protecting group as described herein.

In a specific embodiment, for the methods of the seventeenth embodiment, the compound of formula (12) is reacted with the monomer compound of formula (b) in the presence of a base. Examples of suitable base include, but are not limited to, sodium carbonate, potassium carbonate, cesium carbonate, sodium hydride, or potassium hydride. In one embodiment, the base is potassium carbonate.

In another specific embodiment, the compound of formula (12d) or (12A) is reacted with the monomer compound of formula (d) in the presence of a base. Examples of suitable base include, but are not limited to, sodium carbonate, potassium carbonate, cesium carbonate, sodium hydride, or potassium hydride. In one embodiment, the base is potassium carbonate.

For the methods of the seventeenth embodiment, any suitable solvents can be used. In one embodiment, the solvent is DMF.

In another specific embodiment, excess molar equivalent of the compound of formula (12) relative to the monomer compound of formula (b) is used in the reaction.

In an eighteenth embodiment, the present invention provides a method of preparing a compound of formula (7'),

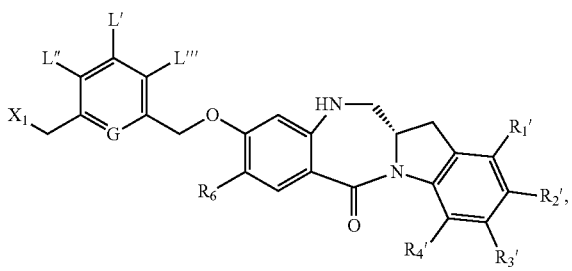

(7')

or a salt thereof, said method comprising reacting a compound of formula (10'),

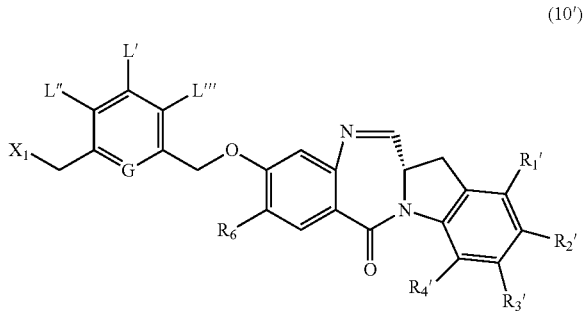

(10')

or a salt thereof, with an imine reducing agent, wherein $X_1$ is —Br, —I, —Cl, a sulfonate ester or an activated ester and the remaining variables are the same as described above in the eleventh embodiment. In one embodiment, $X_1$ is —Br, —I, or a sulfonate ester.

In a specific embodiment, a compound of formula (10') is represented by one of the following formulas:

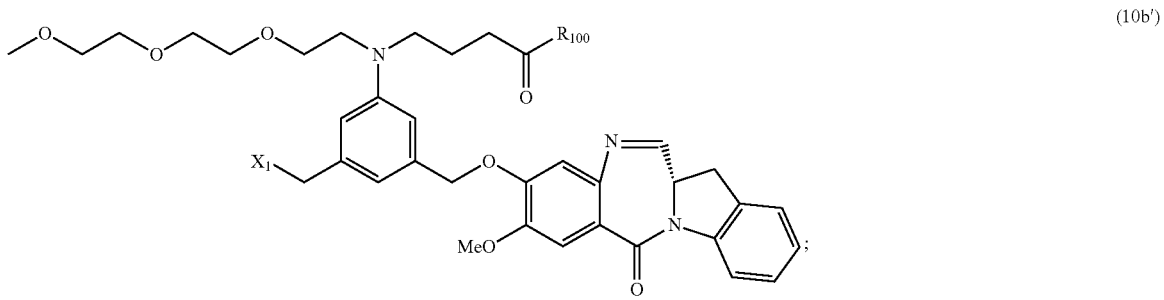

(10b')

-continued

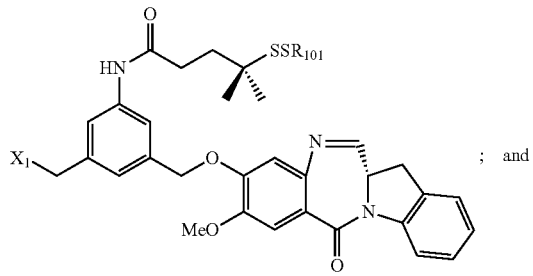 (10c')

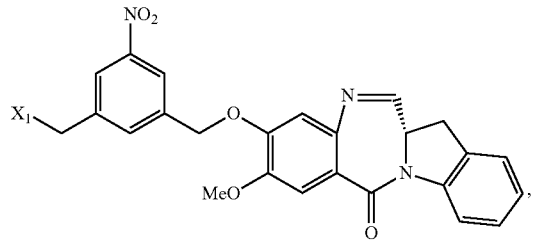 (10A')

In a specific embodiment, for methods of the eighteenth embodiment, $X_1$ is a sulfonate ester. Preferably, $X_1$ is mesylate.

In one embodiment, for methods of the eighteenth embodiment, the imine reducing reagent is a hydride reducing reagent. Alternatively, the imine reducing reagent is sodium borohydride, sodium triacetoxy borohydride, sodium cyanoborohydride, lithium aluminum hydride, hydrogen gas, ammonium formate, borane, 9-borabicyclo[3.3.1]nonane (9-BBN), diisobutylaluminium hydride (DIBAL), lithium borohydride (LiBH$_4$), potassium borohydride (KBH$_4$), or sodium bis(2-methoxyethoxy)aluminumhydride (Red-Al). In a preferred embodiment, the imine reducing reagent is sodium triacetoxy borohydride (NaBH(OAc)$_3$).

Any suitable solvents can be used in the methods of the eighteenth embodiment. In one embodiment, the solvent is dichloroethane.

In a nineteenth embodiment, the present invention provides a method of preparing a compound of formula (I'),

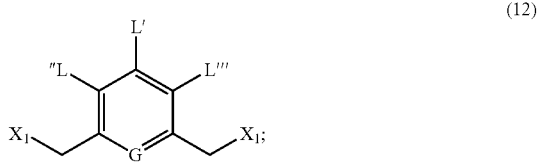 (12)

(2) reacting the compound of formula (12) with a monomer compound of the formula (b),

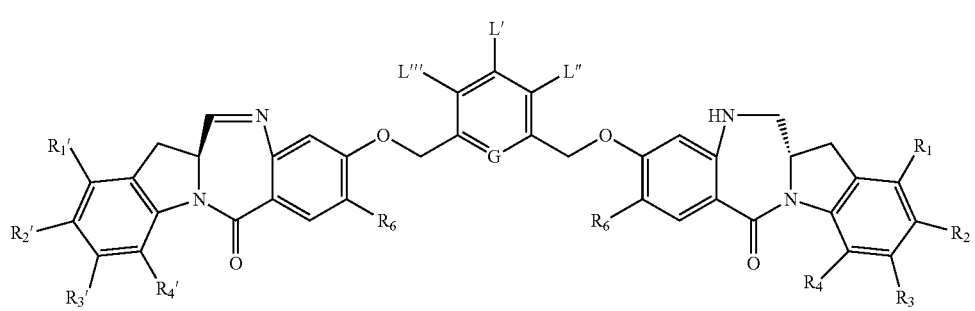 (I')

or a pharmaceutically acceptable salt thereof, said method comprising the steps of:

(1) reacting a halogenating reagent, a sulfonating reagent or an esterification reagent with a compound of formula (1),

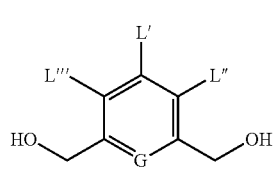 (1)

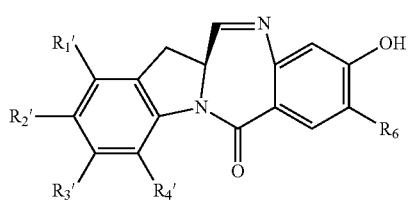 (b)

to form a compound of formula (12), to form a compound of a formula (10'),

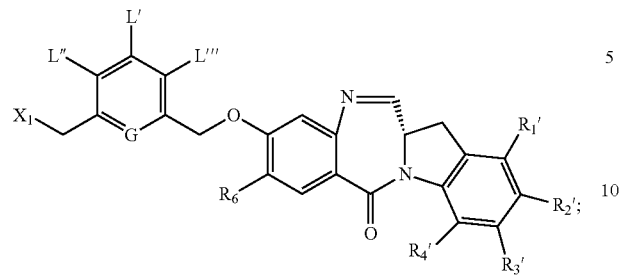
(10')

(3) reacting the compound of formula (10') with a monomer compound of the formula (d),

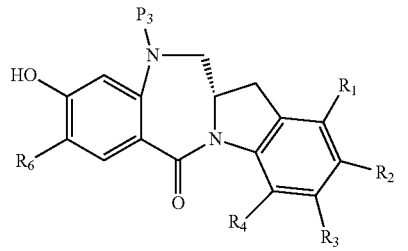
(d)

to form a compound of formula (18),

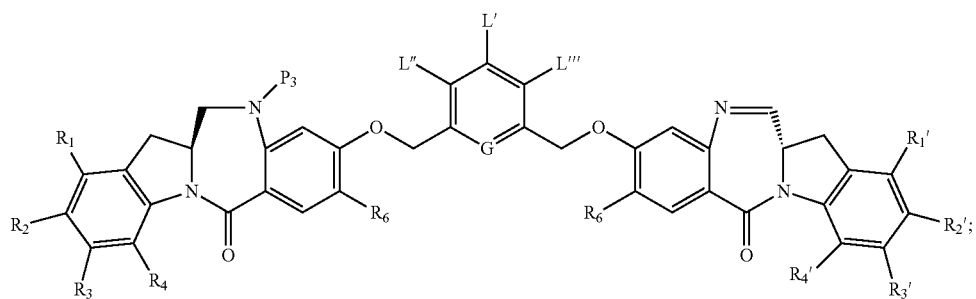
(18)

and (4) when $P_3$ is an amine protecting group, reacting the compound of formula (18) with an amine deprotecting reagent to form the compound of formula (I'); wherein $X_1$ is —Br, —I, —Cl, a sulfonate ester or an activated ester; $P_3$ is H or an amine protecting group, and the remaining variables are the same as described in the eleventh embodiment. In one embodiment, $X_1$ is —Br, —I, or a sulfonate ester.

In one embodiment, the method of the nineteenth embodiment involves preparing a compound of formula (Ib'),

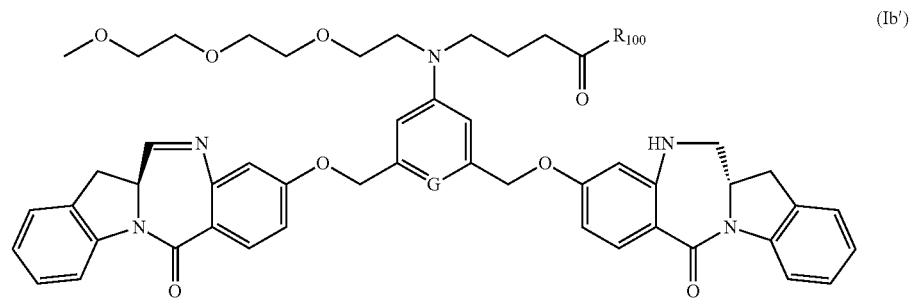
(Ib')

or a pharmaceutically acceptable salt thereof, said method comprising the steps of:

(1) reacting a halogenating reagent or a sulfonating reagent with a compound of formula (1b) to form a compound of formula (12b);

(2) reacting the compound of formula (12b) with a monomer compound of the formula (b₁) to form a compound of a formula (10b');

(3) reacting the compound of formula (10b') with a monomer compound of the formula (d₁) to form a compound of formula (18b); and (4) when P₃ is an amine protecting group, reacting the compound of formula (18b) with an amine deprotecting reagent to form the compound of formula (1b').

In another embodiment, the method of the nineteenth embodiment involves preparing a compound of formula (Ic'), or a pharmaceutically acceptable salt thereof, said method comprising the steps of:

(1) reacting a halogenating reagent or a sulfonating reagent with a compound of formula (1A) to form a compound of formula (12A);

(2) reacting the compound of formula (12A) with a monomer compound of the formula (b₁) to form a compound of a formula (10A');

(3) reacting the compound of formula (10A') with a monomer compound of the formula (d₁) to form a compound of formula (18A); and

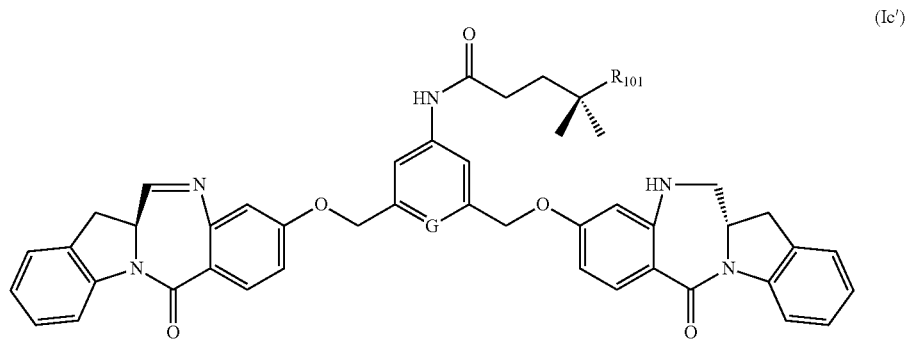

(Ic')

or a pharmaceutically acceptable salt thereof, said method comprising the steps of:

(1) reacting a halogenating reagent or a sulfonating reagent with a compound of formula (Ic) to form a compound of formula (12c);

(2) reacting the compound of formula (12c) with a monomer compound of the formula (b₁) to form a compound of a formula (10c');

(3) reacting the compound of formula (10c') with a monomer compound of the formula (d₁) to form a compound of formula (18c); and (4) when P₃ is an amine protecting group, reacting the compound of formula (18c) with an amine deprotecting reagent to form the compound of formula (Ic').

In still another embodiment, the method of the nineteenth embodiment involves preparing a compound of formula (IA), (4) when P₃ is an amine protecting group, reacting the compound of formula (18A) with an amine deprotecting reagent to form the compound of formula (IA').

In one embodiment, for methods of the nineteenth embodiment, P₃ is H and the compound of (10') is reacted with the monomer compound of (d) to form a compound of (I').

In another embodiment, for methods of the nineteenth embodiment, P₃ is P₂; the monomer compound is represented by formula (c):

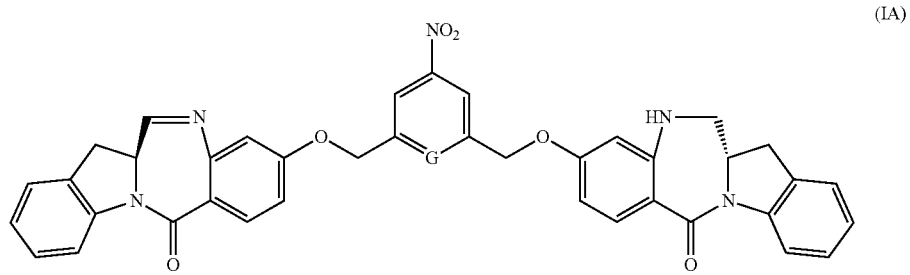

(IA)

77

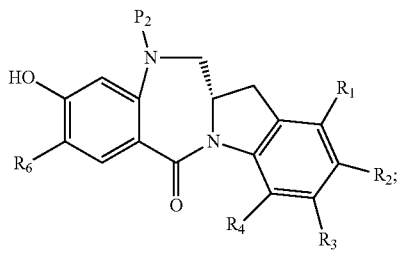
(c)

and the compound of formula (18) is represented by formula (11),

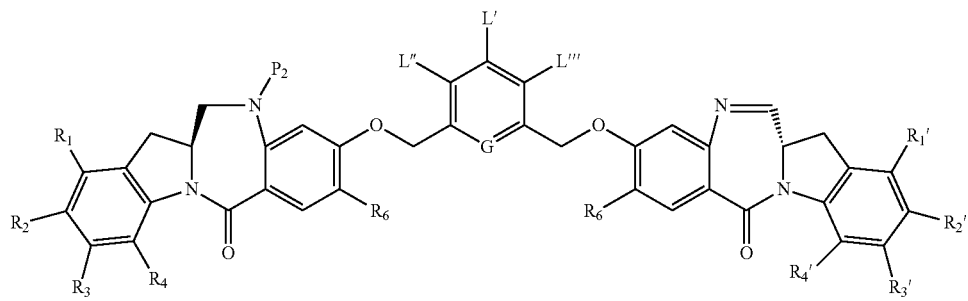
(11)

wherein P₂ is an amine protecting group.

The conditions and reagents for the method of nineteenth embodiment are as described above in the sixteenth, seventeenth, thirteenth and/or fourteenth embodiment(s) and any specific embodiments described therein.

In a twentieth embodiment, the present invention provides a method of preparing a compound of formula (I'),

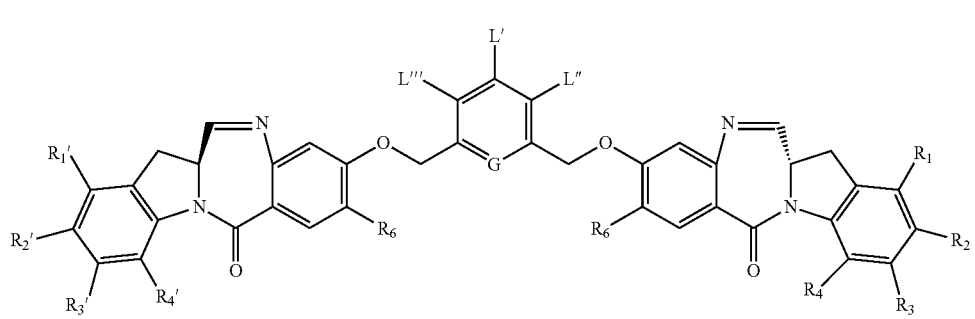
(I')

78 or a pharmaceutically acceptable salt thereof, said method comprising the steps of:

(1) reacting a halogenating reagent, a sulfonating reagent or an esterification reagent with a compound of formula (1),

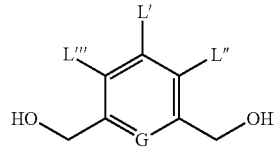
(1)

to form a compound of formula (12),

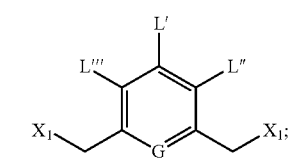
(12)

(2) reacting the compound of formula (12) with a monomer compound of the formula (b),

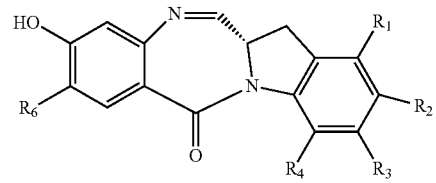

(a)

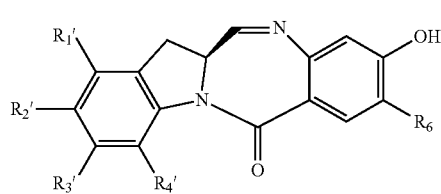

(b)

to form a compound of a formula (10'),

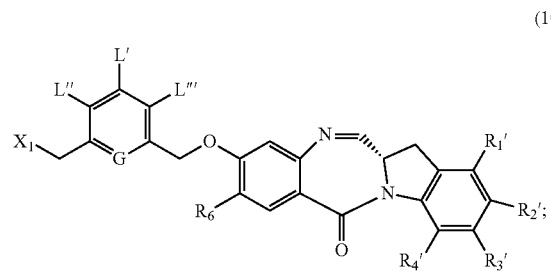

(10')

(3) reacting the compound (10') with an imine reducing reagent to form a compound (7'),

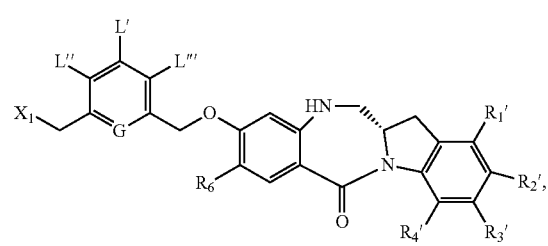

(7')

(4) reacting the compound of formula (7') with a monomer compound of the formula (a), to form a compound of formula (I'), or a pharmaceutically acceptable salt thereof, wherein $X_1$ is —Br, —I, —Cl, a sulfonate ester or an activated ester and the remaining variables are the same as described above in the eleventh embodiment. In one embodiment, $X_1$ is —Br, —I, or a sulfonate ester.

In one embodiment, the method of the twentieth embodiment involves preparing a compound of formula (1b'),

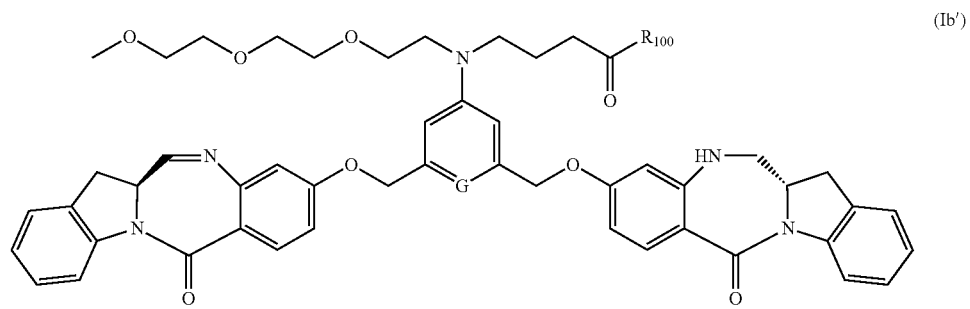

(Ib')

or a pharmaceutically acceptable salt thereof, said method comprising the steps of:

(1) reacting a halogenating reagent or a sulfonating reagent with a compound of formula (1b) to form a compound of formula (12b);

(2) reacting the compound of formula (12b) with a monomer compound of the formula ($a_1$) to form a compound of a formula (10b');

(3) reacting the compound (10b') with an imine reducing reagent to form a compound (7b');

(4) reacting the compound of formula (7b') with a monomer compound of the formula ($a_1$) to form a compound of formula (Ib').

In another embodiment, the method of the twentieth embodiment involves preparing a compound of formula (Ic'),

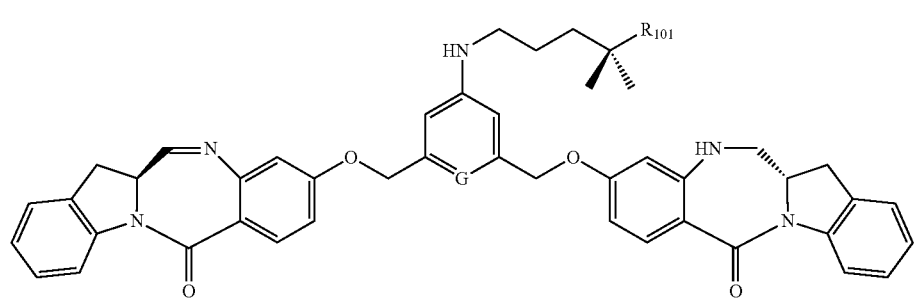

(Ic')

or a pharmaceutically acceptable salt thereof, said method comprising the steps of:

(1) reacting a halogenating reagent or a sulfonating reagent with a compound of formula (1c) to form a compound of formula (12c);

(2) reacting the compound of formula (12c) with a monomer compound of the formula ($a_1$) to form a compound of a formula (10c');

(3) reacting the compound (10c') with an imine reducing reagent to form a compound (7c');

(4) reacting the compound of formula (7c') with a monomer compound of the formula ($a_1$) to form a compound of formula (Ic').

In still another embodiment, the method of the twentieth embodiment involves preparing a compound of formula (IA'), (2) reacting the compound of formula (12A) with a monomer compound of the formula ($a_1$) to form a compound of a formula (10A');

(3) reacting the compound (10A') with an imine reducing reagent to form a compound (7A');

(4) reacting the compound of formula (7A') with a monomer compound of the formula ($a_1$) to form a compound of formula (IA').

In a specific embodiment, $X_1$ is mesylate.

The conditions and reagents for the method of twentieth embodiment are as described above in the sixteenth, seventeenth, eighteenth and/or eighth embodiment(s) and any specific embodiments described therein.

In a twenty-first embodiment, the present invention provides a method of preparing a compound of formula (I'),

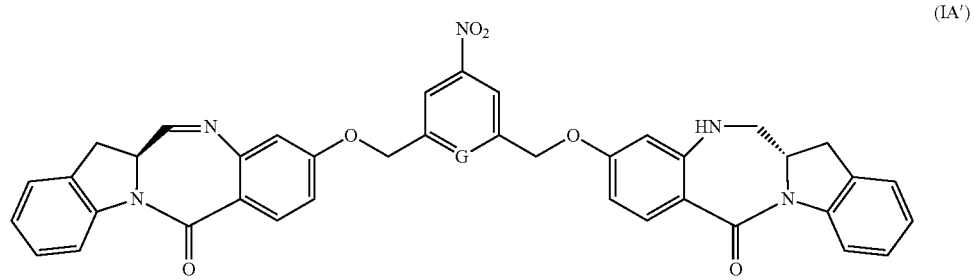

(IA')

or a pharmaceutically acceptable salt thereof, said method comprising the steps of:

(1) reacting a halogenating reagent or a sulfonating reagent with a compound of formula (1A) to form a compound of formula (12A);

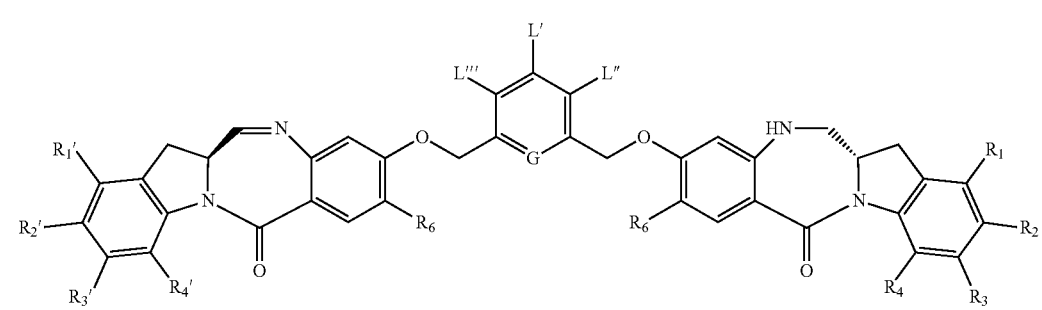

(I')

or a pharmaceutically acceptable salt thereof, said method comprising the steps of:

(1) reacting a halogenating reagent, a sulfonating reagent or an esterification reagent with a compound of formula (1), (1)
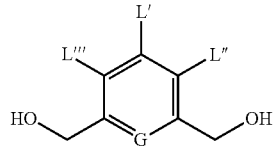

to form a compound of formula (12),

(12)
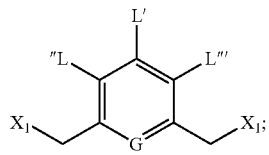

(2) reacting the compound of formula (12) with a monomer compound of the formula (d), (d)
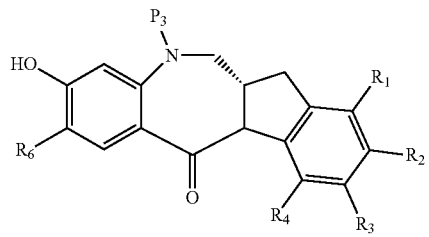

to form a compound of a formula (7-1), (7-1)
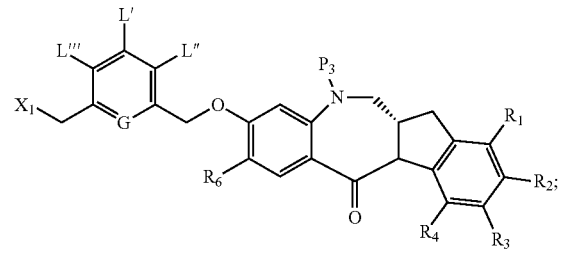

(3) reacting the compound of formula (7-1) with a monomer compound of the formula (b), (b)
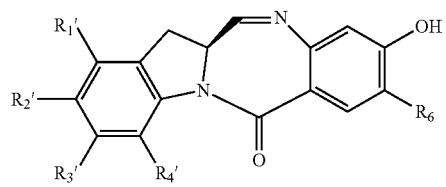

to form a compound of formula (18),

(18)
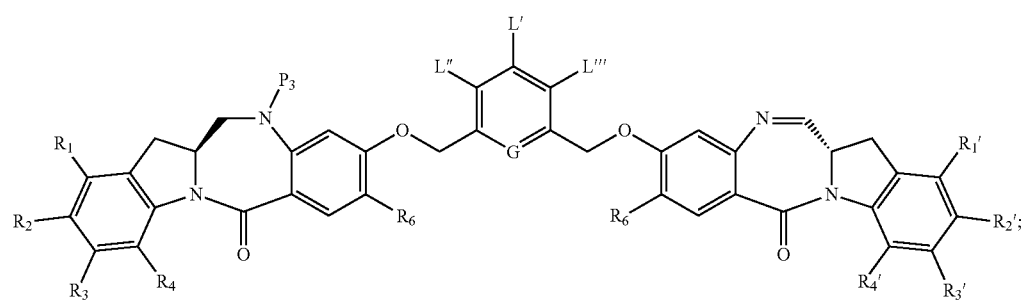

and (4) when $P_3$ is an amine protecting group, reacting the compound of formula (18) with an amine deprotecting reagent to form the compound of formula (I'); wherein $X_1$ is —Br, —I, —Cl, a sulfonate ester or an activated ester; $P_3$ is H or an amine protecting group, and the remaining variables are the same as described above in the eleventh embodiment. In one embodiment, $X_1$ is —Br, —I, or a sulfonate ester.

In one embodiment, the method of the twenty-first embodiment involves preparing a compound of formula (1b'),

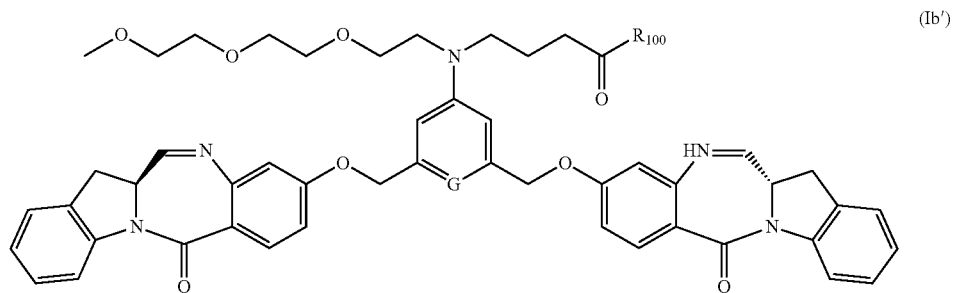

(Ib')

or a pharmaceutically acceptable salt thereof, said method comprising the steps of:

(1) reacting a halogenating reagent or a sulfonating reagent with a compound of formula (1b) to form a compound of formula (12b);

(2) reacting the compound of formula (12b) with a monomer compound of the formula ($d_1$) to form a compound of a formula (7b-1);

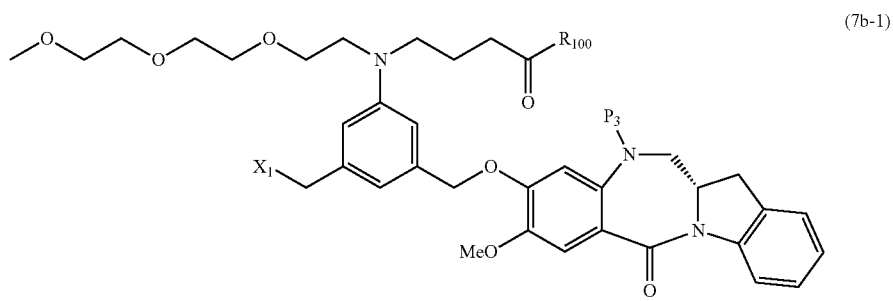

(7b-1)

(3) reacting the compound of formula (7b-1) with a monomer compound of the formula ($a_1$) to form a compound of formula (18b); and (4) when $P_3$ is an amine protecting group, reacting the compound of formula (18b) with an amine deprotecting reagent to form the compound of formula (1b').

In another embodiment, the method of the twenty-first embodiment involves preparing a compound of formula (Ic'),

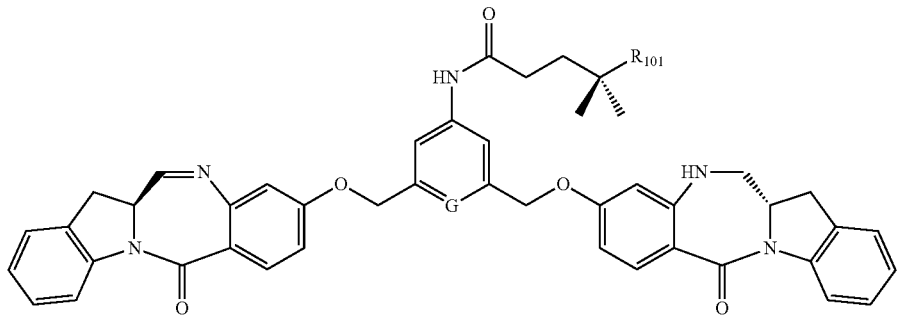
(Ic')

or a pharmaceutically acceptable salt thereof, said method comprising the steps of:

(1) reacting a halogenating reagent or a sulfonating reagent with a compound of formula (1c) to form a compound of formula (12c);

(2) reacting the compound of formula (12c) with a monomer compound of the formula ($d_1$) to form a compound of a formula (7c-1);

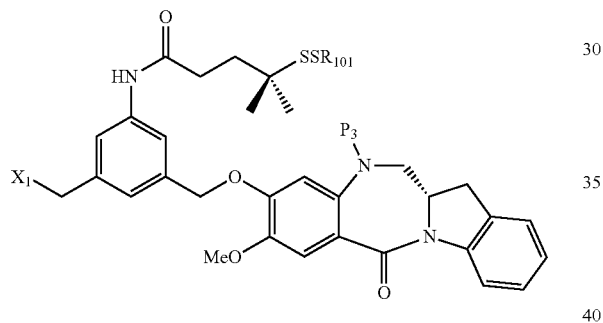
(7c-1)

(3) reacting the compound of formula (7c-1) with a monomer compound of the formula ($a_1$) to form a compound of formula (18c); and (4) when $P_3$ is an amine protecting group, reacting the compound of formula (18c) with an amine deprotecting reagent to form the compound of formula (Ic').

In still another embodiment, the method of the twenty-first embodiment involves preparing a compound of formula (IA'),

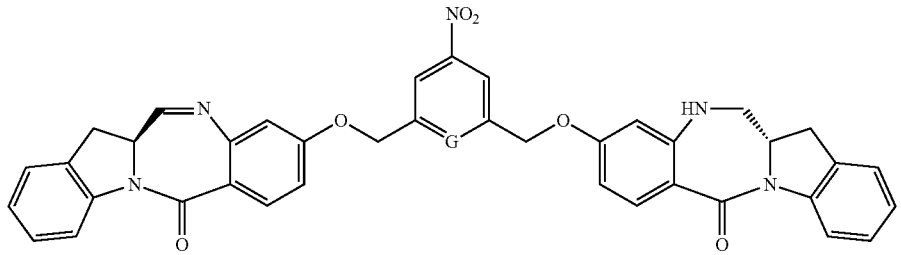
(IA')

or a pharmaceutically acceptable salt thereof, said method comprising the steps of:

(1) reacting a halogenating reagent or a sulfonating reagent with a compound of formula (1A) to form a compound of formula (12A);

(2) reacting the compound of formula (12A) with a monomer compound of the formula ($d_1$) to form a compound of a formula (7A-1);

(7A-1)

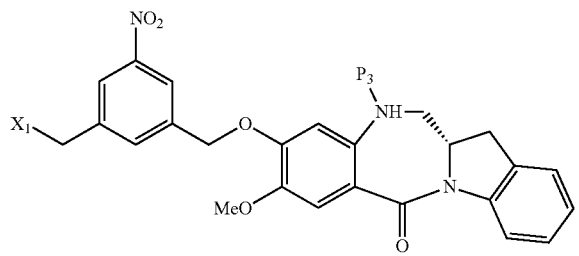

(3) reacting the compound of formula (7A-1) with a monomer compound of the formula ($a_1$) to form a compound of formula (18A); and (4) when $P_3$ is an amine protecting group, reacting the compound of formula (18A) with an amine deprotecting reagent to form the compound of formula (IA').

In one embodiment, for methods of the twenty-first embodiment, $P_3$ is H

In one embodiment, $P_3$ is H and the compound of (7-1) is reacted with the monomer compound of (b) to form a compound of (I').

In another embodiment, $P_3$ is $P_2$; the monomer compound is represented by formula (c):

($c_1$)

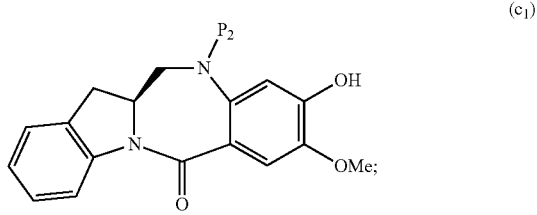

and the compound of formula (18) is represented by formula (11), wherein $P_2$ is an amine protecting group.

In a specific embodiment, $X_1$ is mesylate.

The conditions and reagents for the methods of twenty-first embodiment are as described above in the sixteenth, seventeenth, eighteenth, eighth and/or fourteenth embodiment(s) and any specific embodiments described therein.

In a twenty-second embodiment, the present invention provides a method of preparing a compound of formula (13), (13)

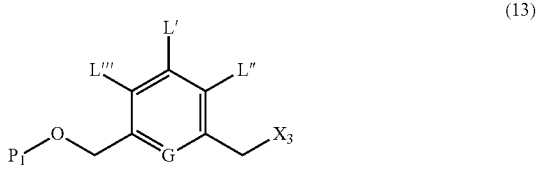

or a salt thereof, said method comprising reacting a chlorinating reagent with a compound of formula (2), (2)

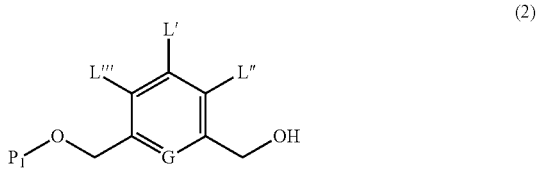

wherein $X_3$ is Cl, and the remaining variables are the same as described above.

In a specific embodiment, the compound of formula (2) is selected from the group consisting of:

(2b)

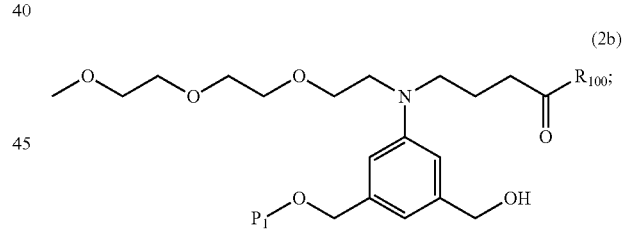

(11)

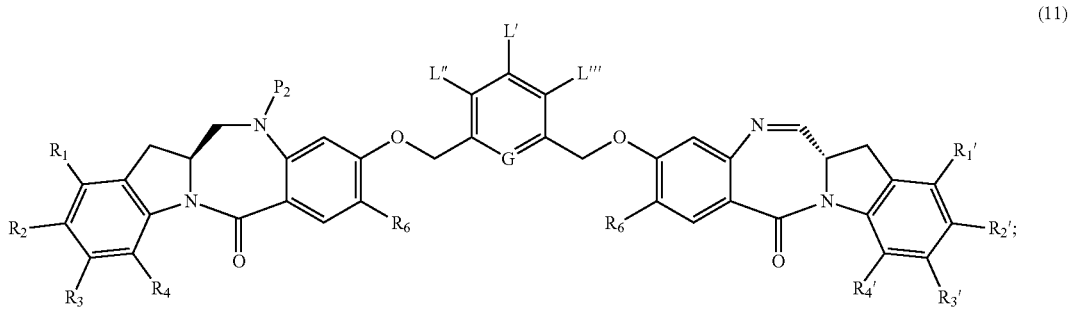

-continued

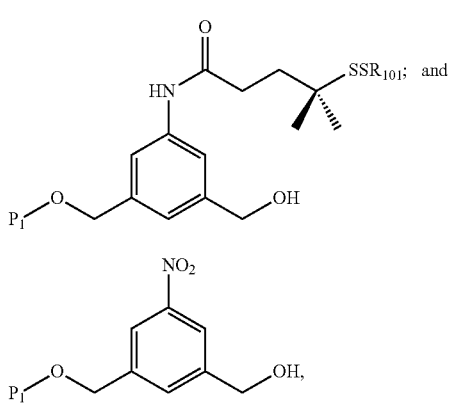

(2c)

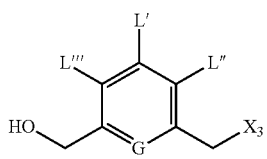

(2A)

wherein $R_{100}$ is a $(C_1-C_3)$alkoxy; and $R_{101}$ is a $(C_1-C_3)$alkyl, pyridyl or nitropyridyl (e.g., 4-nitropyridyl).

In another specific embodiment, the alcohol protecting group is pivoloyl, methoxymethyl, 2-methoxyethoxymethyl, p-methoxybenzyl, 3,4-dimethyoxybenzyl, 2,6-dimethyoxybenzyl, diphenylmethyl, benzyloxymethyl, 2,2,2-trichloroethoxycarbonyl, tetrahydrofuranyl, tetrahydropyranyl, benzyl, benzoyl, para-phenylbenzoyl, 2,4,6-trimethylbenzoyl, para-bromobenzoyl, para-nitrobenzoyl, picolinoyl, nicotinoyl, 5-dibenzosuberyl, trityl/triphenylmethyl, or tris (4-tert-butylphenyl)methyl. Preferably, the alcohol protecting group is methoxymethyl, tetrahydropyranyl, 2-methoxyethoxymethyl, p-methoxybenzyl, benzyloxymethyl, or 2,2,2-trichloroethoxycarbonyl. Even more preferably, the alcohol protecting group is 2,2,2-trichloroethoxycarbonyl.

In another specific embodiment, the alcohol protecting group is a silyl protecting group. For example, the silyl protecting group is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl. Preferably, the silyl protecting group is triethylsilyl, triisopropylsilyl, or tert-butyldimethylsilyl. More preferably, the silyl protecting group is tert-butyldimethylsilyl.

In one embodiment, the base is used. The base can be a non-nucleophilic base. Examples of non-nucleophilic base include, but are not limited to, triethylamine, imidazole, diisopropylethylamine (DIPEA), pyridine, 2,6-lutidine, dimethylformamide, 1,8-diazabicyclo[5.4.0]undec-7-ene (DBU), or tetramethylpiperidine. Preferably, the non-nucleophilic base is pyridine.

Any suitable organic solvents can be used for the methods of the twentieth embodiment. Exemplary solvents include, but are not limited to, DMF, $CH_2Cl_2$, dichloroethane, THF, dimethylacetamide, etc. In certain embodiments, DMF is used as the solvent.

In a twenty-third embodiment, the present invention provides a method of preparing a compound of formula (14),

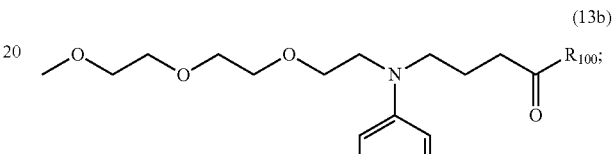

(14)

or a salt thereof, said method comprising reacting a compound of formula (13)

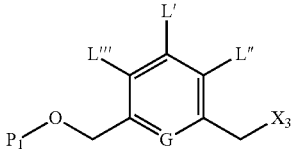

(13)

with an alcohol deprotecting reagent, wherein the variables are the same as described in the twentieth embodiment.

In a specific embodiment, the compound of formula (13) is selected from the group consisting of:

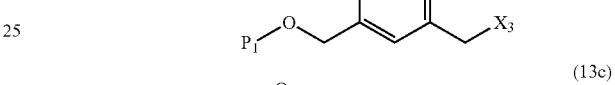

(13b)

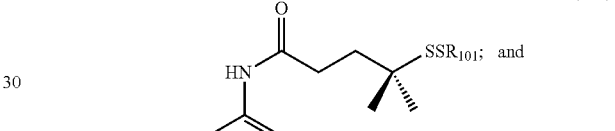

(13c)

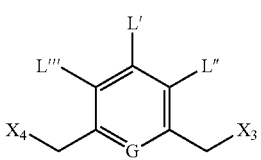

(13A)

wherein $R_{100}$ and $R_{101}$ are the same as defined above.

In another specific embodiment, the alcohol deprotecting reagent is tetra-n-butylammonium fluoride, tris(dimethylamino)sulfonium difluorotrimethylsilicate, hydrogen fluoride or a solvate thereof, hydrogen fluoride pyridine, silicon tetrafluoride, hexafluorosilicic acid, cesium fluoride, hydrochloric acid, acetic acid, trifluoroacetic acid, pyridinium p-toluensulfonate, p-toluenesulfonic acid (p-TsOH), formic acid, or periodic acid. Preferably, the alcohol deprotecting reagent is hydrogen fluoride pyridine.

In a twenty-fourth embodiment, the present invention provides a method of preparing a compound of formula (15):

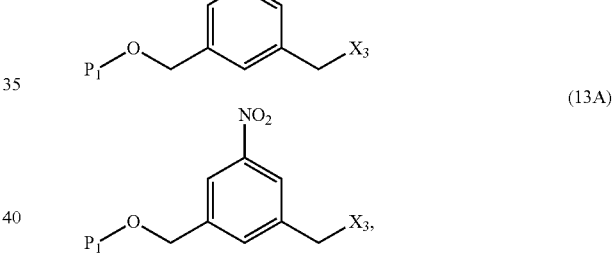

(15)

or a salt thereof, said method comprising reacting a sulfonating reagent or an esterification reagent with a compound of formula (14),

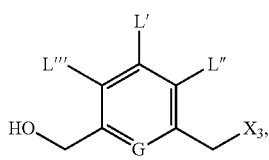
(14)

wherein $X_4$ is a sulfonate ester or an activated ester and the remaining variables are the same as described in the twentieth embodiment.

In a specific embodiment, the compound of formula (14) is selected from the group consisting of:

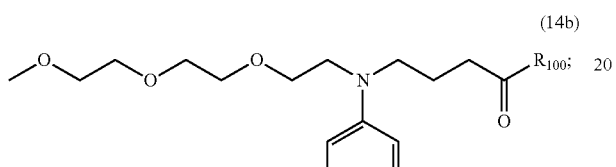
(14b)

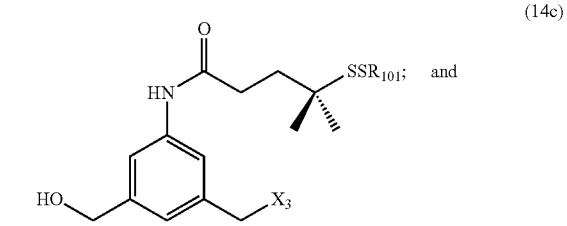
(14c)

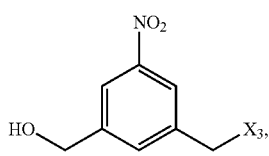
(14A)

wherein $R_{100}$ and $R_{101}$ are the same as defined above.

In a specific embodiment, for methods of the twenty-fourth embodiment, $X_4$ is a sulfonate ester.

In another specific embodiment, methanesufonyl anhydride, methanesufonyl chloride, p-toluenesulfonyl chloride, 4-bromobenzenesulfonyl chloride, or trifluoromethanesulfonyl anhydride.

In another specific embodiment, the sulfonate ester is mesylate, tosylate, brosylate, or triflate. Preferably, the sulfonate ester is mesylate.

In another embodiment, a base is used. The base can be a non-nucleophilic base. Examples of non-nucleophilic base include, but are not limited to, triethylamine, imidazole, diisopropylethylamine, pyridine, 2,6-lutidine, dimethylformamide, 1,8-diazabicyclo[5.4.0]undec-7-ene (DBU), or tetramethylpiperidine. Preferably, the non-nucleophilic base is diisopropylethylamine.

In a twenty-fifth embodiment, the present invention provides a method of preparing a compound of formula (20):

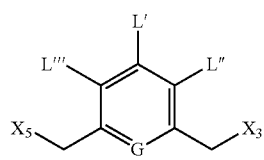
(20)

or a salt thereof, said method comprising reacting a brominating or iodinating reagent with a compound of formula (14),

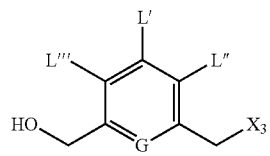
(14)

wherein the variables are the same as described above.

In a specific embodiment, the compound of formula (14) is selected from the group consisting of:

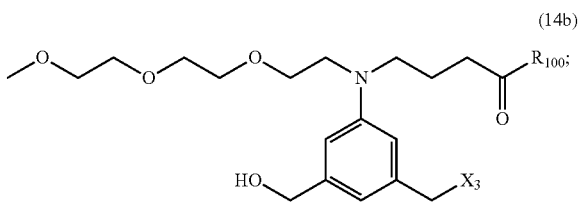
(14b)

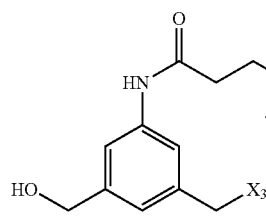
(14c)

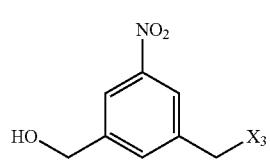
(14A)

wherein $R_{100}$ is a $(C_1$-$C_3)$alkoxy; and $R_{101}$ is a $(C_1$-$C_3)$alkyl, pyridyl or nitropyridyl (e.g., 4-nitropyridyl).

In a particular embodiment, the brominating or iodinating reagent is bromine, hydrobromic acid, carbon tetrabromide, phosphorus tribromide, potassium bromide, hydroiodic acid, iodine, carbon tetraiodide, phosphorus triiodide, sodium iodide, or potassium iodide.

In a twenty-sixth embodiment, the present invention provides a method of preparing a compound of formula (16):

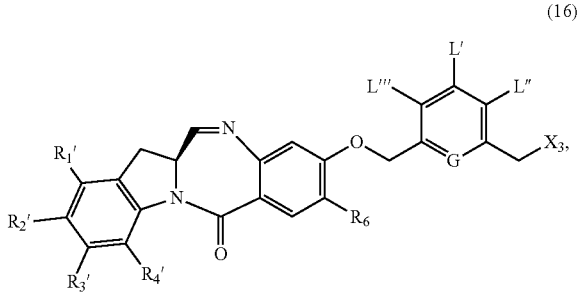

(16)

or a salt thereof, said method comprising reacting a compound of formula (15)

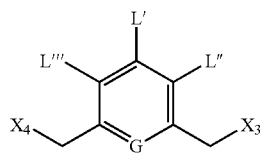

(15)

with a monomer compound of formula (b),

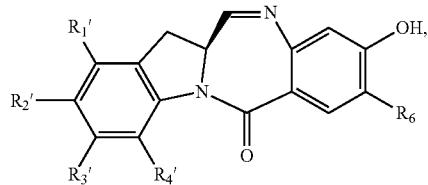

(b)

wherein the variables of $X_3$, $X_4$, L', L'', L''', and G are as described in the twenty-fifth embodiment, and the variables of $R_1'$, $R_2'$, $R_3'$, $R_4'$, and $R_6$ are the same as described above. In one embodiment, $X_4$ is a sulfonate ester In a specific embodiment, the compound of formula (15) is selected from the group consisting of:

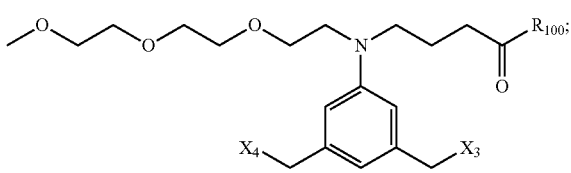

(15b)

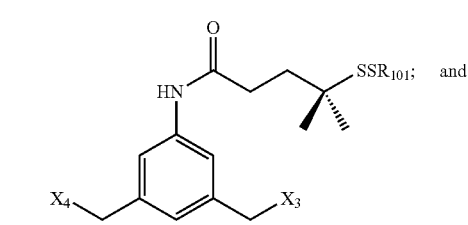

(15c)

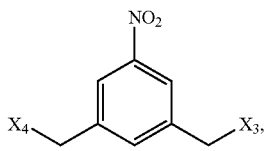

(15A)

and the monomer compound of formula (b) is represented by the following formula:

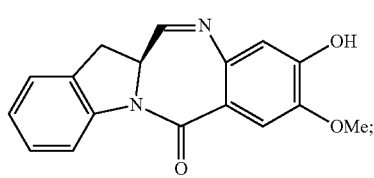

(b1)

wherein $R_{100}$ and $R_{101}$ are the same as defined above.

In an embodiment, a base is used. In specific embodiment, the base is sodium carbonate, potassium carbonate, cesium carbonate, sodium hydride, or potassium hydride. Preferably, the base is potassium carbonate.

Any suitable organic solvents can be used for the methods of the twentieth embodiment. Exemplary solvents include, but are not limited to, DMF, $CH_2Cl_2$, dichloroethane, THF, dimethylacetamide, etc. In certain embodiments, dimethylacetamide is used as the solvent.

In a twenty-seventh embodiment, the present invention provides a method of preparing a compound of formula (16):

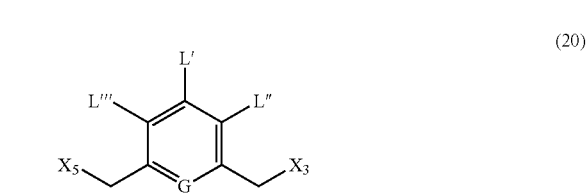

(16)

or a salt thereof, said method comprising reacting a compound of formula (20)

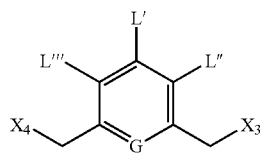

(20)

with a monomer compound of formula (b),

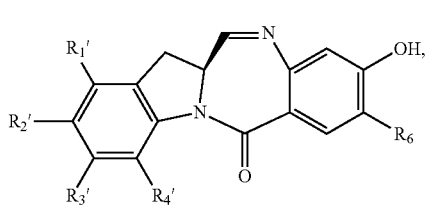

wherein the variables are the same as described above.

In one embodiment, the compound of formula (20) is selected from the group consisting of:

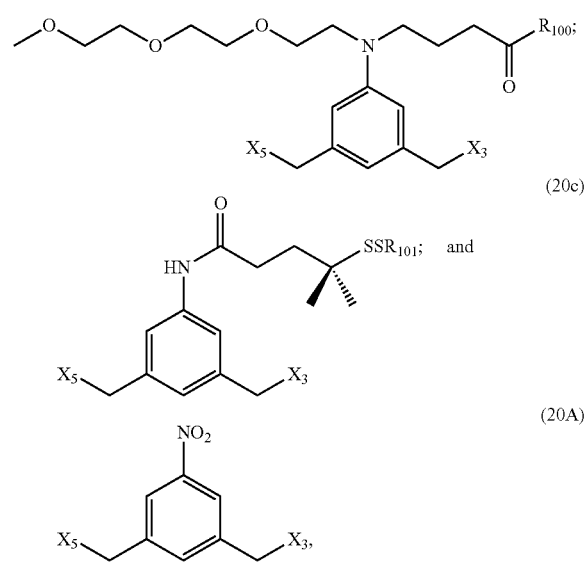

and the monomer compound of formula (b) is represented by the following formula:

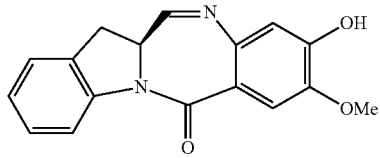

wherein $X_3$ is —Cl; $X_5$ is —Br or —I; $R_{100}$ is a $(C_1\text{-}C_3)$ alkoxy; and $R_{101}$ is a $(C_1\text{-}C_3)$alkyl, pyridyl or nitropyridyl (e.g., 4-nitropyridyl).

In a particular embodiment, the compound of formula (20) is reacted with a monomer compound of formula (b) in the presence of a base. Suitable bases include sodium carbonate, potassium carbonate, cesium carbonate, sodium hydride, or potassium hydride. In a preferred embodiment, the base is potassium carbonate.

In another embodiment, the compound of formula (20) is reacted with a monomer compound of formula (b) in the presence of a polar aprotic solvent. In a preferred embodiment, the polar aprotic solvent is dimethylacetamide.

In a twenty-eighth embodiment, the present invention provides a method of preparing a compound of formula (16):

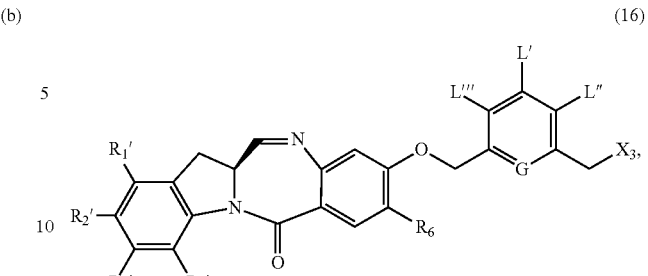

or a salt thereof, said method comprising reacting a compound of formula (14)

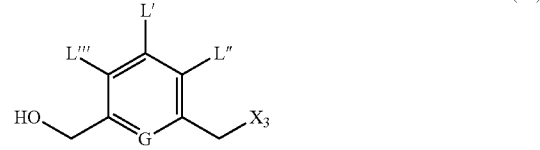

with a monomer compound of formula (b),

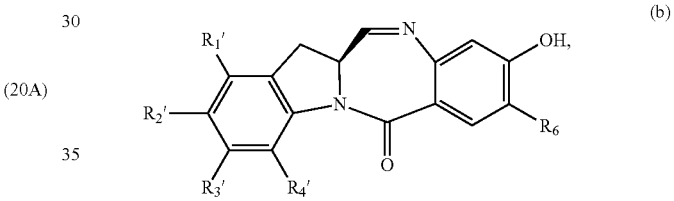

wherein the variables are the same as described above.

In one embodiment, the compound of formula (14) is selected from the group consisting of:

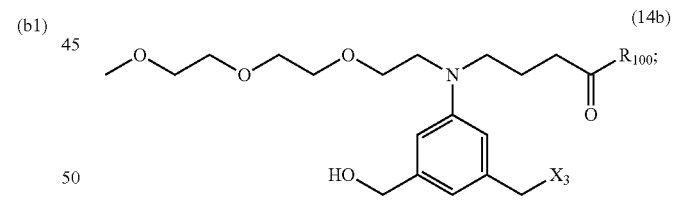

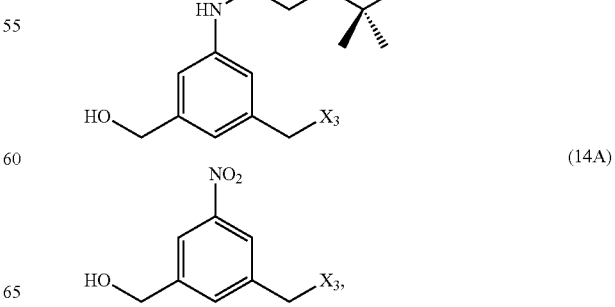

and the monomer compound of formula (b) is represented by the following formula:

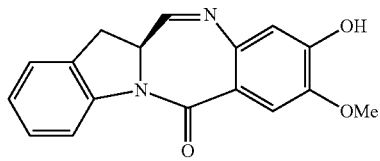

wherein $R_{100}$ is a $(C_1\text{-}C_3)$alkoxy; and $R_{101}$ is a $(C_1\text{-}C_3)$alkyl, pyridyl or nitropyridyl (e.g., 4-nitropyridyl).

In one embodiment, for the methods of the twenty-eighth embodiment, the compound of formula (14) is reacted with a monomer of formula (b) in the presence of an alcohol activating agent. In one embodiment, the alcohol activating agent is a trialkylphosphine, triarylphosphine, or triheteroarylphosphine. In a specific embodiment, the alcohol activating agent is trimethylphosphine, tributylphosphine, tri(o-tolyl)phosphine, tri(m-tolyl)phosphine, tri(p-tolyl)phosphine, tri(2-pyridyl)phosphine, tri(3-pyridyl)phosphine, tri(4-pyridyl)phosphine, or [4-(3,3,4,4,5,5,6,6,7,7,8,8,9,9,10,10,10-Heptadecafluorodecyl)phenyl] diphenylphosphine. In another embodiment, the alcohol activating agent can be a phosphine-like reagent, such as (tributylphosphoranylidene)acetonitrile, (cyanomethylene)tributylphosphorane (CMBP), or (cyanomethylene)trimethylphosphorane (CMMP). In a more specific embodiment, the alcohol activating agent is triphenylphosphine. In one embodiment, the alcohol activating agent can be polymer-bound or polymer-supported, such as polymer-bound or polymer-supported trialkyl phosphine, triarylphosphine (e.g., triphenylphosphine), or triheteroarylphosphine.

In another embodiment, for the methods of the twenty-eighth embodiment, the compound of formula (14) is reacted with a monomer of formula (b) in the presence of an azodicarboxylate. In one embodiment, the azodicarboxylate is selected from the group consisting of: diethyl azodicarboxylate (DEAD), diisopropyl azodicarboxylate (DIAD), 1,1'-(azodicarbonyl)dipiperidine (ADDP), ditertbutyl azodicarboxylate (DTAD), 1,6-dimethyl-1,5,7-hexahydro-1,4,6,7-tetrazocin-2,5-dione (DHTD), di-(4-chlorobenzyl)azodicarboxylate (DCAD), azodicarboxylic dimorpholide, N,N,N',N'-tetramethylazodicarboxamide (TMAD), N,N,N',N'-tetraisopropylazodicarboxamide (TIPA), 4,4'-azopyridine, bis (2,2,2-trichloroethyl) azodicarboxylate, o-(tert-Butyldimethylsilyl)-N-tosylhydroxylamine, di-(4-chlorobenzyl)azodicarboxylate, cyclic 1,6-dimethyl-1,5,7-hexahydro-1,4,6,7-tetrazocin-2,5-dione (DHTD), dimethyl acetylenedicarboxylate (DMAD), di-2-methoxyethyl azodicarboxylate, di-(4-chlorobenzyl)azodicarboxylate and bis(4,4,5,5,6,6,7,7,8,8,9,9,9-tridecafluorononyl) azodicarboxylate. More specifically, the azodicarboxylate is DIAD. In one embodiment, the azodicarboxylate is polymer-bound or polymer supported, such as polymer-supported alkylazodicarboxylate (e.g. polymer-bound DEAD, DIAD, DTAD or ADDP).

In yet another specific embodiment, for methods of the twenty-eighth embodiment, the compound of formula (14) is reacted with a monomer of formula (b) in the presence of triphenylphosphine and an azodicarboxylate. In one embodiment, the azodicarboxylate is selected from the group consisting of: diethyl azodicarboxylate (DEAD), diisopropyl azodicarboxylate (DIAD), 1,1'-(azodicarbonyl)dipiperidine (ADDP), and ditertbutyl azodicarboxylate (DTAD). More specifically, the azodicarboxylate is DIAD.

In a twenty-ninth embodiment, the present invention provides a method of preparing a compound of formula (18):

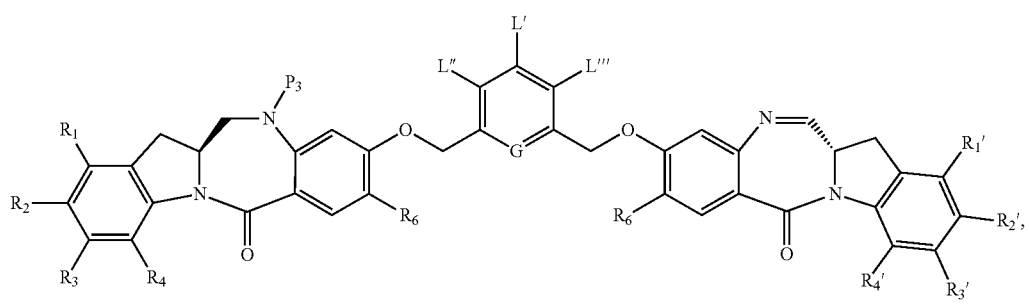

a pharmaceutically acceptable salt thereof, said method comprising reacting a compound of formula of (16):

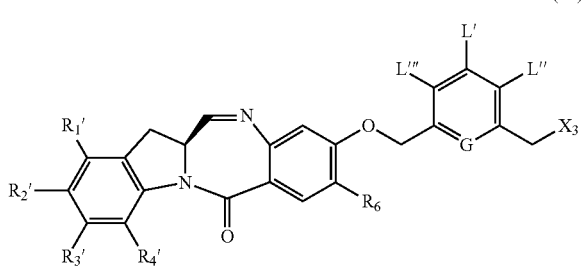

with a reduced monomer of formula (d):

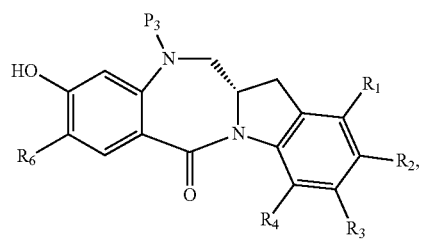

wherein the variables $R_1$, $R_2$, $R_3$, $R_4$, $R_6$ and $P_2$ are as described in the twenty-third embodiment; and wherein $R_1$, $R_2$, $R_3$, and $R_4$ are each independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$_c$, halogen, guanidinium [—NH(C=NH)NH$_2$], —OR, —NR'R'', —NO$_2$, —NCO, —NR'COR'', —SR, —SOR', —SO$_2$R', —SO$_3^-$H, —OSO$_3$H, —SO$_2$NR'R'', cyano, an azido, —COR', —OCOR', and —OCONR'R'';

$R_6$ is —H, —R, —OR, —SR, —NR'R'', —NO$_2$, or halogen; and $P_3$ is H or an amine protecting group.

In a specific embodiment, the compound of formula (16) is selected from the group consisting of:

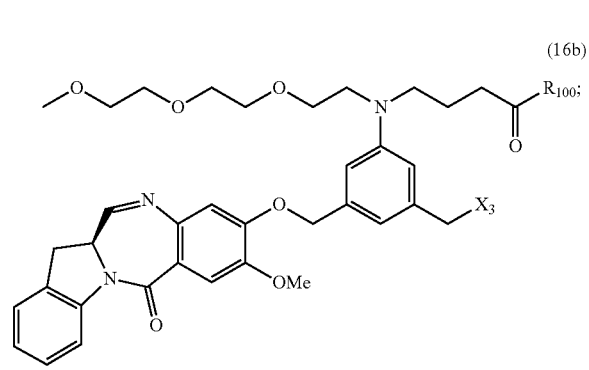

(16b)

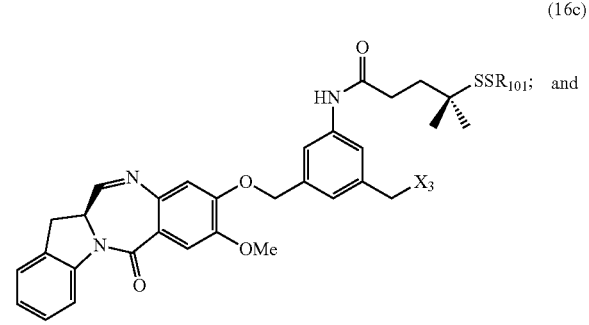

(16c)

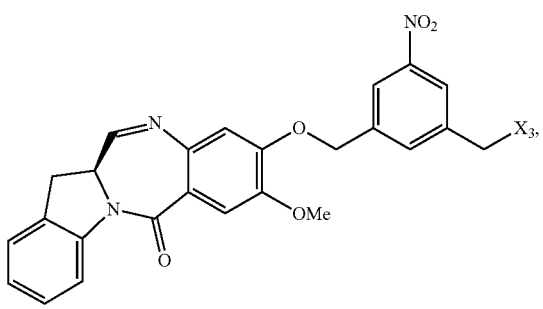

(16A)

and the reduced monomer of formula (d) is represented by the following formula:

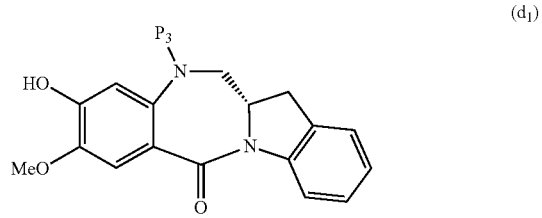

(d$_1$)

wherein $X_3$ is —Cl; $P_3$ is H or an amine protecting group; $R_{100}$ and $R_{101}$ are the same as defined above.

In one embodiment, for methods of the twenty-ninth embodiment, the reaction between the compound of formula (16d) or (16A) and the reduced monomer of formula (d$_1$) is carried out in the presence of a base. In specific embodiment, the base is sodium carbonate, potassium carbonate, cesium carbonate, sodium hydride, or potassium hydride. Preferably, the base is potassium carbonate.

Any suitable organic solvents can be used for the methods of the twentieth embodiment. Exemplary solvents include, but are not limited to, dimethylformamide (DMF), CH$_2$Cl$_2$, dichloroethane, THF, dimethylacetamide, etc. In certain embodiments, dimethylformamide or dimethylacetamide is used as the solvent.

In a specific embodiment of the twenty-fourth embodiment, the compound of formula (16) is reacted with reduced monomer of formula (d), wherein $P_3$ is H, to form a compound of formula (I'):

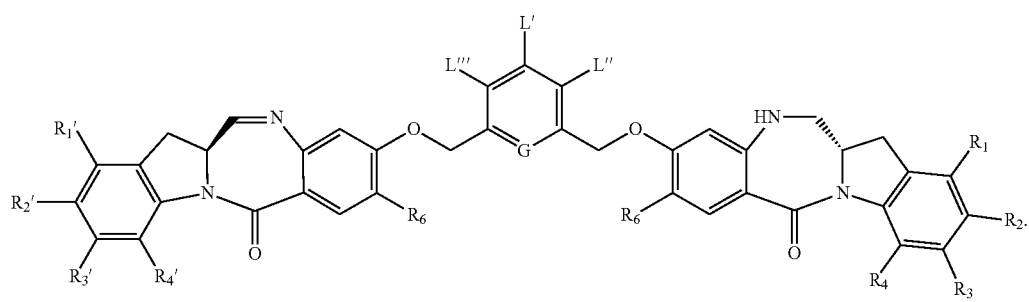

(I')

In another specific embodiment of the twenty-fourth embodiment, $P_3$ is an amine protecting group. Any suitable amine protecting group can be used in the method described above. In one embodiment, the amine protecting group is 2-trimethylsilylethyl, (2-phenyl-2-trimethylsilyl)ethyl, tri-isopropylsiloxy, 2-(trimethylsilyl)ethoxymethyl, allyloxycarbonyl, 9-fluorenylmethoxycarbonyl, 2-(trimethylsilyl)ethoxycarbonyl, or 2,2,2-trichloroethoxycarbonyl.

When $P_3$ is an amine protecting group, the compound of formula (18) is further reacted with an amine deprotecting reagent to form a compound of formula (I'):

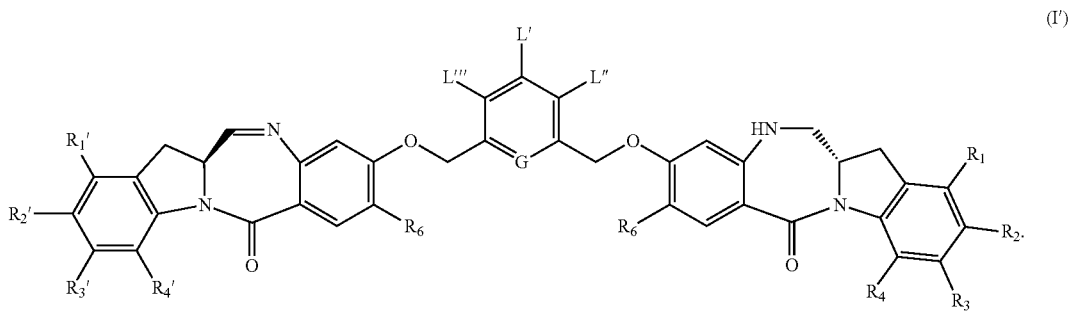

(I')

Examples of suitable amine deprotecting reagent include, but are not limited to, the amine deprotecting reagent is selected from the group consisting of tetra-n-butylammonium fluoride, acetic acid, hydrogen fluoride pyridine, cesium fluoride, piperidine, morpholine, or trifluroacetic acid.

In a thirtieth embodiment, the present invention provides a method for preparing a compound of formula (17):

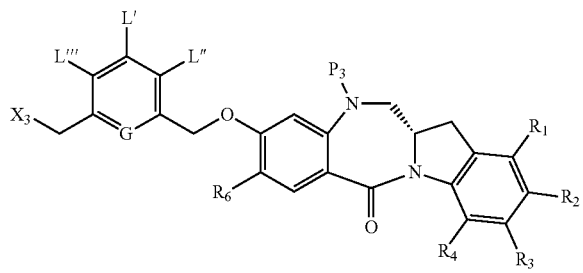

(17)

or a salt thereof, said method comprising reacting a compound of formula (15)

(15)

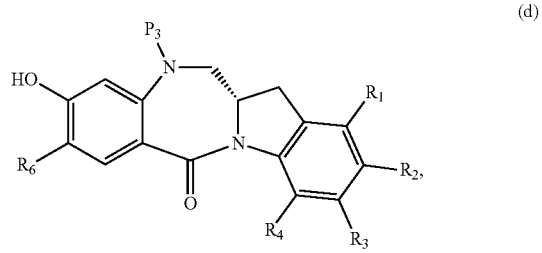

(d)

wherein $X_3$ is —Cl; $X_4$ is a sulfonate ester or an activated ester; $P_3$ is H or an amine protecting group; L', L", L''', and G are as described in the twenty-second embodiment, and the variables $R_1$, $R_2$, $R_3$, $R_4$, $R_6$ and $P_3$ are the same as described in the twenty-fourth embodiment. In one embodiment, $X_4$ is an activated ester.

In a specific embodiment, the compound of formula (15) is selected from the group consisting of:

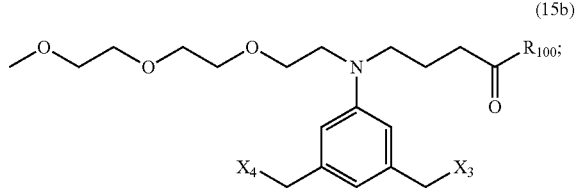

(15b)

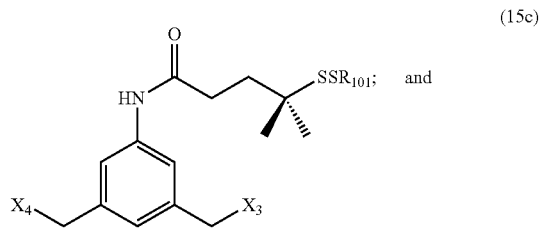

(15c)

and with a monomer compound of formula (d), (15A)

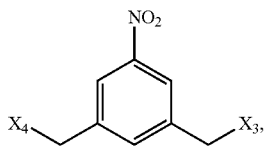

wherein $X_3$ is —Cl; $X_4$ is a sulfonate ester or an activated ester; $R_{100}$ and $R_{101}$ are the same as defined above. In one embodiment, $X_4$ is an activated ester.

In an embodiment, for methods of the thirtieth embodiment, a base is used. In specific embodiment, the base is sodium carbonate, potassium carbonate, cesium carbonate, sodium hydride, or potassium hydride. Preferably, the base is potassium carbonate.

Any suitable organic solvents can be used for the methods of the thirtieth embodiment. Exemplary solvents include, but are not limited to, DMF, $CH_2Cl_2$, dichloroethane, THF, dimethylacetamide, etc. In certain embodiments, dimethylacetamide is used as the solvent.

In a specific embodiment of the thirtieth embodiment, $P_3$ is H and the compound of formula (15) is reacted with the monomer compound of formula (d) to form a compound of formula (17').

In another specific embodiment of the thirtieth embodiment, $P_3$ is an amine protecting group and the method further comprises the step of reacting the compound of formula (17) with an amine deprotecting reagent to form a compound of formula (17'):

(17')

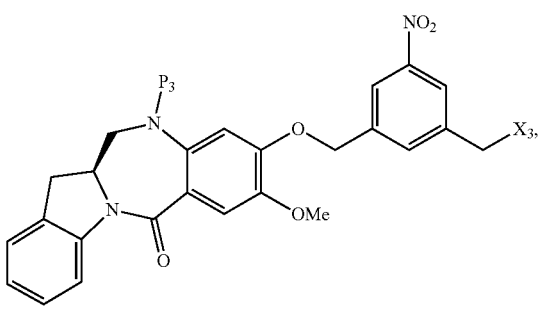

Examples of suitable amine deprotecting reagent include, but are not limited to, the amine deprotecting reagent is selected from the group consisting of tetra-n-butylammonium fluoride, acetic acid, hydrogen fluoride pyridine, cesium fluoride, piperidine, morpholine, or trifluroacetic acid.

In a specific embodiment, the compound of formula (17) is selected from the group consisting of:

(17b)

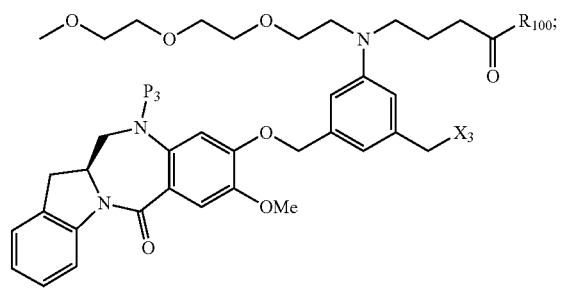

(17c)

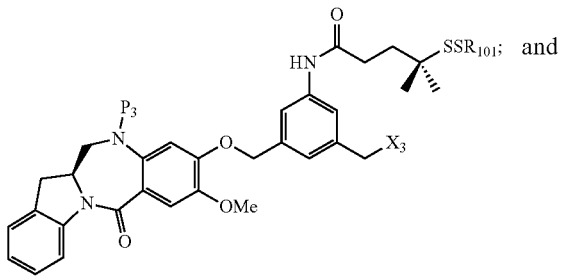
and (17A)

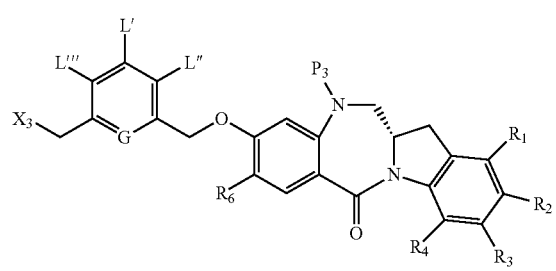

wherein $R_{100}$ and $R_{101}$ are the same as defined above.

In a thirty-first embodiment, the present invention provides a method of preparing a compound of formula (17):

(17)

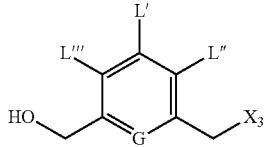

or a salt thereof, said method comprising reacting a compound of formula (14)

(14)

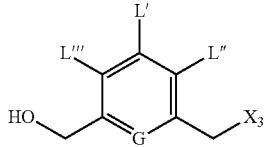

with a monomer compound of formula (d),

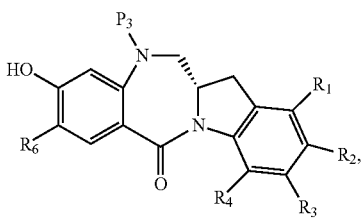

(d)

Wherein $X_3$ is —Cl; $P_3$ is H or an amine protecting group and the remaining variables are as described above.

In a specific embodiment, the compound of formula (14) is selected from the group consisting of:

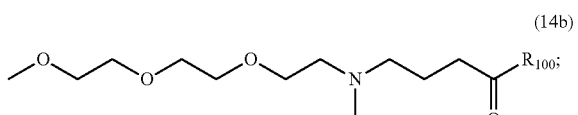

(14b)

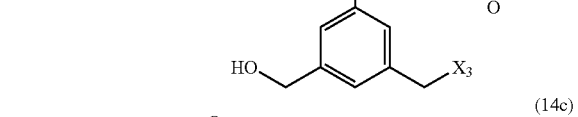

(14c)

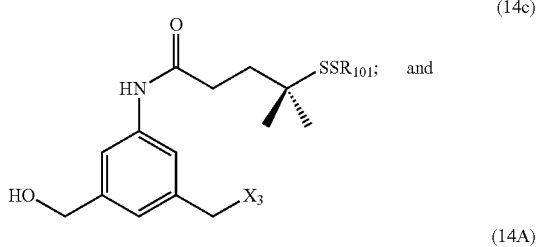

(14A)

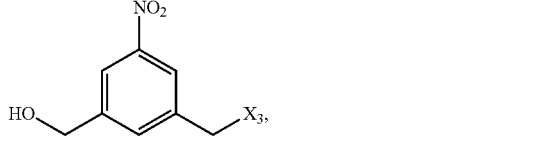

and the monomer compound of formula (d) is represented by formula ($d_1$), wherein $X_3$ is —Cl; $R_{100}$ is a ($C_1$-$C_3$)alkoxy; and $R_{101}$ is a ($C_1$-$C_3$)alkyl, pyridyl or nitropyridyl (e.g., 4-nitropyridyl).

In a specific embodiment, the compound of formula (14) is reacted with a monomer of formula (b) in the presence of an alcohol activating agent. In one embodiment, the alcohol activating agent is a trialkylphosphine, triarylphosphine, or triheteroarylphosphine. In a specific embodiment, the alcohol activating agent is trimethylphosphine, tributylphosphine, tri(o-tolyl)phosphine, tri(m-tolyl)phosphine, tri(p-tolyl)phosphine, tri(2-pyridyl)phosphine, tri(3-pyridyl)phosphine, tri(4-pyridyl)phosphine, or [4-(3,3,4,4,5,5,6,6,7,7,8,8,9,9,10,10,10-Heptadecafluorodecyl)phenyl]diphenylphosphine. In another embodiment, the alcohol activating agent can be a phosphine-like reagent, such as (tributylphosphoranylidene)acetonitrile, (cyanomethylene)tributylphosphorane (CMBP), or (cyanomethylene)trimethylphosphorane (CMMP). In a more specific embodiment, the alcohol activating agent is triphenylphosphine. In one embodiment, the alcohol activating agent can be polymer-bound or polymer-supported, such as polymer-bound or polymer-supported trialkyl phosphine, triarylphosphine (e.g., triphenylphosphine), or triheteroarylphosphine.

In another specific embodiment, the compound of formula (14) is reacted with a monomer of formula (b) in the presence of an azodicarboxylate. In one embodiment, the azodicarboxylate is selected from the group consisting of: diethyl azodicarboxylate (DEAD), diisopropyl azodicarboxylate (DIAD), 1,1'-(azodicarbonyl)dipiperidine (ADDP), ditertbutyl azodicarboxylate (DTAD), 1,6-dimethyl-1,5,7-hexahydro-1,4,6,7-tetrazocin-2,5-dione (DHTD), di-(4-chlorobenzyl)azodicarboxylate (DCAD), azodicarboxylic dimorpholide, N,N,N',N'-tetramethylazodicarboxamide (TMAD), N,N,N',N'-tetraisopropylazodicarboxamide (TIPA), 4,4'-azopyridine, bis (2,2,2-trichloroethyl) azodicarboxylate, o-(tert-Butyldimethylsilyl)-N-tosylhydroxylamine, di-(4-chlorobenzyl)azodicarboxylate, cyclic 1,6-dimethyl-1,5,7-hexahydro-1,4,6,7-tetrazocin-2,5-dione (DHTD), dimethyl acetylenedicarboxylate (DMAD), di-2-methoxyethyl azodicarboxylate, di-(4-chlorobenzyl) azodicarboxylate and bis(4,4,5,5,6,6,7,7,8,8,9,9,9-tridecafluorononyl) azodicarboxylate. More specifically, the azodicarboxylate is DIAD. In one embodiment, the azodicarboxylate is polymer-bound or polymer supported, such as polymer-supported alkylazodicarboxylate (e.g. polymer-bound DEAD, DIAD, DTAD or ADDP).

In yet another specific embodiment, for methods of the twenty-eighth embodiment, the compound of formula (14) is reacted with a monomer of formula (d) in the presence of triphenylphosphine and an azodicarboxylate. In one embodiment, the azodicarboxylate is selected from the group consisting of: diethyl azodicarboxylate (DEAD), diisopropyl azodicarboxylate (DIAD), 1,1'-(azodicarbonyl)dipiperidine (ADDP), and ditertbutyl azodicarboxylate (DTAD). More specifically, the azodicarboxylate is DIAD.

In yet another embodiment, the compound of formula (15) is reacted with the monomer compound of formula (d), wherein $P_3$ is H, to form a compound of formula (17'):

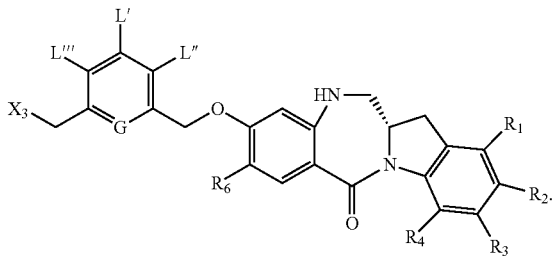

(17')

In a specific embodiment, $P_3$ is an amine protecting group and the method further comprises the step of reacting the compound of formula (17) with an amine deprotecting reagent to form a compound of formula (17'):

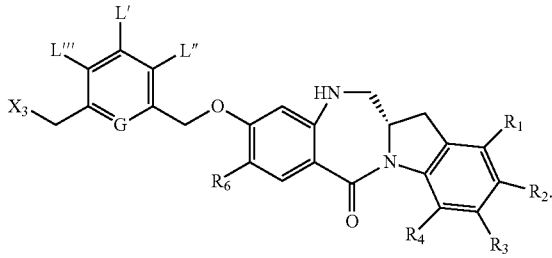

(17')

In a specific embodiment, the compound of formula (17) is selected from the group consisting of:

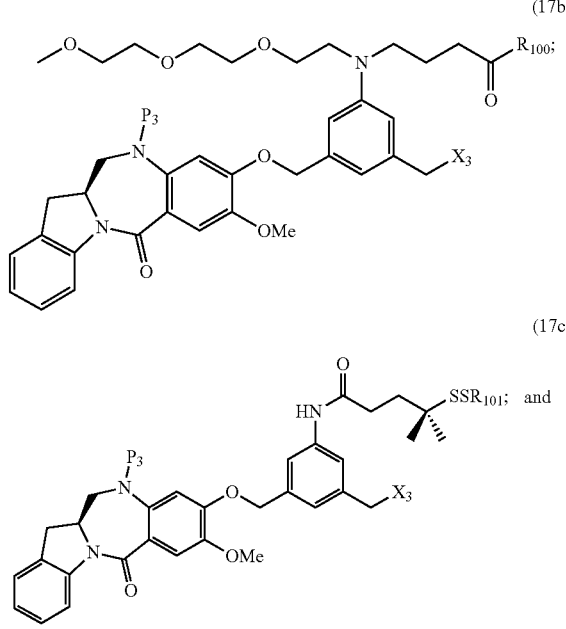

(17b)

(17c)

(17A)

wherein $R_{100}$ is a ($C_1$-$C_3$)alkoxy; and $R_{101}$ is a ($C_1$-$C_3$)alkyl, pyridyl or nitropyridyl (e.g., 4-nitropyridyl).

Examples of suitable amine deprotecting reagent include, but are not limited to, tetra-n-butylammonium fluoride, acetic acid, hydrogen fluoride pyridine, cesium fluoride, piperidine, morpholine, or trifluroacetic acid.

In a thirty-second embodiment, the present invention provides a method of preparing a compound of formula (17):

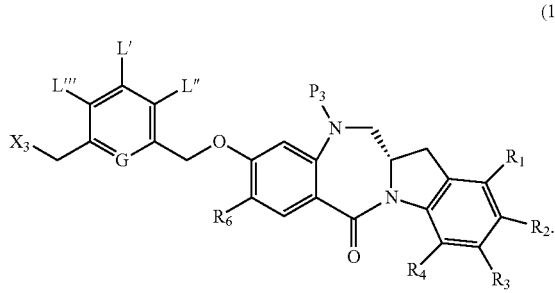

(17)

or a salt thereof, said method comprising reacting a compound of formula (20)

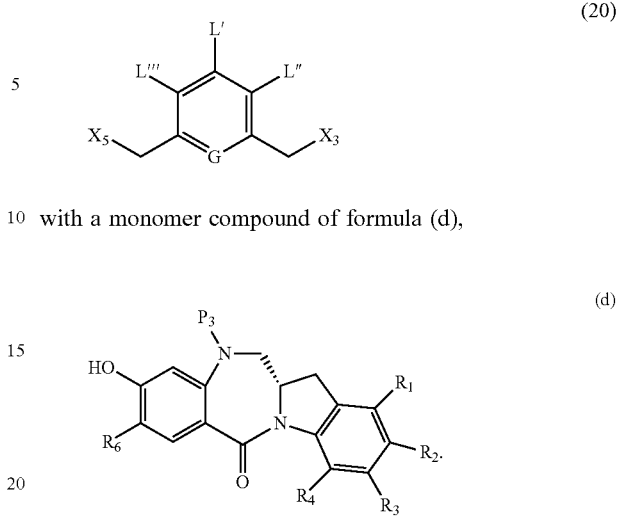

(20)

with a monomer compound of formula (d), (d)

wherein $X_3$ is —Cl; $X_5$ is —Br or —I, $P_3$ is H or an amine protecting group; and the remaining variables are the same as described above.

In a specific embodiment, the compound of formula (20) is selected from the group consisting of:

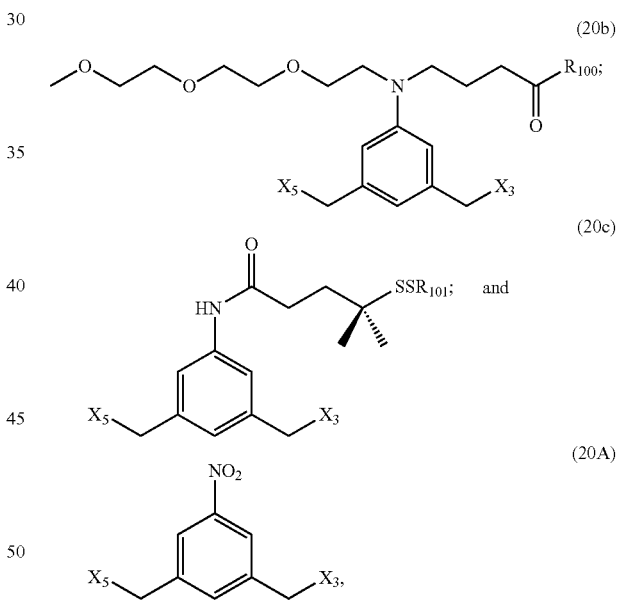

(20b)

(20c)

(20A)

wherein $X_3$ is —Cl; $X_5$ is —Br or —I; $R_{100}$ is a ($C_1$-$C_3$) alkoxy; and $R_{101}$ is a ($C_1$-$C_3$)alkyl, pyridyl or nitropyridyl (e.g., 4-nitropyridyl).

In one embodiment, the compound of formula (20) is reacted with a monomer compound of formula (d) in the presence of a base. Any suitable base can be used. Suitable bases include, but are not limited to, sodium carbonate, potassium carbonate, cesium carbonate, sodium hydride, or potassium hydride. Preferably, the base is potassium carbonate.

In another embodiment, the compound of formula (20) is reacted with a monomer compound of formula (d) in the presence of a polar aprotic solvent. Preferably, the polar aprotic solvent is dimethylacetamide.

In a specific embodiment, the compound of formula (20) is reacted with the monomer compound of formula (d), wherein $P_3$ is H, to form a compound of formula (17'):

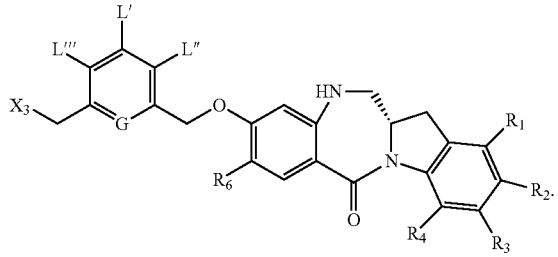

(17')

In another specific embodiment, $P_3$ is an amine protecting group and the method further comprises the step of reacting the compound of formula (17) with an amine deprotecting reagent to form a compound of formula (17'):

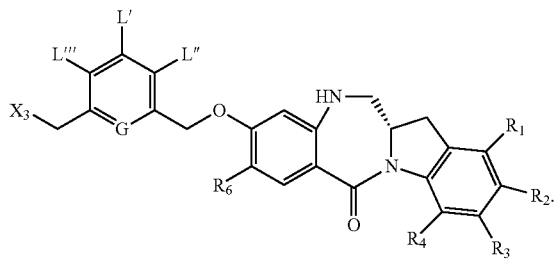

(17')

In one embodiment, the compound of formula (17) is selected from the group consisting of:

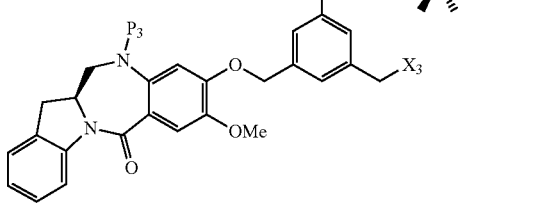

(17b)

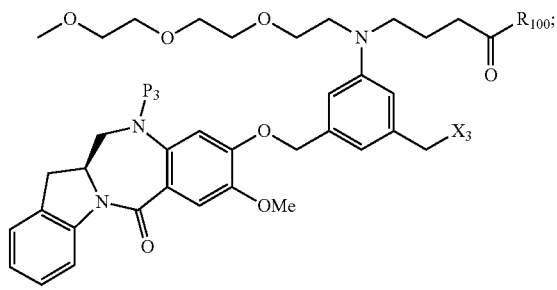

(17c)

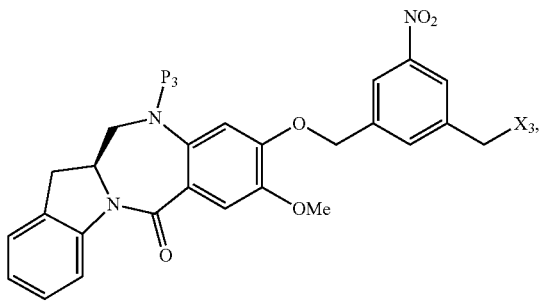

(17A)

wherein $X_3$ is —Cl; $P_3$ is H or an amine protecting group; $R_{100}$ is a ($C_1$-$C_3$)alkoxy; and $R_{101}$ is a ($C_1$-$C_3$)alkyl, pyridyl or nitropyridyl (e.g., 4-nitropyridyl).

Suitable amine deprotecting reagent include, but are not limited to, tetra-n-butylammonium fluoride, acetic acid, hydrogen fluoride pyridine, cesium fluoride, piperidine, morpholine, or trifluroacetic acid.

In a thirty-third embodiment, the present invention provides a method of preparing a compound of formula (17'):

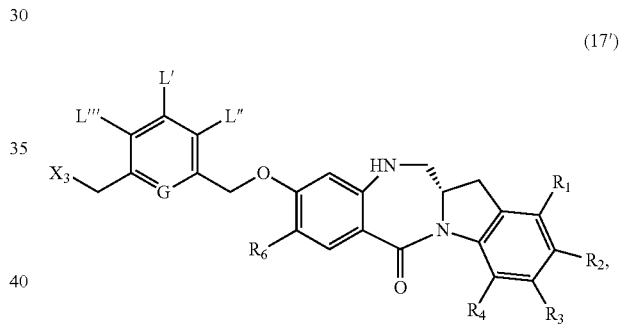

(17')

or a salt thereof, said method comprising reacting a compound of formula (19)

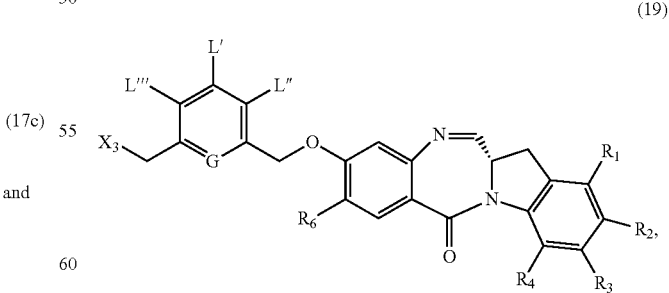

(19)

wherein $X_3$ is —Cl; the remaining variables are the same as described above.

In a specific embodiment, the compound of formula (19) is selected from the group consisting of:

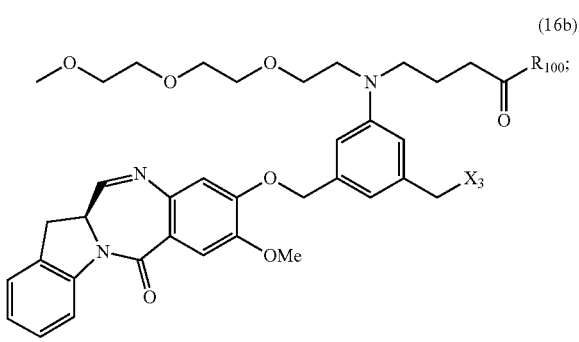

(16b)

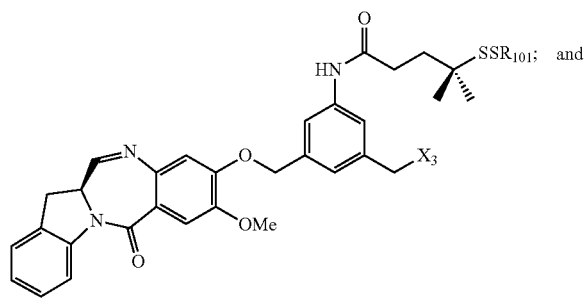

(16A)

wherein X₃ is —Cl; R₁₀₀ and R₁₀₁ are the same as defined above.

In another specific embodiment, the imine reducing agent is a hydride reducing agent. Examples of suitable hydride reducing agents include, but are not limited to, odium borohydride, sodium triacetoxy borohydride, sodium cyanoborohydride, lithium aluminum hydride, hydrogen gas, ammonium formate, borane, 9-borabicyclo[3.3.1]nonane (9-BBN), diisobutylaluminium hydride (DIBAL), lithium borohydride (LiBH₄), potassium borohydride (KBH₄), or sodium bis(2-methoxyethoxy)aluminumhydride (Red-Al). In one particular embodiment, the hydride reducing agent is sodium triacetoxy borohydride (NaBH(OAc)₃).

In a thirty-fourth embodiment, the present invention provides a method of preparing a compound of formula (18),

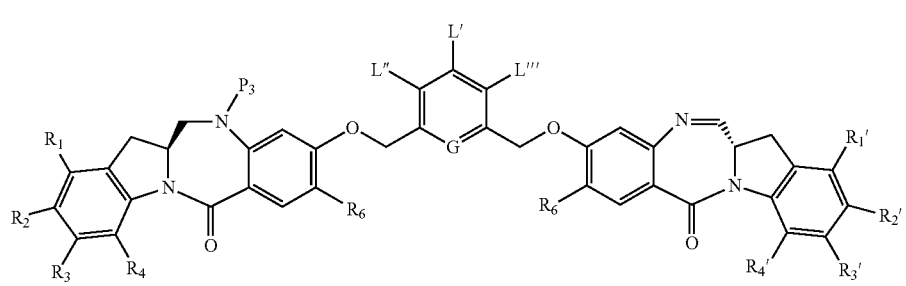

(18)

or a pharmaceutically acceptable salt thereof, said method comprising reacting a compound of formula of (17):

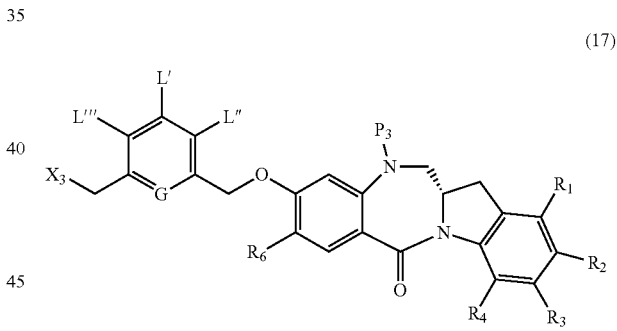

(17)

with a monomer of formula (b):

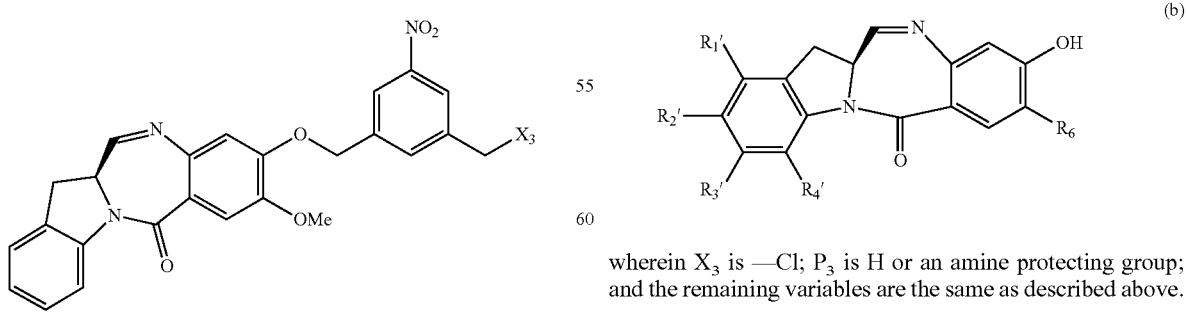

(b)

wherein X₃ is —Cl; P₃ is H or an amine protecting group; and the remaining variables are the same as described above.

In one embodiment, the compound of formula (17) is reacted with a monomer compound of formula (b) in the presence of a base. Suitable bases include, but are not limited to, sodium carbonate, potassium carbonate, cesium carbonate, sodium hydride, or potassium hydride. Preferably, the base is potassium carbonate.

In another embodiment, the compound of formula (17) is reacted with a monomer compound of formula (b) in the presence of a polar aprotic solvent. Preferable polar aprotic solvent include dimethylformamide or dimethylacetamide.

In yet another embodiment, the compound of formula (17) is reacted with reduced monomer of formula (b), wherein $P_3$ is H, to form a compound of formula (I'):

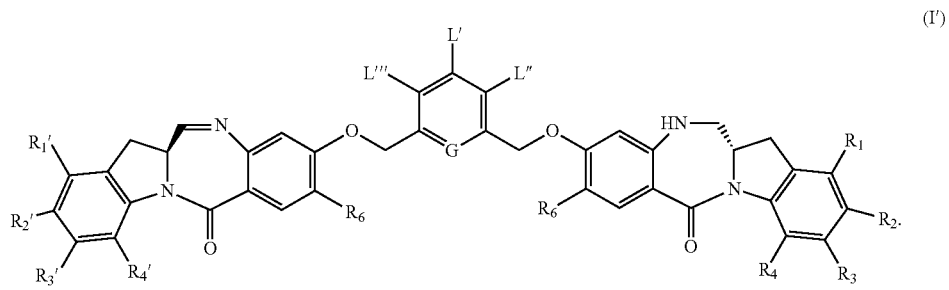

(I')

In a specific embodiment, $P_3$ is an amine protecting group. Suitable amine protecting groups include, but are not limited to, 2-trimethylsilylethyl, (2-phenyl-2-trimethylsilyl)ethyl, triisopropylsiloxy, 2-(trimethylsilyl)ethoxymethyl, allyloxycarbonyl, 9-fluorenylmethoxycarbonyl, 2-(trimethylsilyl)ethoxycarbonyl, or 2,2,2-trichloroethoxycarbonyl.

In still another embodiment, when $P_3$ is an amine protecting group, the compound of formula (18) is further reacted with an amine deprotecting reagent to form a compound of formula (I'):

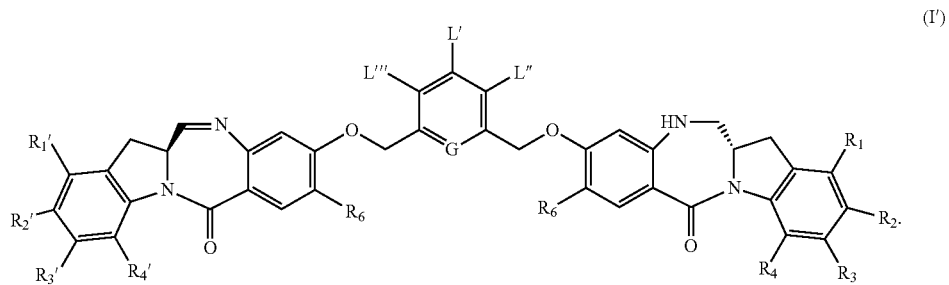

(I')

Examples of suitable amine deprotecting reagent include, but are not limited to, the amine deprotecting reagent is selected from the group consisting of tetra-n-butylammonium fluoride, acetic acid, hydrogen fluoride pyridine, cesium fluoride, piperidine, morpholine, or trifluroacetic acid.

In a thirty-fifth embodiment, the present invention provides a.

method of preparing a compound of formula (18),

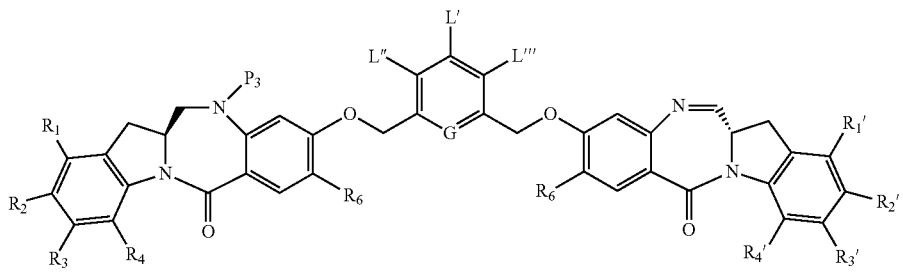

(18)

or a pharmaceutically acceptable salt thereof, said method comprising the steps of:

(1) reacting a sulfonating reagent or an esterification reagent with the compound of formula (14),

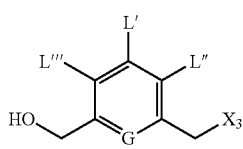

(14)

to form a compound of formula (15):

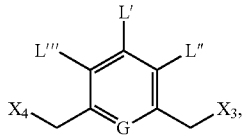

(15)

or a salt thereof;

(2) reacting the compound of formula (15) with a monomer compound of formula (b),

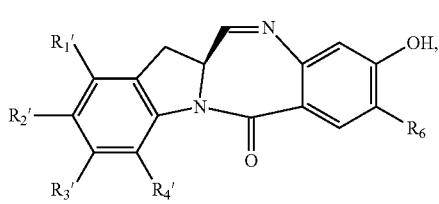

(b)

to form a compound of formula (16):

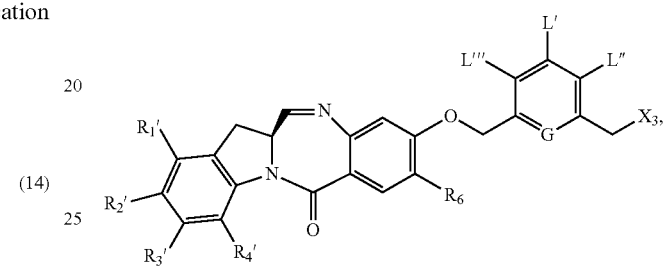

(16)

or a salt thereof;

(3) reacting the compound of formula of (16) with a reduced monomer of formula (d):

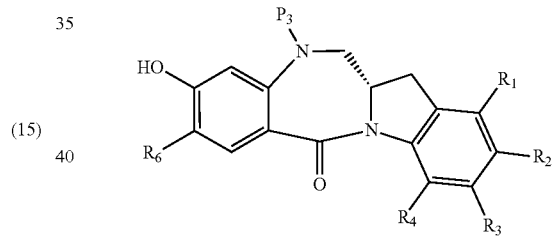

(d)

to form a compound of formula (18), or a pharmaceutically acceptable salt thereof, wherein $X_3$ is —Cl; $X_4$ is a sulfonate ester or an activated ester; $P_1$ is an alcohol protecting group; $P_3$ is H or an amine protecting group; and the remaining variables are the same as described above. In one embodiment, $X_4$ is a sulfonate ester.

In a specific embodiment, the method of the thirty-fifth embodiment involves a method of preparing a compound of formula (Ib'), said method comprising the steps of:

(1) reacting a sulfonating reagent or an esterification reagent with the compound of formula (14b), to form a compound of formula (15b);

(2) reacting the compound of formula (15b) with a monomer compound of formula ($b_1$), to form a compound of formula (16b);

(3) reacting the compound of formula of (16b) with a reduced monomer of formula (d), to form a compound of formula (18b), or a pharmaceutically acceptable salt thereof, wherein when $P_3$ is H, the reaction of the compound of (16b) with the reduced monomer ($d_1$) to form the compound of formula (Ib'); and when $P_3$ is an amine protecting group, the method further comprising reacting the compound of formula (18b) with an amine deprotecting reagent to formula the compound of formula (Ib').

In another specific embodiment, the method of the thirty-fifth embodiment involves a method of preparing a compound of formula (Ic'), said method comprising the steps of:

(1) reacting a sulfonating reagent or an esterification reagent with the compound of formula (14c), to form a compound of formula (15c);

(2) reacting the compound of formula (15c) with a monomer compound of formula ($b_1$), to form a compound of formula (16c);

(3) reacting the compound of formula of (16c) with a reduced monomer of formula ($d_1$), to form a compound of formula (18c), or a pharmaceutically acceptable salt thereof, wherein when $P_3$ is H, the reaction of the compound of (16c) with the reduced monomer ($d_1$) to form the compound of formula (Ib'); and when $P_3$ is an amine protecting group, the method further comprising reacting the compound of formula (18c) with an amine deprotecting reagent to formula the compound of formula (Ib').

In yet another specific embodiment, the method of the thirty-fifth embodiment involves a method of preparing a compound of formula (IA), said method comprising the steps of:

(1) reacting a sulfonating reagent or an esterification reagent with the compound of formula (14b), to form a compound of formula (15A);

(2) reacting the compound of formula (15A) with a monomer compound of formula ($b_1$), to form a compound of formula (16A);

(3) reacting the compound of formula of (16A) with a reduced monomer of formula ($d_1$), to form a compound of formula (18A), or a pharmaceutically acceptable salt thereof, wherein when $P_3$ is H, the reaction of the compound of (16A) with the reduced monomer ($d_1$) to form the compound of formula (IA); and when $P_3$ is an amine protecting group, the method further comprising reacting the compound of formula (18A) with an amine deprotecting reagent to formula the compound of formula (IA).

The conditions and reagents for the methods of thirty-fifth embodiment are as described above in the twenty-fourth, twenty-sixth and/or twenty-ninth embodiment(s) and any specific embodiments described therein.

In a thirty-sixth embodiment, the present invention provides a method of preparing a compound of formula (18), or a pharmaceutically acceptable salt thereof, said method comprising the steps of:

(1) reacting the compound of formula (14):

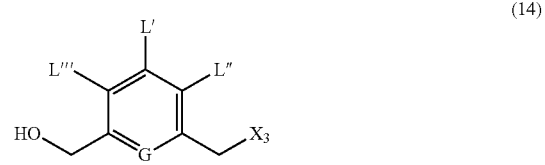

with a monomer compound of formula (b),

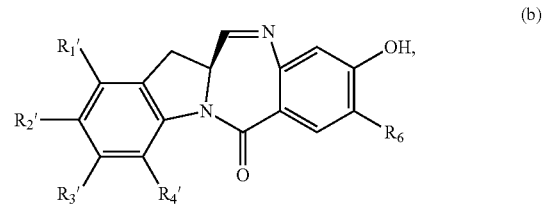

to form a compound of formula (16):

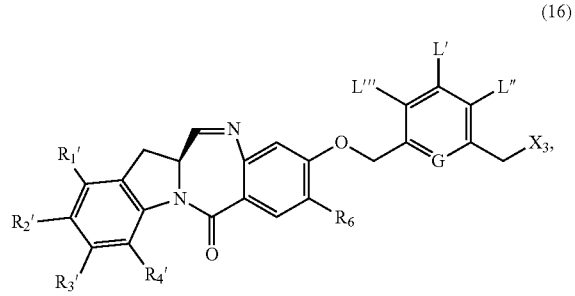

or a salt thereof; and (2) reacting the compound of formula of (16) with a reduced monomer of formula (d):

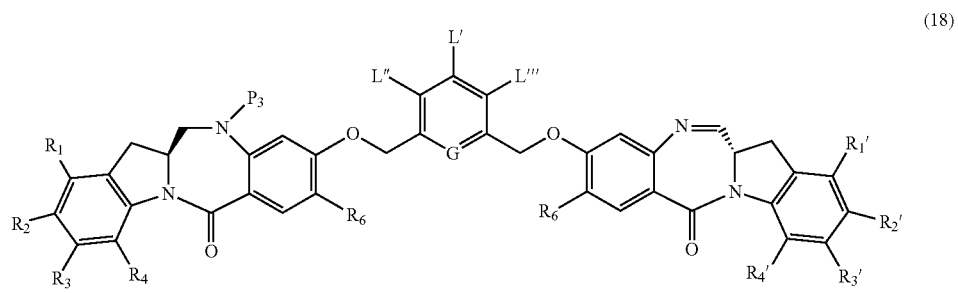

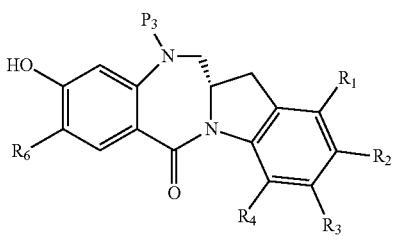

(d)

to form a compound of formula (18), or a pharmaceutically acceptable salt thereof, wherein $X_3$ is —Cl; $P_1$ is an alcohol protecting group; $P_3$ is H or an amine protecting group; and the remaining variables are the same as described above.

In a specific embodiment, the method of the thirty-sixth embodiment involves a method of preparing a compound of formula (Ib'), said method comprising the steps of:

(1) reacting the compound of formula (14b) with a monomer compound of formula ($b_1$), in the presence of an alcohol activating agent to form a compound of formula (16b);

(2) reacting the compound of formula of (16b) with a reduced monomer of formula ($d_1$), to form a compound of formula (18b), or a pharmaceutically acceptable salt thereof, wherein when $P_3$ is H, the reaction of the compound of (16b) with the reduced monomer ($d_1$) to form the compound of formula (Ib'); and when $P_3$ is an amine protecting group, the method further comprising reacting the compound of formula (18b) with an amine deprotecting reagent to formula the compound of formula (Ib').

In another specific embodiment, the method of the thirty-sixth embodiment involves a method of preparing a compound of formula (Ic'), said method comprising the steps of:

(1) reacting the compound of formula (14c) with a monomer compound of formula ($b_1$), in the presence of an alcohol activating agent to form a compound of formula (16c);

(2) reacting the compound of formula of (16c) with a reduced monomer of formula ($d_1$), to form a compound of formula (18c), or a pharmaceutically acceptable salt thereof, wherein when $P_3$ is H, the reaction of the compound of (16c) with the reduced monomer ($d_1$) to form the compound of formula (Ic'); and when $P_3$ is an amine protecting group, the method further comprising reacting the compound of formula (18c) with an amine deprotecting reagent to formula the compound of formula (Ic').

In yet another specific embodiment, the method of the thirty-sixth embodiment involves a method of preparing a compound of formula (IA), said method comprising the steps of:

(1) reacting the compound of formula (14A) with a monomer compound of formula ($b_1$), in the presence of an alcohol activating agent to form a compound of formula (16A);

(2) reacting the compound of formula of (16A) with a reduced monomer of formula ($d_1$), to form a compound of formula (18A), or a pharmaceutically acceptable salt thereof, wherein when $P_3$ is H, the reaction of the compound of (16A) with the reduced monomer ($d_1$) to form the compound of formula (IA); and when $P_3$ is an amine protecting group, the method further comprising reacting the compound of formula (18A) with an amine deprotecting reagent to formula the compound of formula (IA).

The conditions and reagents for the method of thirty-sixth embodiment are as described above in the twenty-eighth, and/or twenty-ninth embodiment(s) and any specific embodiments described therein.

In a thirty-seventh embodiment, the present invention provides a method of preparing a compound of formula (18),

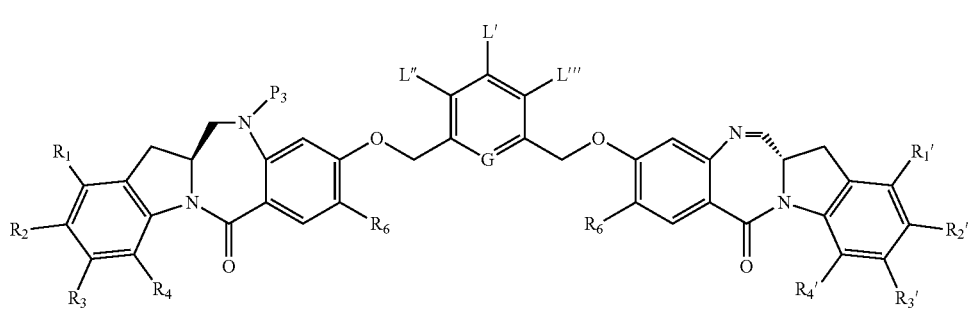

(18)

or a pharmaceutically acceptable salt thereof, said method comprising the steps of:

(1) reacting a halogenating reagent with the compound of formula (14),

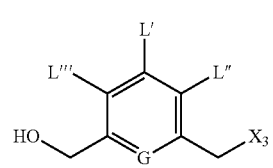

(14)

to form a compound of formula (20):

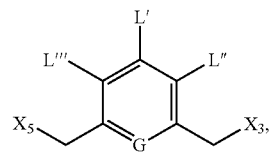

(20)

or a salt thereof;

(2) reacting a compound of formula (20) or a salt thereof with a monomer compound of formula (b),

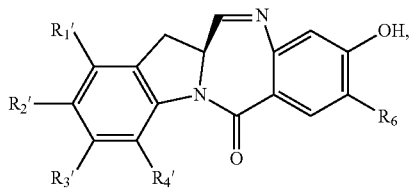

(b)

to form a compound of formula (16):

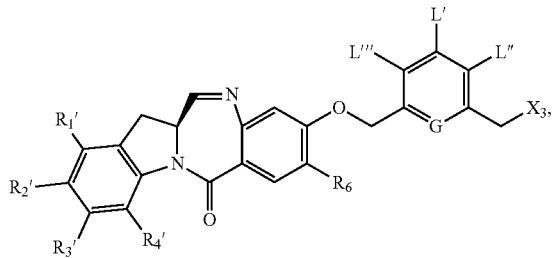

(16)

or a salt thereof; and (3) reacting the compound of formula of (16) with a reduced monomer of formula (d):

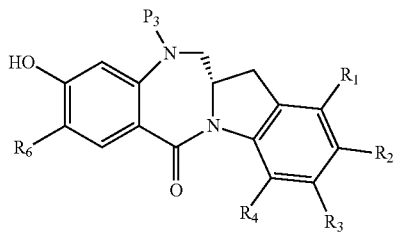

(d)

to form a compound of formula (18), or a pharmaceutically acceptable salt thereof, wherein $X_3$ is —Cl; $X_5$ is —Br or —I; $P_3$ is H or an amine protecting group; and the remaining variables are the same as described above.

In a specific embodiment, the method of the thirty-seventh embodiment involves a method of preparing a compound of formula (Ib'), said method comprising the steps of:

(1) reacting a halogenating reagent with the compound of formula (14b) to form a compound of formula (20b);

(2) reacting a compound of formula (20b) or a salt thereof with a monomer compound of formula ($b_1$), to form a compound of formula (16b)

(3) reacting the compound of formula of (16b) with a reduced monomer of formula ($d_1$), to form a compound of formula (18b), or a pharmaceutically acceptable salt thereof, wherein when $P_3$ is H, the reaction of the compound of (16b) with the reduced monomer ($d_1$) to form the compound of formula (Ib'); and when $P_3$ is an amine protecting group, the method further comprising reacting the compound of formula (18b) with an amine deprotecting reagent to formula the compound of formula (Ib').

In another specific embodiment, the method of the thirty-seventh embodiment involves a method of preparing a compound of formula (Ic'), said method comprising the steps of:

(1) reacting a halogenating reagent with the compound of formula (14c) to form a compound of formula (20c);

(2) reacting a compound of formula (20c) or a salt thereof with a monomer compound of formula ($b_1$), to form a compound of formula (16c)

(3) reacting the compound of formula of (16c) with a reduced monomer of formula ($d_1$), to form a compound of formula (18c), or a pharmaceutically acceptable salt thereof, wherein when $P_3$ is H, the reaction of the compound of (16c) with the reduced monomer ($d_1$) to form the compound of formula (Ib'); and when $P_3$ is an amine protecting group, the method further comprising reacting the compound of formula (18b) with an amine deprotecting reagent to formula the compound of formula (Ic').

In yet another specific embodiment, the method of the thirty-seventh embodiment involves a method of preparing a compound of formula (IA), said method comprising the steps of:

(1) reacting a halogenating reagent with the compound of formula (14A) to form a compound of formula (20A);

(2) reacting a compound of formula (20A) or a salt thereof with a monomer compound of formula ($b_1$), to form a compound of formula (16A)

(3) reacting the compound of formula of (16A) with a reduced monomer of formula ($d_1$), to form a compound of formula (18A), or a pharmaceutically acceptable salt thereof, wherein when $P_3$ is H, the reaction of the compound of (16A) with the reduced monomer ($d_1$) to form the compound of formula (IA); and when $P_3$ is an amine protecting group, the method further comprising reacting the compound of formula (18A) with an amine deprotecting reagent to formula the compound of formula (IA).

The conditions and reagents for the method of thirty-seventh embodiment are as described above in the twenty-fifth, twenty-seventh, and/or twenty-ninth embodiment(s) and any specific embodiments described therein.

In a specific embodiment of the thirty-fifth, thirty-sixth, or thirty-seventh embodiment, the compound of formula (16) is reacted with reduced monomer of formula (d), wherein $P_3$ is H, to form a compound of formula (I'):

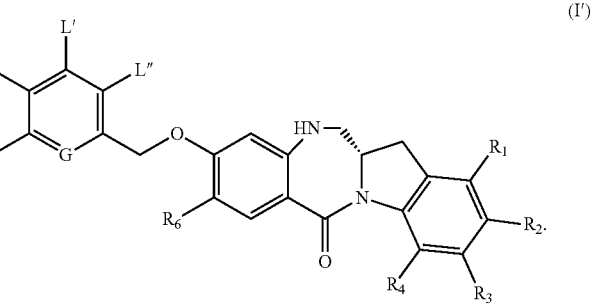

(I')

In another specific embodiment of the thirty-fifth, thirty-sixth, or thirty-seventh embodiment, P₃ is an amine protecting group and the compound of formula (18) is further reacted with an amine deprotecting reagent to form a compound of formula (I'):

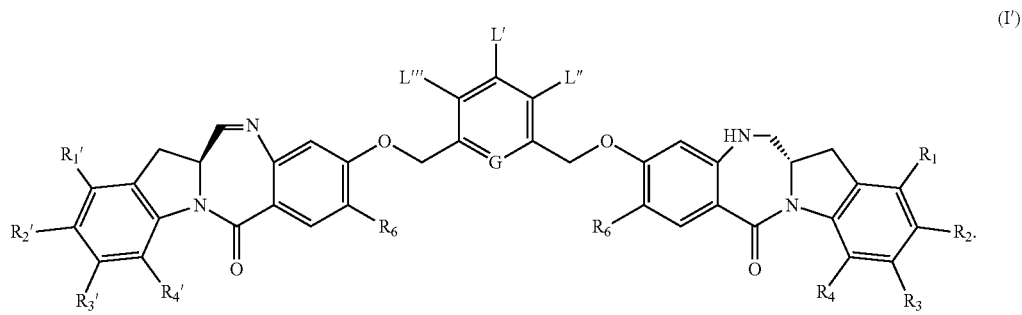

(I')

In a thirty-eighth embodiment, the present invention provides a method of preparing a compound of formula (18),

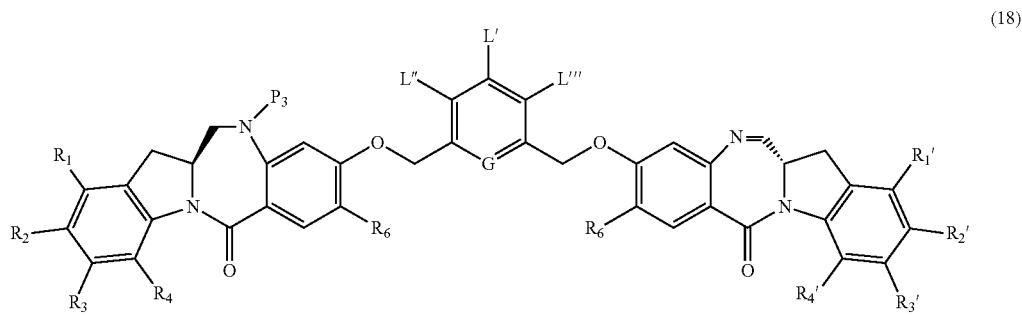

(18)

or a pharmaceutically acceptable salt thereof, said method comprising the steps of:

(1) reacting a sulfonating reagent or an esterification reagent with the compound of formula (14),

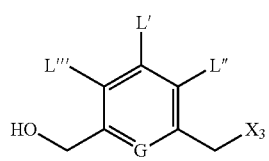

(14)

to form a compound of formula (15):

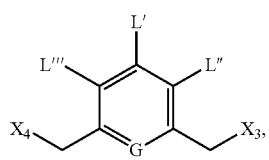

(15)

or a salt thereof;

(2) reacting the compound of formula (15) with a reduced monomer compound of formula (d),

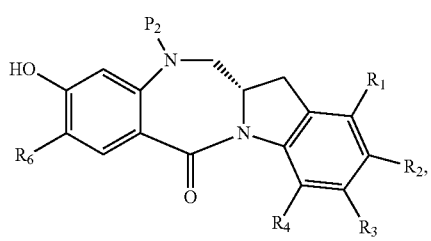

(d)

to form a compound of formula (17):

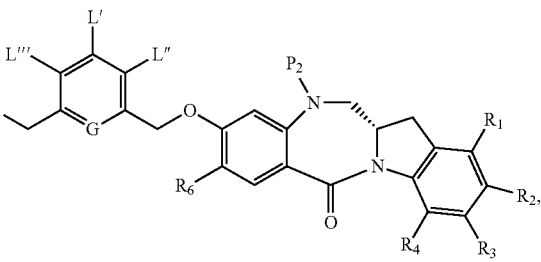

(17)

or a salt thereof; and (3) reacting the compound of formula of (17) with a monomer of formula (b):

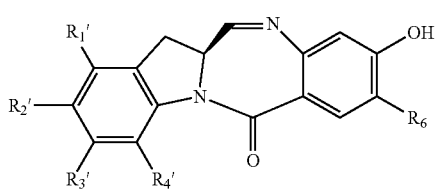
(b)

to form a compound of formula (18) or a pharmaceutically acceptable salt thereof, wherein $X_3$ is —Cl; $X_4$ is a sulfonate ester or an activated ester; $P_1$ is an alcohol protecting group; $P_3$ is H or an amine protecting group; the remaining variables are the same as described above. In one embodiment, $X_4$ is a sulfonate ester.

In a specific embodiment, the method of the thirty-eighth embodiment involves a method of preparing a compound of formula (Ib'), said method comprising the steps of:

(1) reacting a sulfonating reagent or an esterification reagent with the compound of formula (14b) to form a compound of formula (15b);

(2) reacting a compound of formula (15b) or a salt thereof with a reduced monomer compound of formula ($d_1$), to form a compound of formula (17b)

(3) reacting the compound of formula of (17b) with a monomer of formula ($b_1$), to form a compound of formula (18b), or a pharmaceutically acceptable salt thereof, wherein when $P_3$ is H, the reaction of the compound of (17b) with the reduced monomer ($d_1$) to form the compound of formula (Ib'); and when $P_3$ is an amine protecting group, the method further comprising reacting the compound of formula (18b) with an amine deprotecting reagent to formula the compound of formula (Ib').

In another specific embodiment, the method of the thirty-eighth embodiment involves a method of preparing a compound of formula (Ic'), said method comprising the steps of:

(1) reacting a sulfonating reagent or an esterification reagent with the compound of formula (14b) to form a compound of formula (15c);

(2) reacting a compound of formula (15c) or a salt thereof with a reduced monomer compound of formula ($d_1$), to form a compound of formula (17c)

(3) reacting the compound of formula of (17c) with a monomer of formula ($b_1$), to form a compound of formula (18c), or a pharmaceutically acceptable salt thereof, wherein when $P_3$ is H, the reaction of the compound of (17c) with the reduced monomer ($d_1$) to form the compound of formula (Ic'); and when $P_3$ is an amine protecting group, the method further comprising reacting the compound of formula (18c) with an amine deprotecting reagent to formula the compound of formula (Ic').

In yet another specific embodiment, the method of the thirty-eighth embodiment involves a method of preparing a compound of formula (IA), said method comprising the steps of:

(1) reacting a sulfonating reagent or an esterification reagent with the compound of formula (14A) to form a compound of formula (15A);

(2) reacting a compound of formula (15A) or a salt thereof with a reduced monomer compound of formula ($d_1$), to form a compound of formula (17A)

(3) reacting the compound of formula of (17A) with a monomer of formula ($b_1$), to form a compound of formula (18A), or a pharmaceutically acceptable salt thereof, wherein when $P_3$ is H, the reaction of the compound of (17A) with the reduced monomer ($d_1$) to form the compound of formula (IA); and when $P_3$ is an amine protecting group, the method further comprising reacting the compound of formula (18A) with an amine deprotecting reagent to formula the compound of formula (IA).

The conditions and reagents for the method of thirty-eighth embodiment are as described above in the twenty-fifth, thirtieth and/or thirty-fourth embodiment(s) and any specific embodiments described therein.

In a thirty-ninth embodiment, the present invention provides a method of preparing a compound of formula (18),

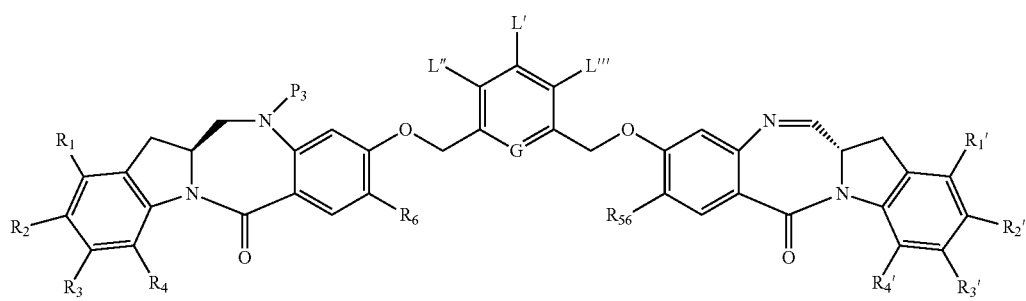
(18)

or a pharmaceutically acceptable salt thereof, said method comprising the steps of:

(1) reacting the compound of formula (14):

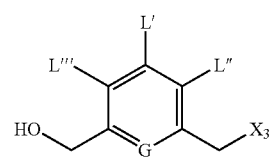
(14)

with a reduced monomer compound of formula (d),

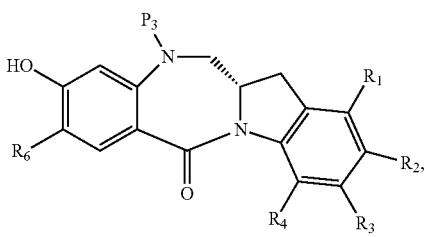

to form a compound of formula (17):

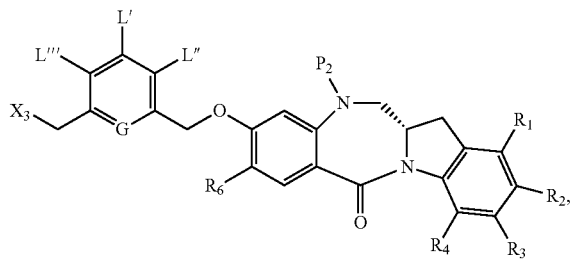

or a salt thereof; and (2) reacting the compound of formula of (17) with a monomer of formula (b):

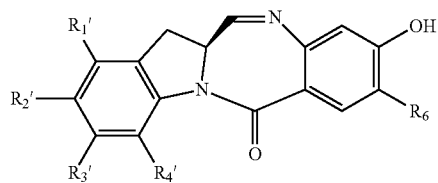

to form a compound of formula (18), or a pharmaceutically acceptable salt thereof, wherein $X_3$ is —Cl; $P_1$ is an alcohol protecting group; $P_3$ is H or an amine protecting group; and the remaining variables are the same as described above.

In a specific embodiment, the method of the thirty-ninth embodiment involves a method of preparing a compound of formula (Ib'), said method comprising the steps of:

(1) reacting a compound of formula (14b) with a reduced monomer compound of formula ($d_1$), to form a compound of formula (17b)

(2) reacting the compound of formula of (17b) with a monomer of formula ($b_1$), to form a compound of formula (18b), or a pharmaceutically acceptable salt thereof, wherein when $P_3$ is H, the reaction of the compound of (17b) with the reduced monomer ($d_1$) to form the compound of formula (Ib'); and when $P_3$ is an amine protecting group, the method further comprising reacting the compound of formula (18b) with an amine deprotecting reagent to formula the compound of formula (Ib').

In another specific embodiment, the method of the thirty-ninth embodiment involves a method of preparing a compound of formula (Ic'), said method comprising the steps of:

(1) reacting a compound of formula (14c) with a reduced monomer compound of formula ($d_1$), to form a compound of formula (17c)

(2) reacting the compound of formula of (17c) with a monomer of formula ($b_1$), to form a compound of formula (18c), or a pharmaceutically acceptable salt thereof, wherein when $P_3$ is H, the reaction of the compound of (17c) with the reduced monomer ($d_1$) to form the compound of formula (Ic'); and when $P_3$ is an amine protecting group, the method further comprising reacting the compound of formula (18c) with an amine deprotecting reagent to formula the compound of formula (Ic').

In yet another specific embodiment, the method of the thirty-ninth embodiment involves a method of preparing a compound of formula (IA), said method comprising the steps of:

(1) reacting a compound of formula (14A) with a reduced monomer compound of formula ($d_1$), to form a compound of formula (17A)

(2) reacting the compound of formula of (17A) with a monomer of formula ($b_1$), to form a compound of formula (18A), or a pharmaceutically acceptable salt thereof, wherein when $P_3$ is H, the reaction of the compound of (17A) with the reduced monomer ($d_1$) to form the compound of formula (IA'); and when $P_3$ is an amine protecting group, the method further comprising reacting the compound of formula (18A) with an amine deprotecting reagent to formula the compound of formula (IA).

The conditions and reagents for the method of thirty-ninth embodiment are as described above in the thirty-first and/or thirty-fourth embodiment(s) and any specific embodiments described therein.

In a fortieth embodiment, the present invention provides a method of preparing a compound of formula (18),

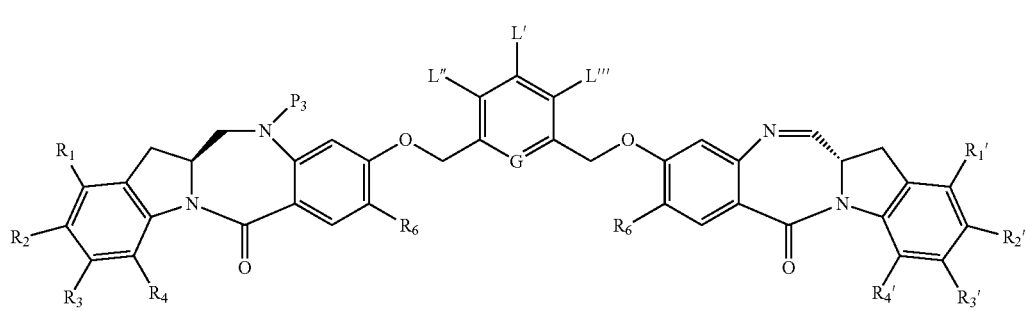

or a pharmaceutically acceptable salt thereof, said method comprising the steps of:

(1) reacting a halogenating reagent with the compound of formula (14):

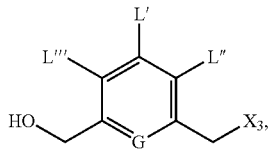
(14)

to form a compound of formula (20):

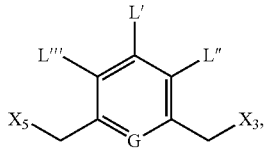
(20)

or a salt thereof;

(2) reacting the compound of formula (20) with a reduced monomer compound of formula (d),

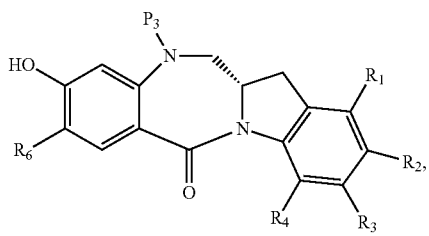
(d)

to form a compound of formula (17):

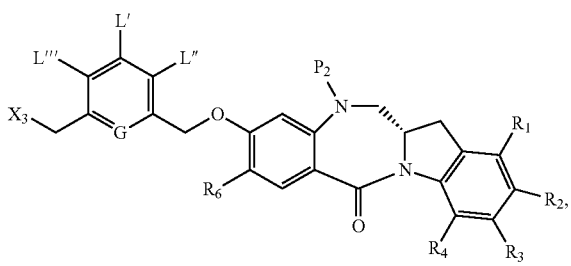
(17)

or a salt thereof; and (3) reacting the compound of formula of (17) with a monomer of formula (b):

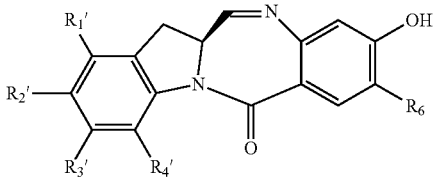
(b)

to form a compound of formula (18), or a pharmaceutically acceptable salt thereof, wherein $X_3$ is —Cl; $X_5$ is —Br or —I; $P_1$ is an alcohol protecting group; $P_3$ is H or an amine protecting group; and the variables are the same as described above.

In a specific embodiment, the method of the fortieth embodiment involves a method of preparing a compound of formula (Ib'), said method comprising the steps of:

(1) reacting a brominating or iodinating reagent with the compound of formula (14b) to form a compound of formula (20b);

(2) reacting a compound of formula (20b) with a reduced monomer compound of formula ($d_1$), to form a compound of formula (17b)

(3) reacting the compound of formula of (17b) with a monomer of formula ($b_1$), to form a compound of formula (18b), or a pharmaceutically acceptable salt thereof, wherein when $P_3$ is H, the reaction of the compound of (17b) with the reduced monomer ($d_1$) to form the compound of formula (Ib'); and when $P_3$ is an amine protecting group, the method further comprising reacting the compound of formula (18b) with an amine deprotecting reagent to formula the compound of formula (Ib').

In another specific embodiment, the method of the fortieth embodiment involves a method of preparing a compound of formula (Ic'), said method comprising the steps of:

(1) reacting a brominating or iodinating reagent with the compound of formula (14c) to form a compound of formula (20c);

(2) reacting a compound of formula (20c) with a reduced monomer compound of formula ($d_1$), to form a compound of formula (17c)

(3) reacting the compound of formula of (17c) with a monomer of formula ($b_1$), to form a compound of formula (18c), or a pharmaceutically acceptable salt thereof, wherein when $P_3$ is H, the reaction of the compound of (17c) with the reduced monomer ($d_1$) to form the compound of formula (Ic'); and when $P_3$ is an amine protecting group, the method further comprising reacting the compound of formula (18c) with an amine deprotecting reagent to formula the compound of formula (Ic').

In yet another specific embodiment, the method of the fortieth embodiment involves a method of preparing a compound of formula (IA), said method comprising the steps of:

(1) reacting a brominating or iodinating reagent with the compound of formula (14A) to form a compound of formula (20A);

(2) reacting a compound of formula (20A) with a reduced monomer compound of formula ($d_1$), to form a compound of formula (17A)

(3) reacting the compound of formula of (17A) with a monomer of formula ($b_1$), to form a compound of formula (18A), or a pharmaceutically acceptable salt thereof, wherein when $P_3$ is H, the reaction of the compound of (17A) with the reduced monomer ($d_1$) to form the compound of formula (Ib'); and when $P_3$ is an amine protecting group, the method further comprising reacting the compound of formula (18A) with an amine deprotecting reagent to formula the compound of formula (Ib').

The conditions and reagents for the method of fortieth embodiment are as described above in the twenty-fifth, thirty-second and/or thirty-fourth embodiment(s) and any specific embodiments described therein.

In a specific embodiment of the thirty-eighth, thirty-ninth, or fortieth embodiment, the compound of formula (17) is reacted with reduced monomer of formula (d), wherein $P_3$ is H, to form a compound of formula (I'):

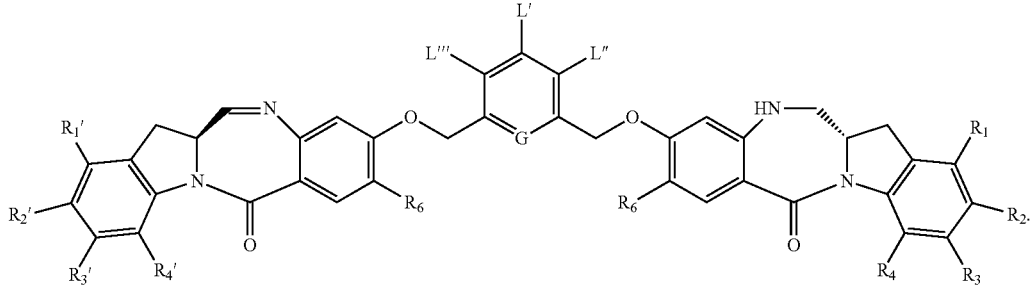

(I')

In another specific embodiment of the thirty-sixth, thirty-seventh, or thirty-eighth embodiment, $P_3$ is an amine protecting group. When $P_3$ is an amine protecting group, the compound of formula (18) is further reacted with an amine deprotecting reagent to form a compound of formula (I'):

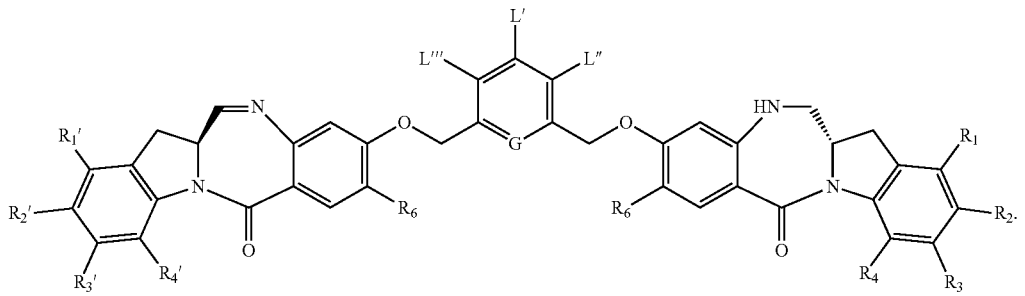

(I')

In a forty-first embodiment, the present invention provides a method of preparing a compound of formula (I'),

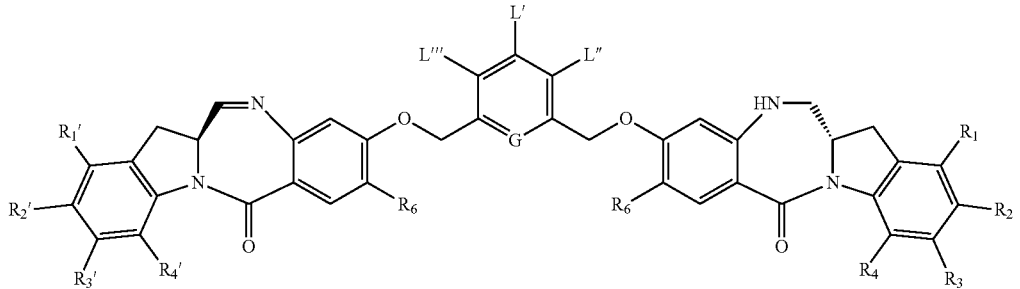

(I')

or a pharmaceutically acceptable salt thereof, said method comprising the steps of:

(1) reacting a sulfonating reagent or an esterification reagent with the compound of formula (14),

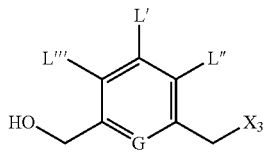

(14)

to form a compound of formula (15):

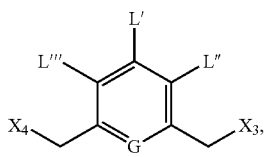

(15)

or a salt thereof;

(2) reacting the compound of formula (15) with a monomer compound of formula (a),

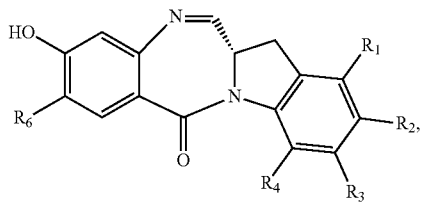

(a)

to form a compound of formula (19):

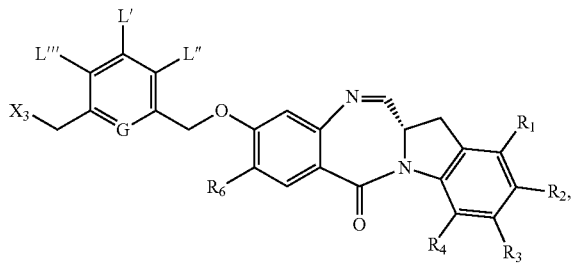

(19)

or a salt thereof;

(3) reacting the compound of formula (19) with an imine reducing agent to form a compound of formula (17'):

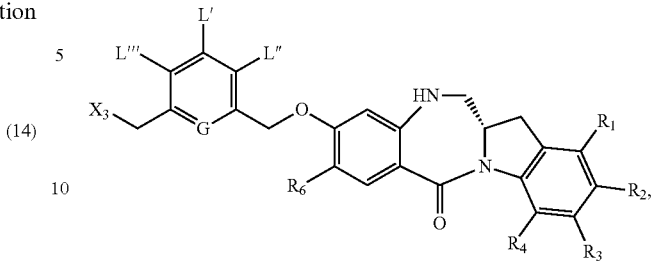

(17')

or a salt thereof; and (6) reacting the compound of formula (17') with a monomer of formula (B):

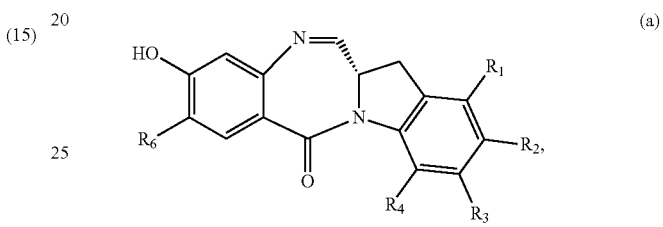

(a)

to form the compound of formula (I'), or a pharmaceutically acceptable salt thereof, wherein $X_3$ is —Cl; $X_4$ is a sulfonate ester or an activated ester; $P_1$ is an alcohol protecting group; $P_2$ is an amine protecting group; and the remaining variables are the same as described above. In one embodiment, $X_4$ is a sulfonate ester.

In one embodiment, the method of the forty-first embodiment involves preparing a compound of formula (Ib'), or a pharmaceutically acceptable salt thereof, said method comprising the steps of:

(1) reacting a sulfonating reagent with the compound of formula (14b), to form a compound of formula (15b), or a salt thereof;

(2) reacting the compound of formula (15b) with a monomer compound of formula ($a_1$) to form a compound of formula (16b), or a salt thereof;

(3) reacting the compound of formula (16b) with an imine reducing agent to form a compound of formula (17b'), or a salt thereof; and (6) reacting the compound of formula (17b') with a monomer of formula ($a_1$) to form the compound of formula (Ib'), or a pharmaceutically acceptable salt thereof.

In another embodiment, the method of the forty-first embodiment involves preparing a compound of formula (Ic'), or a pharmaceutically acceptable salt thereof, said method comprising the steps of:

(1) reacting a sulfonating reagent with the compound of formula (14c), to form a compound of formula (15c), or a salt thereof;

(2) reacting the compound of formula (15c) with a monomer compound of formula ($a_1$) to form a compound of formula (16c), or a salt thereof;

(3) reacting the compound of formula (16c) with an imine reducing agent to form a compound of formula (17c'), or a salt thereof; and (6) reacting the compound of formula (17c') with a monomer of formula ($a_1$) to form the compound of formula (Ic'), or a pharmaceutically acceptable salt thereof.

In still another embodiment, the method of the forty-first embodiment involves preparing a compound of formula (IA'), or a pharmaceutically acceptable salt thereof, said method comprising the steps of:

(1) reacting a sulfonating reagent with the compound of formula (14A), to form a compound of formula (15A), or a salt thereof;

(2) reacting the compound of formula (15A) with a monomer compound of formula (a$_1$) to form a compound of formula (16A), or a salt thereof;

(3) reacting the compound of formula (16A) with an imine reducing agent to form a compound of formula (17A'), or a salt thereof; and (6) reacting the compound of formula (17A') with a monomer of formula (a$_1$) to form the compound of formula (IA'), or a pharmaceutically acceptable salt thereof.

In a forty-second embodiment, the present invention provides a method of preparing a compound of formula (I'),

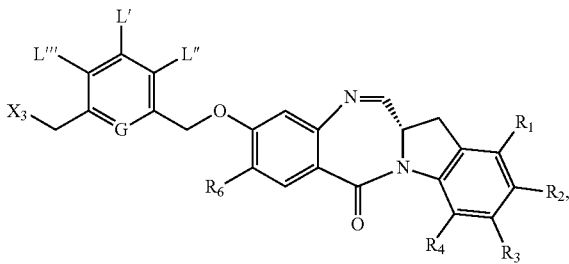

(19)

or a salt thereof;

(2) reacting the compound of formula (19) with an imine reducing agent to form a compound of formula (17'):

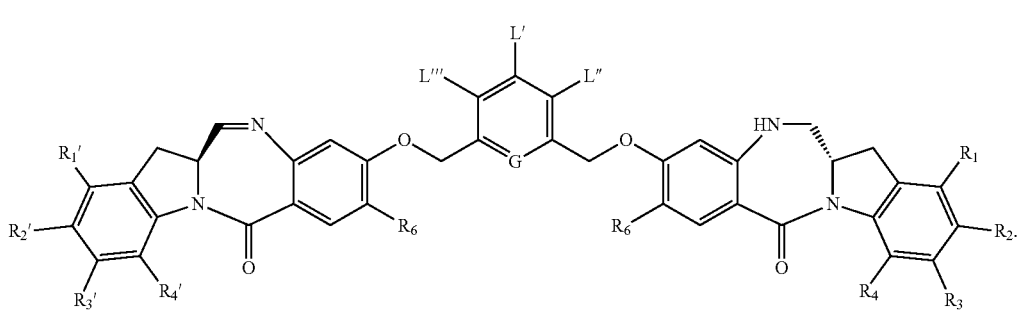

(I')

or a pharmaceutically acceptable salt thereof, said method comprising the steps of:

(1) reacting the compound of formula (14):

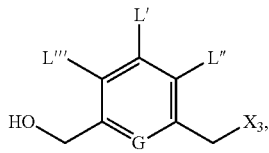

(14)

with a monomer compound of formula (b),

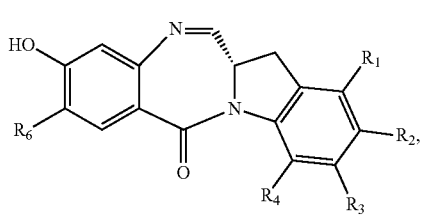

(a)

to form a compound of formula (19):

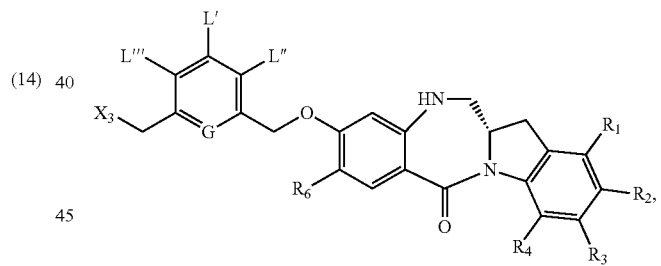

(17')

or a salt thereof; and (3) reacting the compound of formula (17') with a monomer of formula (a):

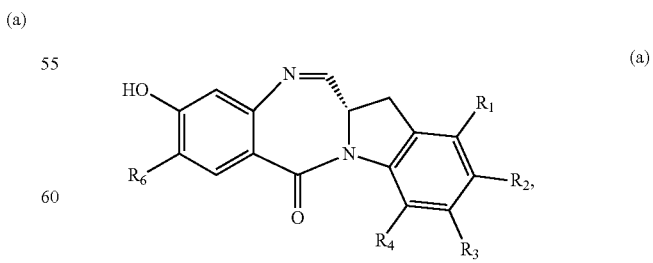

(a)

to form the compound of formula (I'); wherein X$_3$ is —Cl; P$_1$ is an alcohol protecting group; the variables are the same as described above.

In one embodiment, the method of the forty-second embodiment involves preparing a compound of formula (Ib'),

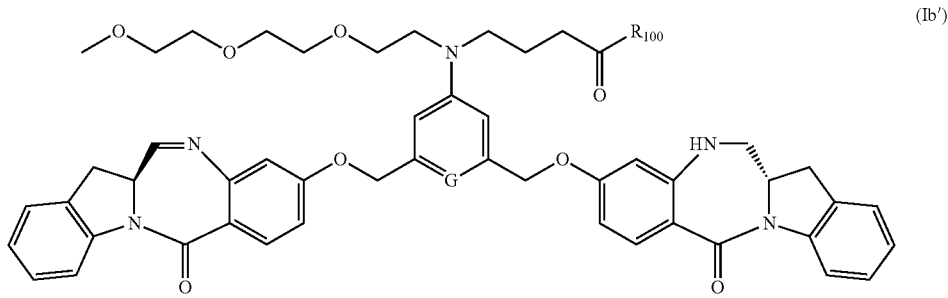

(Ib')

or a pharmaceutically acceptable salt thereof, said method comprising the steps of:

(1) reacting the compound of formula (14b) with a monomer compound of formula (a₁) to form a compound of formula (19b), or a salt thereof;

(2) reacting the compound of formula (19b) with an imine reducing agent to form a compound of formula (17b'), or a salt thereof; and (3) reacting the compound of formula (17b') with a monomer of formula (a₁) to form the compound of formula (Ib').

In another embodiment, the method of the forty-second embodiment involves preparing a compound of formula (Ic'), (1) reacting the compound of formula (14c) with a monomer compound of formula (a₁) to form a compound of formula (19c), or a salt thereof;

(2) reacting the compound of formula (19c) with an imine reducing agent to form a compound of formula (17c'), or a salt thereof; and (3) reacting the compound of formula (17c') with a monomer of formula (a₁) to form the compound of formula (Ic').

In still another embodiment, the method of the forty-second embodiment involves preparing a compound of formula (IA),

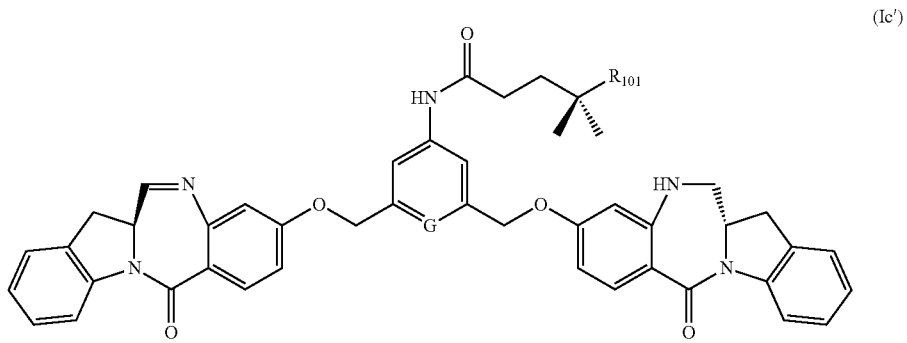

(Ic')

or a pharmaceutically acceptable salt thereof, said method comprising the steps of:

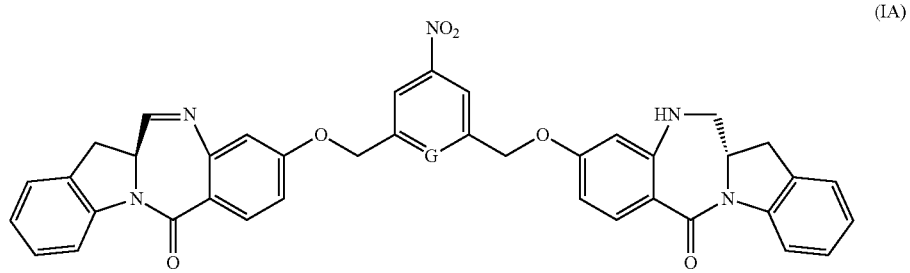

(IA)

or a pharmaceutically acceptable salt thereof, said method comprising the steps of:

(1) reacting the compound of formula (14A) with a monomer compound of formula (a₁) to form a compound of formula (19A), or a salt thereof;

(2) reacting the compound of formula (19A) with an imine reducing agent to form a compound of formula (17A'), or a salt thereof; and (3) reacting the compound of formula (17A') with a monomer of formula (a₁) to form the compound of formula (IA').

The conditions and reagents for the method of forty-second embodiment are as described above in the twenty-eighth, thirty-third and/or thirty-fourth embodiment(s) and any specific embodiments described therein.

In a forty-third embodiment, the present invention provides a method of preparing a compound of formula (I'),

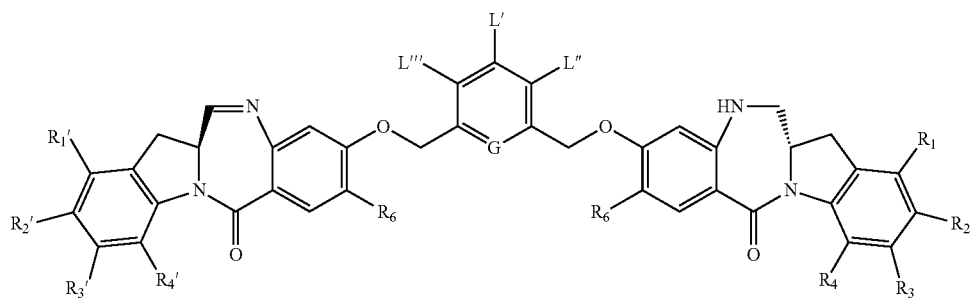

(a)

to form a compound of formula (19):

(I')

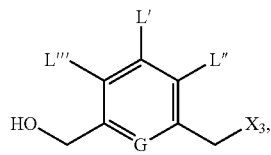

or a pharmaceutically acceptable salt thereof, said method comprising the steps of:

(1) reacting a brominating or iodinating reagent with a compound of formula (14):

(19)

(14)

(3) reacting the compound of formula (19) with an imine reducing agent to form a compound of formula (17'):

or a salt thereof, to form a compound of formula (20):

(17')

(20)

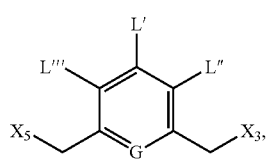

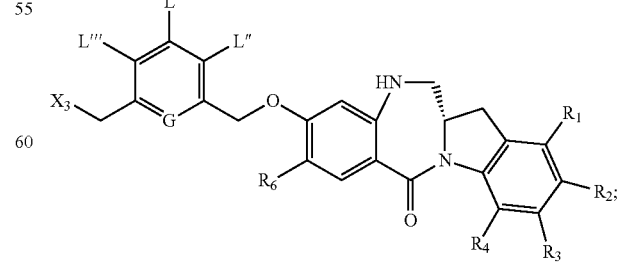

or a salt thereof;

(2) reacting a compound of formula (20) or a salt thereof with a monomer compound of formula (a):

or a salt thereof, and (4) reacting the compound of (17') with a monomer of formula (b):

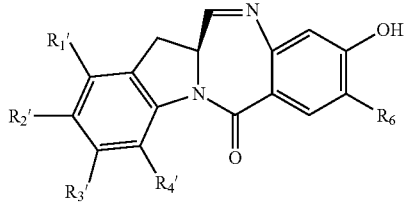
(b)

to form the compound of formula (I'), wherein $X_3$ is —Cl; $X_5$ is —Br or —I; and the remaining variables are the same as described above.

In one embodiment the method of the forty-third embodiment involves preparing a compound of formula (Ib'),

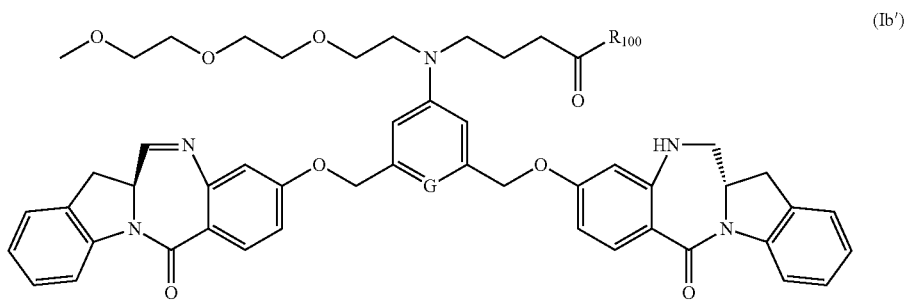
(Ib')

or a pharmaceutically acceptable salt thereof, said method comprising the steps of:

(1) reacting a brominating or iodinating reagent with a compound of formula (14b) or a salt thereof, to form a compound of formula (20b), or a salt thereof;

(2) reacting a compound of formula (20b) or a salt thereof with a monomer compound of formula ($a_1$) to form a compound of formula (19b);

(3) reacting the compound of formula (19b) with an imine reducing agent to form a compound of formula (17b'), or a salt thereof, and (4) reacting the compound of (17b') with a monomer of formula ($a_1$) to form the compound of formula (Ib').

In another embodiment the method of the forty-third embodiment involves preparing a compound of formula (Ic'), or a pharmaceutically acceptable salt thereof, said method comprising the steps of:

(1) reacting a brominating or iodinating reagent with a compound of formula (14c) or a salt thereof, to form a compound of formula (20c), or a salt thereof;

(2) reacting a compound of formula (20c) or a salt thereof with a monomer compound of formula ($a_1$) to form a compound of formula (19c);

(3) reacting the compound of formula (19c) with an imine reducing agent to form a compound of formula (17c'), or a salt thereof, and (4) reacting the compound of (17c') with a monomer of formula ($a_1$) to form the compound of formula (Ic').

In still another embodiment, the method of the forty-third embodiment involves preparing a compound of formula (IA),

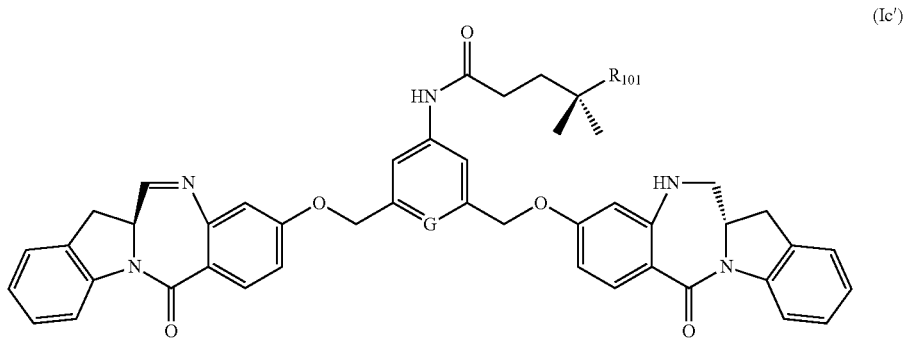
(Ic')

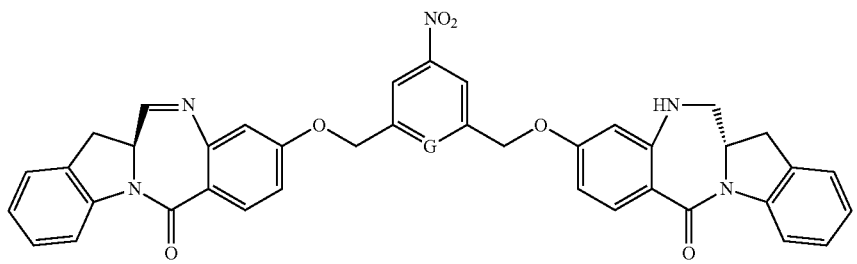

(IA)

or a pharmaceutically acceptable salt thereof, said method comprising the steps of:

(1) reacting a brominating or iodinating reagent with a compound of formula (14A) or a salt thereof, to form a compound of formula (20A), or a salt thereof;

(2) reacting a compound of formula (20A) or a salt thereof with a monomer compound of formula ($a_1$) to form a compound of formula (19A);

(3) reacting the compound of formula (19A) with an imine reducing agent to form a compound of formula (17A'), or a salt thereof, and (4) reacting the compound of (17A') with a monomer of formula ($a_1$) to form the compound of formula (IA').

The conditions and reagents for the method of the forty-third embodiment are as described above in the twenty-fifth, twenty-seventh, thirty-third and/or thirty-fourth embodiment(s) and any specific embodiments described therein.

In one embodiment of any one of the thirty-fifth to forty-third embodiments, the compound of formula (14) or a salt thereof is prepared by a method comprising the steps of:

(1) reacting a chlorinating reagent with a compound of formula (2):

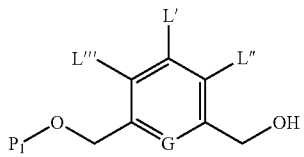

(2)

to form a compound of formula (13):

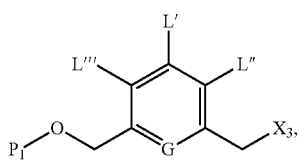

(13)

or a salt thereof; and (2) reacting the compound of formula (13) with an alcohol deprotecting reagent to form the compound of formula (14) or a salt thereof, wherein $X_3$ is —Cl; and $P_1$ is an alcohol protecting group.

In a specific embodiment, the compound of formula (14b) or a salt thereof is prepared by a method comprising the steps of: (1) reacting a chlorinating reagent with a compound of formula (2b) to form a compound of formula (13b) or a salt thereof; and (2) reacting the compound of formula (13b) with an alcohol deprotecting reagent to form the compound of formula (14b) or a salt thereof.

In another specific embodiment, the compound of formula (14c) or a salt thereof is prepared by a method comprising the steps of: (1) reacting a chlorinating reagent with a compound of formula (2c) to form a compound of formula (13c) or a salt thereof; and (2) reacting the compound of formula (13c) with an alcohol deprotecting reagent to form the compound of formula (14c) or a salt thereof.

In yet another specific embodiment, the compound of formula (14A) or a salt thereof is prepared by a method comprising the steps of: (1) reacting a chlorinating reagent with a compound of formula (2A) to form a compound of formula (13A) or a salt thereof; and (2) reacting the compound of formula (13A) with an alcohol deprotecting reagent to form the compound of formula (14A) or a salt thereof.

The conditions and reagents for the method of preparing compound of formula (14), (14b), (14c) or (14A) above are as described above in the twenty-second and/or twenty-third embodiment(s) and any specific embodiments described therein.

In another embodiment, the compound of formula (2) is prepared by reacting a compound of formula (1) with an alcohol protecting reagent

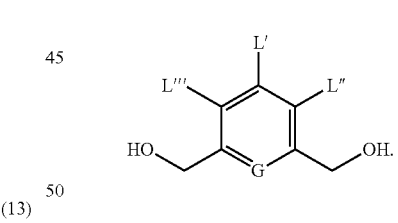

(1)

In a specific embodiment, the compound of formula (2b) is prepared by reacting a compound of formula (1b) with an alcohol protecting reagent.

In another specific embodiment, the compound of formula (2c) is prepared by reacting a compound of formula (Ic) with an alcohol protecting reagent.

In yet another specific embodiment, the compound of formula (2A) is prepared by reacting a compound of formula (1A) with an alcohol protecting reagent.

The conditions and reagents for the method of preparing compound of formula (2), (2b), (2c) or (2A) above are as described above in the first embodiment and any specific embodiments described therein.

In a forty-fourth embodiment, the present invention provides a method of preparing a compound formula (IB)

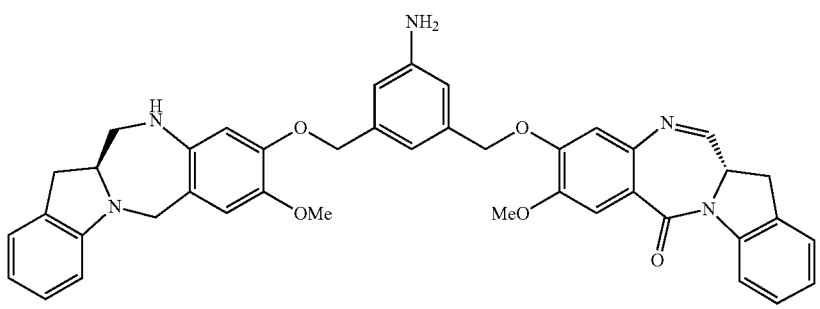

(IB)

or a pharmaceutically acceptable salt thereof, comprising the step of reacting the compound of formula (IA) with a reducing agent. Any suitable reducing agent can be used. In one embodiment, the reducing agent is selected from the group consisting of: hydrogen gas, sodium hydrosulfite, sodium sulfide, stanneous chloride, titanium (II) chloride, zinc, iron and samarium iodide. In a specific embodiment, the reducing agent is Fe/NH$_4$Cl or Zn/NH$_4$Cl.

In one embodiment, the compound of formula (Ic') can be prepared by reacting the compound of formula (IB) with a compound of formula (Lc'):

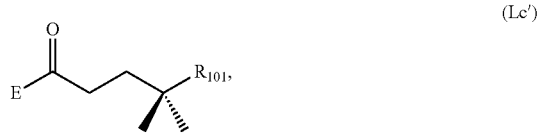

(Lc')

wherein E is —OH, halide or —C(=O)E is an activated ester; and R$_{100}$ is (C$_1$-C$_3$)alkoxy In a specific embodiment, E is —OH and the reaction of the compound of formula (IB) and the compound of formula (Lc') is carried out in the presence of an activating agent.

In one embodiment, the activating agent is a carbodiimide, a uronium, an active ester, a phosphonium, 2-alkyl-1-alkylcarbonyl-1,2-dihydroquinoline, 2-alkoxy-1-alkoxycarbonyl-1,2-dihydroquinoline, or alkylchloroformate. In a specific embodiment, the activating agent is a carbodiimide. In a more specific embodiment, the activating agent is dicyclohexylcarbodiimide (DCC), 1-ethyl-3-(3-dimethylaminopropyl)carbodiimide (EDC), or diisopropylcarbodiimide (DIC). In another specific embodiment, the activating agent is N-ethoxycarbonyl-2-ethoxy-1,2-dihydroquinoline.

In one embodiment, for methods described above, R$_{100}$ is methoxy and R$_{101}$ is methyl.

The method of the present invention can also be any combination of the methods described above (e.g., methods in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-forth, thirty-fifth, thirty-sixth, thirty-seventh, thirty-eighth, thirty-ninth, fortieth, forty-first, forty-second, or forty-third embodiment). For example, the combination of the methods of the first and second embodiments, the combination of methods of the first, second, and third embodiments, the combination of the methods of the fourth and fifth embodiments, the combination of the methods of the fourth, fifth and sixth embodiments, the combination of the methods of the sixth and eighth embodiments, the combination of the methods of thirteenth and fourteenth embodiments, the combination of the methods of thirteenth, fourteenth and fifteenth embodiments, and the combination of the methods of the seventeenth and eighteenth embodiments are also included in the present invention. The variable definitions described in any of the specific embodiments below also apply to any combination of methods described above.

The reactions described herein in the methods of the present invention can be carried out in any suitable solvent(s). In one embodiment, the solvent is an organic solvent. Exemplary organic solvents include, but are not limited to, dichloromethane, dichloroethane, DMF, DMA, acetone, acetonitrile, THF, DMSO, ethyl acetate etc., or a combination thereof.

The reactions described herein in the methods of the present invention can be carried out at any suitable temperature. In one embodiment, the reaction can be carried out at room temperature. In another embodiment, the reaction can carried out at a low temperature, such as 0° C. In yet another embodiment, the reaction can be carried out at an elevated temperature, such as about 40° C., about 50° C. etc.

In a 1$^{st}$ specific embodiment, for methods in the first, second, third, fourth, fifth, sixth, seventh, eighth, ninth, tenth, eleventh, twelfth, thirteenth, fourteenth, fifteenth, sixteenth, seventeenth, eighteenth, nineteenth embodiment, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-forth, thirty-fifth, thirty-sixth, thirty-seventh, thirty-eighth, thirty-ninth, fortieth, forty-first, forty-second, or forty-third embodiment, one of L', L", and L'" is represented by the following formula:

$$-Z_1-P-Z_2-R_x-J \qquad (A)$$

and the other two are the same or different, and are independently selected from —H, an optionally substituted linear, branched or cyclic alkyl, alkenyl or alkynyl having from 1 to 10 carbon atoms, a polyethylene glycol unit —(CH$_2$CH$_2$O)$_n$—R$_c$, halogen, guanidinium [—NH(C=NH)NH$_2$], —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R"; wherein:

one of the Z$_1$ and Z$_2$ is —C(=O)—, and the other is —NR$_5$—;

P is an amino acid residue or a peptide containing between 2 to 20 amino acid residues;

J is a moiety comprising a reactive group that is capable of covalently linking the cytotoxic compound to a cell-binding agent; $R_x$ is an optionally substituted linear, branched or cyclic alkyl, alkenyl or alkynyl having from 1 to 10 carbon atoms; and $R_5$ is —H or an optionally substituted linear or branched alkyl having 1 to 10 carbon atoms.

In a more specific embodiment, one of L', L" and L'" is represented by formula (A), and the others are each independently —H, an linear or branched alkyl having from 1 to 6 carbon atoms, halogen, —OH, $(C_1-C_6)$alkoxy, or —NO$_2$.

In another more specific embodiment, one of L', L" and L'" is represented by formula (A), and the others are —H.

In yet another more specific embodiment, L' is represented by formula (A); and L" and L'" are both —H.

In another more specific embodiment, for formula (A), $R_x$ is a linear, branched or cyclic alkyl having 1 to 6 carbon atoms optionally substituted with halogen, —OH, $(C_1-C_3)$ alkyl, $(C_1-C_3)$alkoxy, halo$(C_1-C_3)$alkyl, or a charged substituent or an ionizable group Q.

In more specific embodiment, J is NHR$^{c1}$, —COOR$^{c1}$ or —COE, wherein —COE represents a reactive ester, and R$^{c1}$ is —H or linear or branched alkyl having 1 to 4 carbon atoms optionally substituted with halogen, —OH or $(C_1-C_3)$ alkoxy. Even more specifically, J is —COOR$^{c1}$ and R$^{c1}$ is a $(C_1-C_3)$alkyl.

In a 2$^{nd}$ specific embodiment, for methods in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-forth, thirty-fifth, thirty-sixth, thirty-seventh, thirty-eighth, thirty-ninth, fortieth, forty-first, forty-second, or forty-third embodiment or the 1$^{st}$ specific embodiment, L' is represented by the following formula:

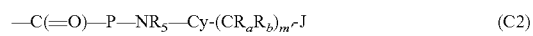
(B1);

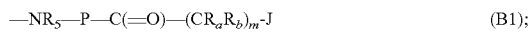
(B2);

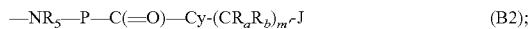
(C1), or

(C2)

wherein:

J is —COOR$^{c1}$;

R$^{c1}$ is —H or linear or branched alkyl having 1 to 4 carbon atoms optionally substituted with halogen, —OH or $(C_1-C_3)$ alkoxy;

$R_a$ and $R_b$, for each occurrence, are each independently —H, $(C_1-C_3)$alkyl or a charged substituent or an ionizable group Q;

m is an integer from 1 to 6;

m' is 0 or an integer from 1 to 6; and,

Cy is a cyclic alkyl having 5 or 6 ring carbon atoms optionally substituted with halogen, —OH, $(C_1-C_3)$alkyl, $(C_1-C_3)$alkoxy, or halo$(C_1-C_3)$alkyl.

In a more specific embodiment, $R_a$ and $R_b$ are both H; Cy is cyclohexane; and $R_5$ is H or Me.

In another more specific embodiment, m' is 0 or 1.

In a 3$^{rd}$ specific embodiment, for methods in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-forth, thirty-fifth, thirty-sixth, thirty-seventh, thirty-eighth, thirty-ninth, fortieth, forty-first, forty-second, or forty-third embodiment or the 1$^{st}$ specific embodiment, L' is represented by the following formula:

(B3); or

—C(=O)—P—NR$_5$—(CR$_a$R$_b$)$_m$—S—Z$^s$ (C3), wherein:

$R_a$ and $R_b$, for each occurrence, are each independently —H, $(C_1-C_3)$alkyl or a charged substituent or an ionizable group Q;

m is an integer from 1 to 6;

Z$^s$ is —H, —SR$^d$, —C(=O)R$^{d1}$ or is selected from any one of the following formulas:

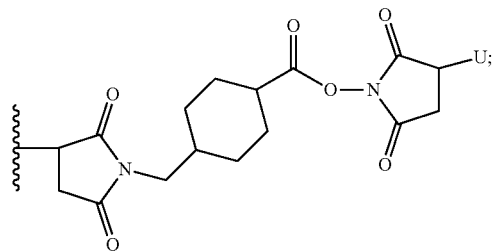
(a1)

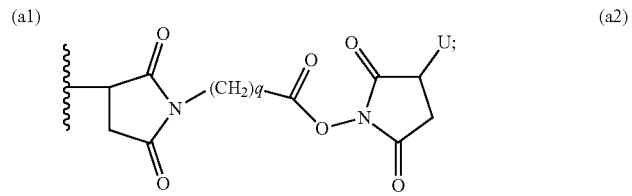
(a2)

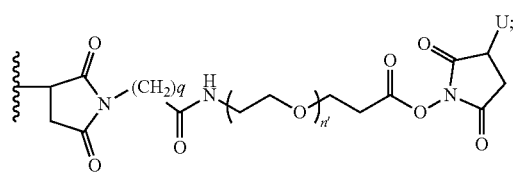
(a3)

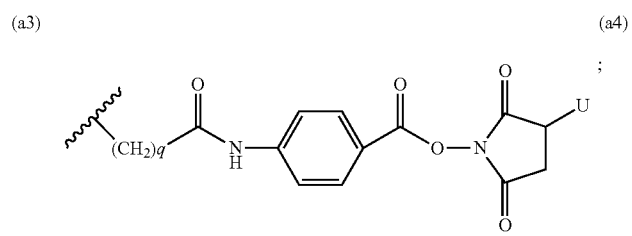
(a4)

-continued

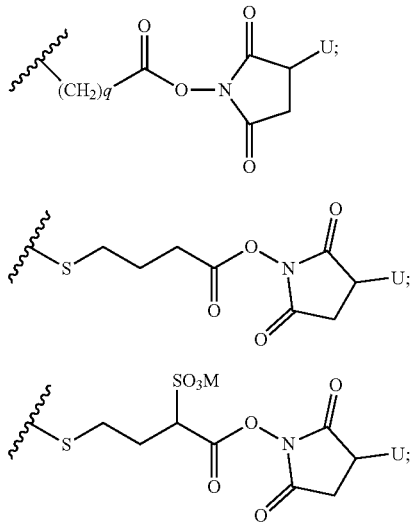

(a5)

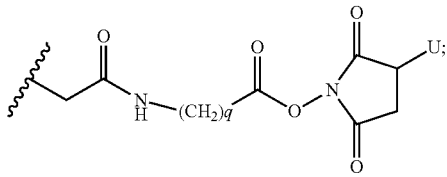

(a6)

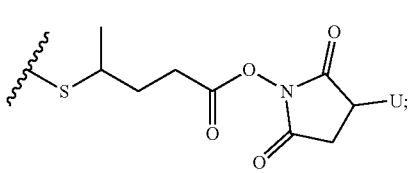

(a7)

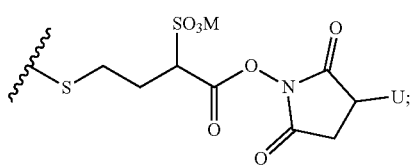

(a8)

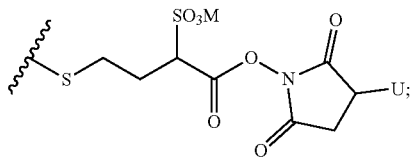

(a9)

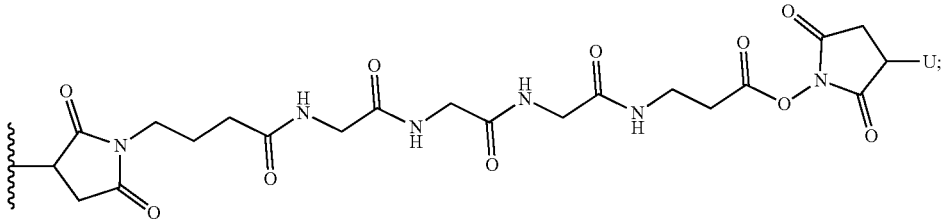

(a10)

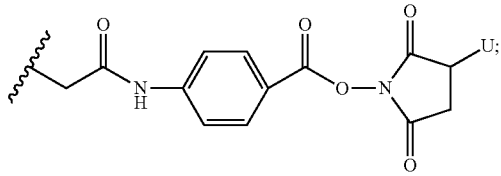

(a11)

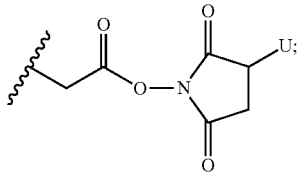

(a12)

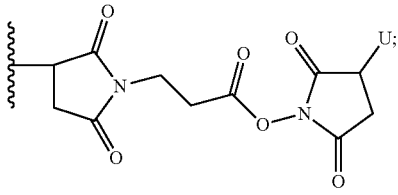

(a13)

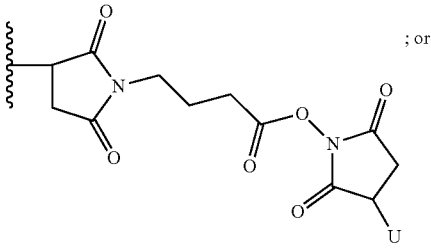

(a14)

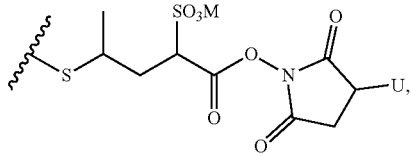

(a15)

wherein:
q is an integer from 1 to 5;
n' is an integer from 2 to 6;
U is —H or $SO_3M$;
M is $H^+$, $Na^+$ or $K^+$;
$R^d$ is a linear or branched alkyl having 1 to 6 carbon atoms or is selected from phenyl, nitrophenyl (e.g., 2 or 4-nitrophenyl), dinitrophenyl (e.g., 2,4-dinitrophenyl), carboxynitrophenyl (e.g., 3-carboxy-4-nitrophenyl), pyridyl or nitropyridyl (e.g., 4-nitropyridyl); and $R^{d1}$ is a linear or branched alkyl having 1 to 6 carbon atoms In a more specific embodiment, $Z^s$ is —$SR^d$ and $R^d$ is a $(C_1$-$C_3)$alkyl, pyridyl or nitropyridyl (e.g., 4-nitropyridyl).

In a more specific embodiment, the charged substituent or an ionizable group Q is i) —$SO_3H$, —Z'—$SO_3H$, —$OPO_3H_2$, —Z'—$OPO_3H_2$, —$PO_3H_2$, —Z'—$PO_3H_2$, —$CO_2H$, —Z'—$CO_2H$, —$NR_{11}R_{12}$, or —Z'—$NR_{11}R_{12}$, or a pharmaceutically acceptable salt thereof; or, ii) —$N^+R_{14}R_{15}R_{16}X^{4-}$ or —Z'—$N^+R_{14}R_{15}R_{16}X^{4-}$; Z' is an optionally substituted alkylene, an optionally substituted cycloalkylene or an optionally substituted phenylene; $R_{11}$, $R_{12}$, $R_{14}$ to $R_{16}$ are each independently H or an optionally substituted alkyl; and $X^{A-}$ is a pharmaceutically acceptable anion. Even more specifically, Q is $SO_3H$ or a pharmaceutically acceptable salt thereof.

In another more specific embodiment, $R_a$ and $R_b$ are both —H and $R_5$ is H or Me.

In yet another more specific embodiment, —$(CR_aR_b)_m$— is —$(CH_2)_{m''}$—$C(Me_2)$- and m" is an integer from 1 to 5.

In a $4^{th}$ specific embodiment, for formula (B1), (B2), (B3), (C1), (C2) or (C3), P is a peptide containing 2 to 10 amino acid residues; and the remaining variables are as described above in the $2^{nd}$ or $3^{rd}$ specific embodiment or any more specific embodiments described therein.

In a more specific embodiment, P is a peptide containing 2 to 5 amino acid residues.

In another more specific embodiment, P is Gly-Gly-Gly, Ala-Val, Val-Ala, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu, β-Ala-Leu-Ala-Leu and Gly-Phe-Leu-Gly, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, or Met-Ala. Even more specifically, P is Gly-Gly-Gly, Ala-Val, Ala-Ala, Ala-D-Ala, D-Ala-Ala, or D-Ala-D-Ala.

In a $5^{th}$ specific embodiment, for methods in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-forth, thirty-fifth, thirty-sixth, thirty-seventh, thirty-eighth, thirty-ninth, fortieth, forty-first, forty-second, and forty-third embodiments, L' is represented by the following formula:

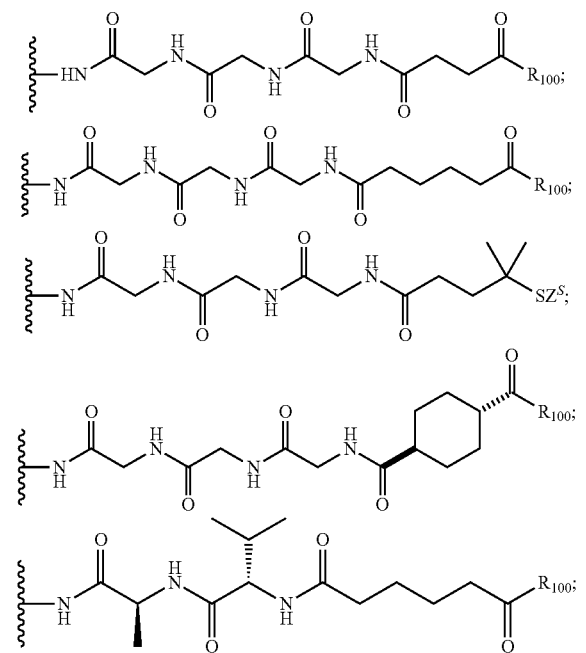

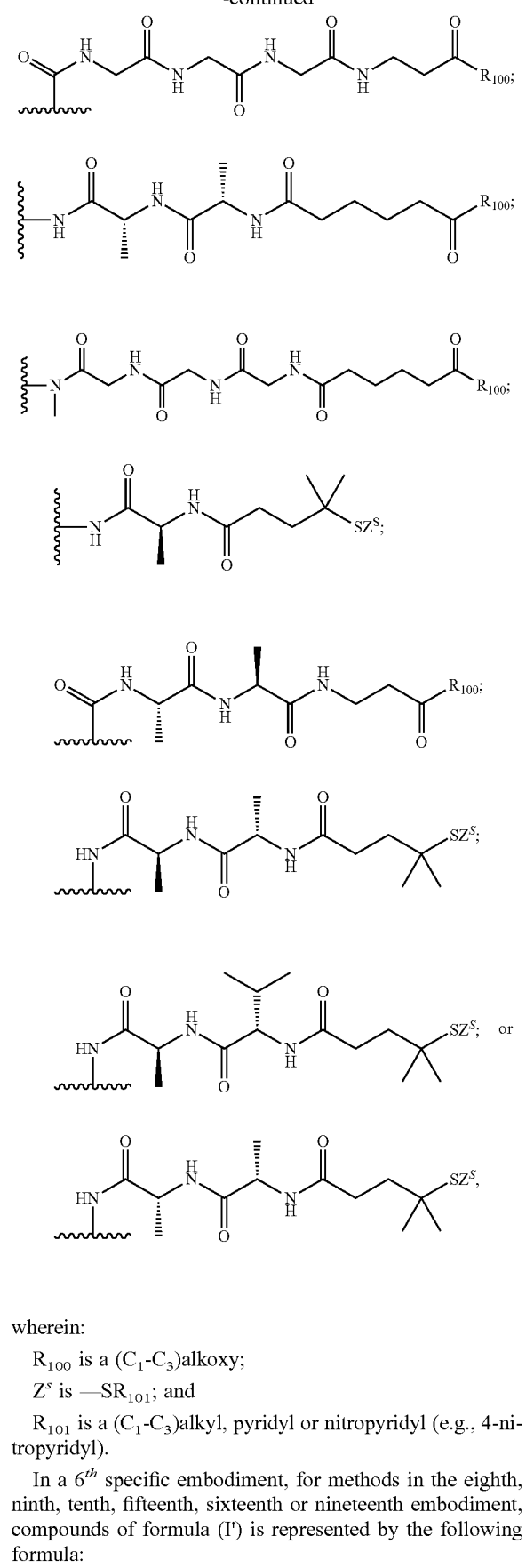

wherein:

$R_{100}$ is a $(C_1-C_3)$alkoxy;

$Z^s$ is —$SR_{101}$; and $R_{101}$ is a $(C_1-C_3)$alkyl, pyridyl or nitropyridyl (e.g., 4-nitropyridyl).

In a $6^{th}$ specific embodiment, for methods in the eighth, ninth, tenth, fifteenth, sixteenth or nineteenth embodiment, compounds of formula (I') is represented by the following formula:

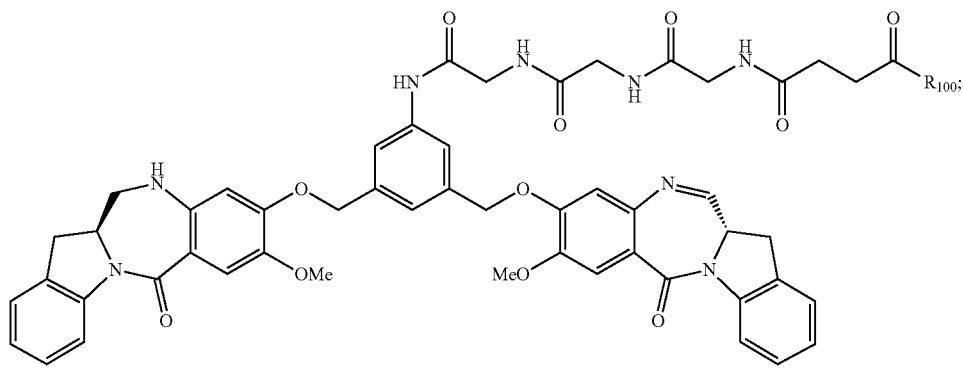
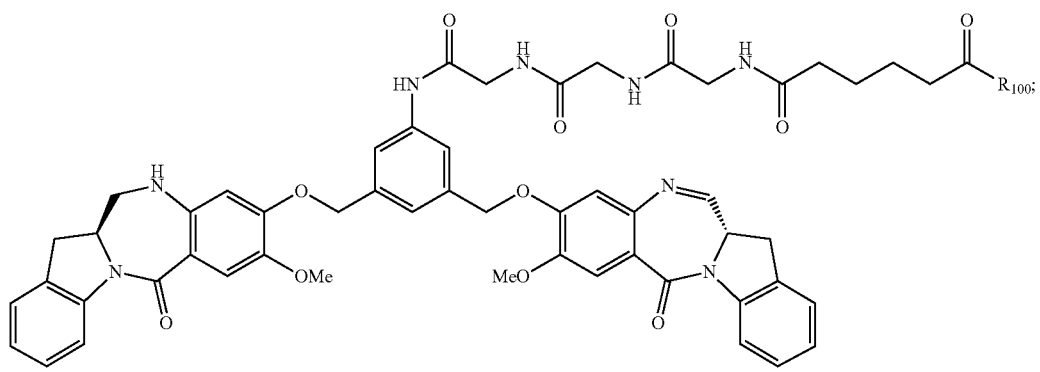
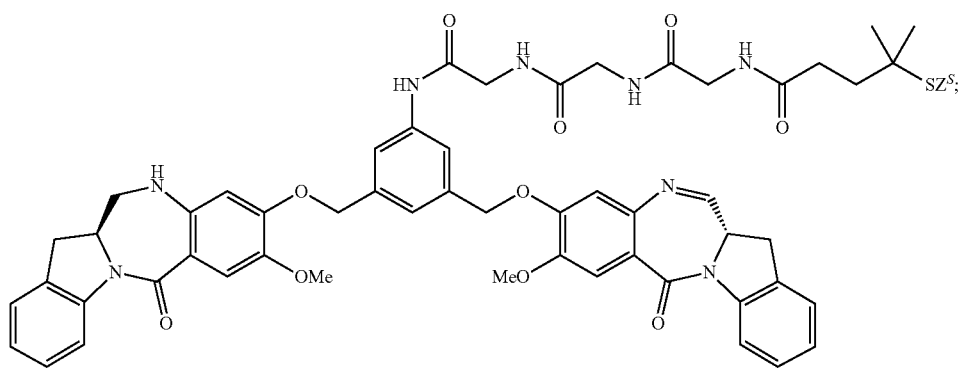
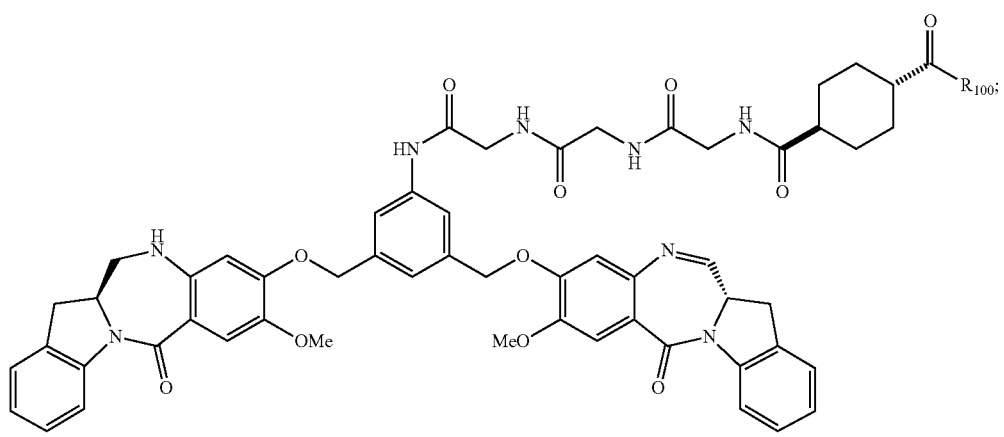

-continued
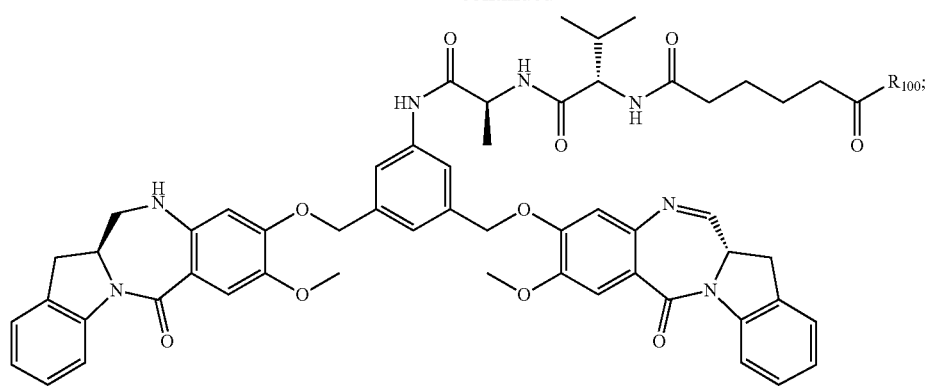
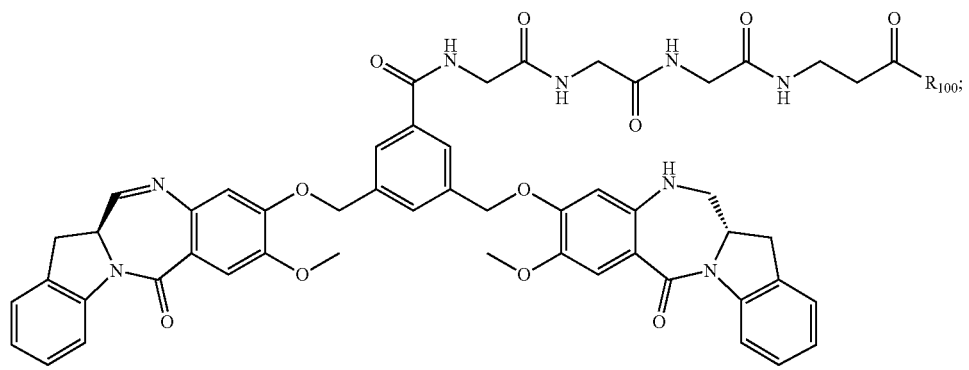
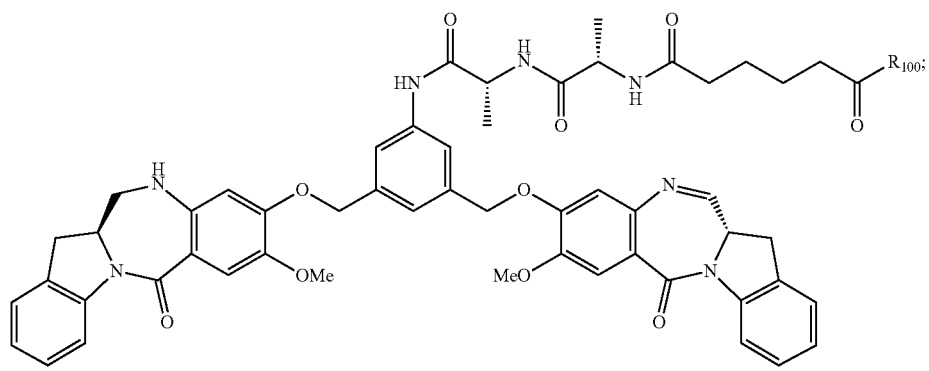
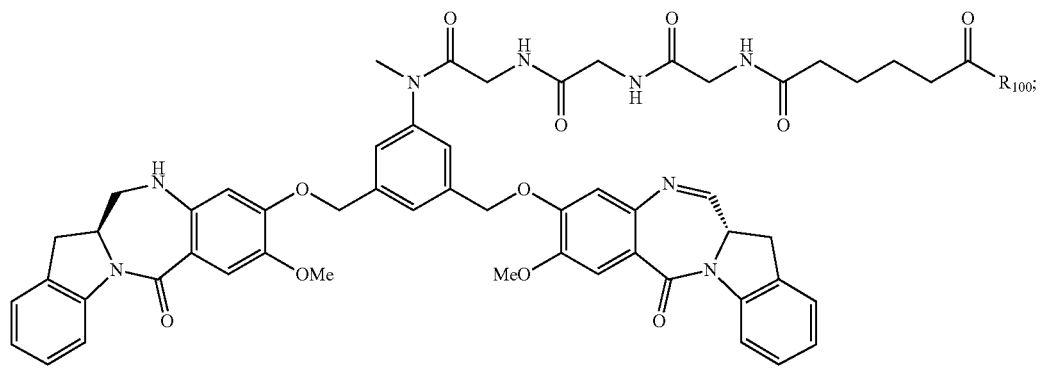

-continued
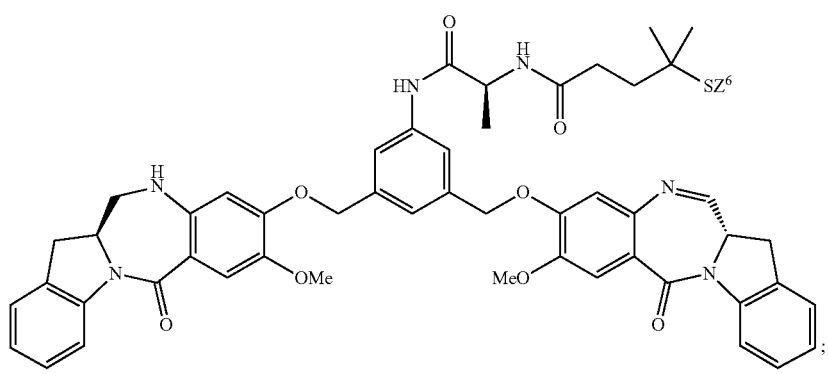
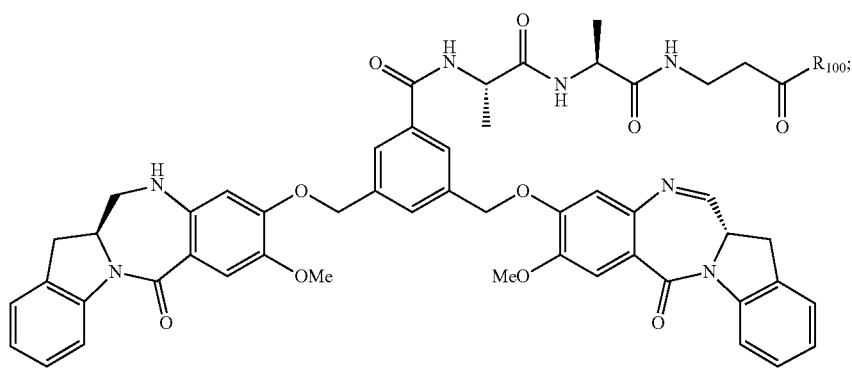
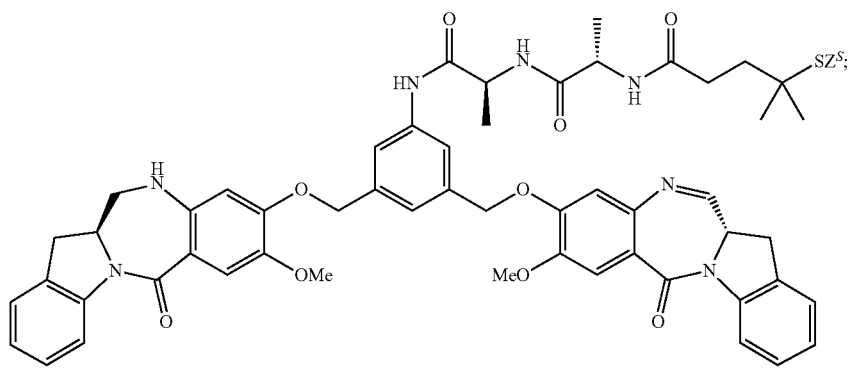
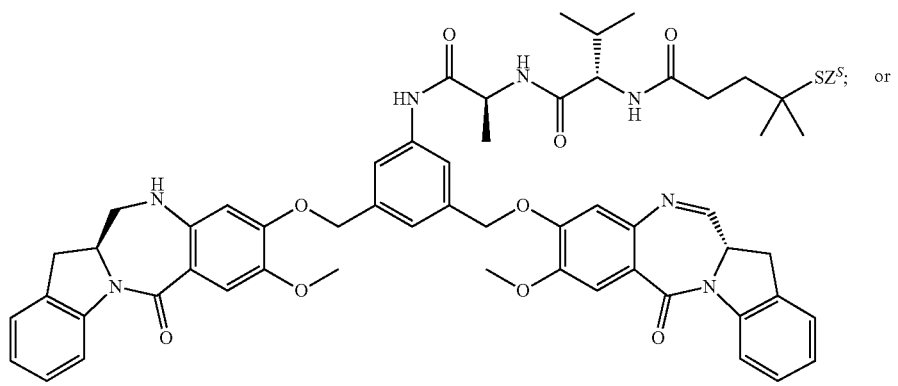

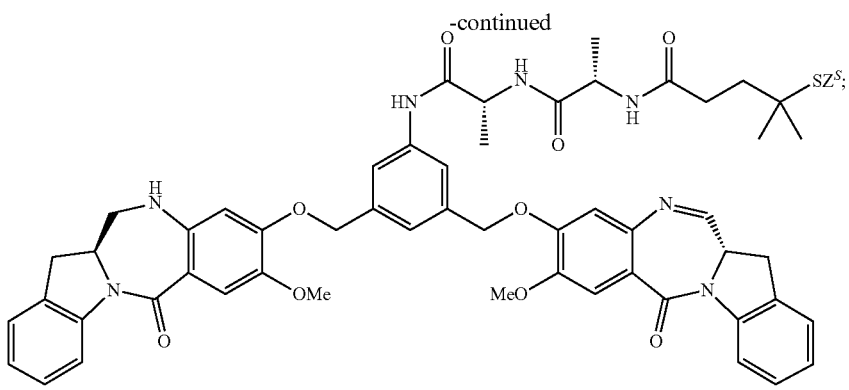

or a pharmaceutically acceptable salt thereof, wherein:

$R_{100}$ is a ($C_1$-$C_3$)alkoxy;

$Z^s$ is —$SR_{101}$; and $R_{101}$ is a ($C_1$-$C_3$)alkyl, pyridyl or nitropyridyl (e.g., 4-nitropyridyl).

In a 7th specific embodiment, for methods described in the 5th or 6th specific embodiment, $R_{100}$ is —OMe and $R_{101}$ is Me or pyridyl.

In a 8th specific embodiment, for methods in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth embodiment, thirtieth, thirty-first, thirty-second, thirty-third, thirty-forth, thirty-fifth, thirty-sixth, thirty-seventh, thirty-eighth, thirty-ninth, fortieth, forty-first, forty-second, and forty-third one of L', L", and L''' is represented by the following formula:

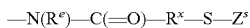

—N($R^e$)—C(=O)—$R^x$—S—$Z^s$ (B);

wherein:

$R^x$ is a linear or branched alkylene having 1 to 6 carbon atoms, optionally substituted with a charged substituent or an ionizable group Q;

Q is i) —$SO_3H$, —Z'—$SO_3H$, —$OPO_3H_2$, —Z'—$OPO_3H_2$, —$PO_3H_2$, —Z'—$PO_3H_2$, —$CO_2H$, —Z'—$CO_2H$, —$NR_{11}R_{12}$, or —Z'—$NR_{11}R_{12}$, or a pharmaceutically acceptable salt thereof; or, ii) —$N^+R_{14}R_{15}R_{16}X^{4-}$ or —Z'—$N^+R_{14}R_{15}R_{16}X^{4-}$; Z' is an optionally substituted alkylene, an optionally substituted cycloalkylene or an optionally substituted phenylene; $R_{11}$, $R_{12}$, $R_{14}$, $R_{15}$ and $R_{16}$ are each independently H or an optionally substituted alkyl; and $X^{4-}$ is a pharmaceutically acceptable anion;

$R^c$ is —H or a linear or branched alkyl having 1 to 6 carbon atoms;

$Z^s$ is —H, —$SR^d$, —C(=O)$R^{d1}$ or is selected from any one of the following formulas:

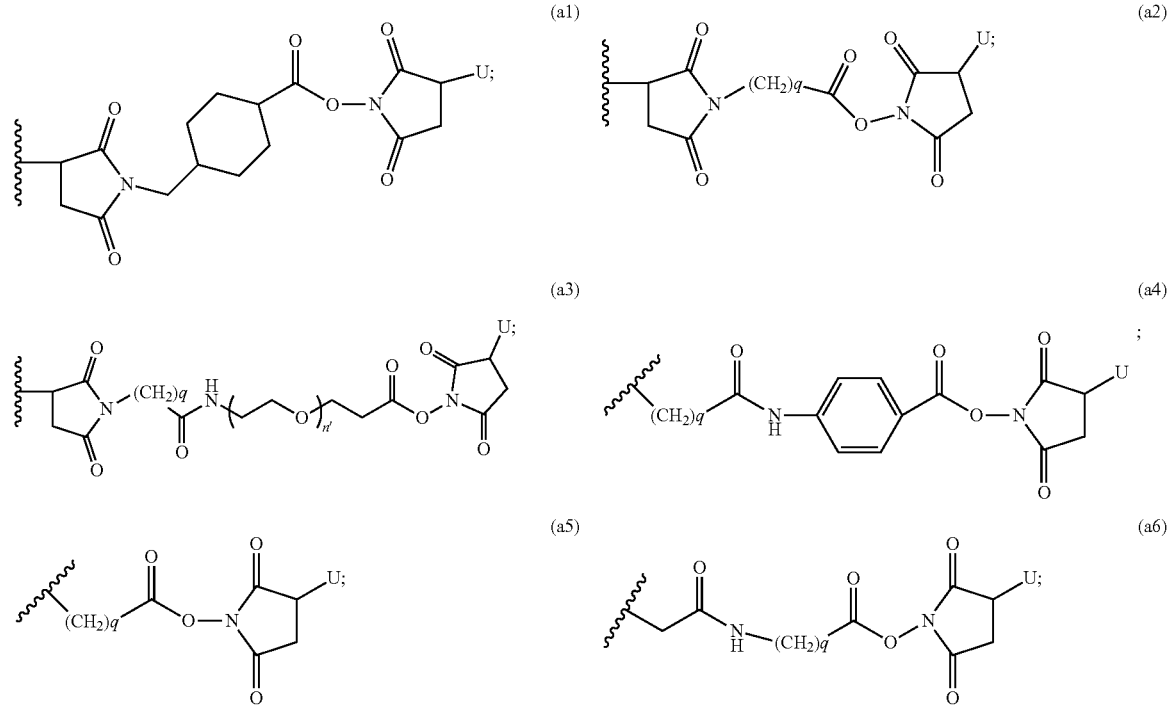

-continued

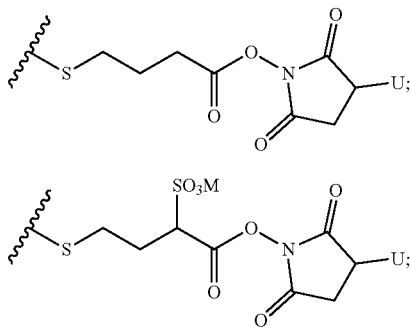

(a7)

(a8)

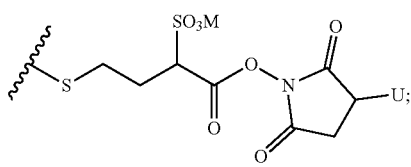

(a9)

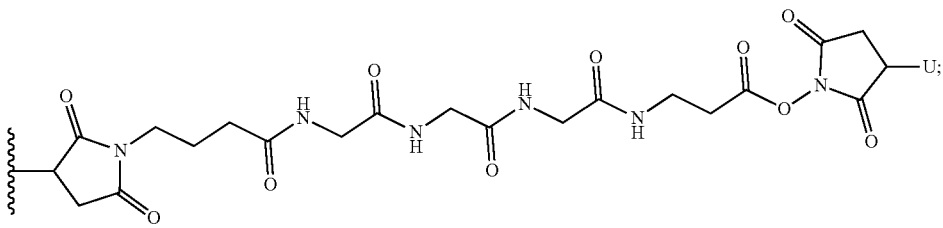

(a10)

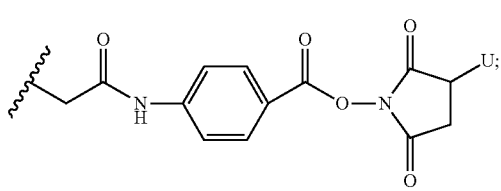

(a11)

(a12)

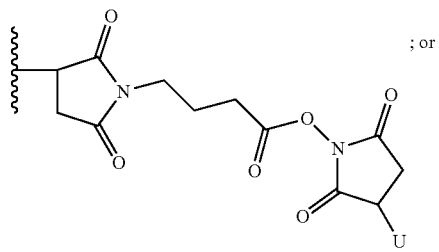

(a13)

(a14)

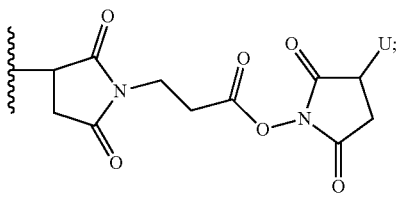

; or

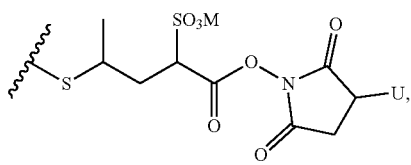

(a15)

wherein:

q is an integer from 1 to 5;

$R^d$ is a linear or branched alkyl having 1 to 6 carbon atoms or is selected from phenyl, nitrophenyl, dinitrophenyl, carboxynitrophenyl, pyridyl and nitropyridyl;

$R^{d1}$ is a linear or branched alkyl having 1 to 6 carbon atoms;

n'' is an integer from 2 to 6;

U is —H or —SO$_3$M; and

M is —H or a cation.

In a more specific embodiment, one of L', L'' and L''' is represented by formula (B), and the others are each independently —H, an linear or branched alkyl having from 1 to 6 carbon atoms, halogen, —OH, (C$_1$-C$_6$)alkoxy, or —NO$_2$.

In another more specific embodiment, one of L', L'' and L''' is represented by formula (B), and the others are —H.

In another more specific embodiment, L' is represented by formula (B); and L'' and L''' are both —H.

In another more specific embodiment, for formula (B), $Z^s$ is —SR$^d$ and R$^d$ is a (C$_1$-C$_3$)alkyl, pyridyl or nitropyridyl (e.g., 4-nitropyridyl).

In a 9$^{th}$ specific embodiment, for formula (B), R$^x$ is —(CH$_2$)$_p$—(CR$^f$R$^g$)—, wherein R$^f$ and R$^g$ are each independently selected from —H or a linear or branched alkyl having 1 to 4 carbon atoms; and p is 0, 1, 2 or 3; and the remaining variables are as described in the 8$^{th}$ specific embodiment or any more specific embodiments described therein.

In a more specific embodiment, R$^f$ and R$^g$ are the same or different, and are selected from —H and -Me.

In another more specific embodiment, R$^f$ and R$^g$ are both -Me; and p is 2.

In a 10th specific embodiment, for formula (B), $R^x$ is a linear or branched alkylene having 1 to 4 carbon atoms substituted with a charged substituent or an ionizable group Q; and the remaining variables are as described in the 8th specific embodiment or any more specific embodiments described therein.

In a more specific embodiment, the charged substituent or an ionizable group Q is: i) —$SO_3H$, —Z'—$SO_3H$, —$OPO_3H_2$, —Z'—$OPO_3H_2$, —$PO_3H_2$, —Z'—$PO_3H_2$, —$CO_2H$, —Z'—$CO_2H$, —$NR_{11}R_{12}$, or —Z'—$NR_{11}R_{12}$, or a pharmaceutically acceptable salt thereof; or, ii) —$N^+R_{14}R_{15}R_{16}X^{A-}$ or —Z'—$N^+R_{14}R_{15}R_{16}X^{A-}$; Z' is an optionally substituted alkylene, an optionally substituted cycloalkylene or an optionally substituted phenylene; $R_{11}$, $R_{12}$, $R_{14}$ to $R_{16}$ are each independently H or an optionally substituted alkyl; and $X^{A-}$ is a pharmaceutically acceptable anion. More specifically, Q is —$SO_3H$ or a pharmaceutically acceptable salt thereof.

In a 11th specific embodiment, $R^e$ is —H or -Me; and the remaining variables as described in the 9th or 10th specific embodiment or any more specific embodiments described therein In a 12th specific embodiment, for methods in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-forth, thirty-fifth, thirty-sixth, thirty-seventh, thirty-eighth, thirty-ninth, fortieth, forty-first, forty-second, or forty-third embodiment, L' is represented by the following formula:

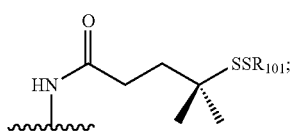

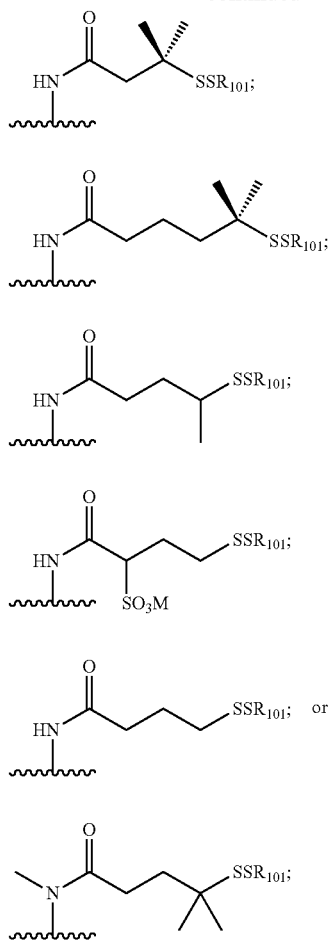

wherein $R_{101}$ is a ($C_1$-$C_3$)alkyl, pyridyl or nitropyridyl (e.g., 4-nitropyridyl); and M is $H^+$, $Na^+$ or $K^+$.

In a 13th specific embodiment, for methods in the eighth, tenth, fourteenth, fifteenth, nineteenth, twentieth, twenty-first, forty-first, forty-second, and forty-third embodiments, the compound of formula (I') is represented by any one of the following:

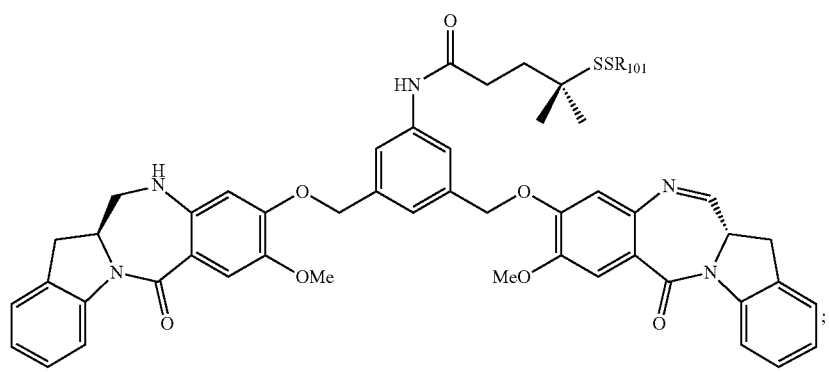

-continued
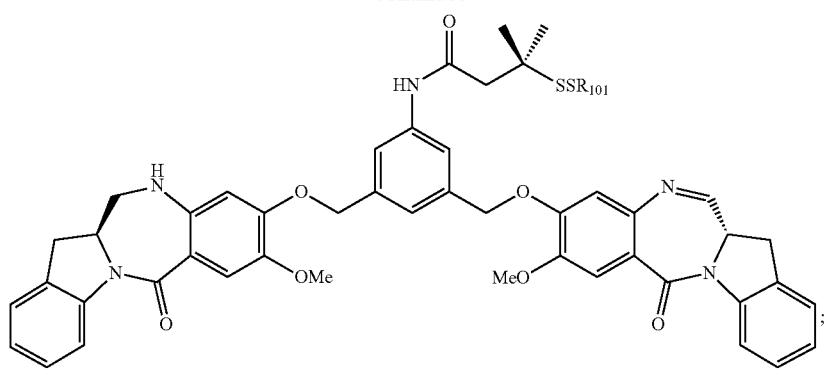
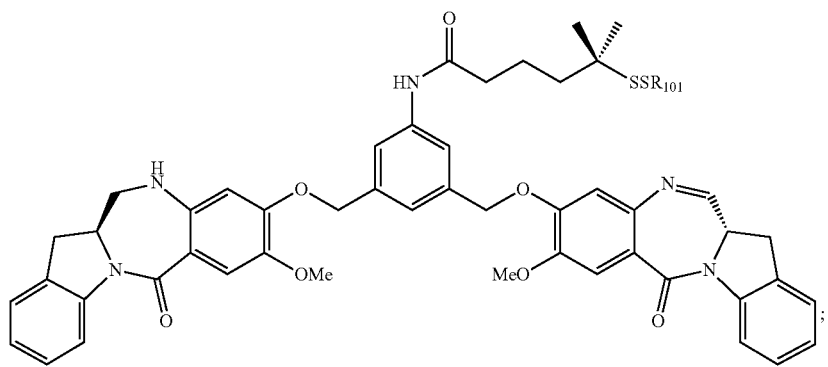
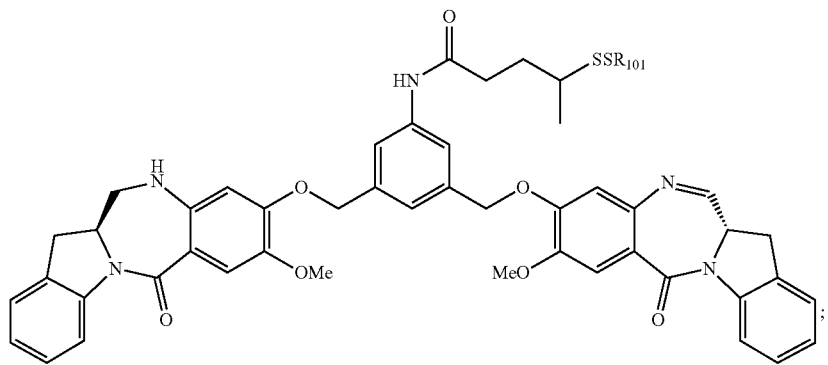
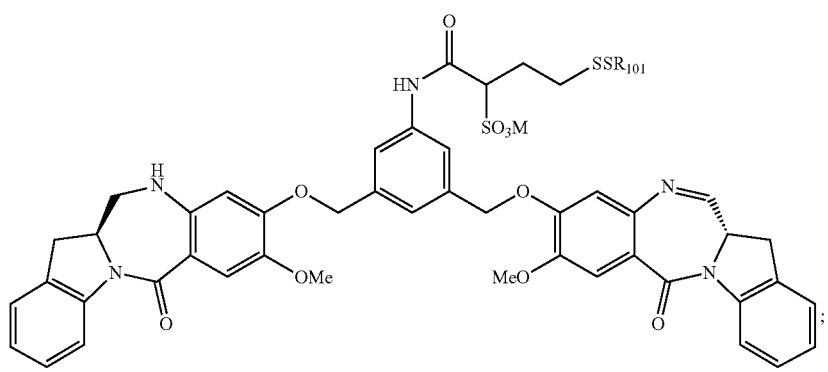

-continued

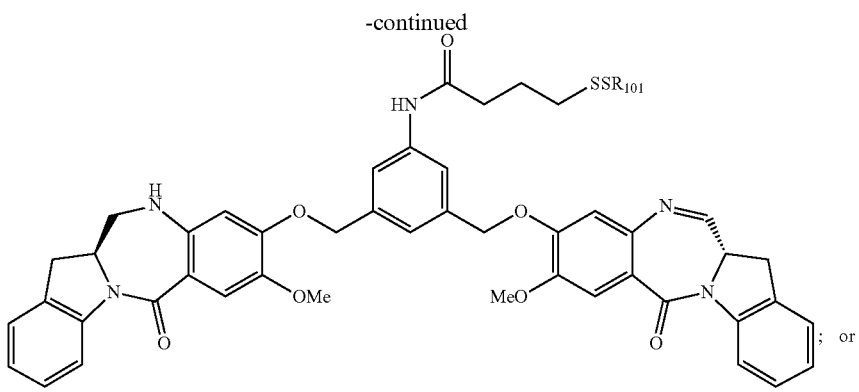

; or

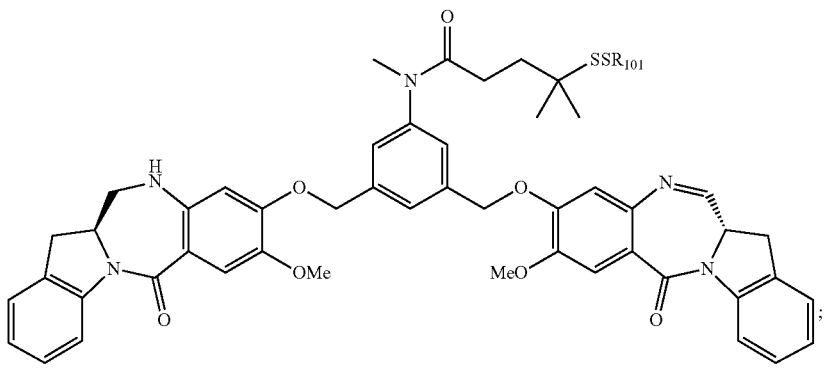

;

or a pharmaceutically acceptable salt thereof, wherein $R_{101}$ is a $(C_1-C_3)$alkyl, pyridyl or nitropyridyl (e.g., 4-nitropyridyl); and M is $H^+$, $Na^+$ or $K^+$.

In a $14^{th}$ specific embodiment, for methods described in the $12^{th}$ or $13^{th}$ specific embodiment, $R_{101}$ is methyl.

In a $15^{th}$ specific embodiment, for methods in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-forth, thirty-fifth, thirty-sixth, thirty-seventh, thirty-eighth, thirty-ninth, fortieth, forty-first, forty-second, or forty-third embodiments, one of L', L", and L'" is represented by the following formula:

$$—W'—R^x—S—Z^s \quad (C);$$

wherein:

W' is $—N(R^e)—$;

$R^e$ is $—H$, a linear, branched or cyclic alkyl, alkenyl or alkynyl having 1 to 10 carbon atoms or $—(CH_2—CH_2—O)_n—R^k$, wherein $R^k$ is a $—H$, a linear, branched cyclic alkyl having 1 to 6 carbon atoms, optionally bearing a secondary amino (e.g., $—NHR^{101}$) or tertiary amino ($—NR^{101}R^{102}$) group or a 5- or 6-membered nitrogen containing heterocycle, such as piperidine or morpholine, wherein $R^{101}$ and $R^{102}$ are each independently a linear, branched, or cyclic alkyl, alkenyl or alkynyl having 1 to 10 carbon atoms;

$R^x$ is a linear, branched or cyclic alkyl having 1 to 10 carbon atoms;

$Z^s$ is $—H$, $—SR^d$, $—C(=O)R^{d1}$ or is selected from any one of the following formulas:

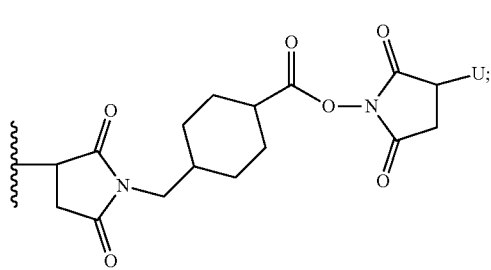
(a1)

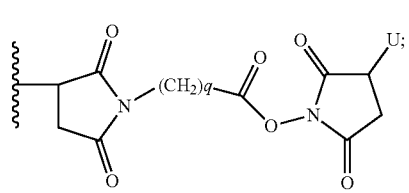
(a2)

-continued
(a3)
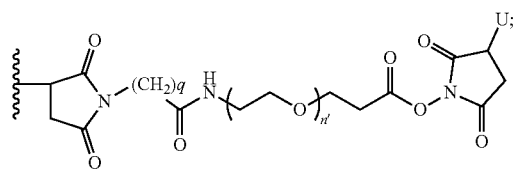
(a4)
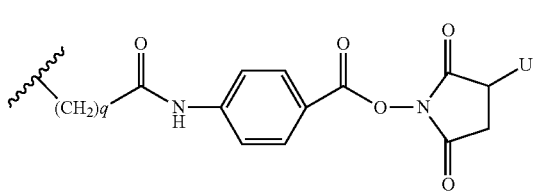
(a5)
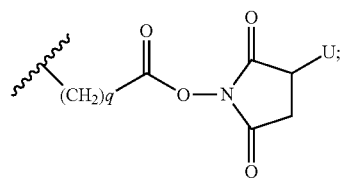
(a6)
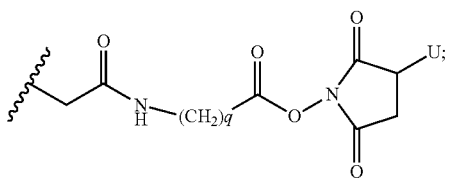
(a7)
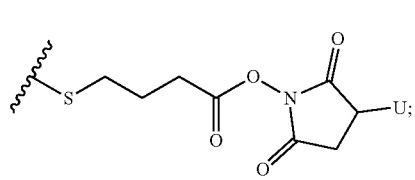
(a8)
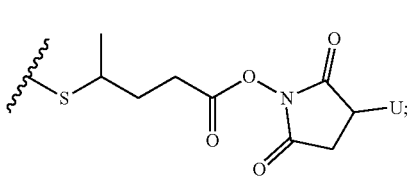
(a9)
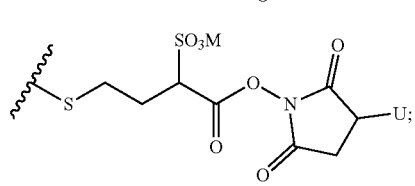
(a10)
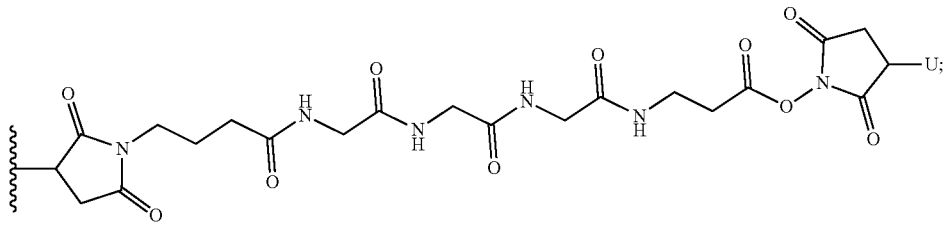
(a11)
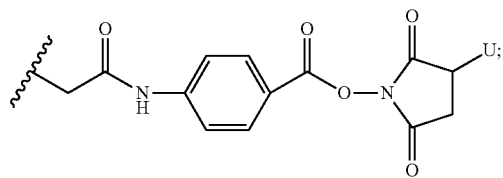
(a12)
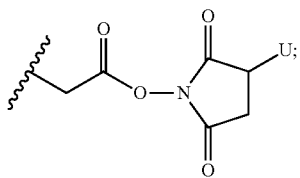
(a13)
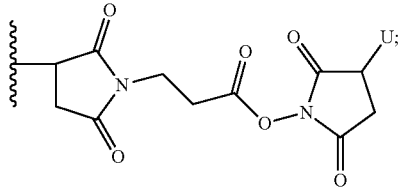
(a14)
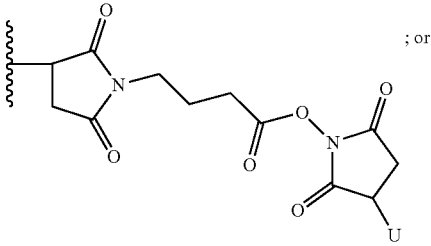
; or
(a15)
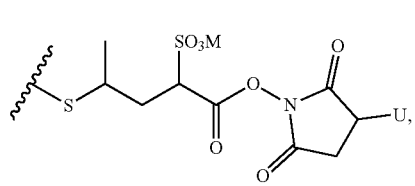

wherein:

$R^d$ is a linear or branched alkyl having 1 to 6 carbon atoms or is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl);

$R^{d1}$ is a linear or branched alkyl having 1 to 6 carbon atoms;

q is an integer from 1 to 5;

n is an integer from 2 to 6;

n' is an integer from 1 to 24;

U is —H or —SO$_3$M; and

M is —H or a cation, such as Na$^+$ or K$^+$.

In a more specific embodiment, one of L', L" and L''' is represented by formula (C), and the others are each independently —H, an linear or branched alkyl having from 1 to 6 carbon atoms, halogen, —OH, (C$_1$-C$_6$)alkoxy, or —NO$_2$.

In another more specific embodiment, one of L', L" and L''' is represented by formula (C), and the others are —H.

In yet another more specific embodiment, L' is represented by formula (C); and L" and L''' are both —H.

In another more specific embodiment, $Z^s$ is —SR$^d$ and $R^d$ is a (C$_1$-C$_3$)alkyl, pyridyl or nitropyridyl (e.g., 4-nitropyridyl).

In a 16$^{th}$ specific embodiment, $R^x$ is a linear or branched alkyl having 1 to 6 carbon atoms; and the remaining variables are as described in the 14$^{th}$ specific embodiment or any more specific embodiments described therein. More specifically, $R^x$ is —(CH$_2$)$_p$—(CR$^f$R$^g$)—, wherein R$^f$ and R$^g$ are each independently selected from —H or a linear or branched alkyl having 1 to 4 carbon atoms; and p is 0, 1, 2 or 3. Even more specifically, R$^f$ and R$^g$ are the same or different, and are selected from —H and -Me; and p is 1.

In a 17$^{th}$ specific embodiment, R$^k$ is —H or -Me, and n is 3; and the remaining variables are as described above in the 15$^{th}$ or 16$^{th}$ specific embodiment.

In a 18$^{th}$ specific embodiment, for methods in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-forth, thirty-fifth, thirty-sixth, thirty-seventh, thirty-eighth, thirty-ninth, fortieth, forty-first, forty-second, and forty-third embodiments, L' is represented by the following formula:

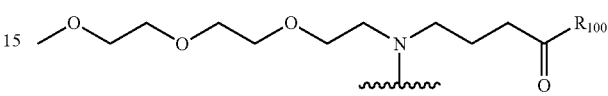

wherein R$_{100}$ is a (C$_1$-C$_3$)alkoxy; and the remaining variables are as described above in the 1$^{st}$ to the 17$^{th}$ specific embodiments. In another embodiment, L' is NO$_2$. In yet another embodiment, L' is represented by the following formula:

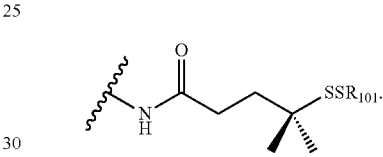

In certain embodiment, the indolinobenzodiazepine dimer compound of formula (I') can be prepared according to Schemes 1-12 shown below.

Scheme 1

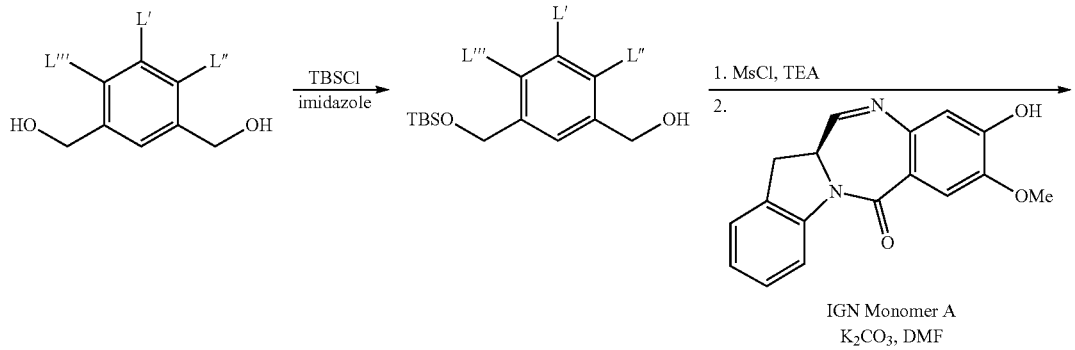

IGN Monomer A
K$_2$CO$_3$, DMF

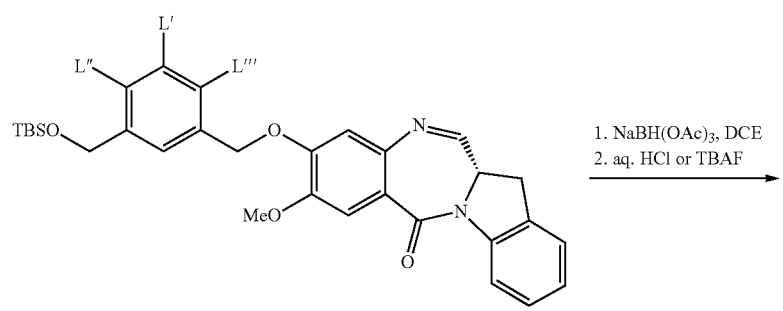

-continued
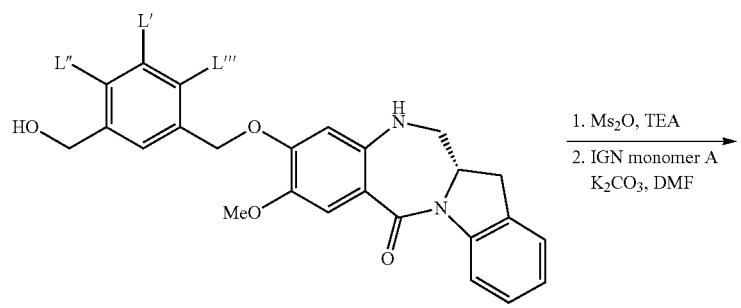
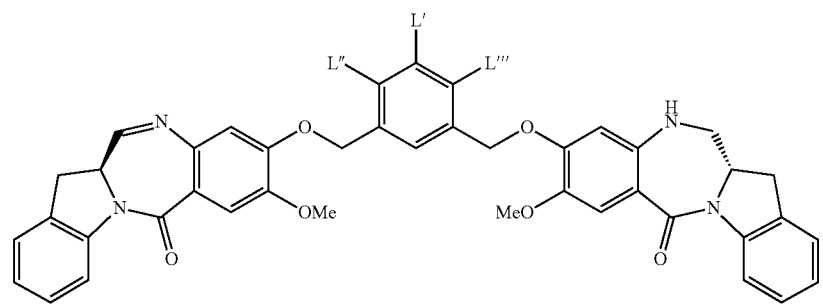
Scheme 2
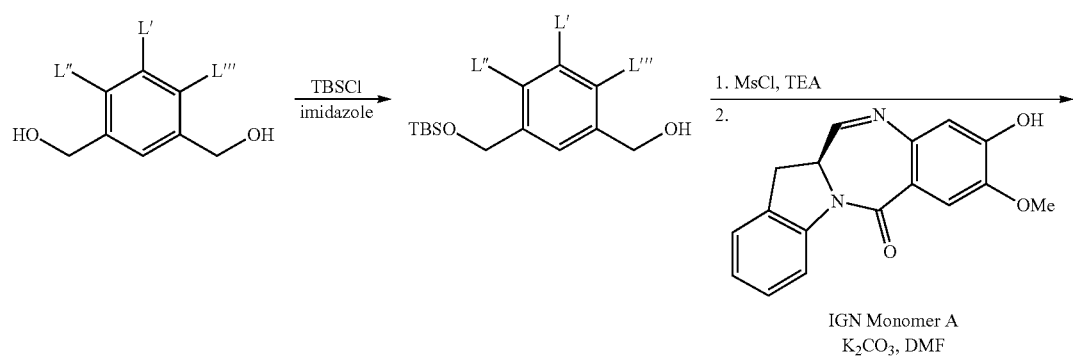
IGN Monomer A
K₂CO₃, DMF
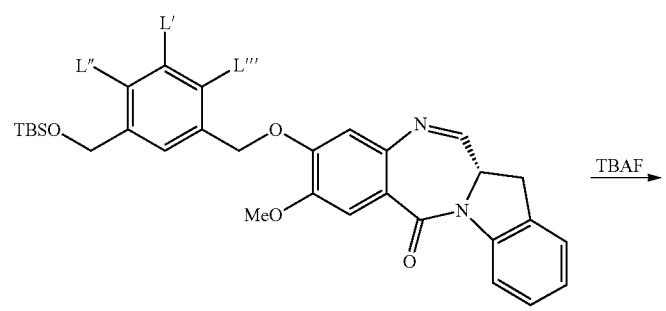

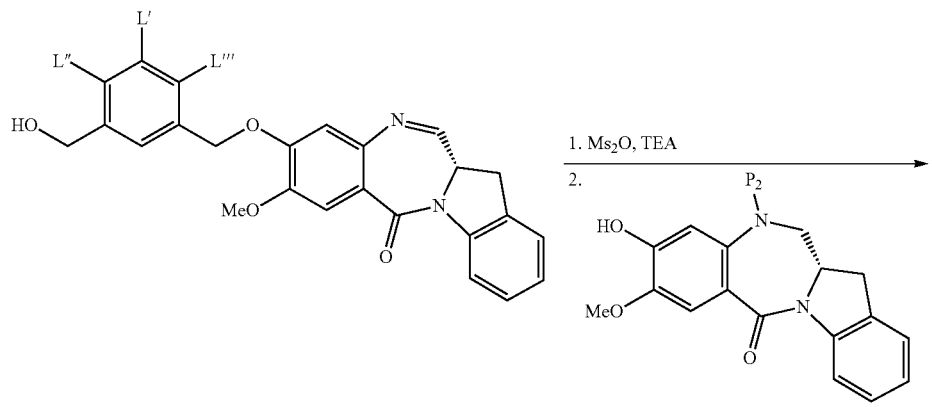
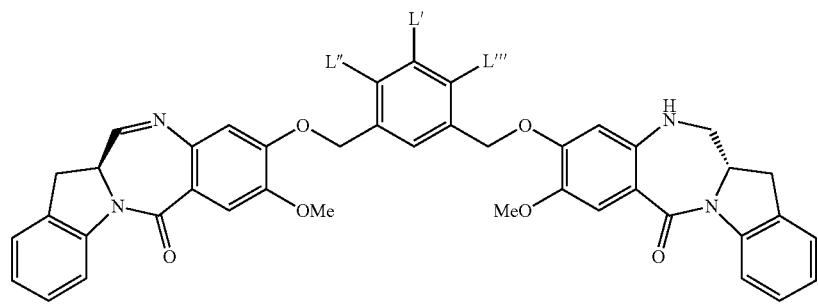
Scheme 3
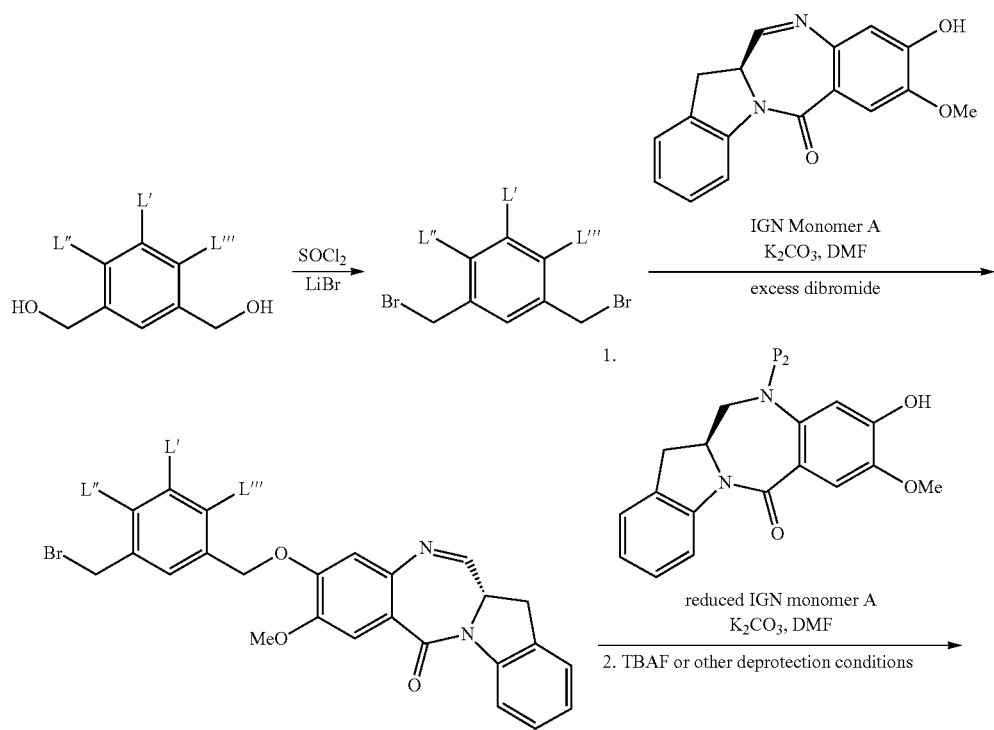

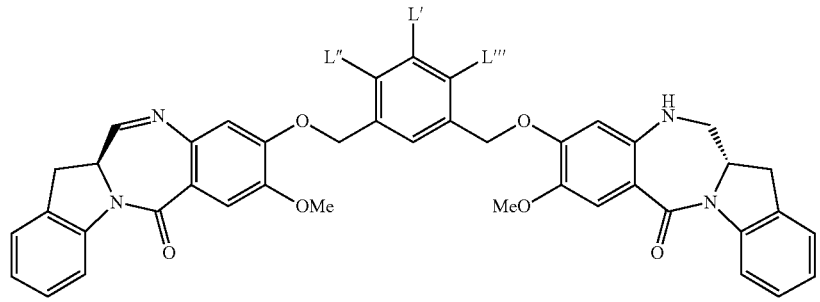
Scheme 4
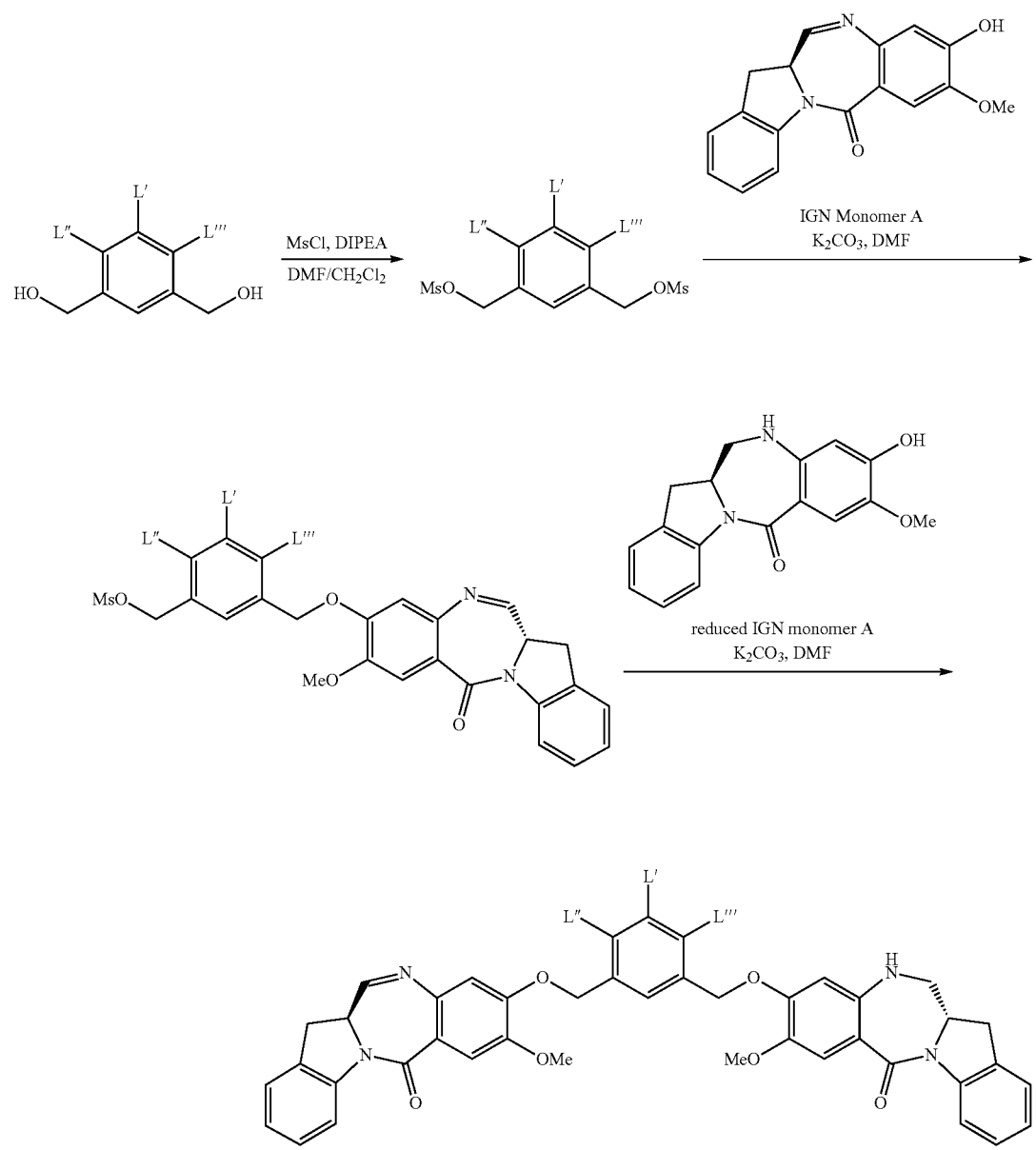

Scheme 5
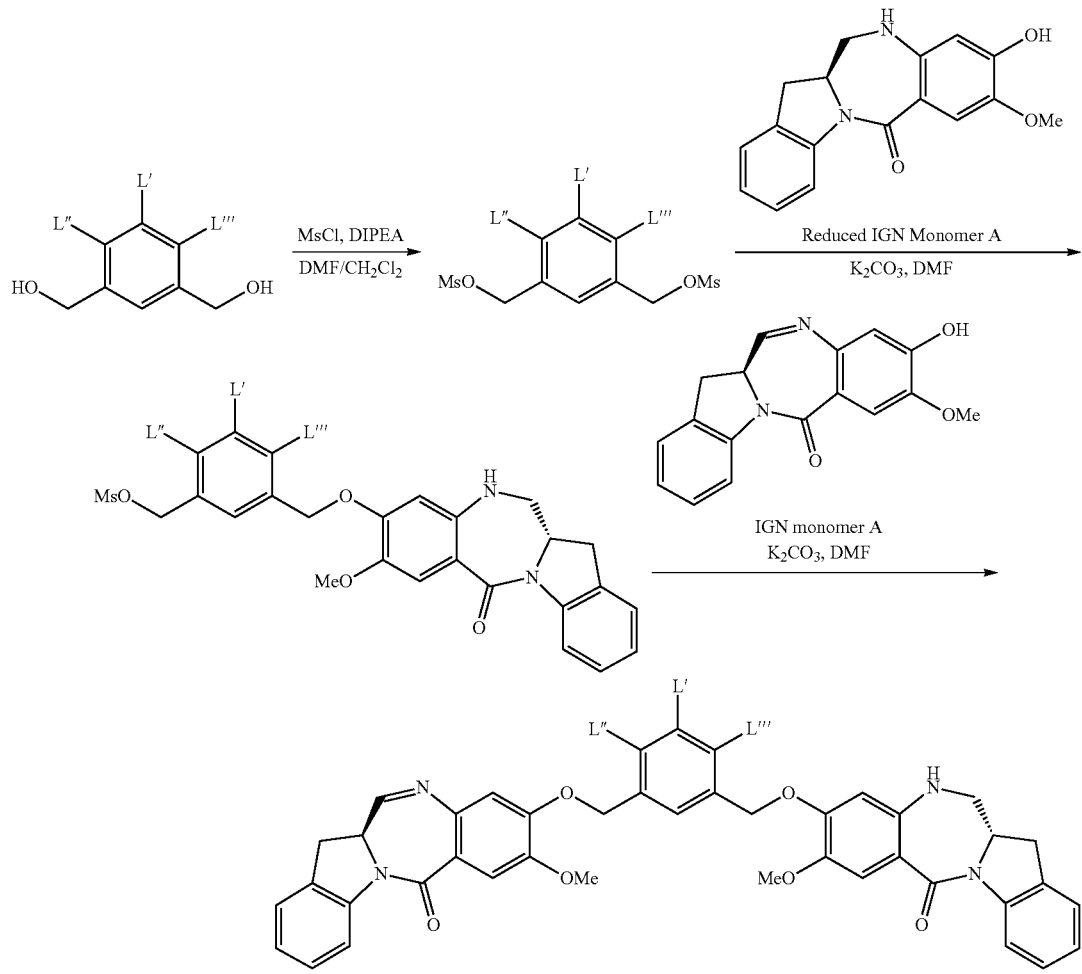
Scheme 6
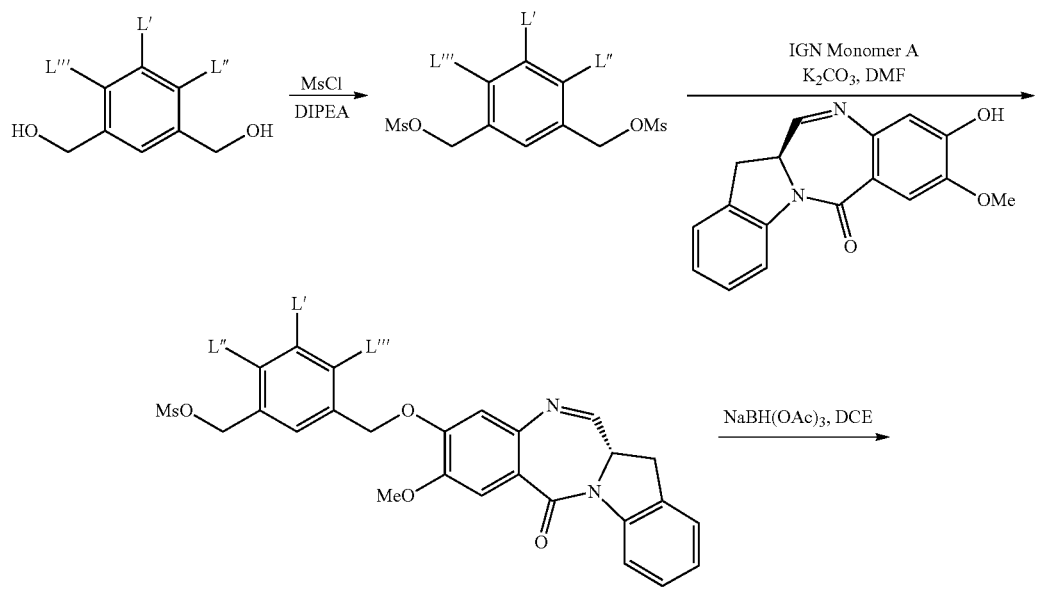

-continued
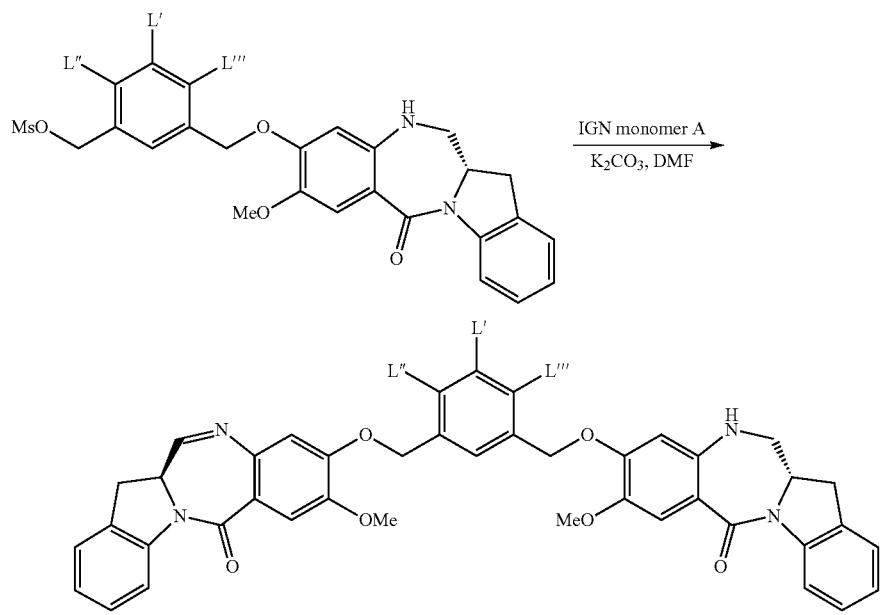
Scheme 7
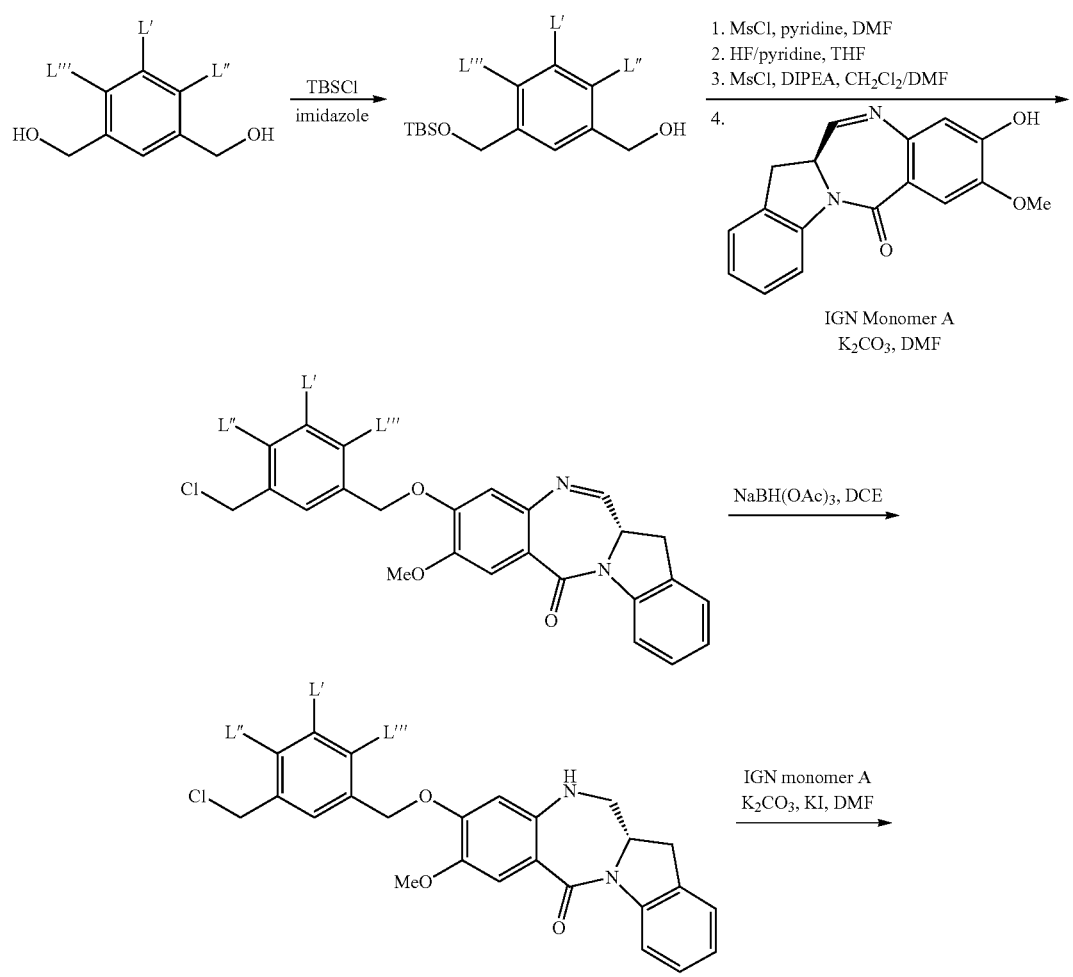

-continued
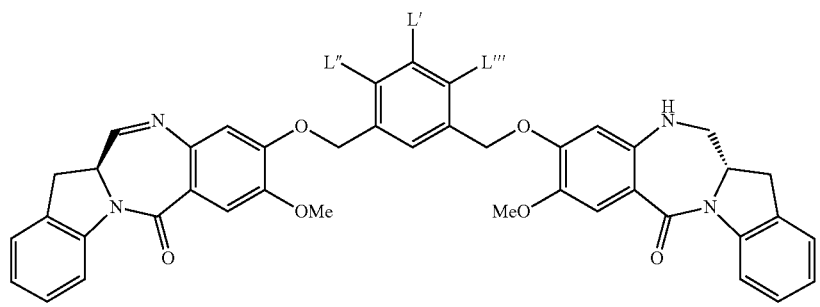
Scheme 8
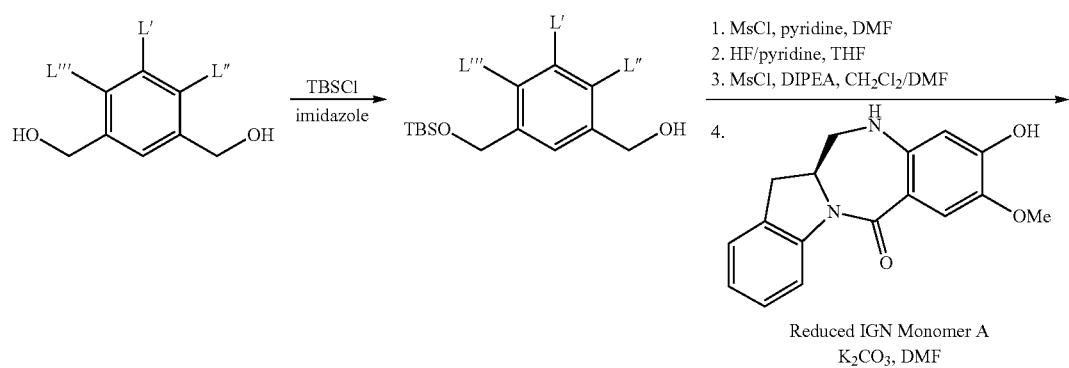
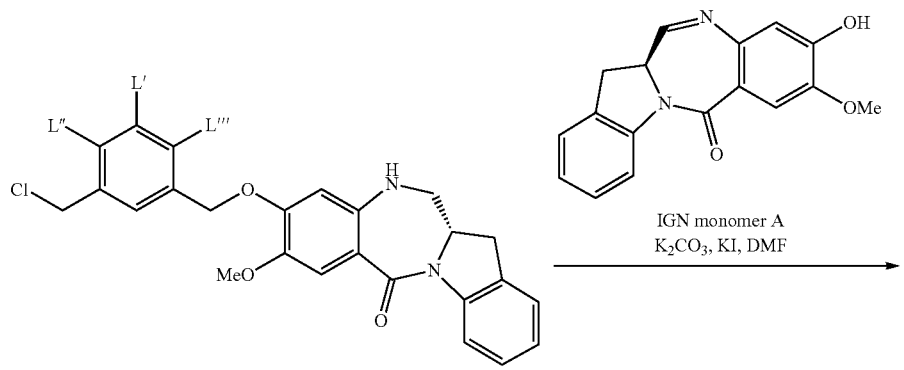
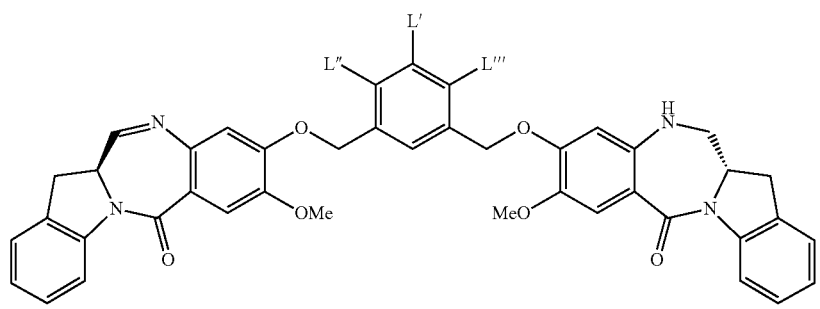

Scheme 9
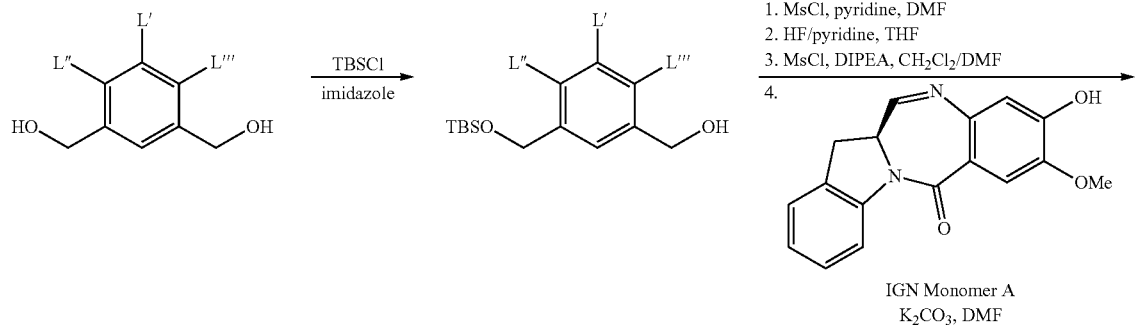
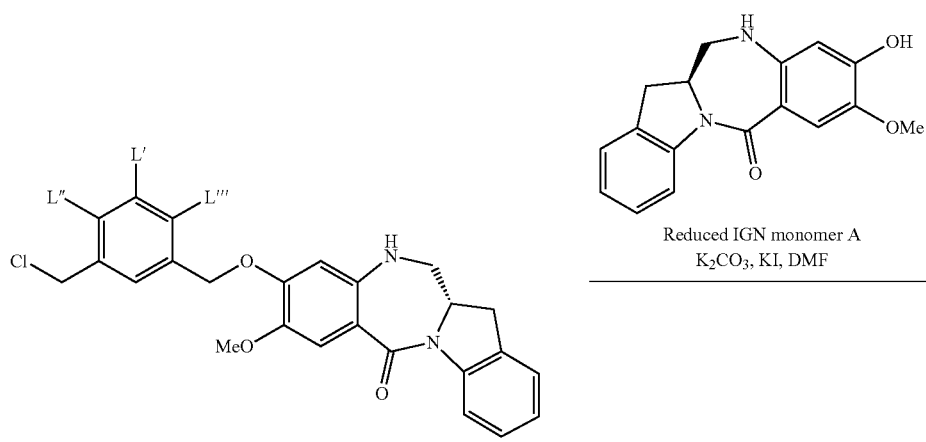
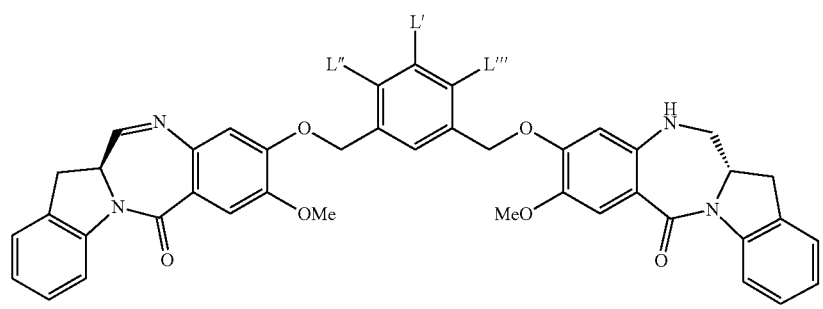
Scheme 10
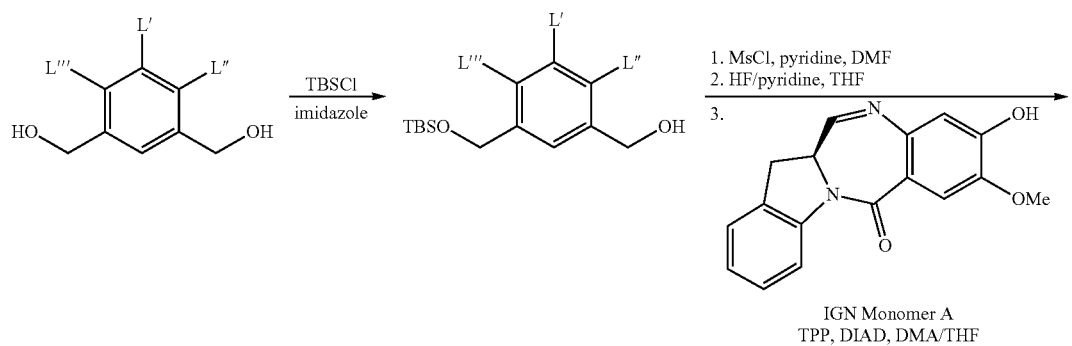

-continued
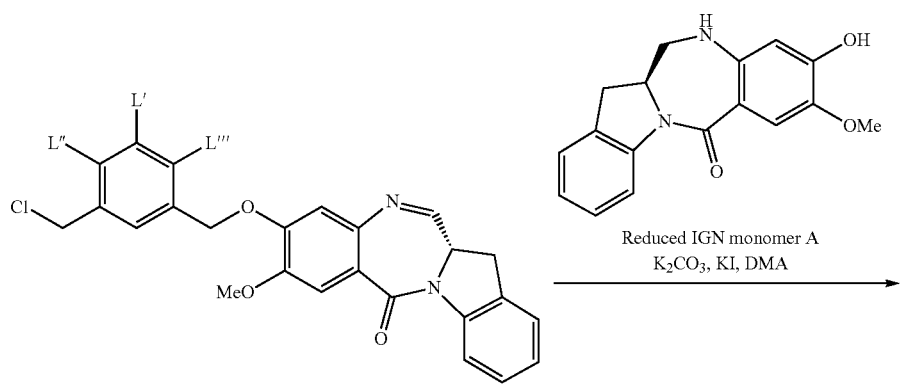
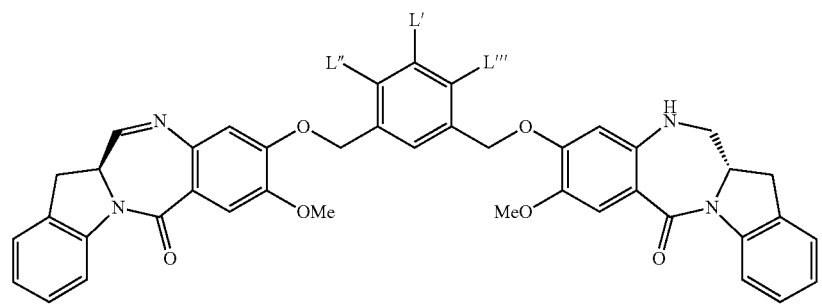
Scheme 11
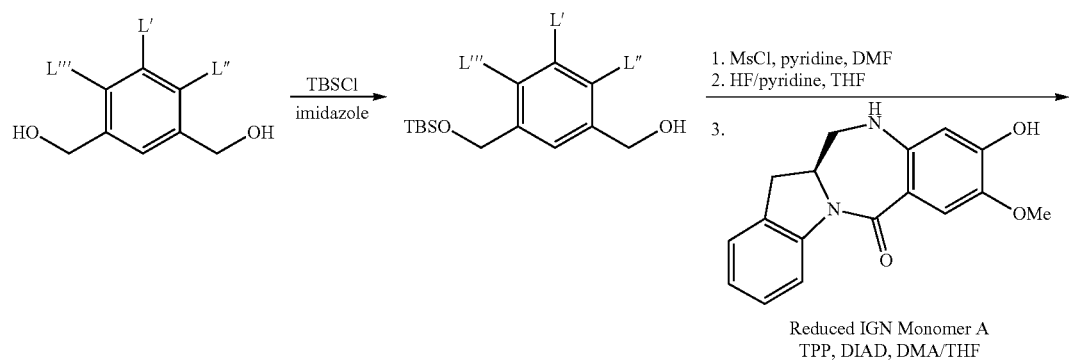
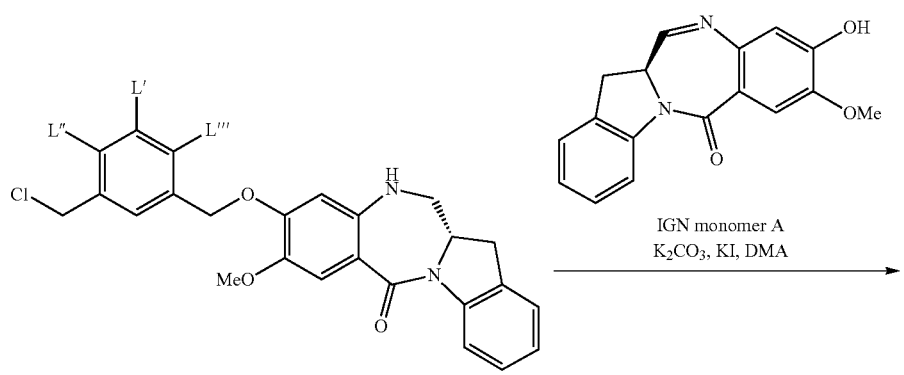

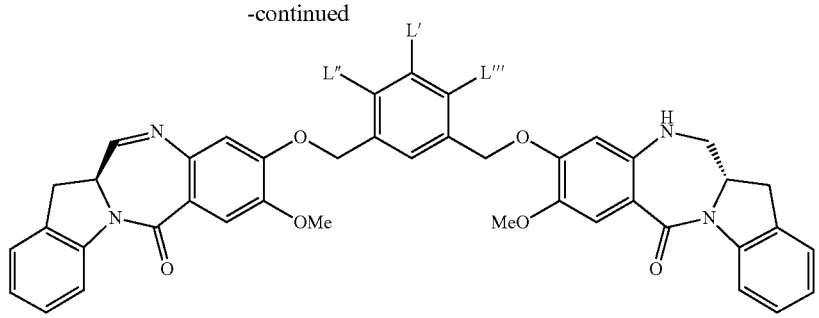

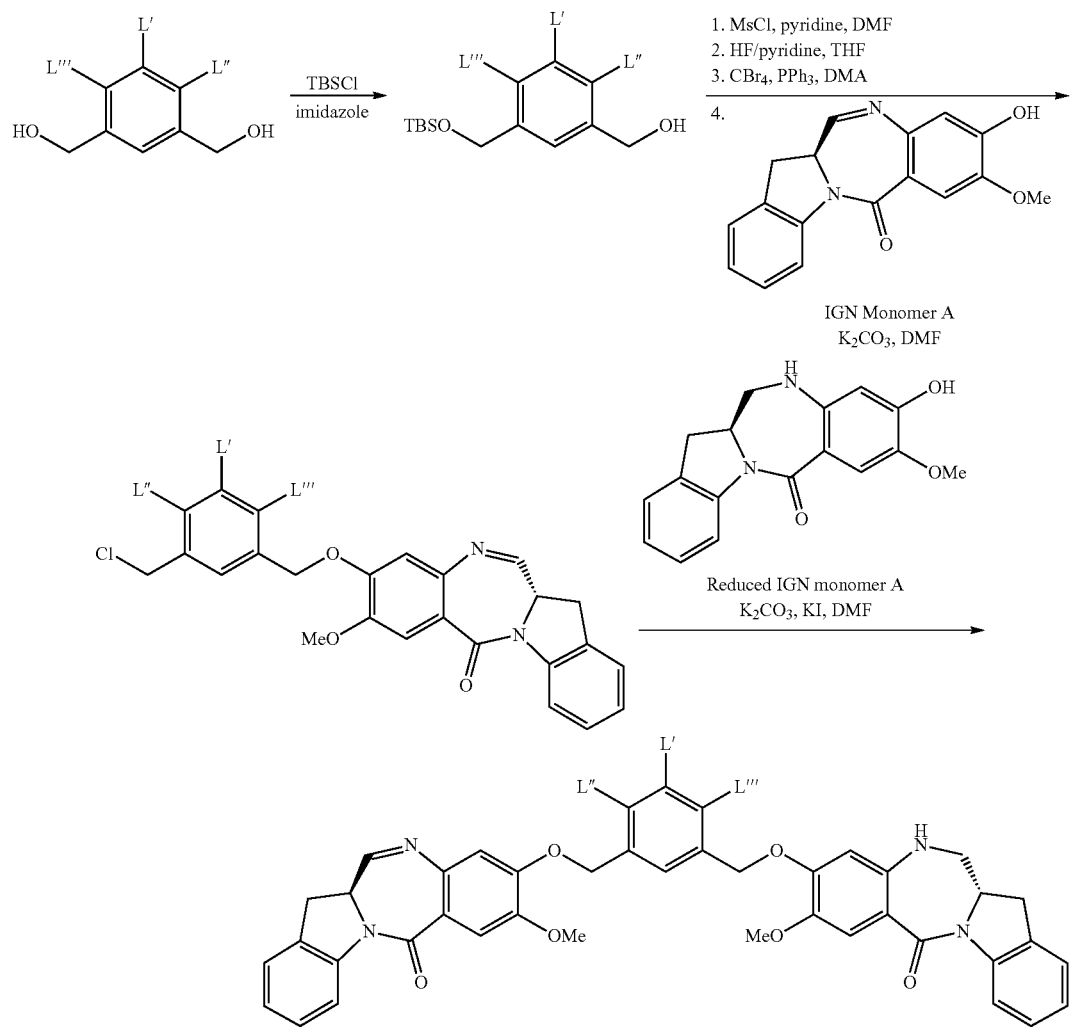

Compounds of the Invention

The present invention also provides novel compounds described herein. In certain embodiments, the compounds of the present invention are compounds of formulas (1), (2), (2"), (3), (3"), (4), (4"), (5), (5"), (6), (7), (7'), (7-1), (7"), (7'''), (8), (9), (10), (10'), (11), (12), (13), (14), (15), (16), (17), (17'), (18), (19), (20), (a), (b), (d), (I'), (IA), and (IB), wherein the variables are as described in the first to forty-third embodiment, or the $1^{st}$ to $18^{th}$ specific embodiment or any more specific embodiment described therein.

In a $19^{th}$ specific embodiment, for the compounds of the present invention, when present, $R_{100}$ is $(C_1-C_3)$alkoxy; $R_{101}$ is $(C_1-C_3)$alkyl, pyridyl or nitropyridyl (e.g., 4-nitropyridyl); $P_1$ is an alcohol protecting group; $X_1$ and $X_2$ for each occurrence are independently —Br, —I, and a sulfonate ester; $P_2$ is an amine protecting group; $P_3$ is H or an amine protecting group; and the remaining variables are as described in any one of the first to forty-fourth embodiment and the 1st to 18th specific embodiment.

In a 20th specific embodiment, for compounds of the present invention, when present, $R_{100}$ is —OMe; and $R_{101}$ is Me or pyridyl; and the remaining variables are as described in any one of the first to forty-fourth embodiment and the 1st to 19th specific embodiment.

In a 21st specific embodiment, for compounds of the present invention, when present, $P_1$ is a silyl protecting group; and the remaining variables are as described in any one of the first to forty-fourth embodiment and the 1st to 20th specific embodiment. More specifically, the silyl protecting group is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, or [2-(trimethylsilyl)ethoxy]methyl. Even more specifically, the silyl protecting group is triethylsilyl, triisopropylsilyl, or tert-butyldimethylsilyl. In another even more specific embodiment, the silyl protecting group is tert-butyldimethylsilyl.

In a 22nd specific embodiment, for compounds of present invention, when present, $X_1$ and $X_2$ for each occurrence, are each independently a sulfonate ester; and the remaining variables are as described in any one of the first to forty-fourth embodiment and the 1st to 21st specific embodiment. More specifically, the sulfonate ester is mesylate, tosylate, brosylate, or triflate. Even more specifically, the sulfonate ester is mesylate.

In a 23rd specific embodiment, for compounds of present invention, when present, $X_3$ is chlorine; and the remaining variables are as described in any one of the first to forty-fourth embodiment and the 1st to 22nd specific embodiment.

In a 24th specific embodiment, for compounds of the present invention, when present, $X_4$ is a sulfonate ester; and the remaining variables are as described in any one of the first to forty-fourth embodiment and the 1st to 23rd specific embodiment. More specifically, the sulfonate ester is mesylate, tosylate, brosylate, or triflate. Even more specifically, the sulfonate ester is mesylate.

In a 25th specific embodiment, for compounds of the present invention, $P_2$ is an amine protecting group selected from 2-trimethylsilylethyl, (2-phenyl-2-trimethylsilyl)ethyl, triisopropylsiloxy, 2-(trimethylsilyl)ethoxymethyl, allyloxycarbonyl, 9-fluorenylmethoxycarbonyl, 2-(trimethylsilyl)ethoxycarbonyl, and 2,2,2-trichloroethoxycarbonyl; and the remaining variables are as described in any one of the first to forty-fourth embodiment and the 1st to 24th specific embodiment.

In a 26th specific embodiment, for the compounds of the present invention, when present, $P_3$ is H or an amine protecting group selected from 2-trimethylsilylethyl, (2-phenyl-2-trimethylsilyl)ethyl, triisopropylsiloxy, 2-(trimethylsilyl)ethoxymethyl, and allyloxycarbonyl, 9-fluorenylmethoxycarbonyl, 2-(trimethylsilyl)ethoxycarbonyl, and 2,2,2-trichloroethoxycarbonyl; and the remaining variables are as described in any one of the first to forty-fourth embodiment and the 1st to 25th specific embodiment.

In a 27th specific embodiment, for compounds of the present invention, when present, $X_5$ is —Br; and the remaining variables are as described in any one of the first to forty-fourth embodiment and the 1st to 26th specific embodiment.

In one embodiment, for the methods and the compounds of the present invention described herein, L' is not represented by:

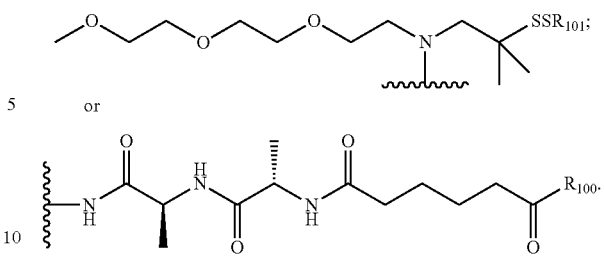

In one embodiment, for the methods and the compounds of the present invention described herein, L' is not represented by:

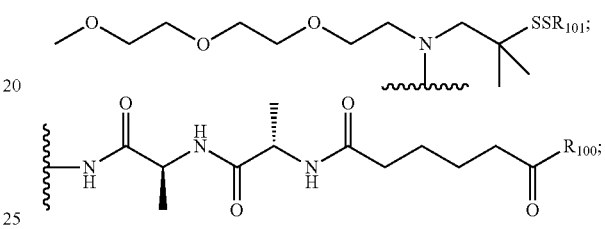

or $NO_2$

All references cited herein and in the examples that follow are expressly incorporated by reference in their entireties.

EXAMPLES

The invention will now be illustrated by reference to non-limiting examples. Unless otherwise stated, all percents, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument. Mass spectra were acquired on a Bruker Daltonics Esquire 3000 instrument and LCMS were acquired on an Agilent 1260 Infinity LC with an Agilent 6120 single quadrupole MS using electrospray ionization and UPLC were acquired on a Waters, Acquity system with a single quadrupole MS Zspray™ (column: Acquity BEH C18, 2.1×50 mm, 1.7 m, method: 2.5 min, flow rate 0.8 mL/min, solvent A: water, solvent B: MeCN, 5 to 95% of MeCN over 2.0 min and 95% MeCN for 0.5 min).

The following solvents, reagents, protecting groups, moieties and other designations may be referred to by their abbreviations in parenthesis:

Me=methyl; Et=ethyl; Pr=propyl; i-Pr=isopropyl; Bu=butyl; t-Bu=tert-butyl; Ph=phenyl, and Ac=acetyl
AcOH or HOAc=acetic acid
ACN or $CH_3CN$=acetonitrile
Ala=alanine
Ar=argon
aq=aqueous
Bn=benzyl
Boc or BOC=tert-butoxycarbonyl
$CBr_4$=carbontetrabromide
Cbz or Z=benzyloxycarbonyl
DCM or $CH_2Cl_2$=dichloromethane
DCE=1,2-dichloroethane
DMAP=4-dimethylaminopyridine
DI water=deionized water
DIBAL=diisobutylaluminum hydride
DIEA or DIPEA=N,N-diisopropylethylamine DMA=N,N-dimethylacetamide
DMF=N,N-dimethylformamide
DMSO=dimethyl sulfoxide
DTT=dithiothreitol
EDC=1-ethyl-3-(3-dimethylaminopropyl)carbodiimide
EEDQ=N-Ethoxycarbonyl-2-ethoxy-1,2-dihydroquinoline
ESI or ES=electrospray ionization
EtOAc=ethylacetate
Gly=glycine
g=grams
h=hour
HATU=N,N,N'N'-tetramethyl-O-(7-azabenzotriazol-1-yl) uronium hexaphosphate
HPLC=high-performance liquid chromatography
HOBt or HOBT=1-hydroxybenzotriazole
LAH=lithium aluminum hydride
LC=liquid chromatography
LCMS=liquid chromatography mass spectrometry
mmin=minutes
mg=miligrams
mL=mililiters
mmol=milimoles
μg=micrograms
μL=microliters
μmol=micromoles
Me=methyl
MeOH=methanol
MeI=methyliodide
MS=mass spectrometry
MsCl=methanesulfonyl chloride (mesyl chloride)
Ms$_2$O=methanesulfonic anhydride
MTBE=Methyl tert-butyl ether
NaBH(OAc)$_3$=sodium triacetoxyborohydride
NHS=N-hydroxysuccinamide
NMR=nuclear magnetic resonance spectroscopy
PPh$_3$=triphenylphosphine
PTLC=preparative thin layer chromatography
rac=racemic mixture
R$_f$=retardation factor
RPHPLC or RP-HPLC=reverse phase high-performance liquid chromarography
RT or rt=room temperature (ambient, about 25° C.)
sat or sat'd=saturated
STAB=sodium triacetoxyborohydride (NaBH(OAc)$_3$)
TBSCl or TBDMSCl=tert-butyldimethylsilyl chloride
TBS=tert-butyldimethylsilyl
TCEP.HCl=tris(2-carboxyethyl)phosphine hydrochloride salt
TEA=triethylamine (Et$_3$N)
TFA=trifluoroacetic acid
THF=tetrahydrofuran
TLC=thin layer chromatography Example 1

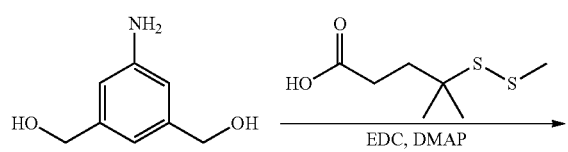

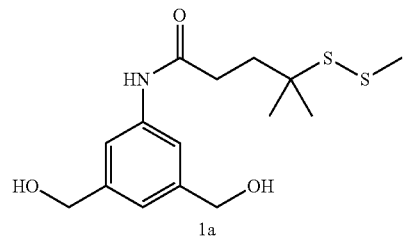

1a

To a stirred solution of (5-amino-1,3-phenylene)dimethanol (1.01 g, 6.59 mmol) in anhydrous dimethylformamide (16.48 mL) and anhydrous tetrahydrofuran (16.48 ml) was added 4-methyl-4-(methyldisulfanyl)pentanoic acid (1.281 g, 6.59 mmol), EDC.HCl (2.53 g, 13.19 mmol), and DMAP (0.081 g, 0.659 mmol). The resulting mixture was stirred for 18 hours at room temperature. The reaction was quenched with saturated ammonium chloride solution and extracted with ethyl acetate (3×50 mL). The organic extracts were washed with water, brine, and dried over anhydrous sodium sulfate. The solution was filtered and concentrated in vacuo and the resulting residue was purified by silica gel chromatography (Hexanes/EtOAc) to obtain compound 1a as a white solid (0.70 g, 35% yield). $^1$H NMR (400 MHz, DMSO-d6): δ 9.90 (s, 1H), 7.43 (s, 2H), 6.93 (s, 1H), 5.16 (t, 2H, J=5.7 Hz), 4.44 (d, 4H, J=5.7 Hz), 2.43 (s, 3H), 2.41-2.38 (m, 2H), 1.92-1.88 (m, 2H), 1.29 (s, 6H). MS (m/z), found 330.0 (M+H)$^+$.

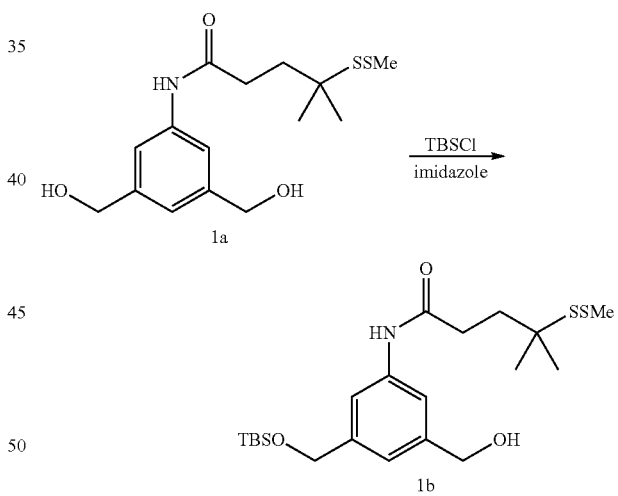

Diol 1a (1.0 g, 3.04 mmol) was dissolved in DMF (10.12 mL). TBSCl (503 mg, 3.34 mmol) and imidazole (238 mg, 3.49 mmol) were added to the solution and the reaction was stirred at rt overnight. Additional TBSCl (600 mg) and imidazole (220 mg) were added to the reaction mixture and was stirred at rt for an additional 5 h. The reaction mixture was diluted with DCM and was washed with sat'd ammonium chloride, brine and was dried over sodium sulfate, filtered and concentrated. The crude product was purified by silca gel chromatography (EtOAc/hexanes, gradient) to obtain 1b as a colorless oil (710 mg, 53% yield). LCMS (8 min method)=6.967 min. Mass observed (ESI$^+$): 445.95 (M+H)$^+$ and 467.90 (M+Na)$^+$.

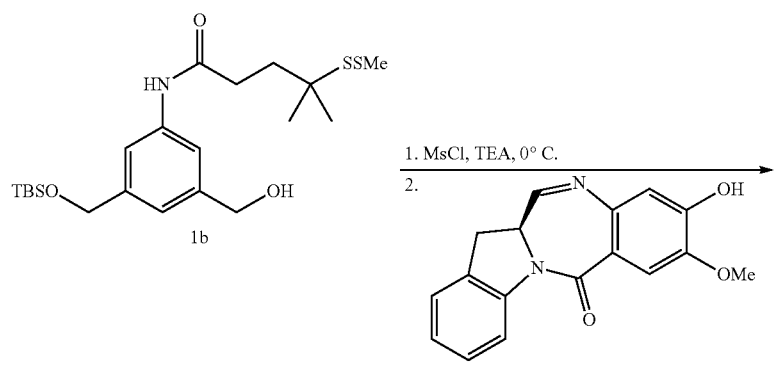

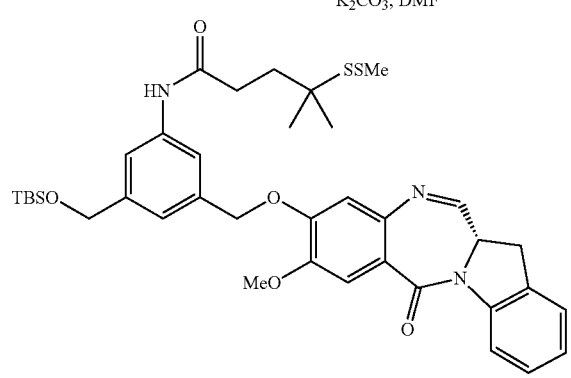

1c

Compound 1b (200 mg, 0.451 mmol) was dissolved in DCM (4.51 mL) and was cooled to 0° C. Et₃N (82 µL, 0.586 mmol) was added to the reaction mixture under Ar, followed by dropwise addition of mehanesulfonyl chloride (42.1 µL, 0.541 mmol). The reaction mixture was stirred at 0° C. for 2 h. The solution was diluted with EtOAc and was washed with cold water (2×). The organic layer was dried over sodium sulfate, filtered and concentrated to obtain the mesylate. The crude mesylate was used in the next step without purification. LCMS (8 min method)=7.444 min. Mass observed (ESI⁺): 521.8 (M+H)⁺ and 543.8 (M+Na)⁺. The crude mesylate (210 mg, 0.402 mmol) was dissolved in DMF (2.68 mL). IGN monomer A (130 mg, 0.443 mmol) and potassium carbonate (111 mg, 0.805 mmol) were added to the mixture and was stirred at rt under Ar overnight. The product was precipitated out with the addition of water (15 mL). The slurry was stirred for 5 min and was filtered. The filter cake was washed with water (3×) and was dried under vacuum/N₂ to obtain compound 1c as a solid (270 mg, 93% yield). LCMS (8 min method)=7.624 min. Mass observed (ESI⁺): 719.8 (M+H)⁺.

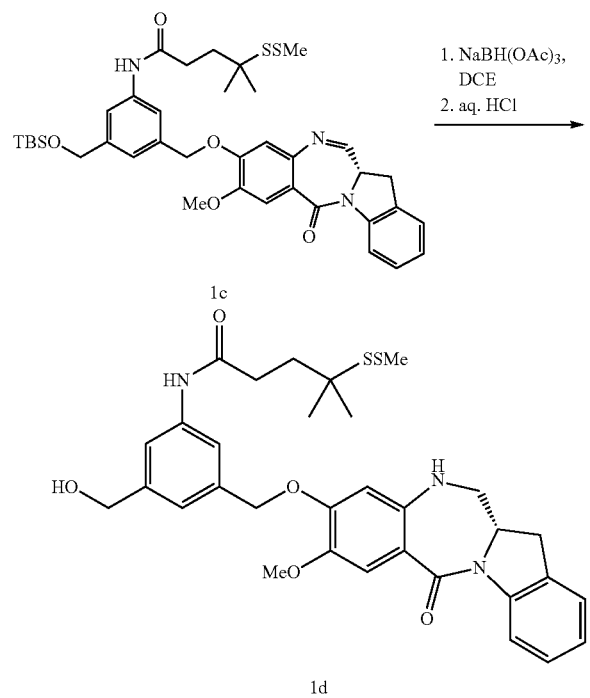

Compound 1c (686 mg, 0.953 mmol) was dissolved in DCE (6.35 mL). Sodium triacetoxyborohydride (400 mg, 1.91 mmol) was added to the reaction mixture and was stirred at rt for 3 h. The reaction mixture was diluted with DCM and was washed with saturated ammonium chloride, brine, dried over sodium sulfate, filtered and concentrated to obtain the reduced imine product. LCMS (8 min method) =4.363 min. Mass observed (ESI⁺): 720.75 (M+H)⁺.

The crude reduced imine (680 mg, 0.942 mmol) was dissolved in THF (5.23 mL). HCl (aq. 5M) (3.77 mL, 9.42 mmol) was added and was stirred at rt for 4 h. The reaction mixture was diluted with DCM and was washed with saturated sodium bicarbonate, brine, dried over sodium sulfate, filtered and concentrated. The crude product was purified by silica gel chromatography (gradient, MeOH/DCM) to obtain compound 1d (420 mg, 73% yield, 2 steps). LCMS (8 min method)=5.905 min. Mass observed (ESI⁺): 607.8 (M+H)⁺.

silica gel chromatography (gradient, MeOH/DCM) to obtain compound 1e as a yellow solid (543 mg, 53% yield). LCMS (8 min method)=6.804 min. Mass observed (ESI⁺): 883.7 (M+H)⁺.

Example 2

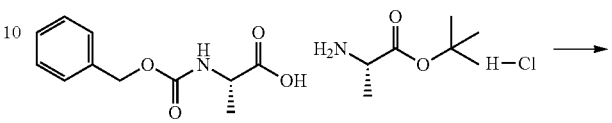

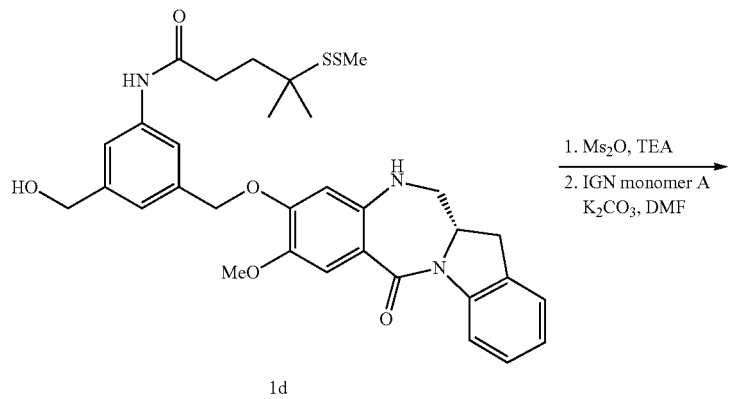

1d

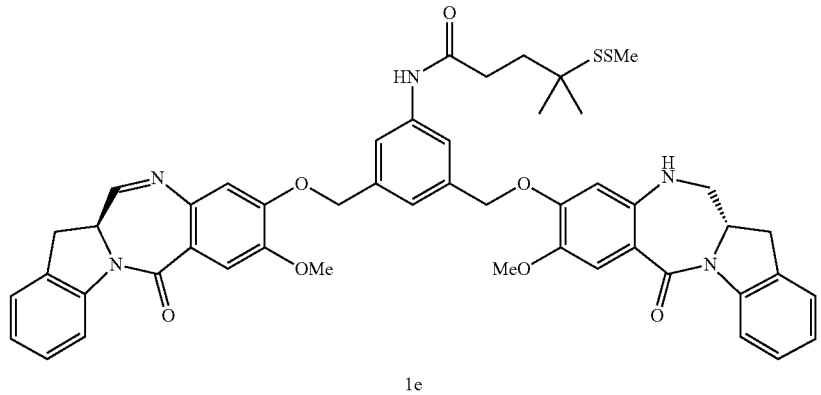

1e

Compound 1d (420 mg, 0.691 mmol) was dissolved in DCM (4.61 mL). The solution was cooled to −5° C. (ice-brine bath) and TEA (125 µL, 0.898 mmol) was added, followed methanesulfonic anhydride (144 mg, 0.829 mmol) under Ar. The reaction mixture was stirred at −5° C. under Ar for 1.5 h. The reaction mixture was quenched with water at −5° C. and was warmed to rt. The mixture was extracted with EtOAc (2×) and the organic layer was washed with water (2×). The organics were dried over sodium sulfate, filtered and concentrated to obtain the mesylated product as a brown foam. LCMS (8 min method)=6.380 min. Mass observed (ESI⁺): 685.7 (M+H)⁺.

The mesylate (470 mg, 0.582 mmol) was dissolved in DMF (3.88 mL). IGN monomer A (189 mg, 0.641 mmol) was added, followed by potassium carbonate (121 mg, 0.874 mmol) at room temperature and the reaction was stirred overnight. Water (~5 mL) was added to precipitate out the product. The slurry was stirred for 5 min, then filtered and dried under vacuum/N₂. The crude product was purified by -continued

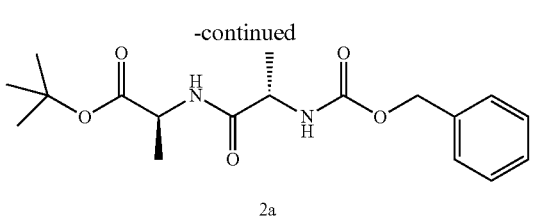

2a (S)-2-(((benzyloxy)carbonyl)amino)propanoic acid (5 g, 22.40 mmol) and (S)-tert-butyl 2-aminopropanoate hydrochloride (4.48 g, 24.64 mmol) were dissolved in anhydrous DMF (44.8 mL). EDC.HCl (4.72 g, 24.64 mmol), HOBt (3.43 g, 22.40 mmol), and DIPEA (9.75 mL, 56.0 mmol) were added. The reaction stirred under argon, at room temperature overnight. The reaction mixture was diluted with dichloromethane and then washed with saturated ammonium chloride, saturated sodium bicarbonate, water, and brine. The organic layer was dried over sodium sulfate and concentrated. The crude oil was purified by silica gel chromatography (Hexanes/Ethyl Acetate) to yield compound 2a (6.7 g, 85% yield). $^1$H NMR (400 MHz, CDCl$_3$): δ 7.38-7.31 (m, 5H), 6.53-6.42 (m, 1H), 5.42-5.33 (m, 1H), 5.14 (s, 2H), 4.48-4.41 (m, 1H), 4.32-4.20 (m, 1H), 1.49 (s, 9H), 1.42 (d, 3H, J=6.8 Hz), 1.38 (d, 3H, J=7.2 Hz).

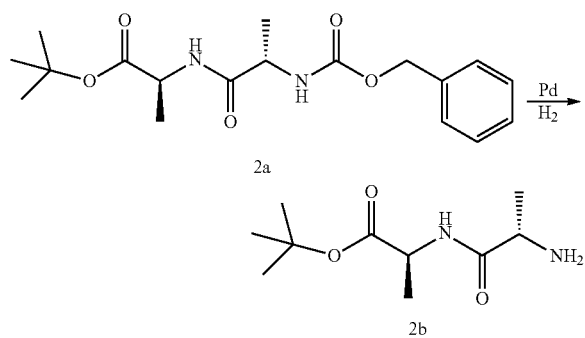

Compound 2a (6.7 g, 19.12 mmol) was dissolved in methanol (60.7 mL) and water (3.03 mL). The solution was purged with argon for five minutes. Palladium on carbon (wet, 10%) (1.017 g, 0.956 mmol) was added slowly. The reaction was stirred overnight under an atmosphere of hydrogen. The solution was filtered through Celite, rinsed with methanol and concentrated. It was azeotroped with methanol and acetonitrile and the resulting oil was placed directly on the high vacuum to give compound 2b (4.02 g, 97% yield) which was used directly in the next step. $^1$H NMR (400 MHz, CDCl$_3$): δ 7.78-7.63 (m, 1H), 4.49-4.42 (m, 1H), 3.55-3.50 (m, 1H), 1.73 (s, 2H), 1.48 (s, 9H), 1.39 (d, 3H, J=7.2 Hz), 1.36 (d, 3H, J=6.8 Hz).

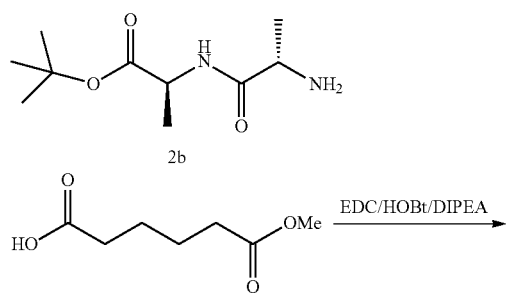

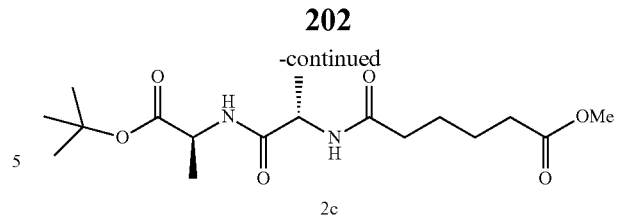

Compound 2b (4.02 g, 18.59 mmol) and mono methyladipate (3.03 mL, 20.45 mmol) were dissolved in anhydrous DMF (62.0 mL). EDC.HCl (3.92 g, 20.45 mmol), HOBt (2.85 g, 18.59 mmol) and DIPEA (6.49 mL, 37.2 mmol) were added. The mixture was stirred overnight at room temperature. The reaction was diluted with dichloromethane/methanol (150 mL, 5:1) and washed with saturated ammonium chloride, saturated sodium bicarbonate, and brine. It was dried over sodium sulfate, filtered and concentrated. The compound was azeotroped with acetonitrile (5×), then pumped on the high vacuum at 35° C. to give compound 2c (6.66 g, 100% yield). The crude material was taken onto next step without purification. $^1$H NMR (400 MHz, CDCl$_3$): δ 6.75 (d, 1H, J=6.8 Hz), 6.44 (d, 1H, J=6.8 Hz), 4.52-4.44 (m, 1H), 4.43-4.36 (m, 1H), 3.65 (s, 3H), 2.35-2.29 (m, 2H), 2.25-2.18 (m, 2H), 1.71-1.60 (m, 4H), 1.45 (s, 9H), 1.36 (t, 6H, J=6.0 Hz).

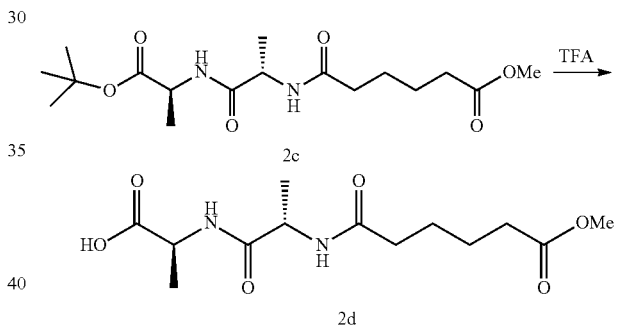

Compound 2c (5.91 g, 16.5 mmol) was stirred in TFA (28.6 mL, 372 mmol) and deionized water (1.5 mL) at room temperature for three hours. The reaction mixture was concentrated with acetonitrile and placed on high vacuum to give crude compound 2d as a sticky solid (5.88 g, 100% yield). $^1$H NMR (400 MHz, CDCl$_3$): δ 7.21 (d, 1H, J=6.8 Hz), 6.81 (d, 1H, J=7.6 Hz), 4.69-4.60 (m, 1H), 4.59-4.51 (m, 1H), 3.69 (s, 3H), 2.40-2.33 (m, 2H), 2.31-2.24 (m, 2H), 1.72-1.63 (m, 4H), 1.51-1.45 (m, 3H), 1.42-1.37 (m, 3H).

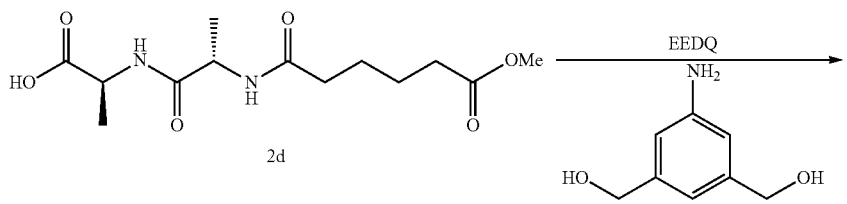

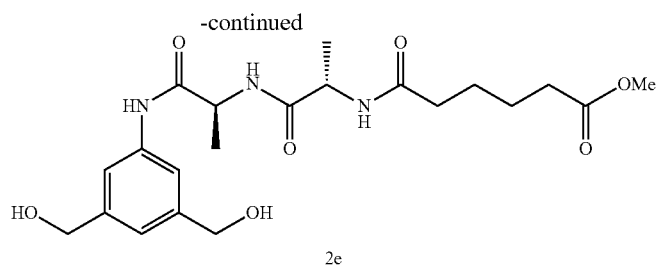

2e

Compound 2d (5.6 g, 18.52 mmol) was dissolved in anhydrous dichloromethane (118 mL) and anhydrous methanol (58.8 mL). (5-amino-1,3-phenylene)dimethanol (2.70 g, 17.64 mmol) and EEDQ (8.72 g, 35.3 mmol) were added and the reaction was stirred at room temperature overnight. The solvent was concentrated and ethyl acetate was added. The resulting slurry was filtered, washed with ethyl acetate and dried under vacuum/$N_2$ to give compound 2e (2.79 g, 36% yield). $^1$H NMR (400 MHz, DMSO-d6): δ 9.82 (s, 1H), 8.05, (d, 1H, J=9.2 Hz), 8.01 (d, 1H, J=7.2 Hz), 7.46 (s, 2H), 6.95 (3, 1H), 5.21-5.12 (m, 2H), 4.47-4.42 (m, 4H), 4.40-4.33 (m, 1H), 4.33-4.24 (m, 1H), 3.58 (s, 3H), 2.33-2.26 (m, 2H), 2.16-2.09 (m, 2H), 1.54-1.46 (m, 4H), 1.30 (d, 3H, J=7.2 Hz), 1.22 (d, 3H, J=4.4 Hz).

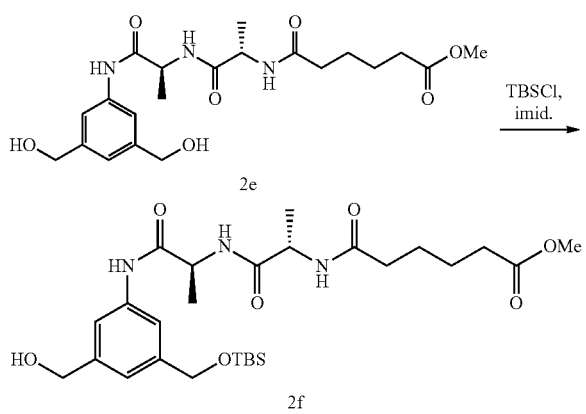

Diol 2e (1.0 g, 2.286 mmol) was dissolved in anhydrous DMF (7.6 mL). TBSCl (0.482 g, 3.20 mmol) and imidazole (0.467 g, 6.86 mmol) were added and the reaction was stirred at room temperature for 2 hrs. The reaction was quenched with saturated ammonium chloride and diluted with water and EtOAc. The aqueous layer was extracted once with EtOAc and the combined organic layers were washed with water and brine, dried over sodium sulfate, filtered and concentrated. The crude residue was purified by silica gel flash chromatography (DCM/MeOH) to obtain compound 2f (360 mg, 28% yield). LCMS (8 min method, 40-98%)=2.35 min. Mass observed (ESI$^+$): 574.4 (M+Na)$^+$.

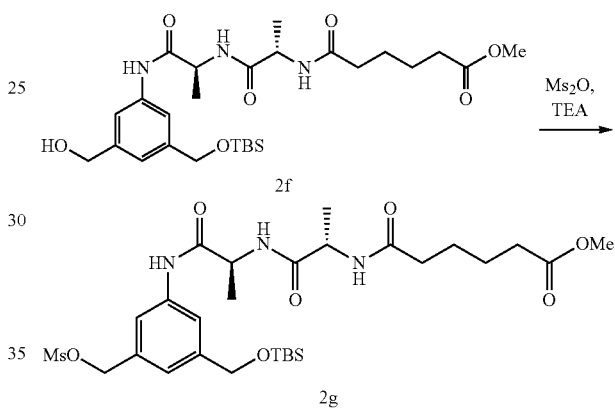

Compound 2f (360 mg, 0.652 mmol) was dissolved in anhydrous dichloromethane (6.52 mL) and cooled in an acetone/ice bath. Triethylamine (227 μL, 1.631 mmol) and methanesulfonic anhydride (146 mg, 0.816 mmol) were added. The reaction stirred at −10° C. in the acetone/ice bath for 1 hr. The reaction was diluted with cold EtOAc and quenched with ice water. The organic layer was washed with ice water and then dried over sodium sulfate and magnesium sulfate, filtered and concentrated to give crude compound 2g as a fluffy solid (390 mg, 95% yield). LCMS (8 min method, 40-98%)=2.81 min; 5.86 min (8 min method, 5-98%). Mass observed (ESI$^-$): 628.0 (M−H)$^-$.

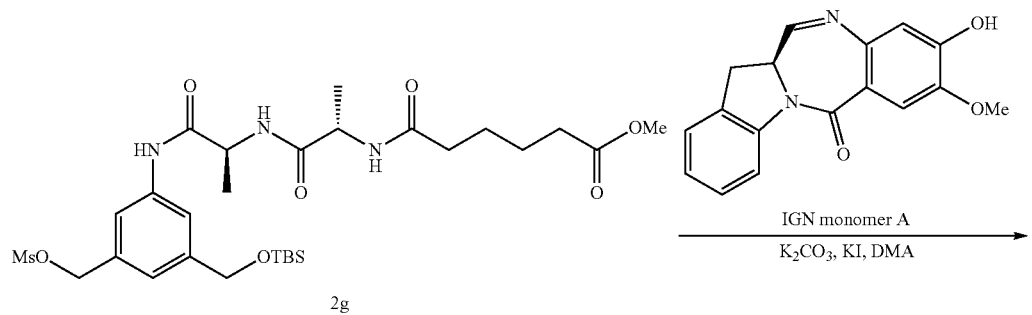

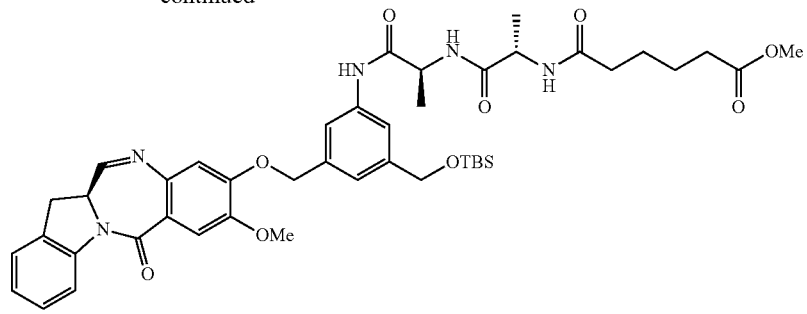

2h

Mesylate 2g (390 mg, 0.619 mmol) and IGN monomer A (264 mg, 0.897 mmol) were dissolved in anhydrous DMA (7.47 mL). Potassium carbonate (207 mg, 1.495 mmol) and potassium iodide (51.4 mg, 0.310 mmol) were added and the reaction was stirred overnight at room temperature. The reaction was precipitated with water, filtered and the filter cake washed with water. The solid was redissolved in DCM, washed with water, dried over magnesium sulfate and concentrated to give crude compound 2h (568 mg, 111% yield). The product was carried on without further purification. LCMS (8 min method, 5-98%)=6.23 min. Mass observed (ESI$^+$): 827.8 (M+H)$^+$.

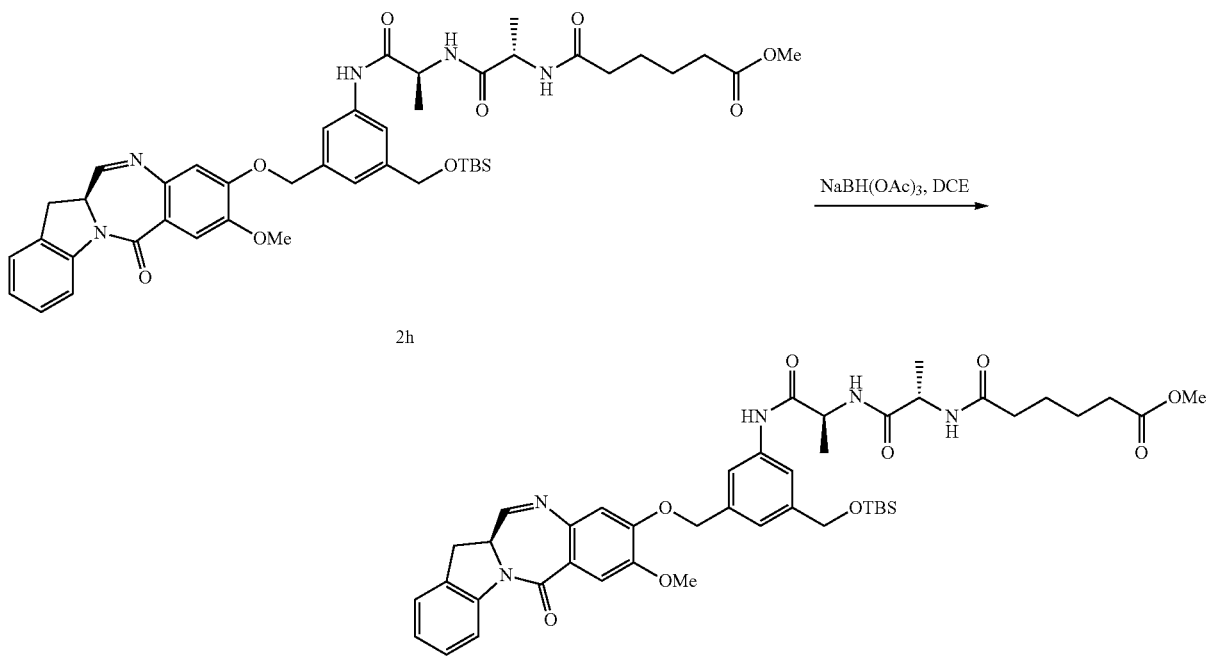

Compound 2h (0.513 g, 0.619 mmol) was dissolved in DCE (7.74 mL). NaBH(OAc)$_3$ (0.276 g, 1.239 mmol) was added and the mixture stirred at room temperature for 1.5 h. The reaction was diluted with DCM, quenched with saturated ammonium chloride and washed with brine. The organic layer was dried over magnesium sulfate, filtered and concentrated to give compound 2i. LCMS (15 min method)=9.93 min.

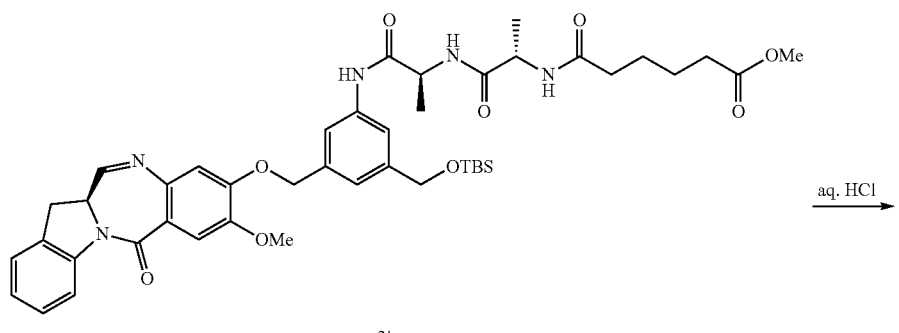

2i

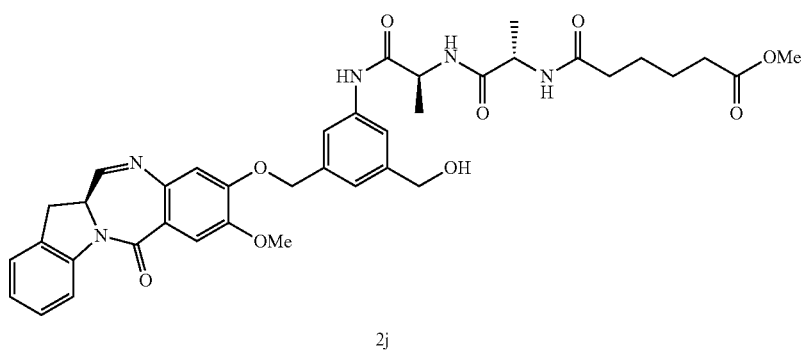

2j

Compound 2i (514 mg, 0.619 mmol) was dissolved in THF (3.44 mL). 5 M aqueous HCl (1.24 mL, 6.19 mmol) was added at room temperature and the reaction stirred for 1 h. The reaction mixture was diluted with DCM/MeOH (20:1) and the organic layer was washed with saturated sodium bicarbonate, brine, dried over magnesium sulfate, filtered and concentrated. The crude residue was purified by silica gel chromatography (DCM/MeOH) to give compound 2j (210 mg, 47% yield). LCMS (8 min method, 5-98%)=4.56 min. Mass observed (ESI+): 715.8 (M+H)+.

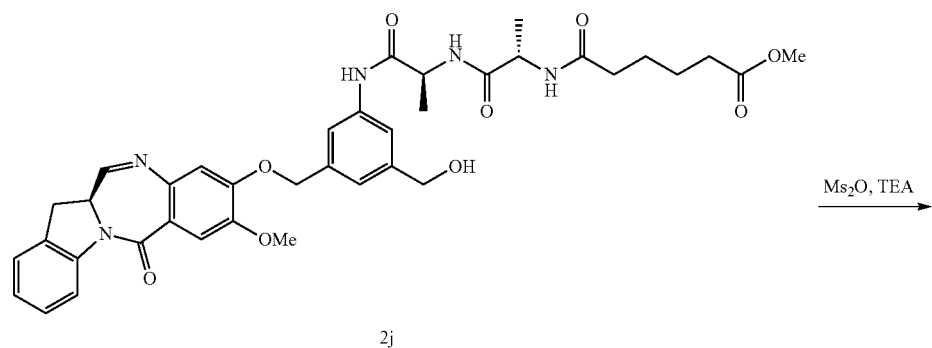

2j

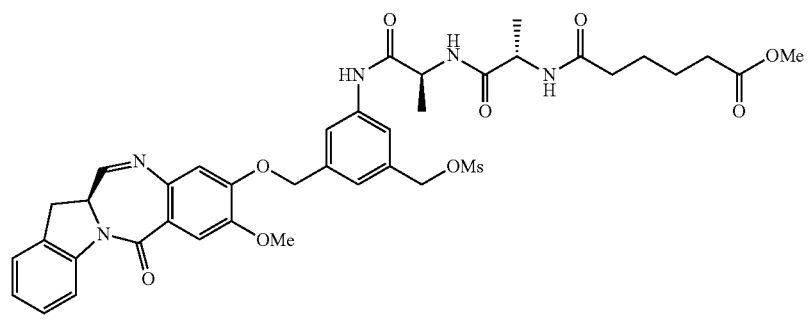

2k

Compound 2j (210 mg, 0.293 mmol) was dissolved in DCM (3.95 mL) and DMF (500 μL) and cooled to −10° C. (ice-acetone bath). TEA (57.2 μL, 0.411 mmol) and methanesulfonic anhydride (46.6 mg, 0.260 mmol) were added and the reaction as stirred for 3 h under Ar. The reaction was quenched with cold water at −5° C. and diluted with EtOAc. The aqueous layer was extracted with cold EtOAc (2×) and the combined organics were washed with cold water (2×). The organic layer was dried over anhydrous sodium/magnesium sulfate, filtered and concentrated. The crude product 2k was pumped on the high vacuum and taken onto next step without purification. LCMS (8 min method, 5-98%)=5.06 min. Mass observed (ESI−): 791.8 (M−H)−.

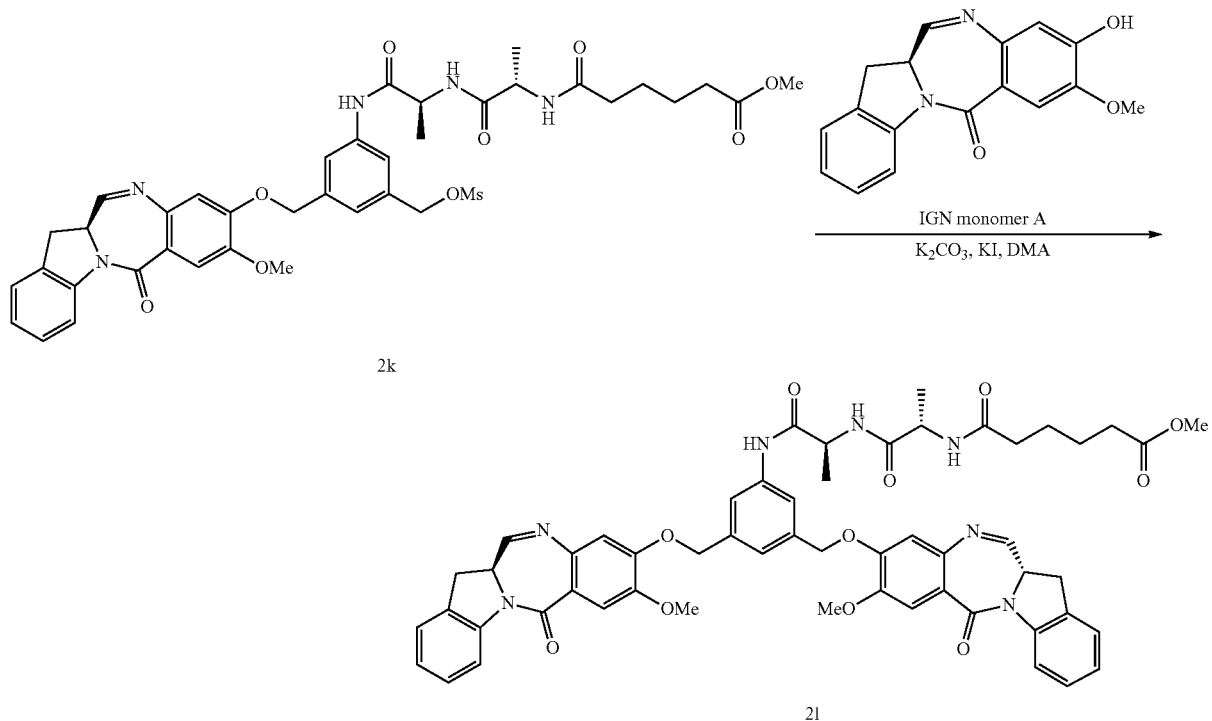

Compound 2k (233 mg, 0.293 mmol) was dissolved in DMA (1.95 mL). IGN monomer A (103 mg, 0.352 mmol) and potassium carbonate (60.7 mg, 0.440 mmol) were added at room temperature and the reaction stirred overnight. DI water was added to the reaction mixture and the resulting solid was filtered and washed with water. The solid was redissolved in DCM/MeOH (20:1), washed with water, dried over magnesium sulfate, filtered and concentrated. The crude residue was purified by RPHPLC (ACN/H$_2$O) to give 2l (44 mg, 15% yield). LCMS (8 min method, 5-98%)=5.4 min. Mass observed (ESI+): 991.7 (M+H)+.

Example 3

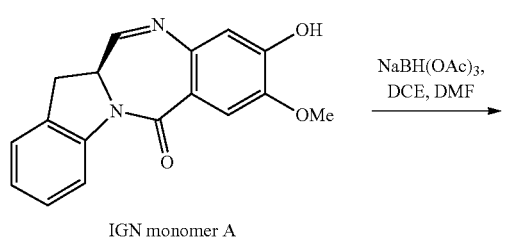

IGN monomer A

-continued reduced IGN monomer A

To a solution of IGN monomer A (1.0 g, 3.4 mmol) in DCE (10 mL) and DMF (4 mL) was added sodium triacetoxyborohydride (1.1 g, 5.1 mmol, 1.5 equiv) and the reaction was stirred until completion of starting material. Upon completion of the starting material after 2 h at room temperature, the reaction was quenched with sat. ammonium chloride (10 mL), and then the layers were separated. The aqueous layer was extracted once with dichloromethane (10 mL) and the combined organic layers were washed with water (2×10 mL) and brine (10 mL). The organic layer was dried over magnesium sulfate, filtered and the solvent was removed in vacuo to give a white/brown powder. The powder was washed with EtOAc (2×10 mL) and dried under vacuum to give reduced IGN monomer A as a white solid (0.87 g, 2.9 mmol, 87% yield) which was used in the next step without further purification. UPLCMS (2.5 min method)=1.34 min. Mass observed (ESI+): 297.4 (M+H)+. 1H NMR (400 MHz, DMSO-d6): δ 9.44 (s, 1H), 8.20 (d, J=8.1 Hz, 1H), 7.30-7.23 (m, 2H), 7.22-7.12 (m, 1H), 7.01 (td, J=7.4, 1.1 Hz, 1H), 6.21 (s, 1H), 6.17 (d, J=6.6 Hz, 1H), 4.37 (tdd, J=10.1, 4.4, 1.9 Hz, 1H), 3.70 (s, 3H), 3.58-3.39 (m, 2H), 3.31-3.15 (m, 2H), 2.88 (dd, J=16.9, 4.4 Hz, 1H).

dried over magnesium sulfate, filtered, and the solvent was removed in vacuo to give an orange oil which was triturated in diethyl ether to give bis mesylate 2m (6.4 g, 10.8 mmol, 85% yield). LCMS (8 min method)=4.019 min. Mass observed (ESI+): 594.8 (M+H)+. The crude material was carried on to the next step without further purification.

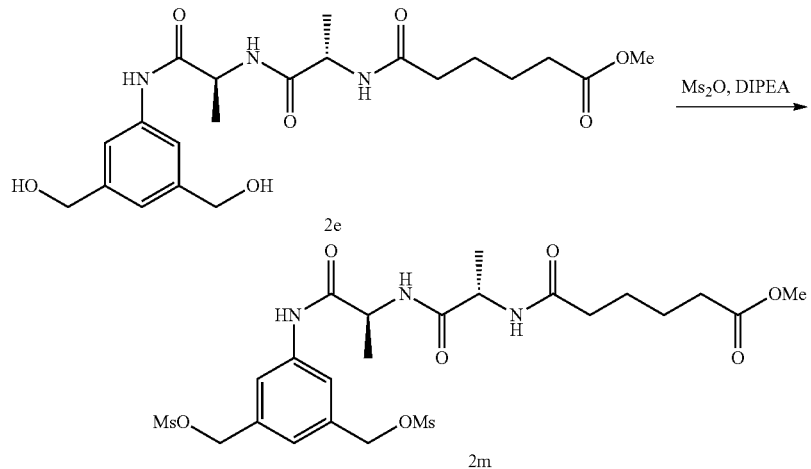

A solution of 2e (5.53 g, 12.6 mmol) in DCM (81 mL) and DMF (64.9 mL) was cooled down to 0° C. and then DIPEA (6.13 mL, 37.9 mmol, 3.0 equiv.) was added followed by a solution of methanesulfonic anhydride (5.06 g, 29.1 mmol, 2.3 equiv.) in DCM (15 mL)/DMF (1 mL) dropwise. The reaction was stirred for 1 h before quenching with cold water. After washing with water and brine the solution was

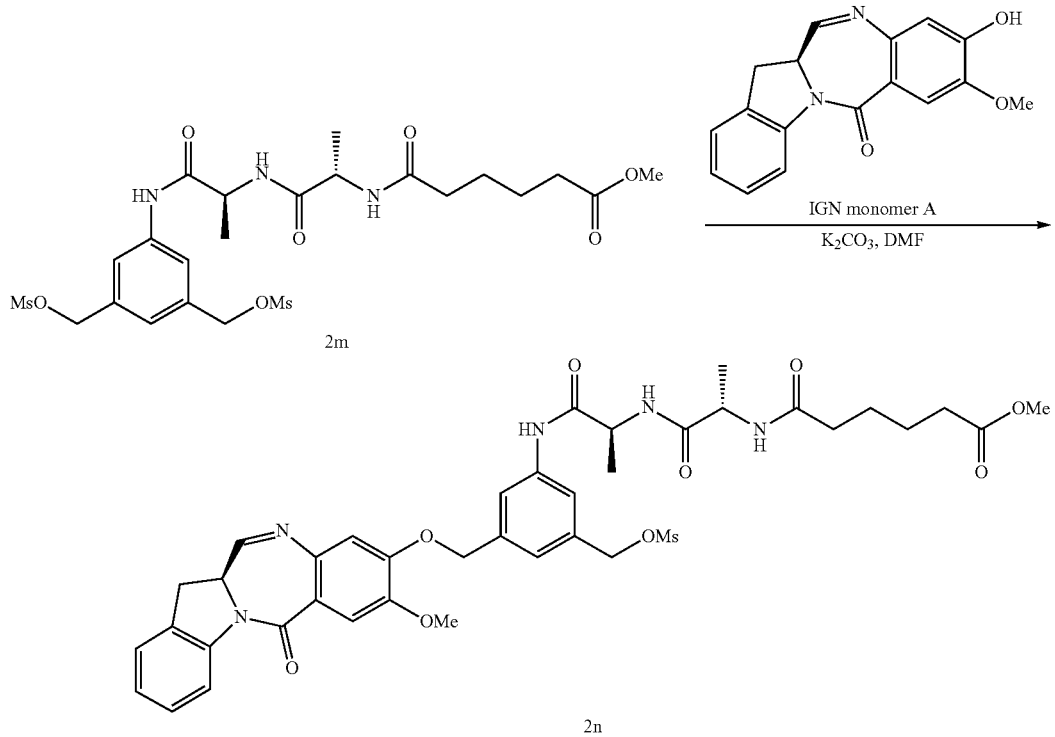

To a solution of 2m (0.52 g, 0.88 mmol) and IGN monomer A (0.18 g, 0.61 mmol, 0.7 equiv.) in DMF (7 mL) was added potassium carbonate (0.24 g, 1.75 mmol, 2.0 equiv.) and the reaction was stirred at room temperature for 12 h. The reaction was quenched with water (30 mL) and was extracted with DCM (3×15 mL). The organic layers were combined and washed with water (3×60 mL), brine (60 mL), dried over magnesium sulfate, filtered and the solvent was removed in vacuo to give a crude yellow oil. The material was purified by silica gel chromatography (DCM/(MeCN/MeOH (4/1) from 100/0 to 65/35) to give desired product 2n (0.09 g, 0.12 mmol, 13% yield). UPLCMS (2.5 min method)=1.46 min. Mass observed (ESI⁺): 792.6 (M+H)⁺.

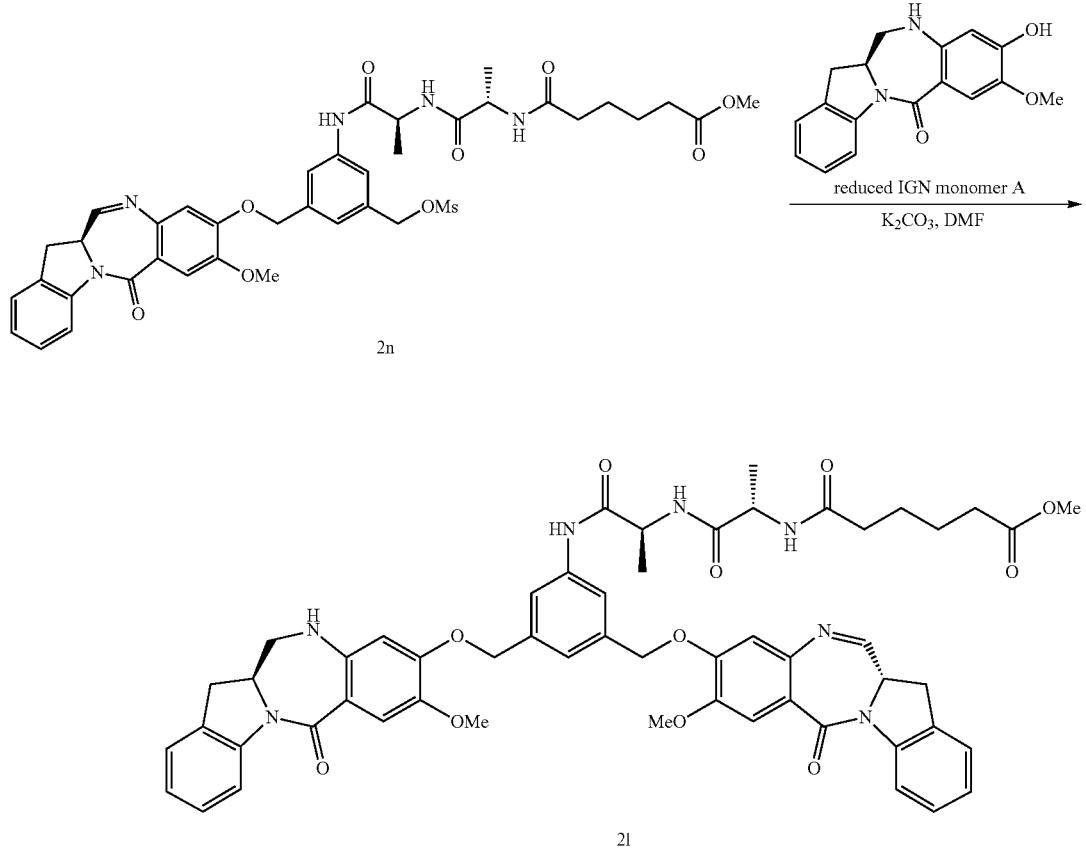

To a solution of 2n (0.05 g, 0.06 mmol) in DMF (0.48 mL, 6.2 mmol) was added potassium carbonate (0.02 g, 0.12 mmol, 2.0 equiv.) followed by reduced IGN monomer A (0.02 g, 0.07 mmol, 1.1 equiv.). The reaction was stirred at room temperature for 12 h. The reaction was quenched with water and the resulting solid was filtered and washed with water. The solid was redissolved in DCM/MeOH (20:1), washed with water, dried with magnesium sulfate, filtered and concentrated. The crude residue was purified by RPHPLC (ACN/H₂O) to give 2l (0.03 g, 0.04 mmol, 55% yield). LCMS (8 min method, 5-98%)=5.4 min. Mass observed (ESI⁺): 991.7 (M+H)⁺. ¹H NMR (400 MHz, DMSO-d₆, reported as a mixture of water adducts): δ 10.10 (d, J=3.7 Hz, 1H), 8.27 (d, J=8.0 Hz, 1H), 8.21-8.10 (m, 1H), 8.05 (d, J=7.4 Hz, 1H), 7.78 (dt, J=8.5, 1.8 Hz, 2H), 7.43-7.13 (m, 7H), 7.16-6.98 (m, 2H), 6.49 (s, 1H), 6.36 (d, J=13.1 Hz, 0.4H), 6.16 (d, J=6.2 Hz, 0.4H), 5.80 (s, 0.4H), 5.67 (s, 0.4H), 5.57 (d, J=5.6 Hz, 0.4H), 5.35-5.09 (m, 2H), 5.03 (t, J=5.9 Hz, 2H), 4.81-4.72 (m, 0.4H), 4.60 (dt, J=9.7, 5.0 Hz, 0.2H), 4.51-4.36 (m, 2H), 4.39-4.23 (m, 1H), 4.17 (td, J=9.7, 2.9 Hz, 0.4H), 3.93 (s, 0.4H), 3.83-3.74 (m, 5H), 3.62 (s, 2H), 3.75-3.44 (m, 2H), 3.32 (d, J=11.6 Hz, 1H), 3.19-3.07 (m, 1H), 2.95 (dd, J=17.1, 4.3 Hz, 1H), 2.38-2.29 (m, 1H), 2.18 (m, 1H), 1.56 (m, J=3.9 Hz, 4H), 1.41-1.31 (m, 3H), 1.30-1.14 (m, 3H).

Example 4

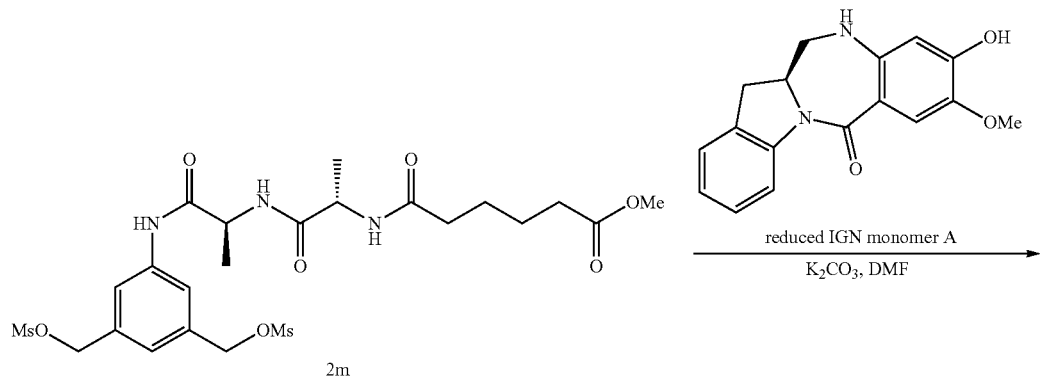

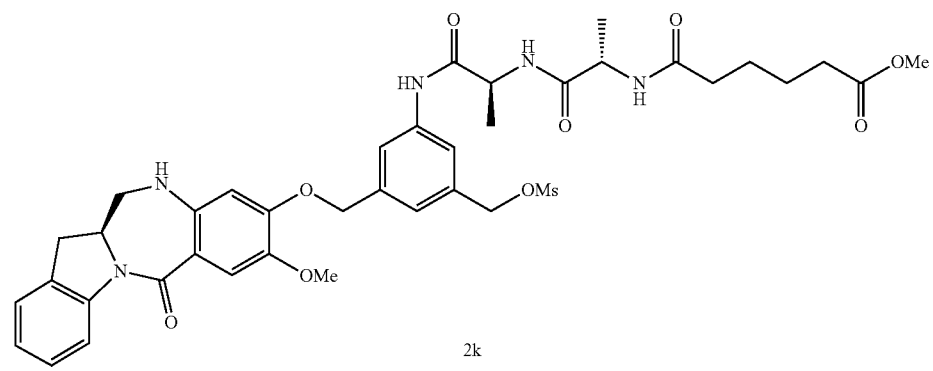

To a solution of 2m (0.88 g, 1.47 mmol) in DMF (11 mL) was added reduced IGN monomer A (0.26 g, 0.88 mmol, 0.6 equiv.) followed by potassium carbonate (0.41 mg, 2.95 mmol, 2.0 equiv.). After the reaction was stirred for 12 h, the reaction was diluted with water (50 mL) and EtOAc (30 mL). The aqueous layer was extracted with EtOAc (3×10 mL). The combined organic layers were washed with brine (20 mL), dried over magnesium sulfate and filtered. The solvent was removed and the crude mixture was purified by silica gel chromatography (DCM/MeOH) to give desired product 2k (0.11 g, 0.14 mmol, 10% yield). LCMS (8 min method)=5.013 min. Mass observed (ESI$^+$): 794.3 (M+H)$^+$.

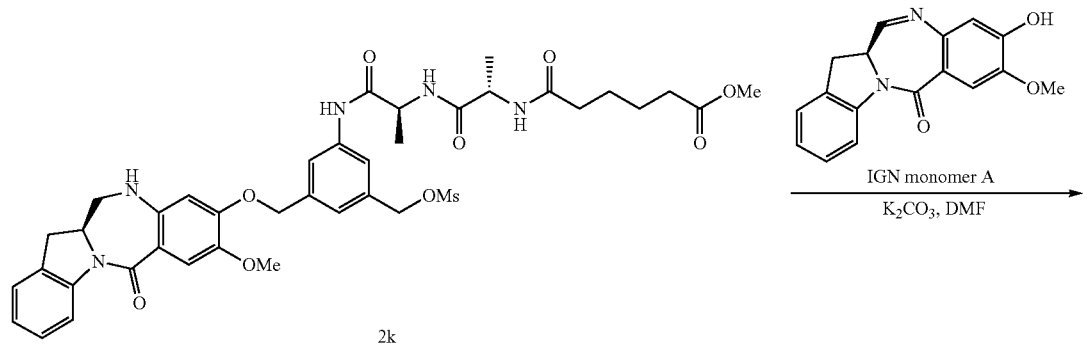

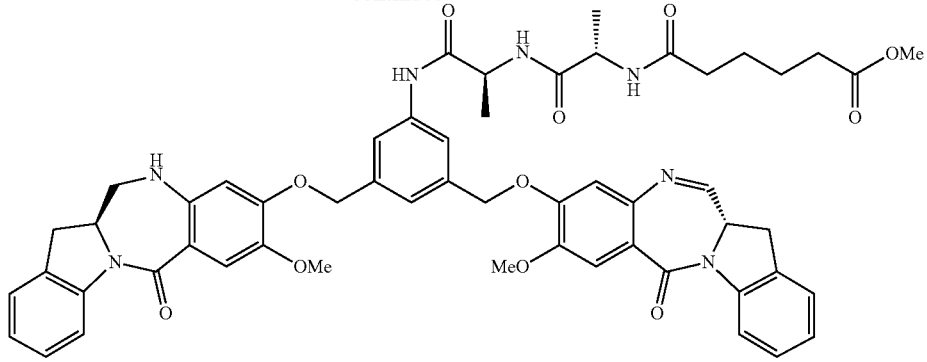

21

To a solution of 2k (0.11 g, 0.14 mmol) in DMF (2 mL) was added potassium carbonate (0.04 g, 0.29 mmol, 2.0 equiv.) IGN monomer A (0.04 g, 0.14 mmol, 1.0 equiv.) was added and the reaction was stirred at rt for 12 h. The reaction was quenched with water (10 mL) and the resulting solid was filtered and washed with water. The solid was redissolved in DCM/MeOH (20:1), washed with water (10 mL), dried with magnesium sulfate, filtered and concentrated. The crude residue was purified by RPHPLC (ACN/H$_2$O) to give 2l (0.08 g, 0.09 mmol, 59% yield). LCMS (8 min method, 5-98%)=5.4 min. Mass observed (ESI$^+$): 991.7 (M+H)$^+$.

Example 5

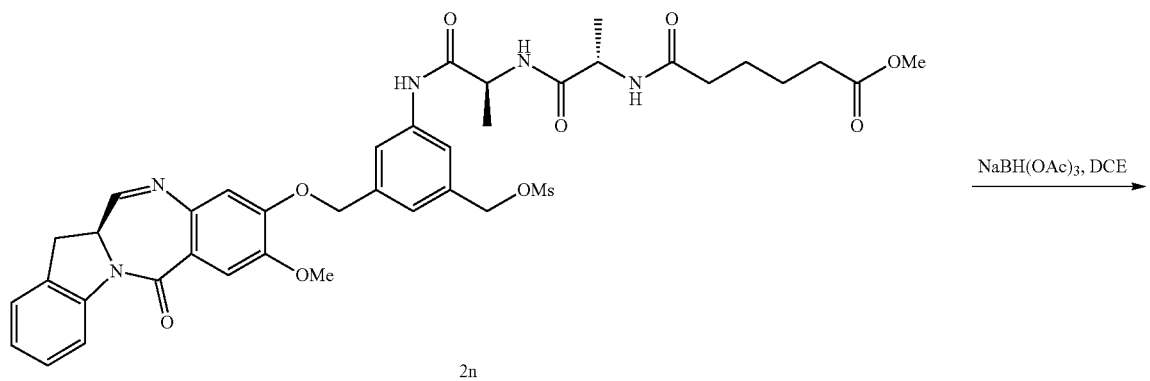

2n

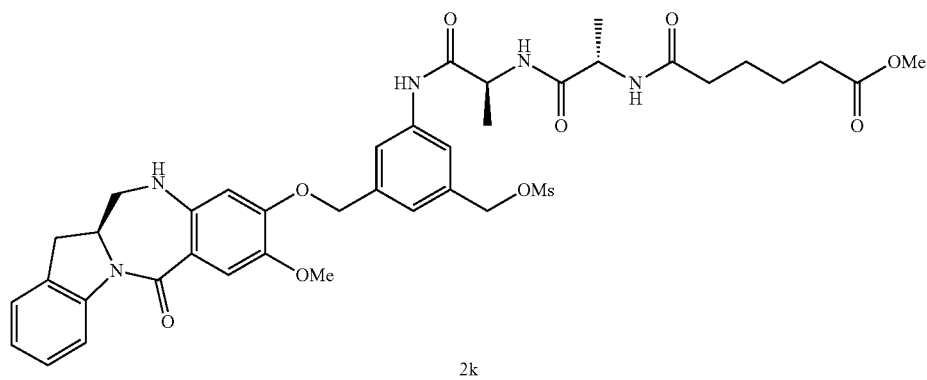

2k

To a solution of 2n (0.1 g, 0.13 mmol) in DCE (2 mL) was added sodium triacetoxyborohydride (0.03 g, 0.13 mmol, 1.0 equiv.) and the reaction was stirred at rt for 2 h. The reaction was quenched with saturated ammonium chloride (2 mL) and the layers were separated. The aqueous layer was extracted with DCM (5 mL) and the combined organic layers were washed with water, brine, dried over magnesium sulfate and filtered. The crude yellow solid was purified using silica gel chromatography (EtOAc/MeOH (95/5)) to afford the desired reduced product 2k (0.035 g, 0.044 mmol, 35% yield). LCMS (8 min method)=5.021 min. Mass observed (ESI$^+$): 794.3 (M+H)$^+$.

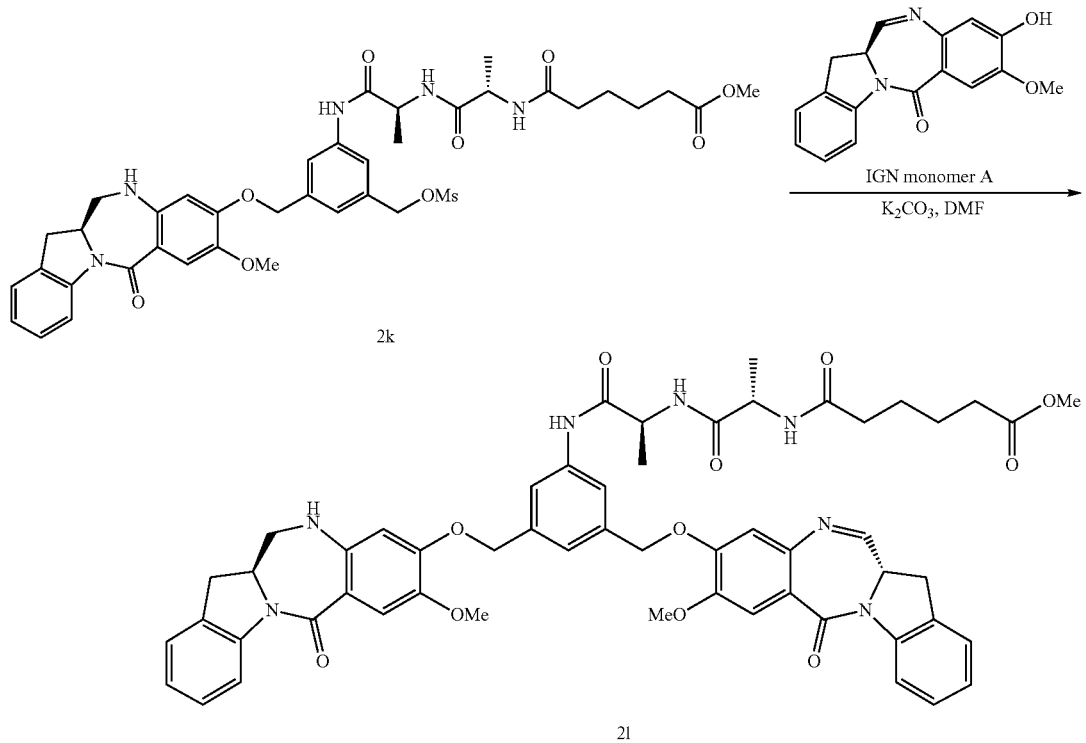

To a solution of 2k (0.035 g, 0.044 mmol) in DMF (1.0 mL) was added potassium carbonate (0.013 g, 0.09 mmol, 2.0 equiv.). IGN monomer A (0.013 g, 0.04 mmol, 1.0 equiv.) was added and the reaction was stirred at room temperature for 12 h. The reaction was quenched with water (10 mL) and the resulting solid was filtered and washed with water. The solid was redissolved in DCM/MeOH (20:1, 20 mL), washed with water (20 mL), dried with magnesium sulfate, filtered and concentrated. The crude residue was purified by RPHPLC (ACN/H$_2$O) to give 2l (0.017 g, 0.01 mmol, 38% yield). LCMS (8 min method, 5-98%)=5.4 min. Mass observed (ESI$^+$): 991.7 (M+H)$^+$.

Example 6

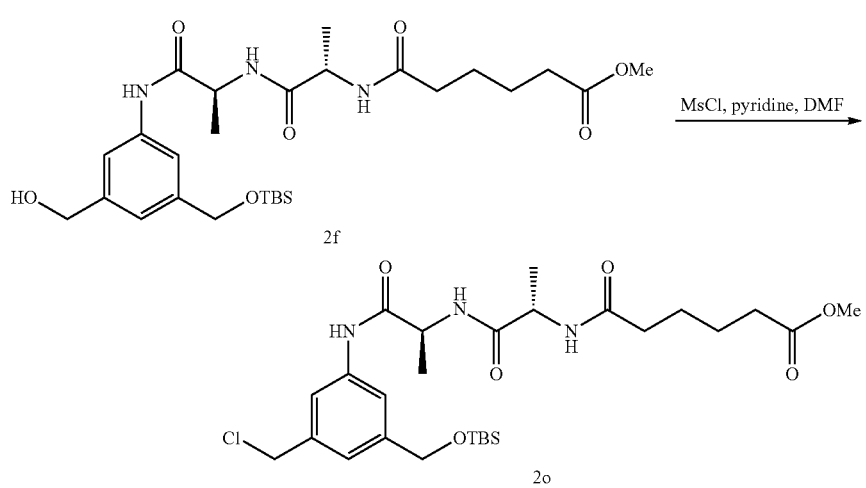

To a solution of 2f (8.8 g, 16.0 mmol) in DMF (100 mL) was added pyridine (4.51 ml, 55.8 mmol, 3.5 equiv.). The reaction was cooled down to 0° C. then methanesulfonyl chloride (2.5 mL, 31.9 mmol, 2.0 equiv.) was added dropwise and reaction stirred for 2 h. The mixture was quenched with sat. sodium bicarbonate (30 mL), EtOAc was added and the layers were separated. The aqueous layer was extracted with EtOAc (3×50 mL) and the combined organic layers were washed with water, brine, dried over magnesium sulfate and filtered. The solvent was removed and the crude white solid 2o was used in the next step without purification (6.2 g, 10.9 mmol, 68%). UPLCMS (2.5 min method)=1.96 min. Mass observed (ESI+): 570.7 (M+H)+.

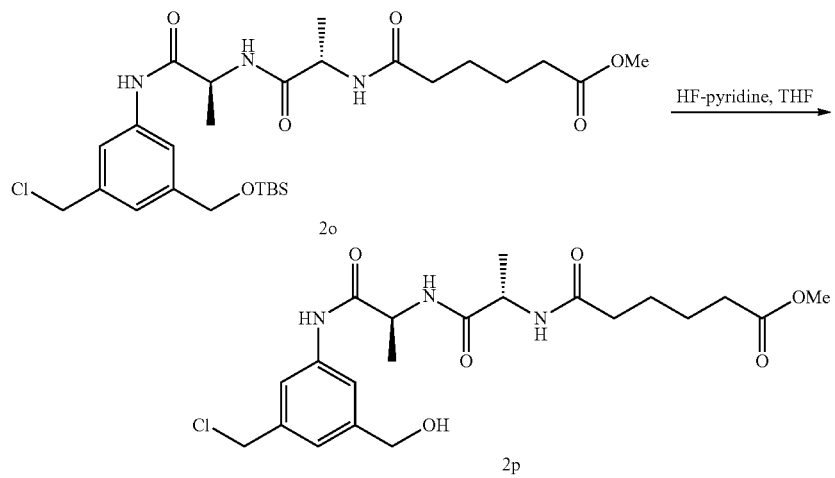

To a solution of 2o (1.7 g, 2.98 mmol) in THF (36.6 mL) was added DIPEA (2.1 mL, 11.9 mmol, 4.0 equiv.) followed by HF-pyridine (0.84 mL, 6.0 mmol, 2.0 equiv.). The reaction was stirred at room temperature for 3 h. The reaction was quenched with sat. sodium bicarbonate (20 mL) and then the layers were separated. The aqueous layer was extracted with EtOAc (3×10 mL). The combined organic layers were washed with brine (30 mL), dried over magnesium sulfate, filtered and the solvent removed in vacuo to give a crude white oil which was purified by silica gel chromatography (DCM/MeOH) to give desired product 2p as a white solid (0.75 g, 1.6 mmol, 55% yield). UPLCMS (2.5 min method)=1.23 min. Mass observed (ESI+): 456.4 (M+H)+.

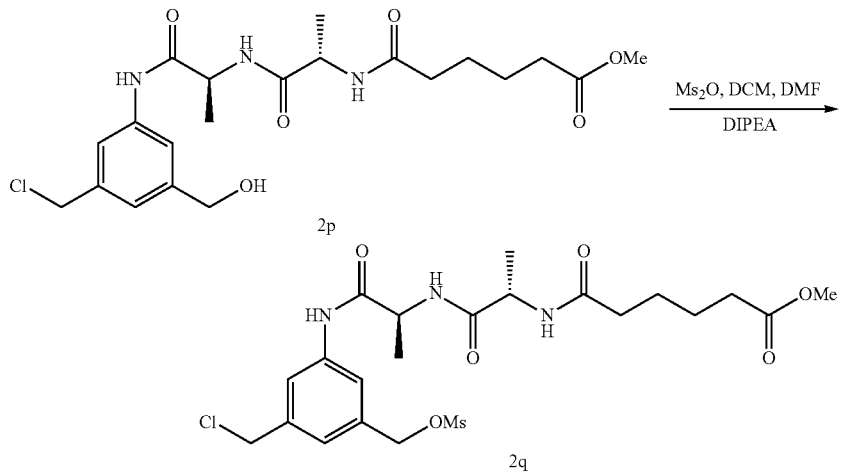

To a solution of 2p (0.65 g, 1.43 mmol) in DCM (10 mL) and DMF (2 mL) was added DIPEA (0.51 mL, 2.85 mmol, 2.0 equiv.) and the reaction was cooled down to 0° C. A solution of methanesulfonic anhydride (0.3 g, 1.71 mmol) in DCM (2 mL) was added slowly. The reaction was completed after 30 min, quenched with water (20 mL), the layers were extracted, aqueous layer washed with DCM (2×10 mL). Organic layers were combined, washed with water (20 mL), brine (10 mL), dried over magnesium sulfate and filtered. The solvent was removed in vacuo to give desired product 2q (0.76 g, 1.42 mmol, 100% yield) which was carried crude into the next step without further purification. UPLCMS (2.5 min method)=1.37 min. Mass observed (ESI+): 534.4 (M+H)+.

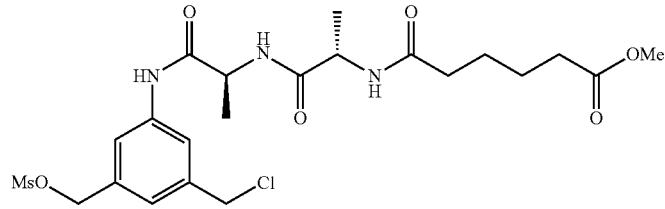

2q

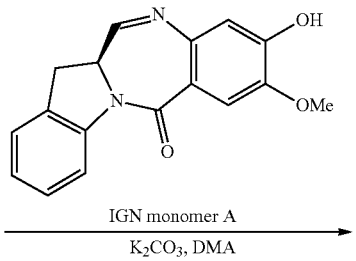

IGN monomer A
$\xrightarrow{K_2CO_3, DMA}$

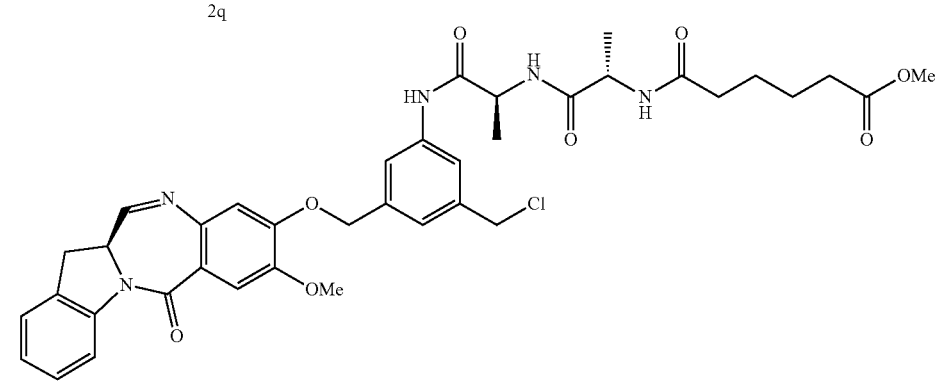

2r

To a solution of 2q (0.76 g, 1.42 mmol) in DMA (13 mL) was added potassium carbonate (0.59 g, 4.27 mmol) followed by a solution of IGN monomer A (0.5 g, 1.71 mmol) in DMA (1 mL). The reaction was stirred at room temperature for 12 h. The reaction was quenched with water (30 mL) and the mixture was stirred for 10 min. The solid was filtered and then dissolved in DCM/MeOH (9/1, 20 mL) and washed with brine (10 mL). The organic layer was separated and dried over magnesium sulfate, filtered and concentrated in vacuo to give a crude yellow solid 2r (0.76 g, 1.04 mmol, 73% yield) which was carried crude into the next step without further purification. UPLCMS (2.5 min method) =1.55 min. Mass observed (ESI+): 732.9 (M+H)+.

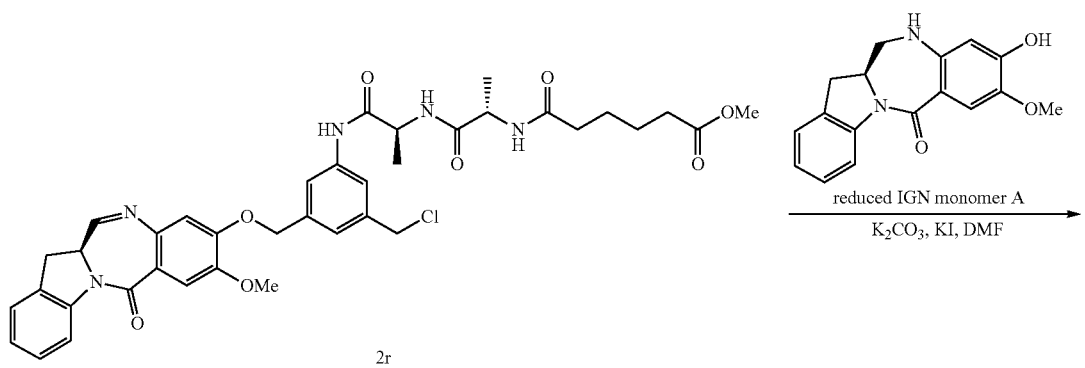

2r reduced IGN monomer A
$\xrightarrow{K_2CO_3, KI, DMF}$

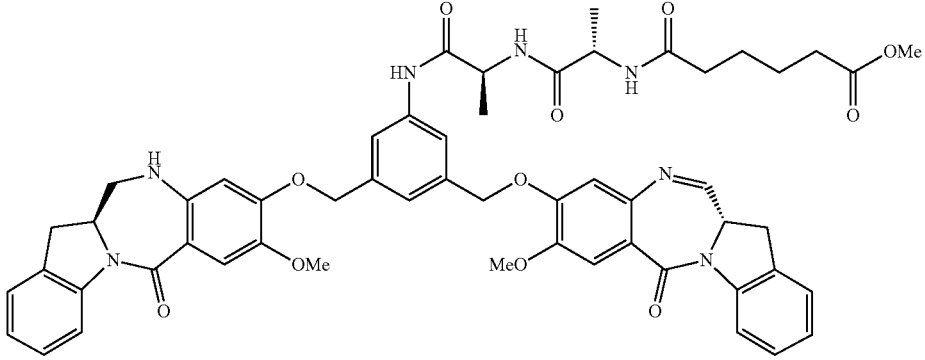

21

To a solution of 2r (0.26 g, 0.36 mmol) in DMA (10 mL) was added potassium iodide (0.06 g, 0.355 mmol, 1.0 equiv.), reduced IGN monomer A (0.1 g, 0.37 mmol, 1.05 equiv.) and potassium carbonate (0.15 g, 1.06 mmol, 3.0 equiv.). The reaction was warmed up to 40° C. and stirred for 4 h. The reaction was quenched with water (20 mL) and the mixture stirred for 10 min. The resulting solid was filtered. The solid was redissolved in DCM/MeOH (20:1, 20 mL), washed with water (20 mL), dried with magnesium sulfate, filtered and concentrated. The crude residue was purified by RPHPLC (ACN/H$_2$O) to give 2l (0.097 g, 0.097 mmol, 28% yield). LCMS (8 min method, 5-98%)=5.4 min. Mass observed (ESI$^+$): 991.7 (M+H)$^+$.

Example 7

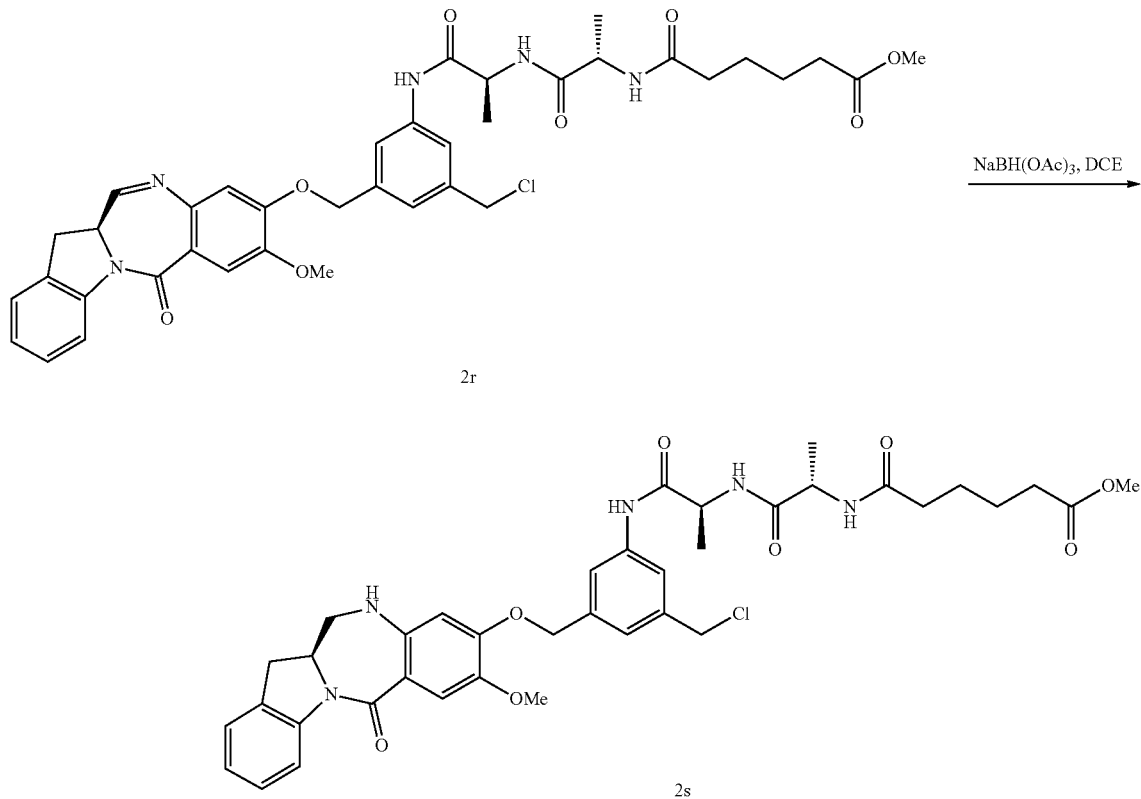

To a solution of 2r (0.76 g, 1.04 mmol) in DCE (10 mL) was added DMF (3.0 mL) followed by addition of sodium triacetoxyborohydride (0.33 g, 1.56 mmol) at 0° C. The reaction was stirred at room temperature for 4 h. The reaction was quenched with sat. ammonium chloride (20 mL) and the layers were separated. The aqueous layer was extracted with DCM (3×10 mL) and the combined organic layers were washed with water (10 mL), brine (10 mL), dried over magnesium sulfate, filtered and the solvent removed in vacuo to give the desired crude material 2s as an oil (0.65 g, 0.88 mmol, 85% yield) which was used in the next step without further purification. UPLCMS (2.5 min method)=1.80 min. Mass observed (ESI$^+$): 735.3 (M+H)$^+$.

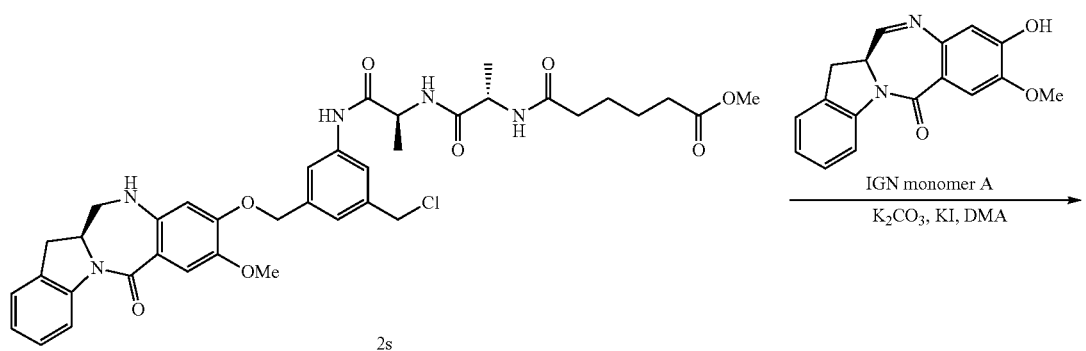

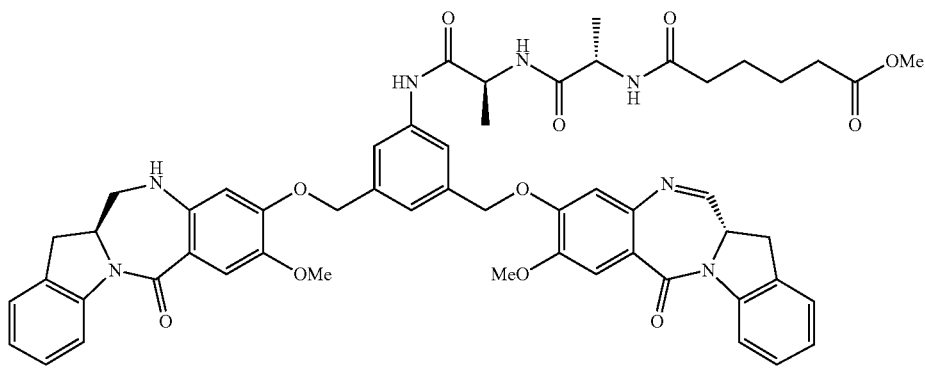

To a solution of 2s (0.65 g, 0.88 mmol) in DMA (15 mL) was added potassium carbonate (0.25 g, 1.78 mmol, 2.0 equiv.) followed by potassium iodide (0.073 g, 0.44 mmol, 0.5 equiv.) and a solution of IGN monomer A (0.29 g, 0.974 mmol, 1.1 equiv.) in DMA (2 mL) was added to the reaction mixture at room temperature. The reaction was heated at 40° C. for 5 h. The reaction was quenched with water (30 mL) and then solid was filtered off. The solid was redissolved in DCM/MeOH (20:1, 30 mL), washed with water (20 mL), dried with magnesium sulfate, filtered and concentrated. The crude residue (0.78 g) was purified by RPHPLC (ACN/H$_2$O) to give 2l (0.43 g, 0.43 mmol, 49% yield). LCMS (8 min method, 5-98%)=5.4 min. Mass observed (ESI$^+$): 991.7 (M+H)$^+$.

Example 8

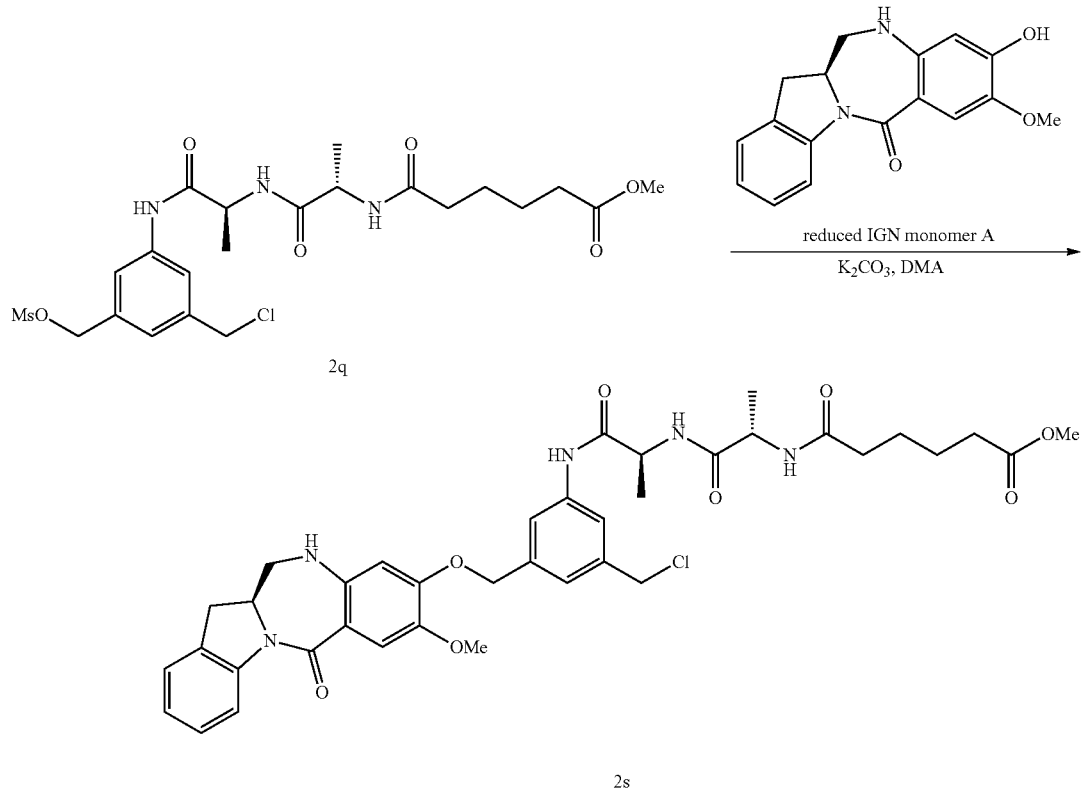

To a solution of 2q (0.14 g, 0.27 mmol) in DMA (3 mL) was added potassium carbonate (0.11 g, 0.81 mmol) followed by a solution of reduced IGN monomer A (0.084 g, 0.28 mmol) in DMA (1 mL). The reaction was stirred at room temperature for 12 h. The reaction was quenched with water (20 mL) and the mixture stirred for 10 min. The solid was filtered and then dissolved in DCM/MeOH (9/1, 20 mL) and washed with brine (10 mL). The organic layer was separated and dried over magnesium sulfate, filtered and solvent removed in vacuo. The crude material was purified by silica gel chromatography using DCM (MeOH/EtOAc, 1/4) to give desired product 2s (0.08 g, 0.11 mmol, 40% yield). UPLCMS (2.5 min method)=1.63 min. Mass observed (ESI+): 735.2 (M+H)+

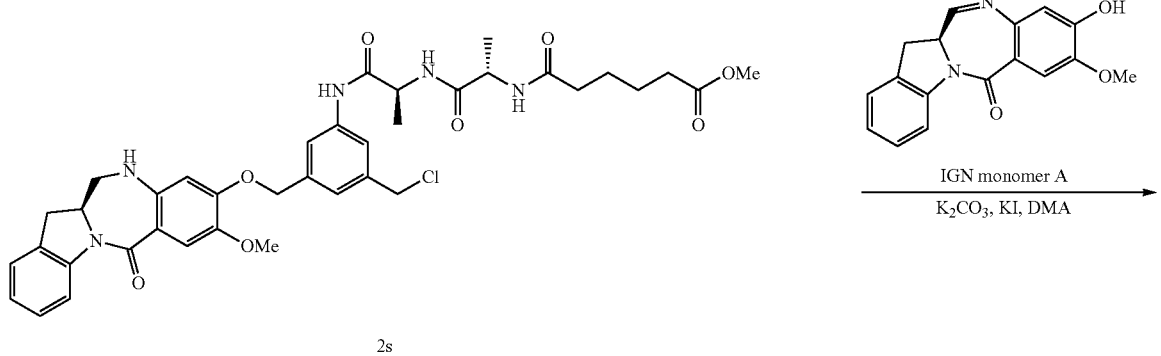

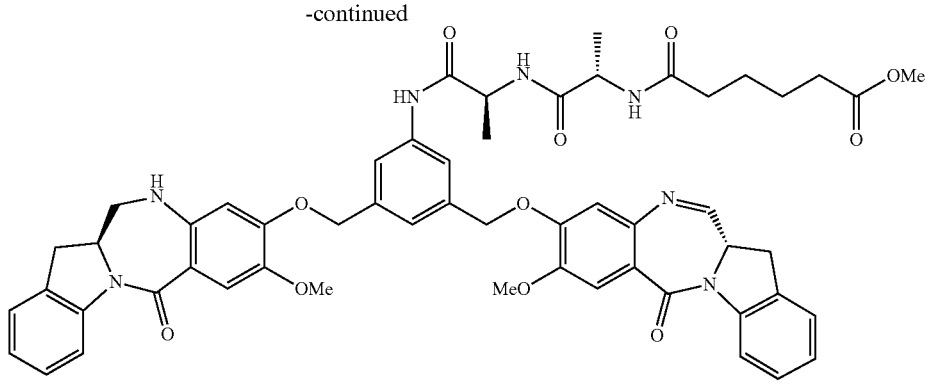

21

To a solution of 2s (0.06 g, 0.09 mmol) in DMA (2 mL) was added potassium carbonate (0.025 g, 0.18 mmol) followed by potassium iodide (0.007 g, 0.044 mmol). A solution of IGN monomer A (0.03 g, 0.097 mmol) in DMA (1 mL) was added to the reaction mixture at room temperature. The reaction was heated at 40° C. for 5 h., The reaction was cooled down and quenched with water (20 mL) and the solid was filtered off. The solid was redissolved in DCM/MeOH (20:1, 20 mL), washed with water (10 mL), dried with magnesium sulfate, filtered and concentrated. The crude residue (0.07 g) was purified by RPHPLC (ACN/H$_2$O) to give 2l (0.035 g, 0.035 mmol, 51% yield). LCMS (8 min method, 5-98%)=5.4 min. Mass observed (ESI$^+$): 991.7 (M+H)$^+$.

Example 9

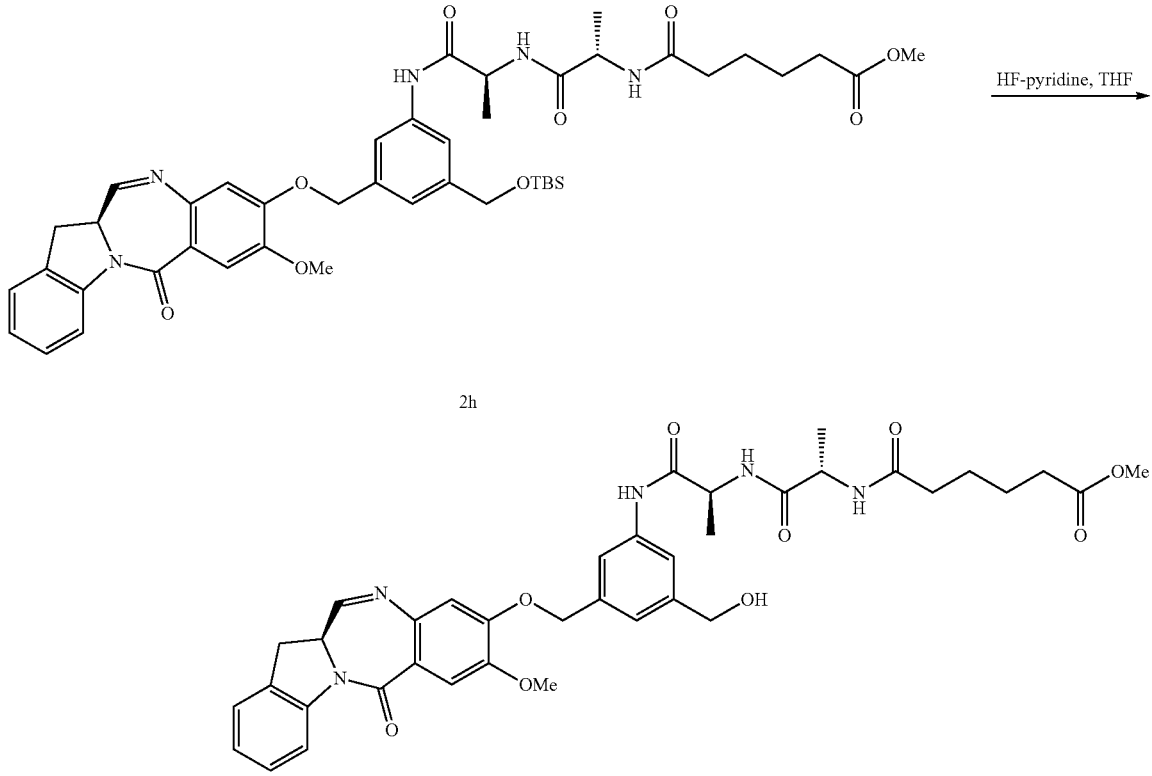

To a solution of 2 h (0.85 g, 1.027 mmol) in THF (9 mL) was added DIPEA (0.54 mL, 3.1 mmol, 3.0 equiv.) followed by HF-pyridine (0.3 mL, 2.053 mmol, 2.0 equiv.) at room temperature. The reaction was stirred for 3 h at room temperature. The reaction was quenched with sat. sodium bicarbonate (10 mL), the layers were separated and the aqueous layer extracted with DCM (3×10 mL). The combined organic layers were washed with brine (10 mL), dried over magnesium sulfate, and filtered. The solvent was removed in vacuo to give crude product as a solid which was washed with EtOAc to give the desired product 2t (0.64 g, 0.89 mmol, 87% yield). UPLCMS (2.5 min method)=1.36 min. Mass observed (ESI$^+$): 714.6 (M+H)$^+$.

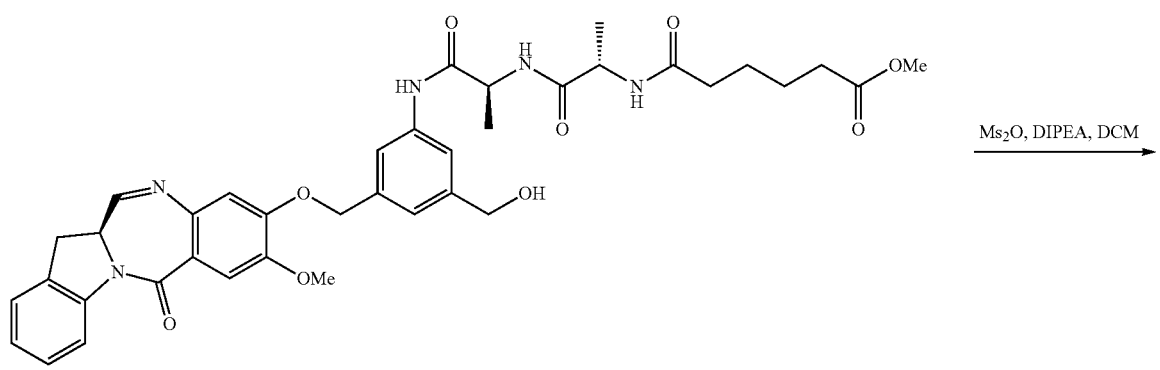

2t

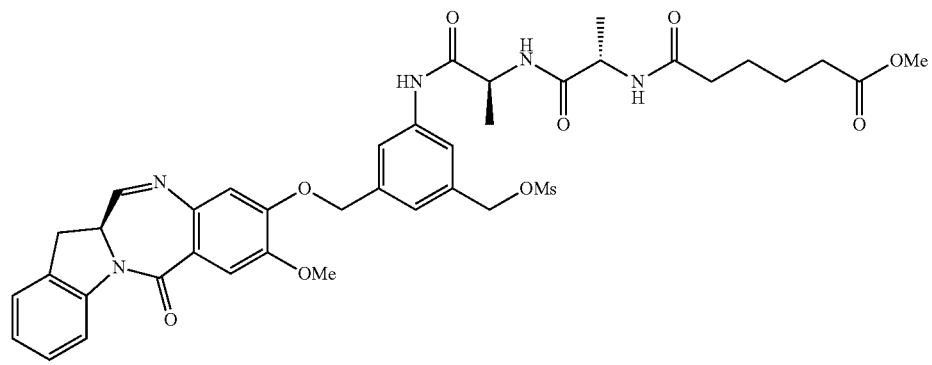

2n

To a solution of 2t (0.23 g, 0.322 mmol) in dichloromethane (3 mL) was added DIPEA (0.11 ml, 0.644 mmol, 2.0 equiv.) followed by methanesulfonic anhydride (0.084 g, 0.48 mmol, 1.5 equiv.) as a solution in DCM (1 mL) at 0° C. The reaction was stirred for 1 h. The reaction was quenched with water (3 mL) and diluted with DCM (3 mL). The layers were separated and the organic layer was washed with brine (3 mL), dried over magnesium sulfate and filtered. The solvent was removed in vacuo and the crude material 2n (0.25 g, 0.31 mmol, 98% yield) was used in the next step without further purification. UPLCMS (2.5 min method)=1.45 min. Mass observed (ESI$^+$): 792.5 (M+H)$^+$.

235 236

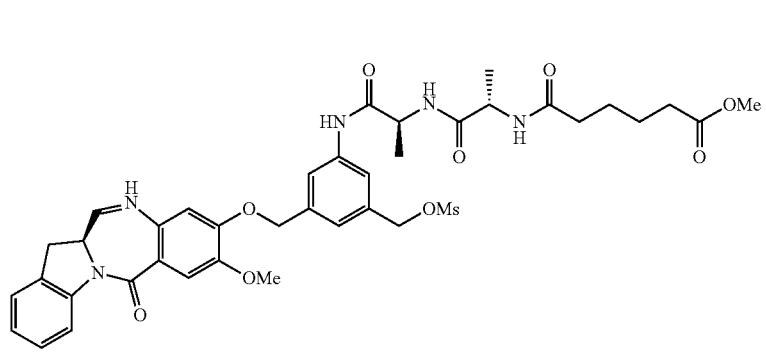

2n

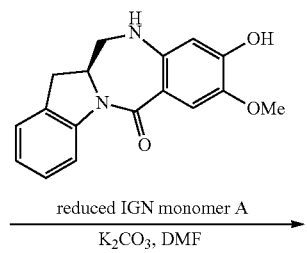

reduced IGN monomer A
─────────────────→
K₂CO₃, DMF

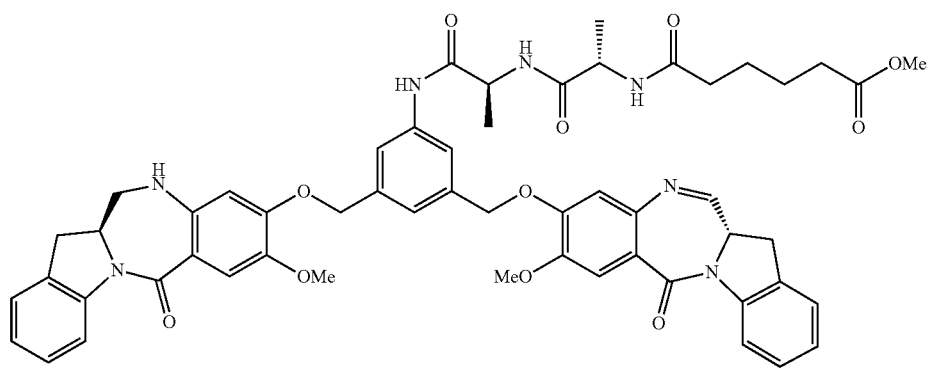

2l

To a solution of 2n (0.02 g, 0.027 mmol) in DMF (0.2 ml) was added potassium carbonate (0.007 g, 0.053 mmol, 2.0 equiv.) followed by reduced IGN monomer A (0.009 g, 0.029 mmol, 1.1 equiv.) and the reaction was stirred at room temperature for 18 h. Water (3 mL) was added to the reaction mixture and the resulting solid was filtered. The solid was redissolved in DCM/MeOH (20:1, 5 mL), washed with water (5 mL), dried with magnesium sulfate, filtered and concentrated. The crude residue was purified by RPHPLC (ACN/H₂O) to give 2l (0.005 g, 0.005 mmol, 19% yield). LCMS (8 min method, 5-98%)=5.4 min. Mass observed (ESI⁺): 991.7 (M+H)⁺.

Example 10

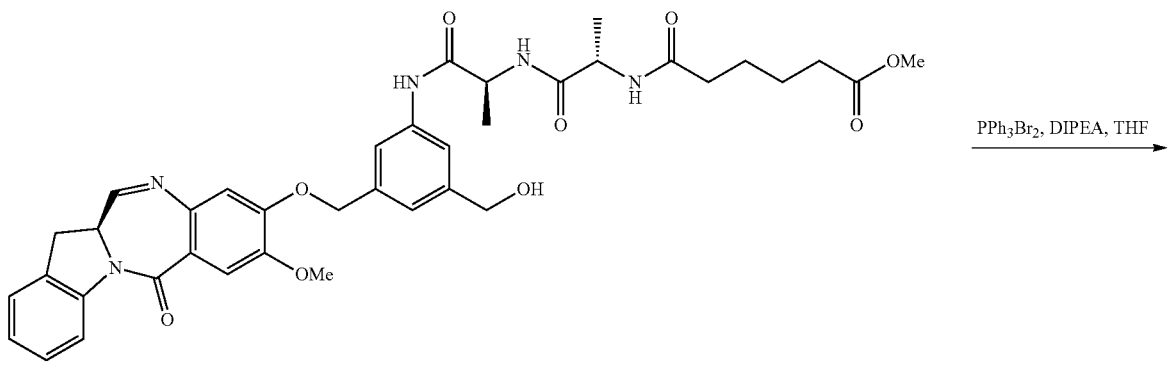

2t

PPh₃Br₂, DIPEA, THF
─────────────────→

-continued

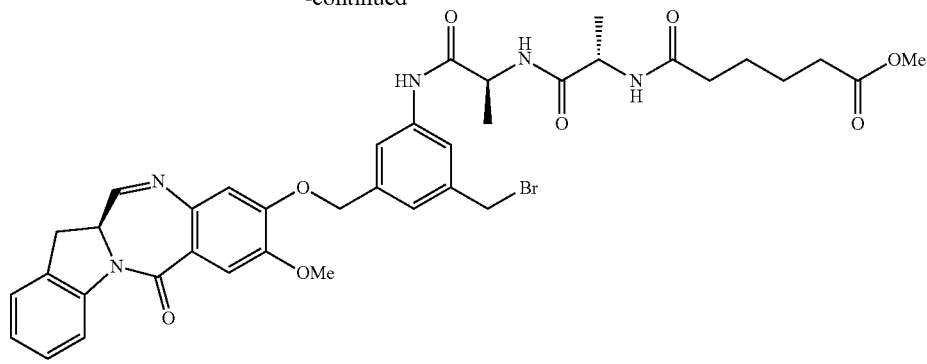

2u

To a solution of 2t (0.02 g, 0.031 mmol) in THF (2 mL) was added DIPEA (0.016 mL, 0.092 mmol, 3.0 equiv.) followed by a solution of dibromotriphenylphosphorane (0.03 g, 0.062 mmol, 2.0 equiv.) in THF (0.5 mL). The reaction was stirred at room temperature for 12 h., The reaction was stopped by evaporation of solvent and then the crude material was purified by silica gel chromatography to give 2u (0.006 g, 0.007 mmol, 25% yield). UPLCMS (2.5 min method)=1.56 min. Mass observed (ESI$^+$): 778.2 (M+H)$^+$.

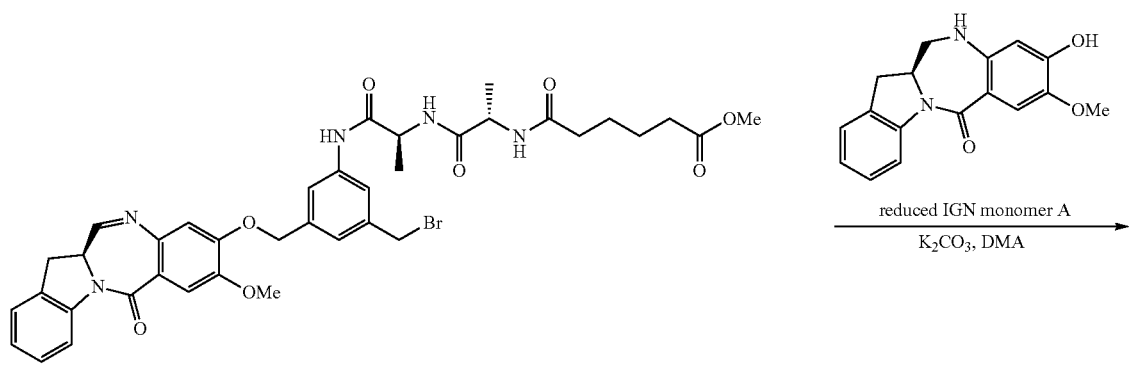

2u

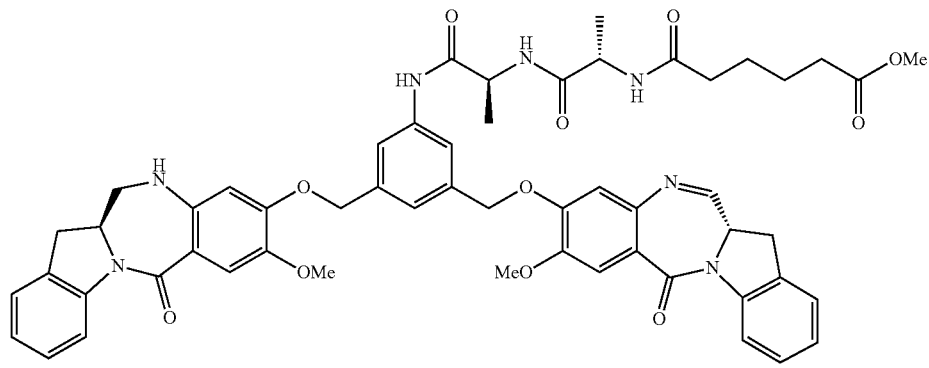

21

To a solution of 2u (0.006 g, 7.73 μmol) in DMA (1 mL) was added reduced IGN monomer A (0.003 g, 9.27 μmol) followed by potassium carbonate (0.002 g, 0.015 mmol) and the reaction was stirred at room temperature for 18 h. Water (3 mL) was added to the reaction mixture and the resulting solid was filtered and washed with water. The solid was redissolved in DCM/MeOH (20:1, 5 mL), washed with water (5 mL), dried with magnesium sulfate, filtered and concentrated. The crude residue was purified by RPHPLC (ACN/H$_2$O) to give 2l (0.001 g, 0.001 mmol, 13% yield). LCMS (8 min method, 5-98%)=5.4 min. Mass observed (ESI$^+$): 991.7 (M+H)$^+$.

Example 11

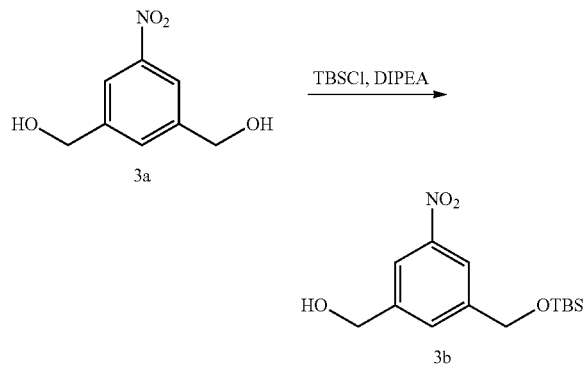

To a solution of (5-nitro-1,3-phenylene)dimethanol 3a (4.0 g, 21.84 mmol) in DCM (40 mL) and DMF (5 mL) was added DIPEA (3.86 mL, 21.84 mmol, 1.0 equiv.) followed by TBSCl (3.29 g, 21.84 mmol, 1.0 equiv.) as a solution in DMF (5 mL). The reaction was stirred at 0° C. for 1 h. The reaction was quenched with sat. ammonium chloride (20 mL) and the layers were separated. The aqueous layer was extracted with DCM (2×20 mL) and the combined organic layers were washed with water (2×50 mL), brine, dried over magnesium sulfate, filtered and solvent was removed in vacuo to give a crude yellow oil. The crude product was purified by silica gel chromatography (DCM/MeOH) to give desired product 3b (3.69 g, 12.41 mmol, 57% yield). UPLCMS (2.5 min method)=1.96 min. Mass observed (ESI$^+$): 298.5 (M+H)$^+$.

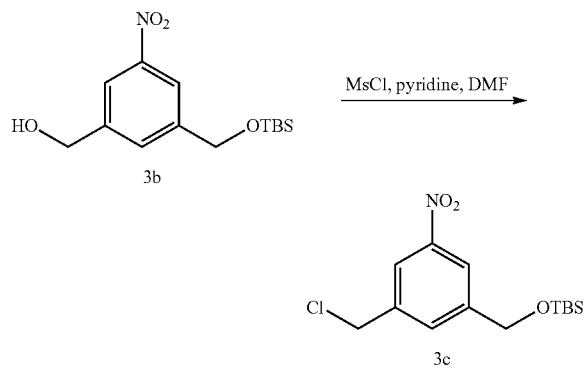

To a solution of 3b (2.0 g, 6.72 mmol) in DMF (50 mL) was added pyridine (1.6 ml, 20.17 mmol, 3.0 equiv.) followed by methanesulfonyl chloride (1.1 mL, 13.45 mmol, 2.0 equiv.) at 0° C. The reaction was warmed to rt and was stirred for 3 h. The reaction was quenched with sat. sodium bicarbonate (20 mL) and the layers were separated. The aqueous layer was extracted with EtOAc (3×30 mL). The combined organic layers were washed with water (2×100 mL), brine (100 mL), dried over magnesium sulfate and filtered. The solvent removed in vacuo and the crude material 3c (2.0 g, 6.7 mmol, 94% yield) was carried crude onto the next step. UPLCMS (2.5 min method)=2.22 min. Mass observed (ESI$^+$): 316.7 (M+H)$^+$.

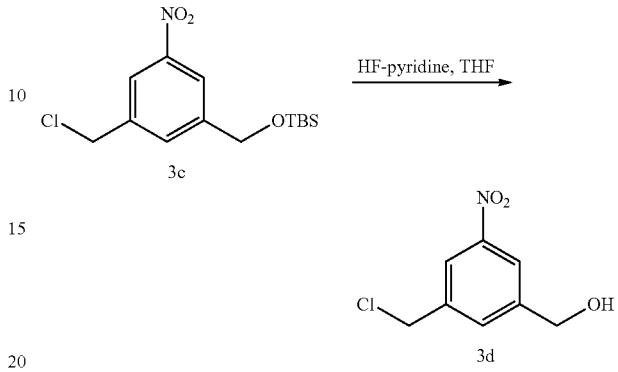

To a solution of 3c (2.0 g, 6.33 mmol) in THF (38.9 mL) was added DIPEA (5.5 mL, 31.6 mmol, 5.0 equiv.) followed by HF-pyridine (2.7 mL, 19.0 mmol, 3.0 equiv.) and the reaction was stirred at room temperature for 2 h. The reaction was then quenched with sat. sodium bicarbonate (100 mL). The layers were separated and then the aqueous layer was extracted with EtOAc (3×20 mL). The combined organic layers were then washed with water (30 mL), brine (30 mL), dried over magnesium sulfate and filtered. The excess of solvent was removed in vacuo to give desired product 3d (1.1 g, 5.46 mmol, 86% yield). UPLCMS (2.5 min method)=1.31 min. Mass observed (ESI$^+$): 202.4 (M+H)$^+$.

To a solution of 3d (1.0 g, 4.96 mmol) in DCM (10 mL) was added DIPEA (2.6 mL, 14.9 mmol, 3.0 equiv.) at 0° C. then a solution of methanesulfonic anhydride (1.1 g, 6.45 mmol, 1.3 equiv.) in DCM was added to the reaction mixture. The reaction was stirred for 1 h. The reaction was quenched with water (10 mL) and the layers were separated and the aqueous layer was extracted with DCM (2×20 mL). The combined organic layers were washed with sat. sodium bicarbonate (10 mL), brine (20 mL), dried over magnesium sulfate and filtered. The solvent was removed in vacuo and the crude material 3e (1.3 g, 4.65 mmol, 94% yield) was used in the next step without further purification. UPLCMS (2.5 min method)=1.51 min. Mass observed (ESI$^+$): 280.6 (M+H)$^+$.

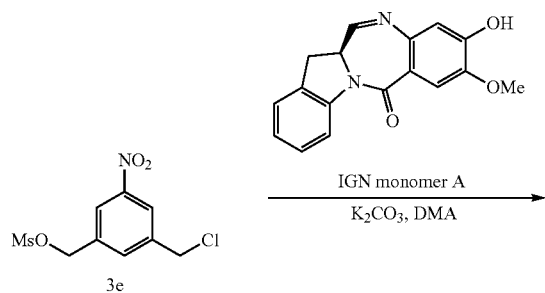

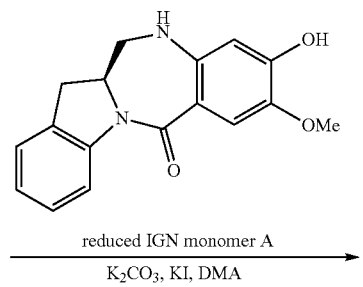

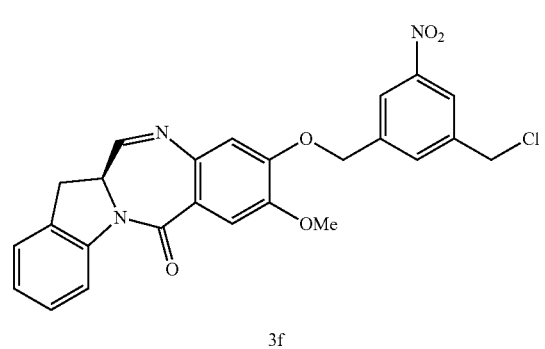

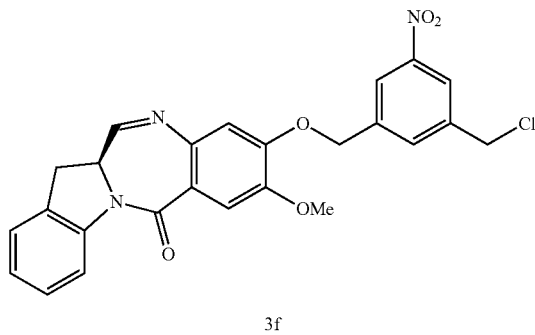

To a solution of 3e (0.4 g, 1.43 mmol) and potassium carbonate (0.6 g, 4.29 mmol, 3.0 equiv.) in DMA (13.4 mL) was added a solution of IGN monomer A (0.46 g, 1.57 mmol, 1.1 equiv.) in DMA (2 mL) at room temperature and the reaction was stirred for 5 h. The reaction was quenched with water (30 mL), the layers were separated and the aqueous layer was extracted with EtOAc (3×30 mL). The combined organic layers were washed with water (30 mL), brine (30 mL), dried over magnesium sulfate and the solvent was removed in vacuo. The crude oil was purified over silica gel chromatography using DCM/MeOH to give compound 3f (0.37 g, 0.77 mmol, 54% yield). UPLCMS (2.5 min method)=1.69 min. Mass observed (ESI$^+$): 478.3 (M+H)$^+$.

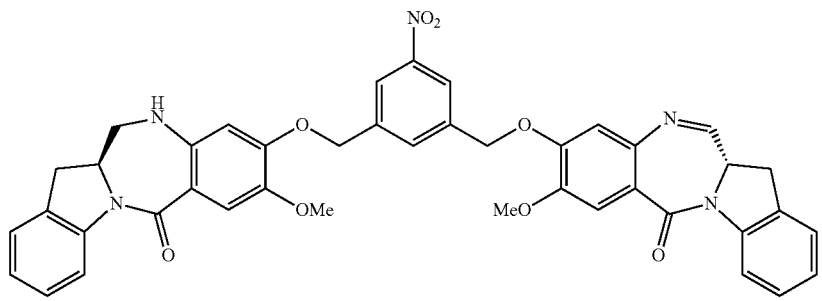

To a solution of 3f (0.11 g, 0.23 mmol) in DMA (3.0 mL) was added potassium carbonate (0.095 g, 0.69 mmol, 3.0 equiv.), followed by potassium iodide (0.02 g, 0.11 mmol, 0.5 equiv.). A solution of reduced IGN monomer A (0.07 g, 0.25 mmol, 1.1 equiv.) in DMA (1 mL) was added. The reaction was then gently heated at 35° C. for 5 h. The reaction was quenched with water, and the solid was filtered off. The solid was redissolved in DCM/MeOH (20:1), washed with water, dried with magnesium sulfate, filtered and concentrated. The crude residue (0.13 g) was purified by RPHPLC (ACN/H$_2$O) to give 3g (0.063 g, 0.085 mmol, 36% yield). UPLCMS (2.5 min method)=1.79 min. Mass observed (ESI$^+$): 738.3 (M+H)$^+$. $^1$H NMR (400 MHz, DMSO-d$_6$, reported as a mixture of water adducts)$^1$H NMR (400 MHz, DMSO-d6): δ 8.43-8.36 (m, 2H), 8.27 (d, J=8.1 Hz, 1H), 8.13-8.02 (m, 2H), 7.44-7.14 (m, 6H), 7.14-6.99

(m, 2H), 6.79 (s, 0.5H), 6.56 (s, 0.5H), 6.50 (d, J=2.2 Hz, 1H), 6.39 (d, J=6.9 Hz, 1H), 6.17 (d, J=6.8 Hz, 0.5H), 5.69 (s, 0.5H), 5.59 (d, J=5.7 Hz, 0.5H), 5.47-5.27 (m, 4H), 5.03 (t, J=6.1 Hz, 0.5H), 4.77 (dd, J=9.1, 6.8 Hz, 0.5H), 4.61 (dt, J=9.7, 5.1 Hz, 0.15H), 4.50-4.39 (m, 0.5H), 4.27 (dd, J=10.9, 4.2 Hz, 0.5H), 4.16 (td, J=9.6, 2.9 Hz, 0.5H), 3.95 (s, 0.5H), 3.89-3.76 (m, 6H), 3.76-3.44 (m, 4H), 3.20-3.08 (m, 1H), 2.96 (dd, J=17.0, 4.4 Hz, 1H).

Example 12

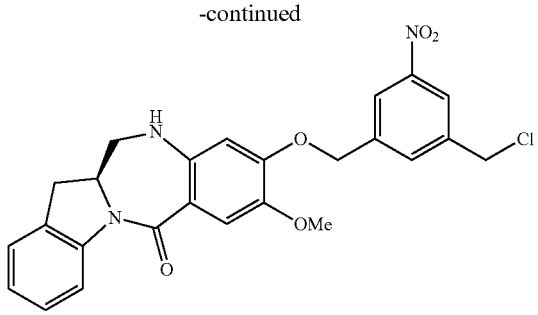

3h

To a solution of 3e (0.45 g, 1.61 mmol) in DMA (15.1 mL) was added potassium carbonate (0.67 g, 4.83 mmol, 3.0 equiv.) followed by a solution of reduced IGN monomer A (0.5 g, 1.69 mmol, 1.1 equiv.) in DMA (2 mL). The reaction was stirred at room temperature for 5 h. The reaction was quenched with water (30 mL) and the mixture was stirred for 10 min. The solid was filtered and then dissolved in DCM/MeOH (9/1, 30 mL) and washed with brine (20 mL). The organic layer was separated and dried over magnesium sulfate, filtered and the solvent removed in vacuo. The crude material was purified by silica gel chromatography using Hexane/EtOAc to give compound 3h (0.28 g, 0.58 mmol, 36% yield) as colorless oil. UPLCMS (2.5 min method) =1.82 min. Mass observed (ESI+): 480.3 (M+H)+.

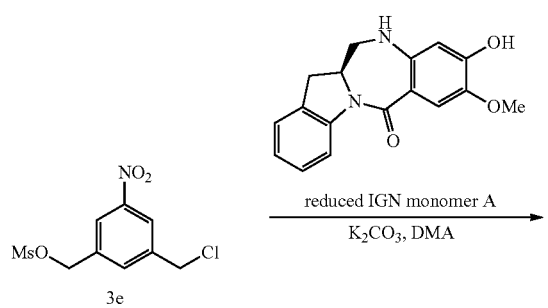

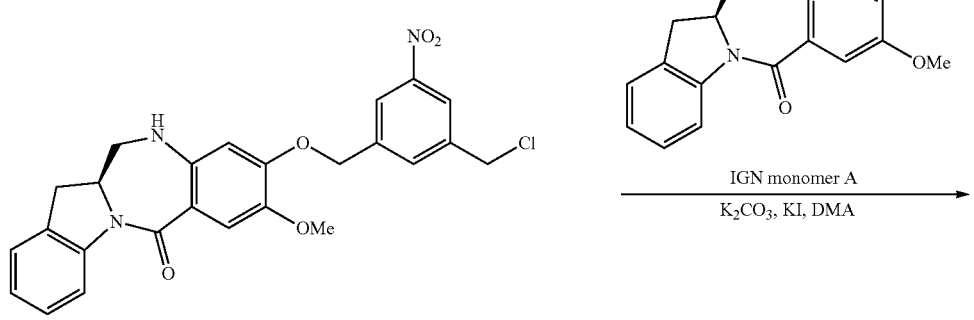

3h

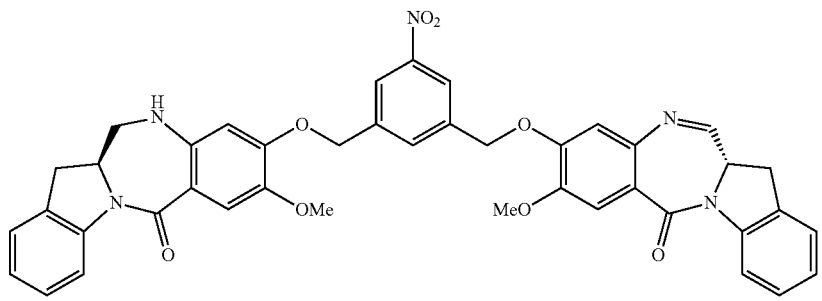

3g

To a solution of 3 h (0.27 g, 0.56 mmol) in DMA (10 mL) was added potassium carbonate (0.16 g, 1.12 mmol, 2.0 equiv.) followed by potassium iodide (0.05 g, 0.28 mmol, 0.05 equiv.). A solution of IGN monomer A (0.18 g, 0.62 mmol, 1.1 equiv.) in DMA (2 mL) was added to the reaction mixture at room temperature. The reaction was then stirred at 40° C. for 3 h. The reaction was quenched with water (20 mL) and the solid was filtered off and washed with water. The crude yellow solid was dissolved in DCM/MeOH (9/1, 30 mL) and then washed with water (10 mL), dried over magnesium sulfate and filtered. The solvent was removed in vacuo to give a crude yellow solid. The crude product was purified by silica gel chromatography using DCM/MeOH (0% to 5% MeOH/DCM) to give the product 3g as a yellow powder (0.35 g, 0.48 mmol, 86% yield). UPLCMS (2.5 min method)=1.79 min (2.5 min method). Mass observed (ESI+): 738.4 (M+H)+.

Example 13

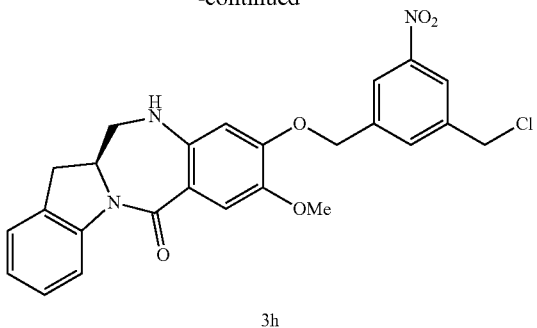

3h

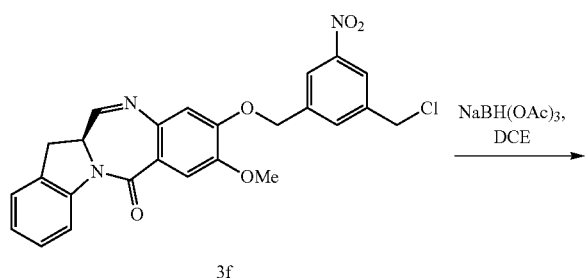

3f

To a solution of 3f (0.15 g, 0.31 mmol) in DCE (2 mL) was added sodium triacetoxyborohydride (0.067 g, 0.31 mmol, 1.0 equiv.) and the reaction was stirred at room temperature for 1 h. The reaction was quenched with sat. ammonium chloride (1 mL) and then the layers were separated. The aqueous layer was extracted with DCM (3×10 mL) and the combined organic layers were washed with brine (20 mL), dried over magnesium sulfate, filtered and the solvent removed in vacuo. The crude brown oil was purified by silica gel chromatography to give desired product 3 h (0.08 g, 0.16 mmol, 52% yield). UPLCMS (2.5 min method)=1.80 min. Mass observed (ESI+): 480.5 (M+H)+.

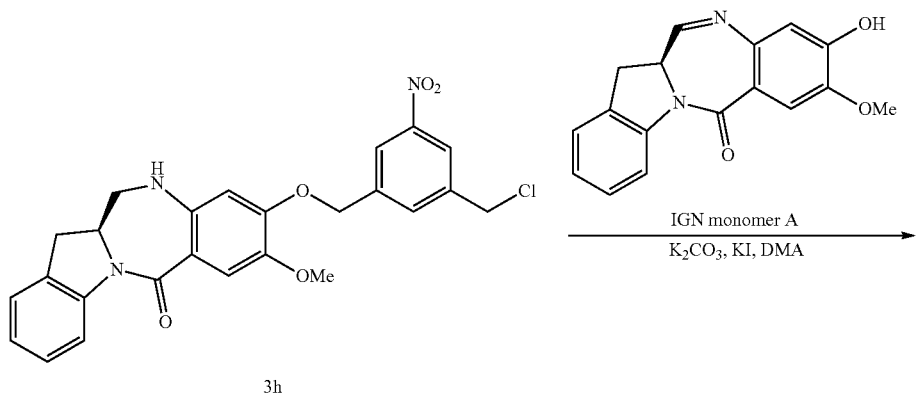

3h

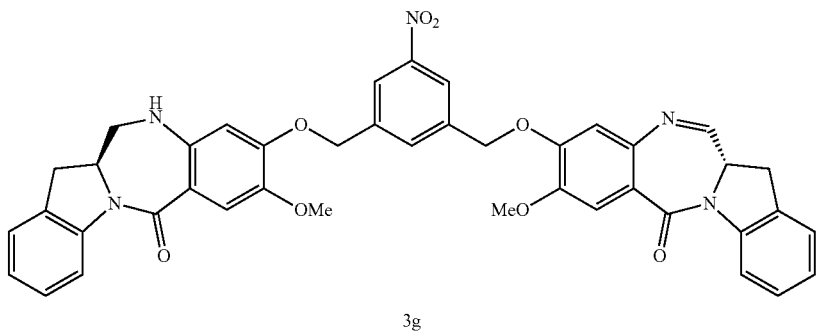

3g

To a solution of 3 h (0.07 g, 0.16 mmol) in DMA (2 mL) was added potassium carbonate (0.07 g, 0.47 mmol, 3.0 equiv.) followed by potassium iodide (0.013 g, 0.08 mmol, 0.05 equiv.) and then a solution of IGN monomer A (0.05 g, 0.17 mmol, 1.1 equiv.) in DMA (0.5 mL) was added. The reaction was stirred at room temperature for 12 h. Water (20 mL) was added to the mixture and the mixture was stirred for 10 min at which point the solid was filtered. The solid was solubilized in DCM (10 mL) and then washed with brine (10 mL). The organic layer was dried over magnesium sulfate and filtered. The solvent was removed to obtain a yellow oil (0.09 g, 0.12 mmol, 80% yield). UPLCMS (2.5 min method)=1.79 min (2.5 min method). Mass observed (ESI$^+$): 738.5 (M+H)$^+$.

Example 14

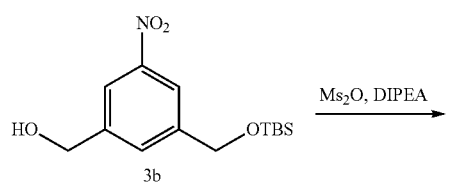

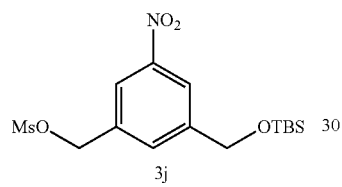

To a solution of 3b (1.00 g, 3.4 mmol) in DCM (33 mL) was added DIPEA (1.781 ml, 10.09 mmol, 3.0 equiv.), followed by a solution of methanesulfonic anhydride (0.703 g, 4.03 mmol, 1.2 equiv.) at 0° C. The reaction was stirred for 1 h. The solvent was evaporated to give the crude product 3j (1.2 g, 3.2 mmol, 95% yield) which was used in the next step without further purification. UPLCMS (2.5 min method)=2.04 min. Mass observed (ESI$^+$): 376.5 (M+H)$^+$.

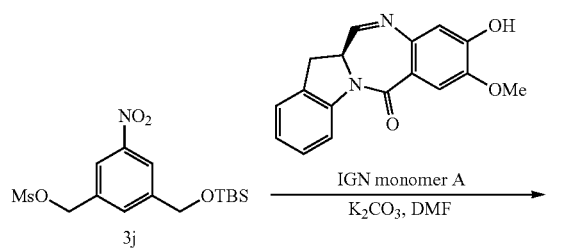

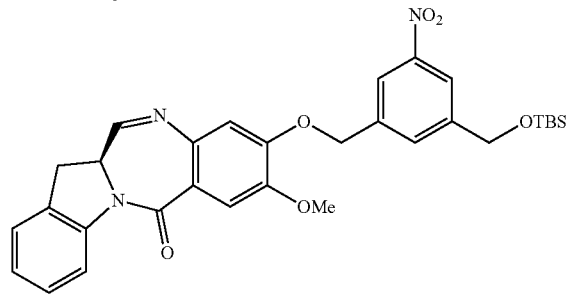

To a solution of 3j (1.24 g, 3.30 mmol) in DMF (26 mL) was added potassium carbonate (0.91 g, 6.60 mmol, 2.0 equiv.) followed by IGN monomer A (0.97 g, 3.30 mmol, 1.0 equiv.) at room temperature for 12 h. The reaction was quenched with water (60 mL) and the solid was filtered off and then dissolved in DCM/MeOH (20/1, 20 mL). The organic layer was washed with brine, dried over magnesium sulfate and filtered. The solvent was removed in vacuo and the crude material was purified over silica gel chromatography to give the desired product 3k (1.3 g, 2.27 mmol, 69% yield). UPLCMS (2.5 min method)=2.12 min (2.5 min method). Mass observed (ESI$^+$): 574.4 (M+H)$^+$.

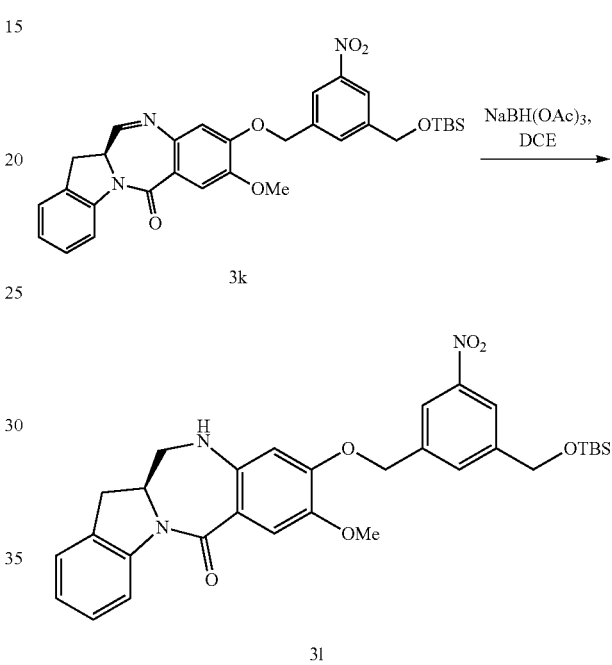

3k (0.63 g, 1.1 mmol) was dissolved in anhydrous DCE (11 mL). Sodium triacetoxyborohydride (0.70 g, 3.3 mmol, 3.0 equiv.) was added and the reaction mixture was stirred for 1 h at room temperature. The mixture was quenched with sat. ammonium chloride (10 mL). The layers were separated and the aqueous layer was extracted with DCM (2×20 mL). The combined organic layers were washed with brine (20 mL), dried over anhydrous magnesium sulfate, filtered and concentrated to obtain 3l (0.58 g, 1.0 mmol, 92% yield). UPLCMS (8.0 min method)=7.797 min (8.0 min method). Mass observed (ESI$^+$): 576.3 (M+H)$^+$.

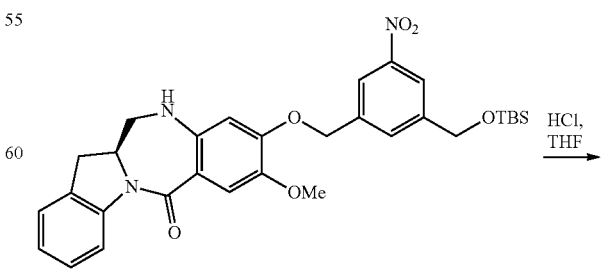

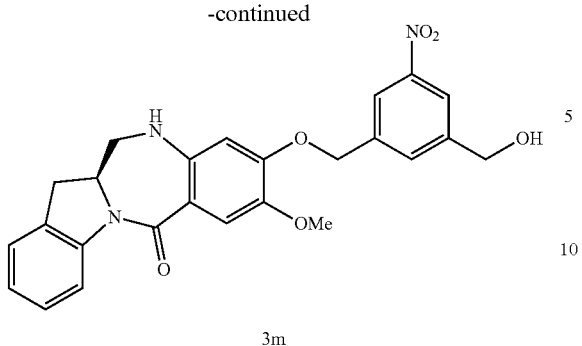

3m

A solution of 3l (0.58 g, 1.0 mmol) was dissolved in anhydrous THF (5 mL) and 5 M aqueous hydrochloride acid solution (2.01 mL, 10.07 mmol) was added. The mixture was stirred at room temperature for 2 h. The reaction was quenched with sat. sodium bicarbonate (5 mL) and the layers were separated and the aqueous layer was extracted with DCM (2×10 mL). The combined organic layers were washed with brine (20 mL), dried over magnesium sulfate and concentrated to give a bright orange solid. The resulting solid was purified by silica gel chromatography (DCM/MeOH) to give compound 3m (0.33 g, 0.71 mmol, 71% yield). UPLCMS (8.0 min method)=5.166 min. Mass observed (ESI+): 462.1 (M+H)+.

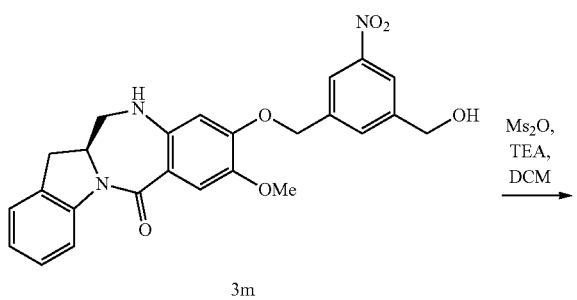

3m $\xrightarrow{\text{Ms}_2\text{O, TEA, DCM}}$

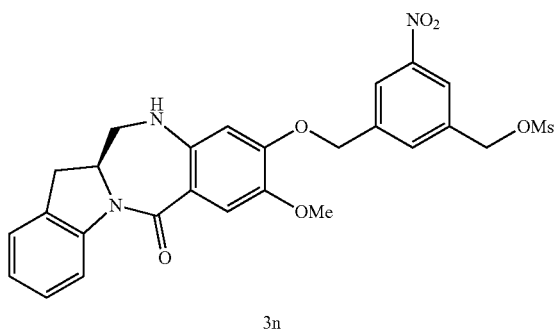

3n 3m (0.1 g, 0.22 mmol) was dissolved in anhydrous DCM (1.5 mL) and anhydrous DMF (0.7 mL). The reaction was cooled to 0° C. and triethylamine (0.12 mL, 0.88 mmol) and methanesulfonic anhydride (0.08 g, 0.44 mmol) were added. The reaction was stirred at 0° C. for 1 h. The reaction mixture was diluted with ethyl acetate (20 mL), washed with water (2×20 mL), dried over magnesium sulfate, filtered and concentrated. The compound was initially purified by silica gel chromatography (DCM/EtOAc) followed by additional purification by RPPHPLC (MeCN/water) to give the desired product 3n (0.041 g, 0.076 mmol, 34% yield). Mass observed (ESI+): 540.3 (M+H)+.

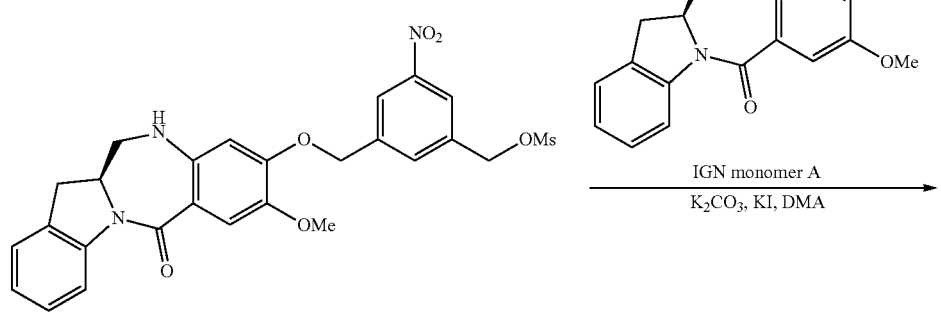

3n $\xrightarrow[\text{K}_2\text{CO}_3,\text{ KI, DMA}]{\text{IGN monomer A}}$

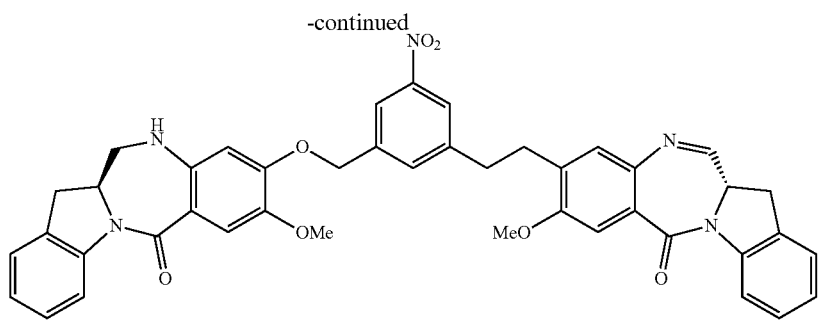

3g

Compound 3n (0.041 g, 0.076 mmol) and IGN monomer A (0.027 g, 0.091 mmol) were dissolved in anhydrous DMA (0.5 mL). Potassium carbonate (0.012 g, 0.091 mmol) and potassium iodide (0.006 g, 0.038 mmol) were added and the mixture stirred for 12 h. Water (5 mL) was added to the reaction mixture. The solid was filtered off and then redissolved in DCM (20 mL) and washed with water (10 mL). After drying over magnesium sulfate, filtration and concentration, the solid was purified by RPHPLC (ACN/H$_2$O) to give 3g (0.012 g, 0.016 mmol, 21% yield). UPLCMS (2.5 min method)=1.79 min. Mass observed (ESI$^+$): 738.5 (M+H)$^+$.

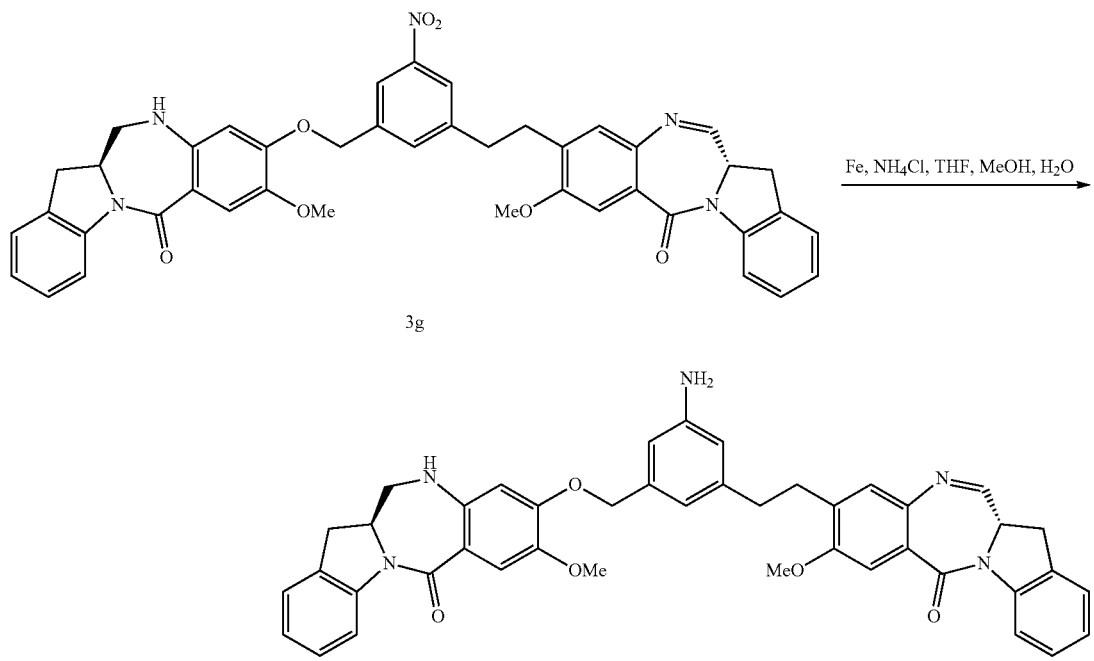

Compound 3g (0.017 g, 0.023 mmol) was dissolved in anhydrous THF (1 mL), anhydrous MeOH (0.5 mL) and water (0.1 mL). Ammonium chloride (0.012 g, 0.23 mmol, 10.0 equiv.) and iron (0.006 g, 0.115 mmol, 5.0 equiv.) were added. The mixture was stirred at 60° C. for 2 h. The reaction mixture was cooled to room temp, filtered through Celite and rinsed with 20% MeOH/DCM (10 mL). The filtrate was concentrated and the crude product was purified by silica gel chromatography (DCM/MeOH) to give compound 3o as a white solid (0.012 g, 0.018 mmol, 76% yield). UPLCMS (2.5 min method)=1.84 min. Mass observed (ESI$^+$): 708.5 (M+H)$^+$. $^1$H NMR (400 MHz, DMSO-d6, reported as a mixture of water adducts, T=330K): δ 8.26 (d, J=7.9 Hz, 1H), 8.17 (d, J=7.8 Hz, 1H), 8.03 (d, J=4.5 Hz, 1H), 7.49 (s, 1H), 7.42-7.33 (m, 2H), 7.36-7.08 (m, 4H), 7.09-6.95 (m, 2H), 6.76-6.64 (m, 3H), 6.47 (s, 1H), 6.15 (d, J=6.5 Hz, 1H), 5.11 (m, 2H), 4.98 (m, 2H), 4.58 (dt, J=9.9, 4.7 Hz, 1H), 4.47-4.36 (m, 1H), 3.87 (m, 1H), 3.76 (s, 3H), 3.71-3.46 (m, 4H), 3.39-3.28 (m, 1H), 2.93 (dd, J=16.8, 4.7 Hz, 1H).

Example 15

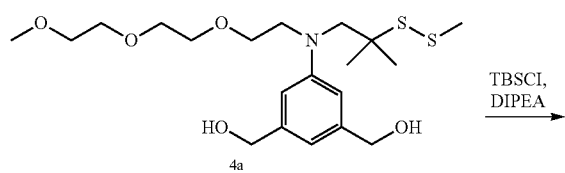

4a

TBSCl, DIPEA →

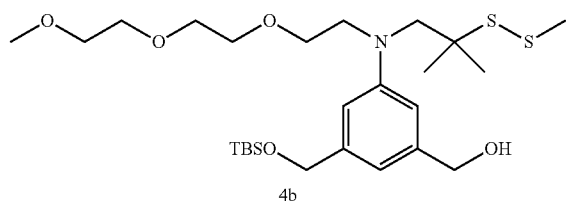

4b

To a solution of 4a (5.6 g, 12.9 mmol, 1.0 equiv.) in DCM (83 mL) was added DIPEA (6.77 mL, 38.7 mmol, 3.0 equiv.) followed by a solution of TBS-Cl (2.336 g, 15.50 mmol, 1.2 equiv.) in DCM (10 mL) at 0° C. The reaction was stirred at room temperature for 3 h. The reaction was quenched with sat. ammonium chloride (30 mL) and the layers were separated. The aqueous solution was extracted with DCM (2×30 mL) and the combined organic layers were washed with water (2×50 mL), brine (50 mL), dried over magnesium sulfate, filtered and the solvent removed in vacuo to give crude yellow oil. The crude product was purified by silica gel chromatography (Hexane/EtOAc) to give the desired product 4b (3.0 g, 5.48 mmol, 43% yield). UPLCMS (2.5 min method)=2.29 min. Mass observed (ESI+): 549.0 (M+H)+.

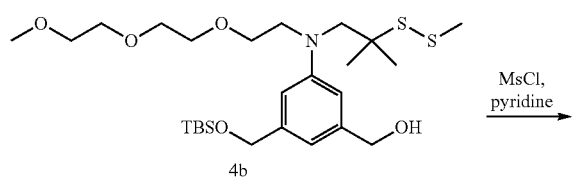

4b

MsCl, pyridine →

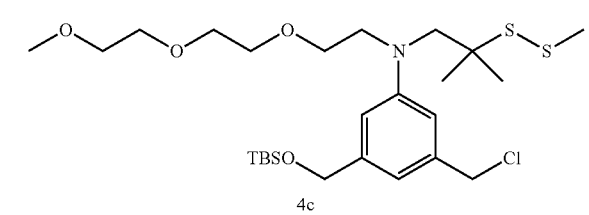

4c

To a solution of 4b (3.00 g, 5.48 mmol, 1.0 equiv.) in DMF (30 mL) was added pyridine (1.33 mL, 16.4 mmol, 3.0 equiv.) followed by a solution of methanesulfonyl chloride (0.64 mL, 8.21 mmol, 1.5 equiv.) at 0° C. The reaction was stirred for 1 h and was quenched with sat. sodium bicarbonate (30 mL), and diluted with EtOAc (40 mL). The layers were separated and the aqueous layer was extracted with EtOAc (2×30 mL). The combined organic layers were washed with water (2×40 mL), brine (40 mL), dried over magnesium sulfate, filtered and the solvent was removed in vacuo to give crude product 4c (2.5 g, 4.41 mmol, 81% yield). UPLCMS (10.0 min method)=8.23 min. Mass observed (ESI+): 567.6 (M+H)+.

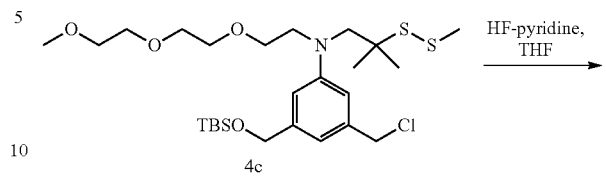

4c

HF-pyridine, THF →

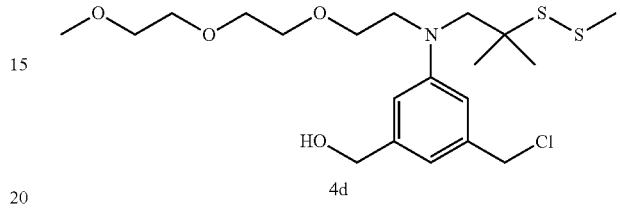

4d

To a solution of 4c (2.5 g, 4.41 mmol, 1.0 equiv.) in THF (43 mL) was added DIPEA (2.46 mL, 14.1 mmol, 4.0 equiv.), followed by HF-pyridine (1.48 mL, 10.6 mmol, 3.0 equiv.) and the reaction was stirred at room temperature for 2 h. The reaction was quenched with sat. sodium bicarbonate (100 mL) and the layers were separated. The aqueous layer was extracted with EtOAc (3×20 mL) and the combined organic layers were washed with water (30 mL), brine (30 mL) dried over magnesium sulfate and filtered. The solvent was removed in vacuo to give desired product 4d (0.9 g, 2.0 mmol, 56% yield). UPLCMS (10.0 min method)=5.20 min. Mass observed (ESI+): 435.4 (M+H)+.

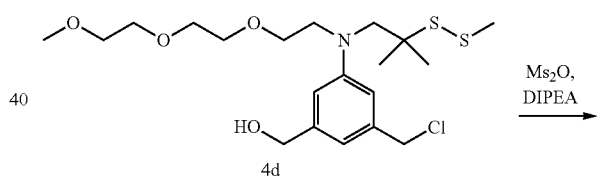

4d

Ms2O, DIPEA →

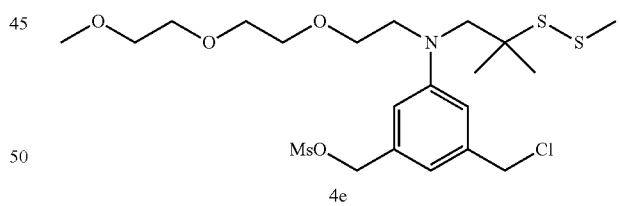

4e

To a solution of 4d (0.9 g, 2.0 mmol, 1.0 equiv.) in DCM (10 mL) was added DIPEA (0.69 mL, 3.98 mmol, 2.0 equiv.) at 0° C., followed by a solution of methanesulfonic anhydride (0.52 g, 2.99 mmol, 1.5 equiv.) in DCM (2 mL). The reaction was stirred for 1 h. The reaction was quenched with water (10 mL), the layers were separated and the aqueous layer was extracted with DCM (2×20 mL). The combined organic layers were washed with sat. sodium bicarbonate (10 mL), brine (20 mL), dried over magnesium sulfate and filtered. The solvent was removed in vacuo and the crude material 4e (1.0 g, 1.88 mmol, 95% yield) was used in the next step without further purification. UPLCMS (10 min method)=5.7 min. Mass observed (ESI+): 531.4 (M+H)+.

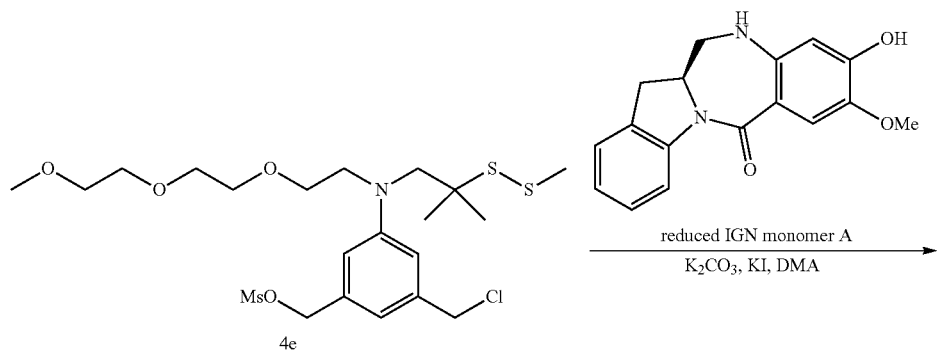

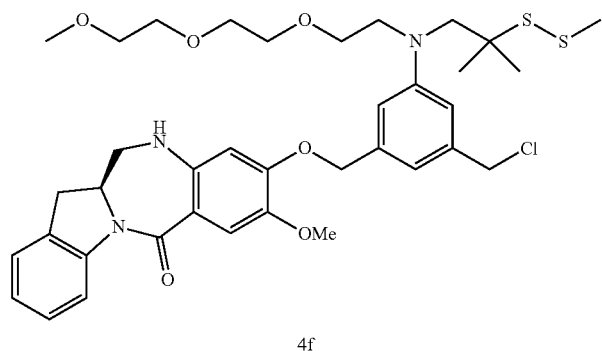

To a solution of 4e (0.21 g, 0.39 mmol, 1.0 equiv.) in DMA (2.0 mL) was added potassium carbonate (0.16 g, 1.19 mmol, 3.0 equiv.) followed by a solution of reduced IGN monomer A (0.12 g, 0.41 mmol, 1.05 equiv.) in DMA (1 mL). The reaction was stirred at room temperature for 5 h. The reaction was quenched with water (30 mL) and the mixture stirred for 10 min. The solid was filtered and was dissolved in DCM/MeOH (9/1, 30 mL) and washed with brine (20 mL). The organic layer was separated and dried over magnesium sulfate, filtered and the solvent removed in vacuo. The crude material was purified by silica gel chromatography (Hexane/EtOAc) to give the desired product 4f (0.11 g, 0.15 mmol, 38% yield) as colorless oil. UPLCMS (10 min method)=6.55 min. Mass observed (ESI+): 730.9 (M+H)+.

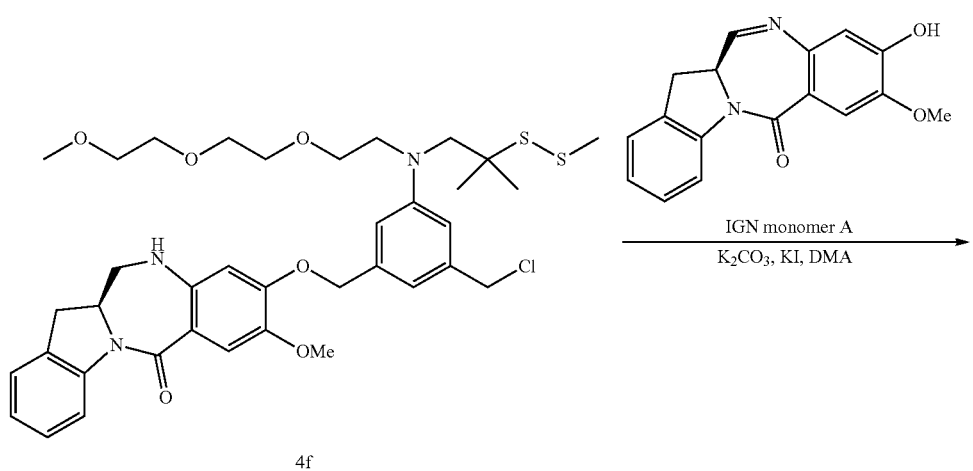

-continued

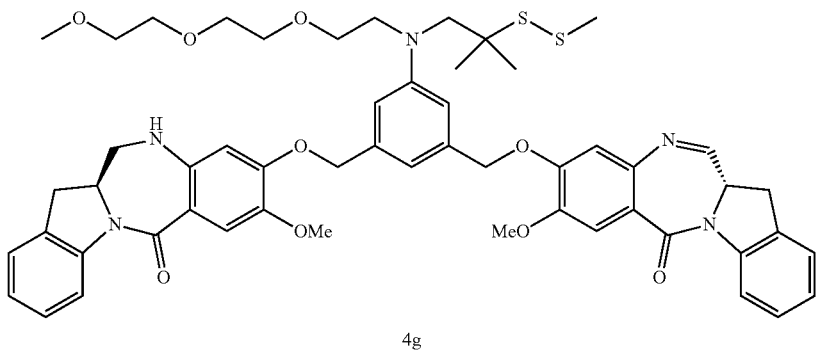

4g

A solution of 4f (0.11 g, 0.15 mmol, 1.0 equiv.) and IGN monomer A (0.053 g, 0.18 mmol) were dissolved in anhydrous DMA (1.0 mL). Potassium carbonate (0.041 g, 0.30 mmol) and potassium iodide (0.025 g, 0.15 mmol) were added. The mixture was stirred for 4 h at 40° C. Water (5 mL) was added to the reaction mixture and the solid was filtered off and then redissolved in DCM (20 mL) and washed with water (10 mL). The organic layer was dried over magnesium sulfate, filtration and concentrated. The crude solid was purified by silica gel chromatography (Hexane/EtOAc) to give 4g (0.099 g, 0.10 mmol, 66% yield). UPLCMS (10 min method)=6.38 min. Mass observed (ESI$^+$): 988.7 (M+H)$^+$. $^1$H NMR (400 MHz, DMSO-d6): δ 8.22 (d, J=7.9 Hz, 1H), 8.12 (d, J=8.1 Hz, 1H), 8.03 (d, J=4.5 Hz, 1H), 7.38-7.25 (m, 2H), 7.24 (t, J=7.9 Hz, 2H), 7.24-7.06 (m, 2H), 7.11-6.94 (m, 1H), 6.98 (s, 1H), 6.91 (d, J=15.2 Hz, 2H), 6.79 (s, 1H), 6.45 (s, 1H), 6.32 (d, J=6.8 Hz, 1H), 5.18 (q, J=12.3 Hz, 2H), 5.01 (m, 2H), 4.54 (dt, J=9.7, 5.2 Hz, 1H), 4.37 (dt, J=10.6, 5.4 Hz, 1H), 3.87 (s, 3H), 3.71 (s, 3H), 3.60 (m, 6H), 3.57-3.50 (m, 2H), 3.47 (qd, J=4.3, 1.0 Hz, 4H), 3.47 (s, 3H), 3.42-3.33 (m, 2H), 3.32-3.16 (m, 2H), 3.21 (s, 3H), 2.97-2.85 (m, 1H), 2.44 (s, 3H), 1.30 (s, 6H).

Example 16

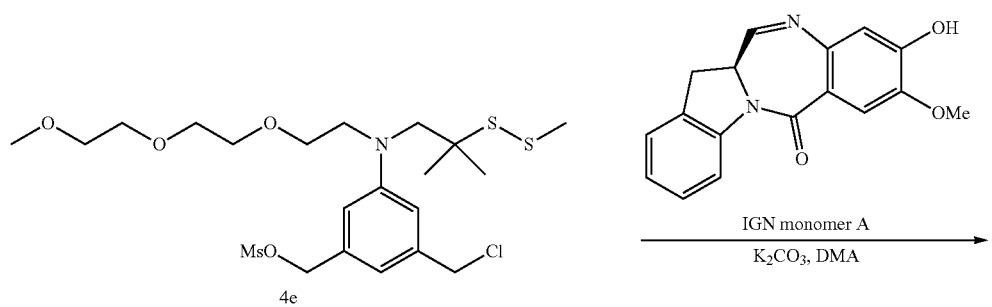

4e

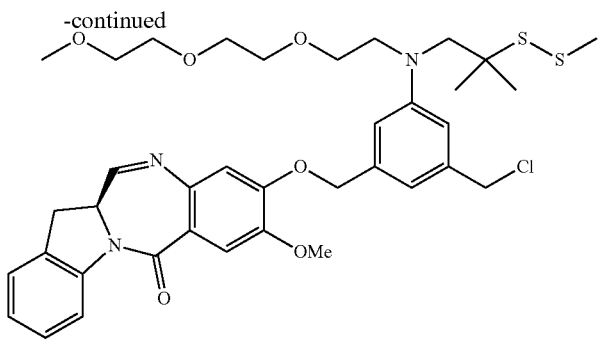

4h

To a solution of 4e (0.52 g, 0.98 mmol, 1.0 equiv.) and potassium carbonate (0.41 g, 2.94 mmol, 3.0 equiv.) in DMA (10 ml) was added a solution of IGN monomer A (0.30 g, 1.03 mmol, 1.05 equiv.) in DMA (2 mL) at room temperature and the reaction was stirred for 5 h. The reaction was quenched with water (30 mL), the layers were separated and the aqueous layer extracted with EtOAc (3×30 mL). The combined organic layers were washed with water (30 mL), brine (30 mL), dried over magnesium sulfate and excess of solvent removed in vacuo. The crude oil was purified by silica gel chromatography (Hexane/EtOAc) to give desired product 4 h (0.35 g, 0.48 mmol, 49% yield). UPLCMS (10 min method)=6.19 min. Mass observed (ESI$^+$): 728.7 (M+H)$^+$.

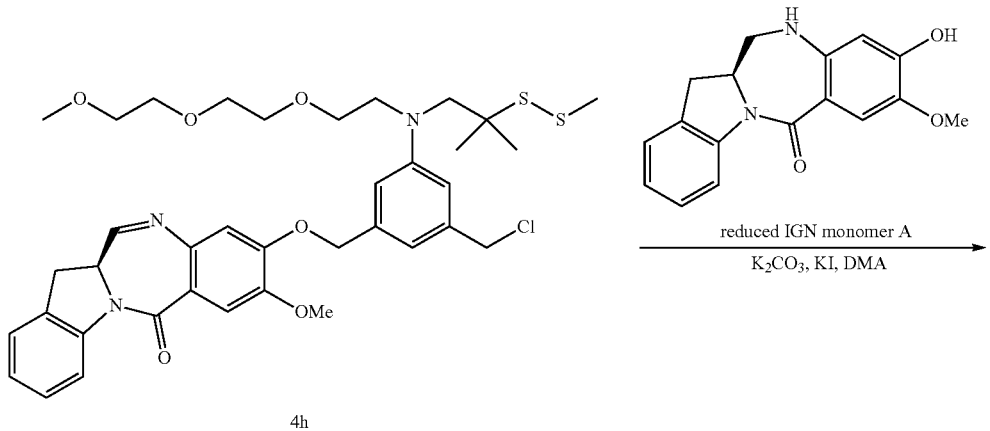

4h

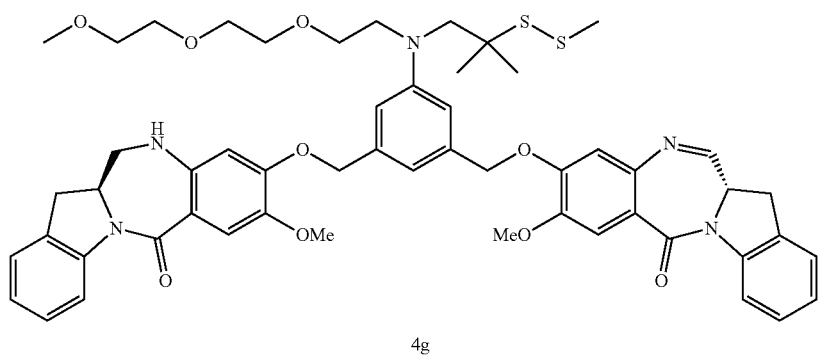

4g

To a solution of 4 h (0.18 g, 0.25 mmol, 1.0 equiv.) in DMA (5.0 mL) was added potassium carbonate (0.10 g, 0.74 mmol, 3.0 equiv.) followed by potassium iodide (0.04 g, 0.2 mmol, 1.0 equiv.). A solution of reduced IGN monomer A (0.08 g, 0.27 mmol, 1.1 equiv.) in DMA (1 mL) was added and the reaction was then heated at 40° C. for 5 h. The reaction was quenched with water, and then solid was filtered off. The solid was redissolved in DCM/MeOH (20:1), washed with water, dried over magnesium sulfate, filtered and concentrated. The crude residue was purified by silica gel chromatography (Hexane/EtOAc) to give 4g (0.05 g, 0.05 mmol, 21% yield). UPLCMS (10 min method)=6.39 min. Mass observed (ESI$^+$): 989.0 (M+H)$^+$.

Example 17

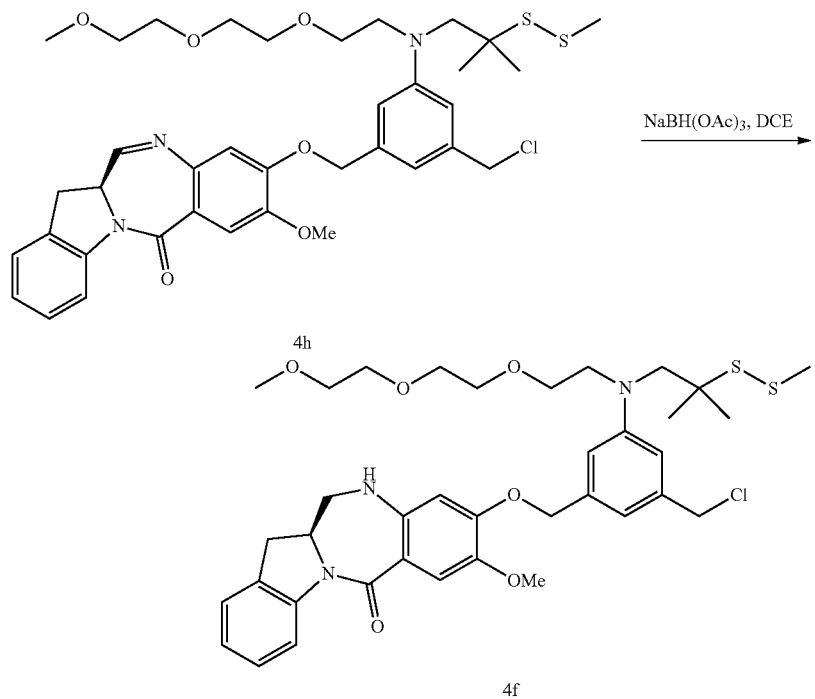

Compound 4h (0.17 g, 0.24 mmol, 1.0 equiv.) was dissolved in anhydrous DCE (3 mL) and sodium triacetoxyborohydride (0.10 g, 0.48 mmol, 3.0 equiv.) was added at room temperature. The reaction mixture was stirred for 1 h. The mixture was quenched with sat. ammonium chloride (10 mL). The layers were separated and the aqueous layer extracted with DCM (2×20 mL). The combined organic layers were washed with brine (20 mL), dried over anhydrous magnesium sulfate, filtered and concentrated to obtain 4f (0.13 g, 0.18 mmol, 77% yield) which was used in the next step without further purification. UPLCMS (2.5 min method)=2.13 min. Mass observed (ESI$^+$): 731.2 (M+H)$^+$.

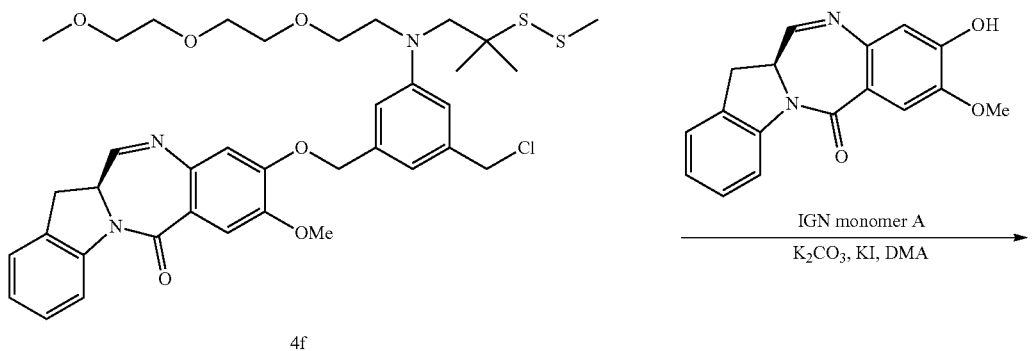

-continued

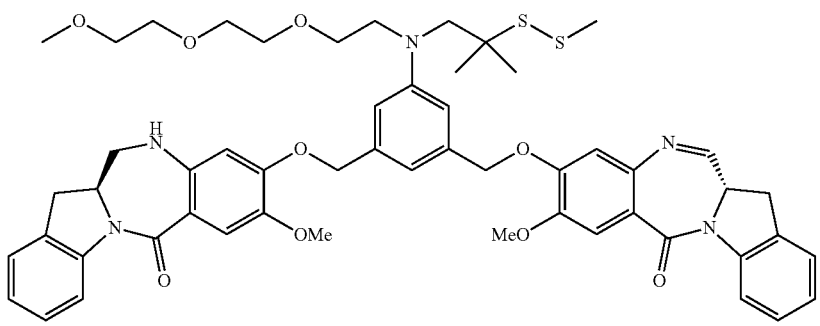

4g

Compound 4f (0.19 g, 0.26 mmol, 1.0 equiv.) and IGN monomer A (0.084 g, 0.28 mmol, 1.1 equiv.) were dissolved in anhydrous DMA (4.0 mL). Potassium carbonate (0.11 g, 0.78 mmol, 3.0 equiv.) and potassium iodide (0.043 g, 0.26 mmol, 1.0 equiv.) were added. The mixture was stirred for 4 h at 40° C. Water (5 mL) was added to the reaction mixture. The solid was filtered off and was redissolved in DCM (20 mL) and washed with water (10 mL). After drying over magnesium sulfate, filtration and concentration, the solid was purified by silica gel chromatography (Hexane/EtOAc) to give 4g (0.065 g, 0.06 mmol, 25% yield). UPLCMS (10 min method)=6.38 min. Mass observed (ESI$^+$): 988.7 (M+H)$^+$.

Example 18

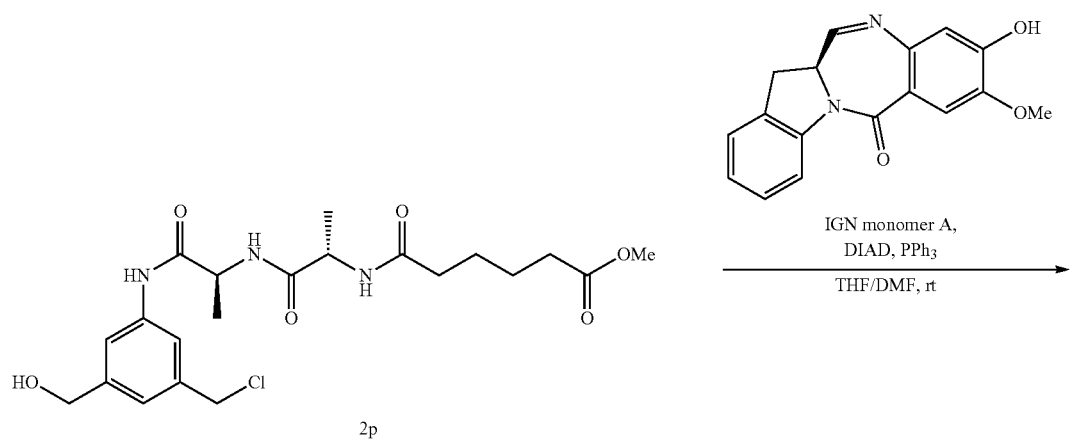

Compound 2p (0.03 g, 0.066 mmol, 1.0 equiv.) and IGN monomer A (0.021 g, 0.072 mmol, 1.1 equiv.) were dissolved in THF (0.65 mL) and DMF (0.3 mL). Triphenylphosphine was added (0.021 g, 0.079 mmol, 1.2 equiv.), followed by a slow addition of DIAD (0.015 mL, 0.079 mmol, 1.2 equiv.). The reaction was stirred at rt under argon for 2 h. The reaction mixture was concentrated and water (~2 mL) was added to triturate the product. The precipitate was filtered and the remaining solid was washed with water. The crude residue was purified by RPHPLC (C18 column, MeCN/water, gradient, 40% to 60%) to give compound 2r as a white fluffy solid (0.015 g, 0.02 mmol, 31% yield). UPLCMS (2.5 min method)=1.62 min. Mass observed (ESI$^+$)=732.9 (M+H)$^+$.

Example 19

Example 20

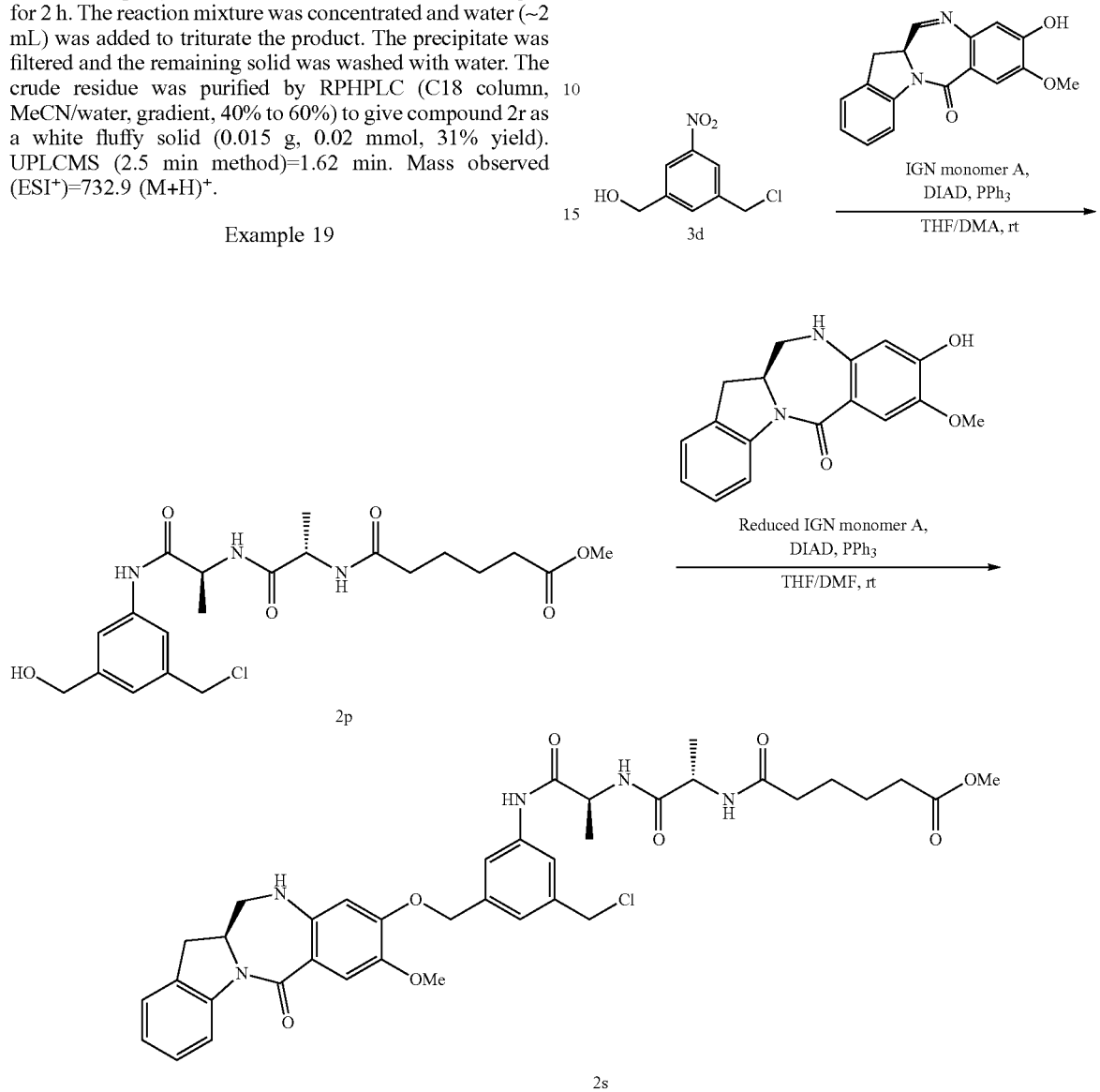

Compound 2p (0.03 g, 0.066 mmol, 1.0 equiv.) and reduced IGN monomer A (0.02 g, 0.072 mmol, 1.1 equiv.) were dissolved in THF (0.66 mL) and DMF (0.1 mL). Triphenylphosphine (0.021 g, 0.079 mmol, 1.2 equiv.) was added, followed by a slow addition of DIAD (0.015 mL, 0.079 mmol, 1.2 equiv.). The reaction mixture was stirred at rt under argon for 2 h. The reaction mixture was diluted with DCM and was washed with water (2×). The organic layer was dried over magnesium sulfate, filtered and concentrated. The crude residue was purified by RPHPLC (C18 column, MeCN/water, gradient, 40% to 65%) to yield 2s as a white fluffy solid (0.017 g, 0.02 mmol, 35% yield). UPLCMS (2.5 min method)=1.71 min. Mass observed (ESI$^+$)=735.4 (M+H)$^+$.

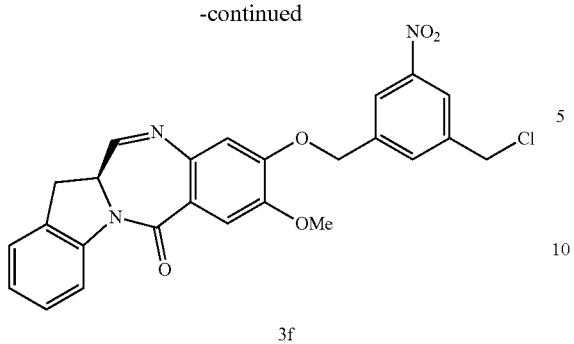

3f

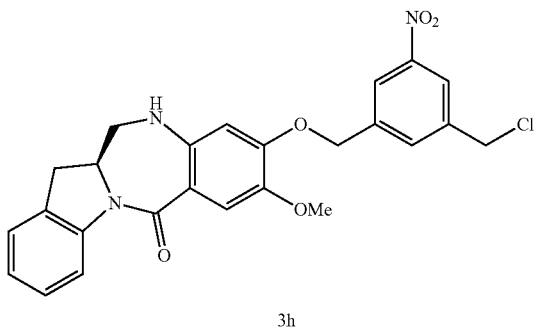

3h

Compound 3d (0.03 g, 0.149 mmol, 1.0 equiv.) and IGN monomer A (0.046 g, 0.156 mmol, 1.05 equiv.) were dissolved in THF (1.5 mL) and DMF (0.3 mL). Triphenylphosphine was added (0.047 g, 0.179 mmol, 1.2 equiv.), followed by a slow addition of DIAD (0.032 mL, 0.164 mmol, 1.1 equiv.). The reaction was stirred at rt under argon for 12 h. The reaction mixture was concentrated and water (~2 mL) was added to triturate the product. The precipitate was filtered and the remaining solid was washed with water. The crude residue was purified by silica gel chromatography (hexane/EtOAc) to give compound 3f as a white yellow solid (0.013 g, 0.027 mmol, 18% yield). UPLCMS (2.5 min method)=1.80 min. Mass observed (ESI$^+$)=478.4 (M+H)$^+$.

Example 21

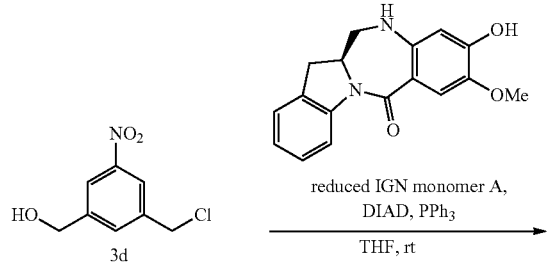

Compound 3d (0.03 g, 0.149 mmol, 1.0 equiv.) and reduced IGN monomer A (0.046 g, 0.156 mmol, 1.05 equiv.) were dissolved in THF (1.5 mL). Triphenylphosphine was added (0.047 g, 0.179 mmol, 1.2 equiv.), followed by a slow addition of DIAD (0.032 mL, 0.164 mmol, 1.1 equiv.). The reaction was stirred at rt under argon for 2 h. The reaction mixture was concentrated and coevaporated with toluene (2 ×). The crude residue was purified by silica gel chromatography (hexane/EtOAc) to give compound 3h as a orange yellow solid (0.055 g, 0.115 mmol, 77% yield). UPLCMS (2.5 min method)=1.90 min. Mass observed (ESI$^+$)=480.5 (M+H)$^+$.

Example 22

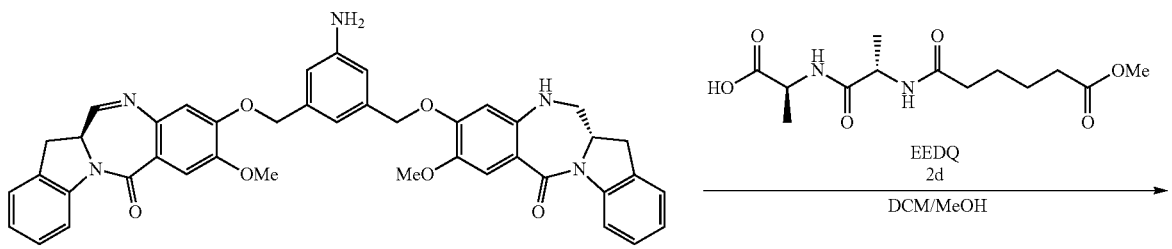

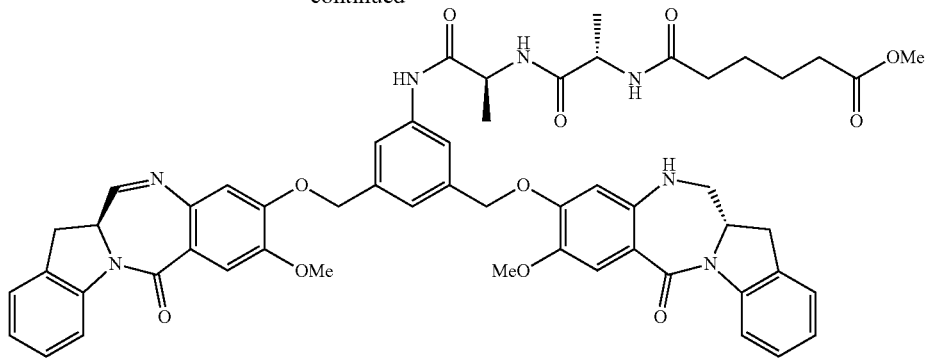

21

To a solution of 2d (0.024 g, 0.078 mmol, 1.1 equiv.) in DCM (1 mL) was added EEDQ (0.019 g, 0.078 mmol, 1.1 equiv.). The reaction was stirred for 5 min and MeOH (0.1 mL) was added, followed by a solution of 3o (0.05 g, 0.071 mmol) in DCM (1 mL). The reaction was stirred at rt for 2 h or until completion of starting material. The reaction was concentrated to form a white precipitate to which MTBE (5 mL) was added and the resulting mixture was stirred for 30 min at room temperature. The solid was filtered off to give compound 21 which was then purified by RPHPLC (C18 column, MeCN/water) to give 2l (0.023 g, 0.023 mmol, 33% yield). UPLCMS (2.5 min method)=1.75 min. Mass observed (ESI$^+$)=993.2 (M+H)$^+$.

Example 23

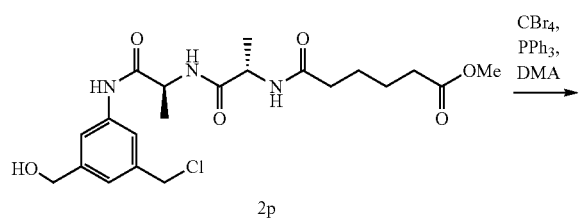

2p

To a solution of 2p (0.05 g, 0.110 mmol, 1.0 equiv.) in DMA (1 mL), was added carbon tetrabromide (0.044 g, 0.132 mmol, 1.2 equiv.) followed by triphenylphosphine (0.043 g, 0.164 mmol, 1.5 equiv.) and the reaction was stirred at room temperature for 2 h. The solvent was removed to give a white solid which was triturated with MTBE and the solid was filtered off to give compound 2v. (0.03 g, 0.058 mmol, 57% yield, 52% purity), which was carried onto the next step without further purification. UPLCMS (2.5 min method)=1.59 min. Mass observed (ESI$^+$)=518.2 (M+H)$^+$.

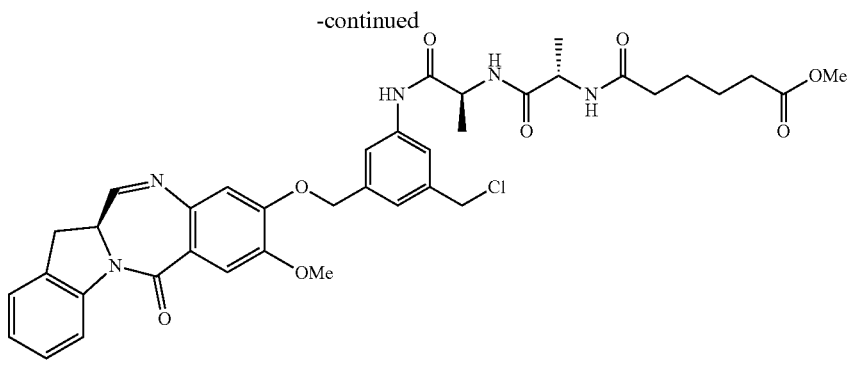

2r

To a solution of 2v (0.03 g, 0.043 mmol, 1.0 equiv.) in DMA (0.5 mL) was added potassium carbonate (0.012 g, 0.087 mmol, 2.0 equiv.) followed by IGN monomer A (0.013 g, 0.046 mmol, 1.05 equiv.). The reaction mixture was stirred for 4 h at room temperature. The reaction mixture was diluted with water (5 mL) and the solid was filtered off. The solid was dissolved in DCM/MeOH (9/1, 2 mL). The organic layer was washed with water (10 mL), brine (10 mL), and dried over magnesium sulfate. After filtration and solvent removal, the crude product was purified by RPHPLC (C18 column, MeCN/water) to give 2r (0.011 g, 0.015 mmol, 35% yield). UPLCMS (2.5 min method)=1.62 min. Mass observed (ESI+)=733.3 (M+H)+.

Example 24

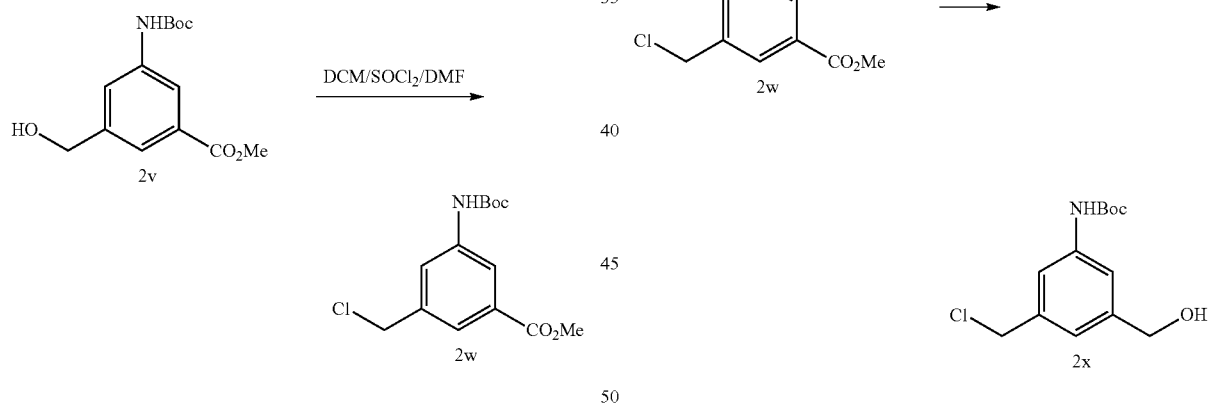

To a slurry of compound 2v (14.7 g, 0.052 mol, 1.0 equiv. prepared as described described in literature, see: Beilstein J. Org. Chem. 2014, 10, 535-543) in DCM and (100 mL) DMF (1 ml), was charged with $SOCl_2$ (12.6 g, 0.104 mol, 2.0 equiv.) in one portion. The resulting solution was stirred at 35° C. overnight resulting in a thick tan slurry. The slurry was filtered and the solid was dried to give 7.5 g as an off-white solid. NMR revealed cleavage of the Boc protecting group. The dark filtrate was charged with solid sodium carbonate (10.6 g, 0.1 mol) followed by buffering to pH ~6-7 by further addition of sodium bicarbonate. To the resulting solution $Boc_2O$ (12.7 g, 0.058 mol, 1.1 equiv.) was added and was stirred for 0.5 h. The filtered solid (7.5 g) was added to the reaction mixture, followed by the addition of $Boc_2O$ (6.5 g, 0.030 mol, 1.7 equiv.) (pH~6) and continued to stir at rt overnight. Then sat. sodium bicarbonate (10 mL) was added to reach pH 6-7. Additional $Boc_2O$ (9.3 g, 42.6 mmol), and DMAP (0.2 g, 1.63 mmol) were added and continued to stir overnight. The dark reaction was filtered to remove some precipitate. The DCM layer was washed with 1 N HCl to remove un-Boc product, which was basified and extracted with DCM and recovered 3.0 g colorless crispy solid (un-Boc product). The DCM layer was washed with brine and concentrated to a dark slush. The crude product was purified by silica gel chromatography (EtOAc/Hexanes) to give 2w as a pale brown solid (9.5 g, 0.031 mmol, 62% yield). $^1H$ NMR (400 MHz, $CDCl_3$): δ 7.84 (m, 2H), 7.75 (m, 1H), 6.60 (s, 1H, NH), 4.58 (s, 2H), 3.91 (s, 3H), 1.53 (s, 9H).

A solution of LAH/THF (0.6M, 60 mL, 1.15 equiv.) was stirred at rt for 30 min and then cooled down to −65° C. with an acetone-dry ice bath. Compound 2w (9.3 g, 0.031 mol, 1.0 equiv.) was slowly added in portions (Ti ~−60° C.) resulting in a yellow brown slurry which was stirred for 4 h. The reaction was quenched with water (1.3 mL), 15% NaOH (1.3 mL), and water (4 mL) and was stirred for 20 min (Ti~5° C.). The reaction was filtered and rinsed with ethyl acetate (~90 mL). The filtrate was washed with brine, and concentrated to yield 2x (8.0 g, 0.029 mol, 93% yield) as brown oil. $^1H$ NMR (400 MHz, $CDCl_3$): δ 7.45 (s, 1H), 7.40 (s, 1H), 7.10 (s, 1H), 6.60 (s, 1H, NH), 4.75 (s, 2H), 4.50 (s, 2H), 1.53 (s, 9H).

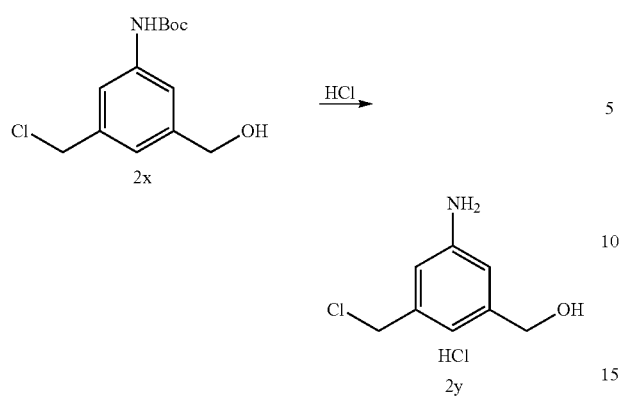

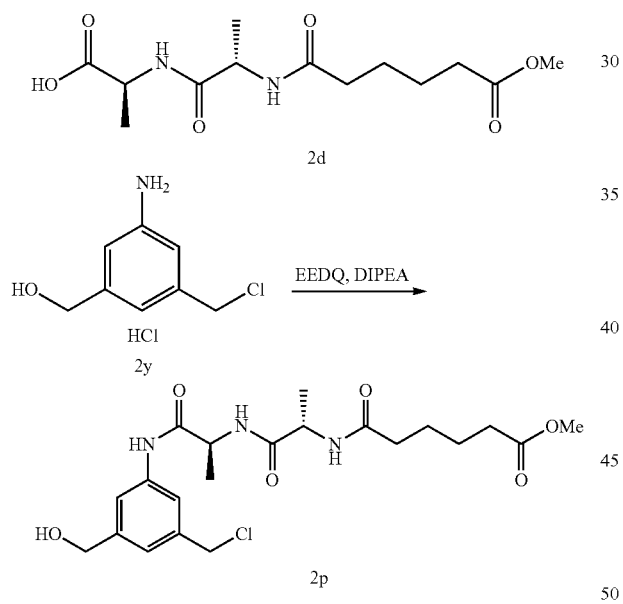

Compound 2x (8.0 g, 0.029 mol, 1.0 equiv.) was dissolved in DCM (20 mL) and cooled in ice-water bath. 4 N HCl/dioxane (15 mL, 1.5 equiv.) was added and the resulting mixture was heated at 50° C. for 1 h and then cooled down to rt. The slurry was concentrated and the solvent switched to heptane. The slurry was filtered, rinsed with hexane, and dried in oven (60° C.) to afford 2y (5.4 g, 0.026 mol, 88% yield) as light brown solid. $^1$H NMR (400 MHz, DMSO-d6): δ 7.45 (s, 1H), 7.25 (s, 2H), 4.76 (s, 2H), 4.52 (s, 2H).

To a solution of 2d (0.969 g, 3.20 mmol, 1.1 equiv.) in DCM (25 mL) was added EEDQ (0.79 g, 3.2 mmol, 1.1 equiv) at room temperature. After 8 min, a solution of 2y (0.5 g, 2.91 mmol, 1.0 equiv.), DIPEA (0.51 mL, 2.91 mmol, 1.0 equiv.) in MeOH (5 mL) was added dropwise over 1 minute. The reaction was stirred for 2 h. The reaction mixture was quenched with water (30 mL), the layers were separated and the aqueous layer extracted with DCM (2×20 mL). The combined organic layers were washed with sat. sodium bicarbonate (20 mL), brine (20 mL), dried over magnesium sulfate, filtered and concentrated to minimal amount of solvent left. The resulting white solid was diluted in MBTE and was filtered to give the desired product 2p as a white solid (0.64 g, 1.40 mmol, 48% yield). UPLCMS (2.5 min method)=1.30 min. Mass observed (ESI$^+$)=456.3 (M+H)$^+$.

The invention claimed is:

1. A method of preparing a compound of formula (3A),

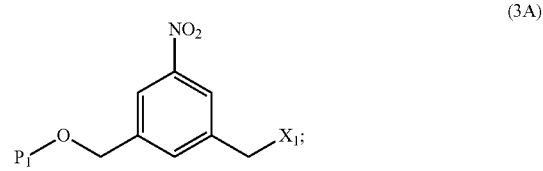

(3A)

or a salt thereof, said method comprising the steps of:
(i) introducing an alcohol protecting group onto one of the primary alcohols of a compound of formula (1) by reacting the compound of formula (1A) with an alcohol protecting reagent,

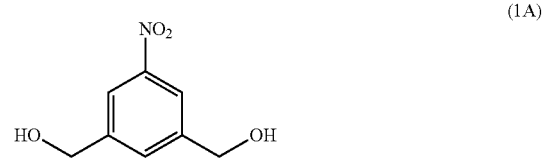 [SMILES: O=[N+]([O-])c1cc(CO)cc(CO)c1]

(1A)

to form a compound of formula (2A),

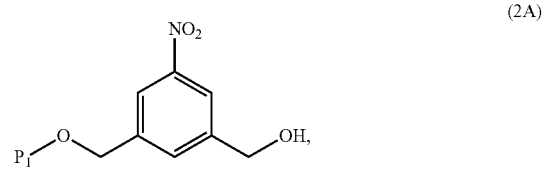

(2A)

or a salt thereof; and
(ii) reacting a halogenating reagent, a sulfonating reagent or an esterification reagent with the compound of formula (2A),
wherein:
  $P_1$ is an alcohol protecting group; and,
  $X_1$ is a leaving group selected from the group consisting of: —Br, —I, —Cl, a sulfonate ester, and an activated ester.

2. The method of claim 1, wherein the sulfonate ester represented by $X_1$ is mesylate, tosylate, brosylate, or triflate.

3. The method of claim 2, wherein the sulfonate ester represented by $X_1$ is mesylate.

4. The method of claim 1, wherein the method comprising reacting the compound of formula (2A) with a sulfonating reagent in the presence of a non-nucleophilic base.

5. The method of claim 4, wherein the non-nucleophilic base is triethylamine, imidazole, diisopropylethylamine, pyridine, 2,6-lutidine, dimethylformamide, 1,8-diazabicyclo[5.4.0]undec-7-ene (DBU), or tetramethylpiperidine.

6. The method of claim 5, wherein the non-nucleophilic base is triethylamine or diisopropylethylamine.

7. The method of claim 4, wherein the sulfonating reagent is methanesulfonic anhydride or methanesulfonyl chloride (MsCl).

8. The method of claim 1, wherein the method comprising reacting a halogenating reagent with the compound of formula (2A) and the halogenating reagent is methanesulfonyl chloride, thionyl chloride, bromine, hydrobromic acid, carbon tetrabromide, phosphorus tribromide, potassium bromide, hydroiodic acid, iodine, carbon tetraiodide, phosphorus triiodide, sodium iodide, or potassium iodide.

9. A method of preparing a compound of formula (IA),

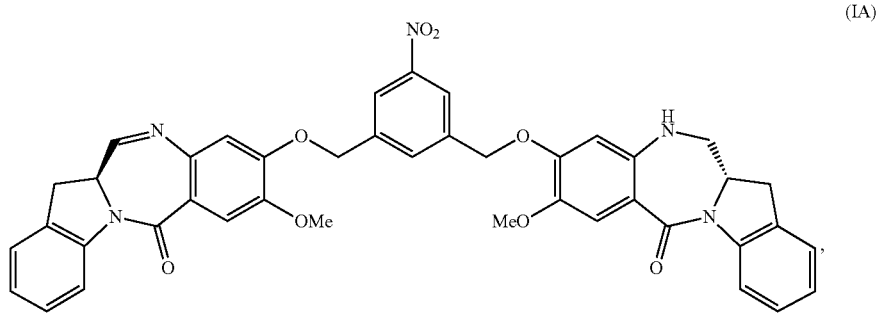 [SMILES: COc1cc2c(cc1OCc1cc(COc3cc4c(cc3OC)C(=O)N3c5ccccc5C[C@H]3CN4)cc([N+](=O)[O-])c1)N=C[C@@H]1Cc3ccccc3N1C2=O]

(IA)

or a pharmaceutically acceptable salt thereof, said method comprising the steps of:

(1) introducing an alcohol protecting group onto one of the primary alcohols of a compound of formula (1A),

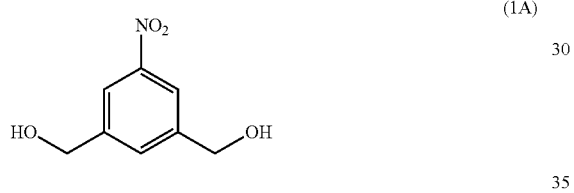

(1A)

to form a compound of formula (2A),

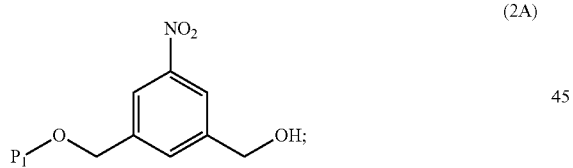

(2A)

(2) reacting the compound of formula (2A) with a halogenating reagent, a sulfonating reagent or an esterification reagent to form a compound of formula (3A),

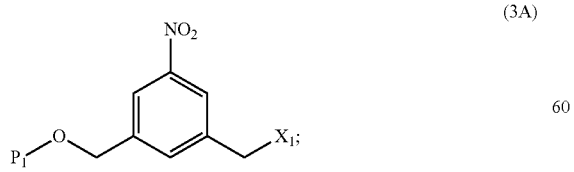

(3A)

(3) reacting the compound of formula (3A) with a monomer compound of the formula (a₁),

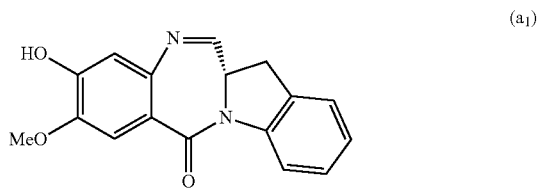 [SMILES: COc1cc2c(cc1O)N=C[C@@H]1Cc3ccccc3N1C2=O]

(a₁)

to form a compound of formula (4A),

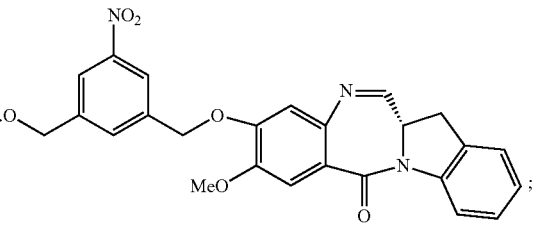

(4A)

(4) reacting the compound of formula (4A) with an imine reducing agent to form a compound of formula (5A),

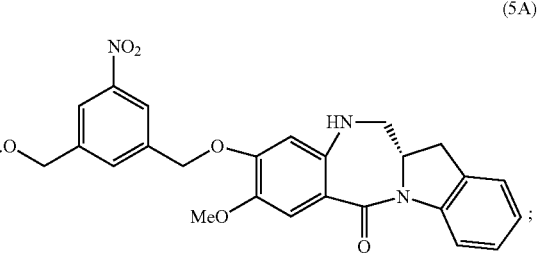

(5A)

(5) reacting the compound of formula (5A) with an alcohol deprotecting reagent to form a compound of formula (6A), (6A)

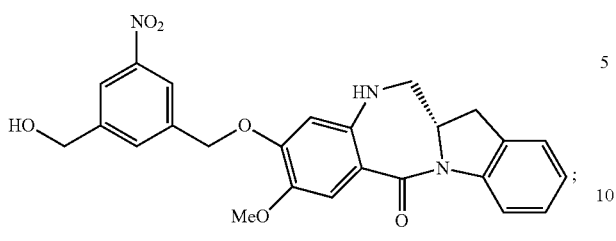

(6) reacting the compound of formula (6A) with a second halogenating reagent, a second sulfonating reagent or a second esterification reagent to form a compound of formula (7A), (7A)

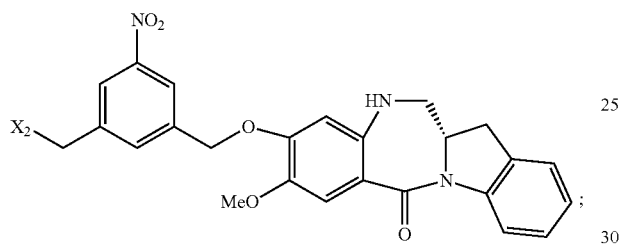

and
(7) reacting the compound of formula (7A) with a monomer compound of the formula (b1), (b1)

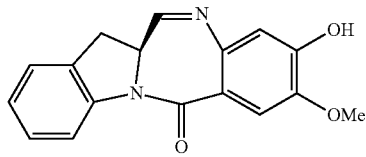

to form the compound of formula (IA); wherein:
P₁ is an alcohol protecting group; and,
X₁ and X₂ are each independently a leaving group selected from the group consisting of: —Br, —I, —Cl, a sulfonate ester and an activated ester.

10. A method of preparing a compound of formula (IA),

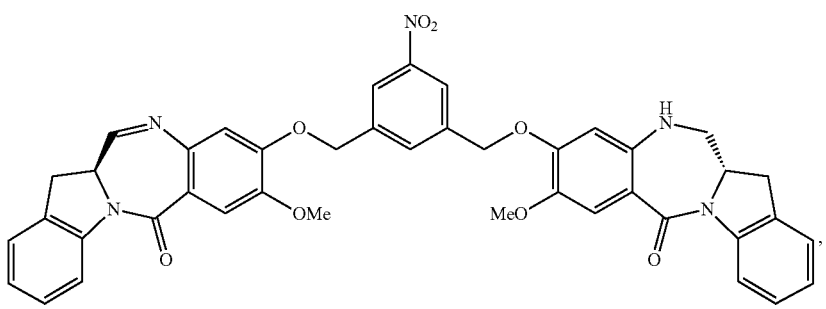

or a pharmaceutically acceptable salt thereof, said method comprising the steps of:

(1) introducing an alcohol protecting group onto one of the primary alcohols of the compound of formula (1A), (1A)

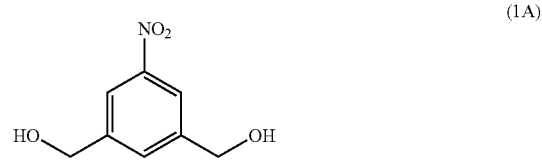 [SMILES: O=[N+]([O-])c1cc(CO)cc(CO)c1]

to form a compound of formula (2A), (2A)

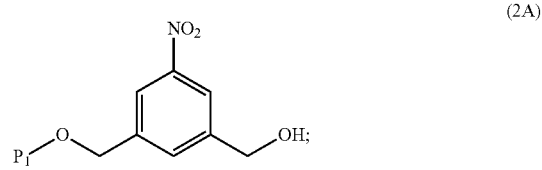

(2) reacting a halogenating reagent, a sulfonating reagent or an esterification reagent with the compound of formula (2) to form a compound of formula (3A), (3A)

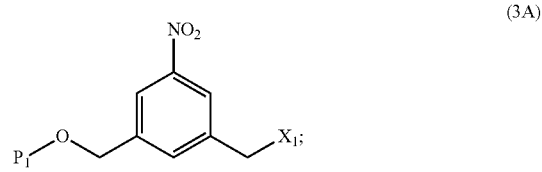

(3) reacting the compound of formula (3A) with a monomer compound of the formula (b1), (b1)

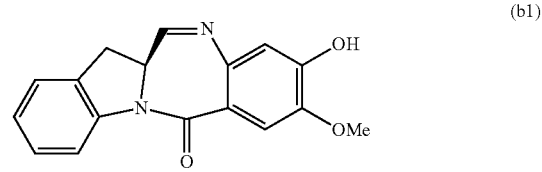 [SMILES: COc1cc2c(cc1O)N=C[C@@H]1Cc3ccccc3N1C2=O]

to form a compound of formula (8A),

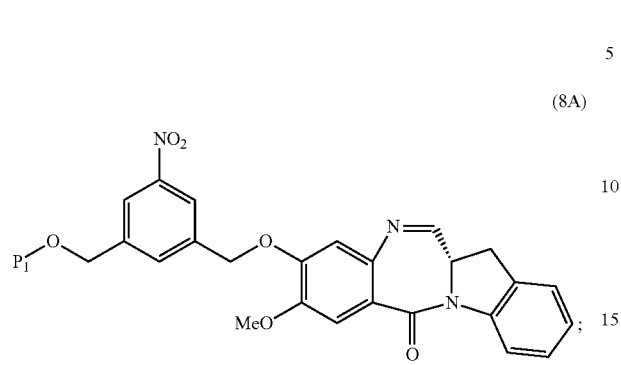
(8A)

(4) reacting the compound of formula (8A) with an alcohol deprotecting reagent to form a compound of formula (9A),

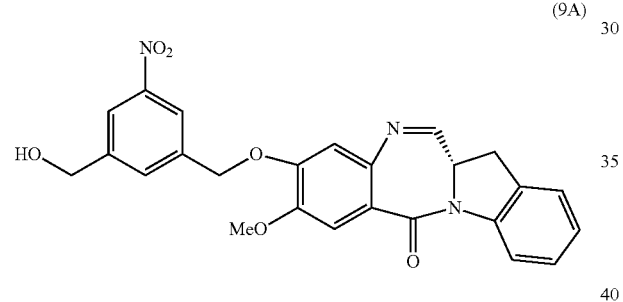
(9A)

(5) reacting a second halogenating reagent, a second sulfonating reagent or a second esterification reagent with the compound of formula (9A) to form a compound of formula (10A),

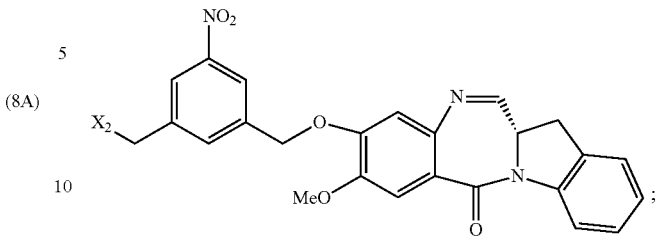
(10A)

(6) reacting the compound of formula (10A) with a monomer compound of the formula ($d_1$)

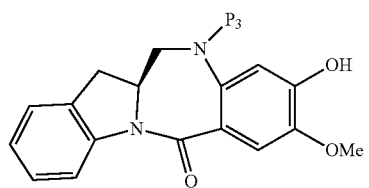
($d_1$)

to form a compound of formula (18A),

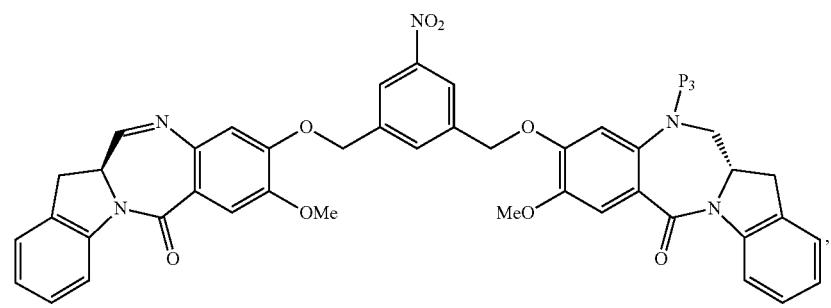
(18A)

(7) when $P_3$ is an amine protecting group; reacting the compound of formula (18A) with an amine deprotecting reagent to form the compound of formula (IA), wherein:

$P_3$ is H or an amine protecting group;

$P_1$ is an alcohol protecting group; and $X_1$ and $X_2$ are each independently a leaving group selected from the group consisting of: —Br, —I, —Cl, a sulfonate ester, and an activated ester.

11. The method of claim 10, wherein $P_3$ is H and the compound of (10A) is reacted with the monomer compound of ($d_1$) to form the compound of (IA).

12. The method of claim 1, wherein the alcohol protecting group is a silyl protecting group.

13. The method of claim 12, wherein the silyl protecting group is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, tert-butyldiphenylsilyl, 2-trimethyethylsilyl (TEOC), or [2-(trimethylsilyl)ethoxy]methyl.

14. The method of claim 12, wherein the silyl protecting group is triethylsilyl, triisopropylsilyl, or tert-butyldimethylsilyl.

15. The method of claim 12, wherein the silyl protecting group is tert-butyldimethylsilyl.

16. The method of claim 13, wherein the silyl protecting group is introduced by reacting the compound of formula (1A) with $R^3$—Cl, $R^3$—Br, $R^3$—I or $R^3$—$OSO_2CF_3$ in the presence of a base, wherein $R^3$ is dimethylisopropylsilyl, diethylisopropylsilyl, dimethylhexylsilyl, trimethylsilyl, triisopropylsilyl, tribenzylsilyl, triphenylsilyl, 2-norbornyldimethylsilyl, tert-butyldimethylsilyl, or tert-butyldiphenylsilyl.

17. The method of claim 16, wherein the base is imidazole, triethylamine, diisopropylethylamine, pyridine, 2,6-lutidine, 1,8-diazabicycloundec-7-ene, or tetramethylpiperidine.

18. The method of claim 16, wherein the reaction is carried out in the presence of a catalyst selected from the group consisting of 4-dimethylaminopyridine (DMAP), 1,1,3,3-tetramethylguanidine and 1,8-diazabicyclo[5.4.0]undec-7-ene (DBU).

19. The method of claim 9, wherein $X_1$ is —Cl, $P_1$ is tert-butyldimethylsilyl; and $X_2$ is mesylate.

20. The method of claim 9, wherein $X_1$ is mesylate, $P_1$ is tert-butyldimethylsilyl; and $X_2$ is mesylate.

21. The method of claim 10, wherein $X_1$ is —Cl, $P_1$ is tert-butyldimethylsilyl; and $X_2$ is mesylate.

22. The method of claim 10, wherein $X_1$ is mesylate, $P_1$ is tert-butyldimethylsilyl; and $X_2$ is mesylate.

\* \* \* \* \*